(12) United States Patent
Russell et al.

(10) Patent No.: US 9,383,360 B2
(45) Date of Patent: Jul. 5, 2016

(54) COMPOSITIONS AND METHODS RELATING TO LYME DISEASE

(71) Applicant: The United States of America, as represented by the Secretary, Department of Health and Human Services, Atlanta, GA (US)

(72) Inventors: Theresa M. Russell, Fort Collins, CO (US); Barbara J. B. Johnson, Fort Collins, CO (US)

(73) Assignee: The United States of America, as represented by the Secretary, Department of Health and Human Services, Rockville, MD (US)

( * ) Notice: Subject to any disclaimer, the term of this patent is extended or adjusted under 35 U.S.C. 154(b) by 45 days.

(21) Appl. No.: 14/372,171

(22) PCT Filed: Jan. 21, 2013

(86) PCT No.: PCT/US2013/022379
§ 371 (c)(1),
(2) Date: Nov. 24, 2014

(87) PCT Pub. No.: WO2013/110026
PCT Pub. Date: Jul. 25, 2013

(65) Prior Publication Data
US 2015/0293096 A1 Oct. 15, 2015

Related U.S. Application Data

(60) Provisional application No. 61/588,820, filed on Jan. 20, 2012.

(51) Int. Cl.
*G01N 33/573* (2006.01)
*G01N 33/58* (2006.01)
*G01N 33/68* (2006.01)
*G01N 33/569* (2006.01)
*C07K 16/12* (2006.01)

(52) U.S. Cl.
CPC .............. *G01N 33/573* (2013.01); *C07K 16/12* (2013.01); *G01N 33/56911* (2013.01); *G01N 33/581* (2013.01); *G01N 33/6863* (2013.01); *G01N 33/6869* (2013.01); *C07K 2317/32* (2013.01); *G01N 2333/20* (2013.01); *G01N 2333/952* (2013.01); *G01N 2469/10* (2013.01); *G01N 2469/20* (2013.01); *G01N 2800/26* (2013.01); *G01N 2800/52* (2013.01)

(58) Field of Classification Search
CPC ................... G01N 2333/20; G01N 2333/952; G01N 2469/10; G01N 2469/20; G01N 2800/26; G01N 2800/52; G01N 33/56911; G01N 33/573; G01N 33/581; G01N 33/6863; G01N 33/6869
See application file for complete search history.

(56) References Cited

U.S. PATENT DOCUMENTS 6,248,517 B1   6/2001   Guo et al.

FOREIGN PATENT DOCUMENTS

| WO | WO-91/13630 | 9/1991 |
| WO | WO-93/08306 | 4/1993 |
| WO | WO-2011/160048 | 12/2011 |

OTHER PUBLICATIONS

Toledo, A. et al., The Enolase of Borrelia burgdorferi Is a Plasminogen Receptor Released in Outer Membranes Vesicles, *Infection and Immunity*, 80(1): 359-68, Jan. 1, 2012.
Kumru, O. et al., Specificity and Role of the Borrelia burgdorferi CtpA Protease in Outer Membrane Protein Processing, *Journal of Bacteriology*, 193(20): 5759-65, Oct. 15, 2011.
Guyard, C. et al., Relapsing fever spirochaetes produce a serine protease that provides resistance to oxidative stress and killing by neutrophils, *Molecular Microbiology*, 60(3): 710-22, May 1, 2006.
Behera, A. et al., Role of Aggrecanase 1 in Lyme Arthritis, *Arthritis & Rheumatism*, 54(10): 3319-29, Oct. 2006.
Hu, L. et al., Host metalloproteinases in Lyme Arthritis, *Arthritis & Rheumatism*, 44(6): 1401-10, Jun. 2001.
Parveen, N. et al., Identification of a candidate glycosaminoglycan-binding adhesin of the Lyme disease spirochete Borrelia burgdorferi, *Molecular Microbiology*, 35(5): 1220-34, 2000.

*Primary Examiner* — Padma V Baskar
(74) *Attorney, Agent, or Firm* — Dinsmore & Shohl LLP

(57) ABSTRACT

Compositions and methods of the present invention relating to *B. burgdorferi* HtrA sensu lato (BbHtrA) protease activity, its substrates, cleavage products, biological effects and use in detection, diagnosis and/or treatment of Lyme disease are provided.

10 Claims, 26 Drawing Sheets

Figure 1A BbHtrA
Figure 1B BbHtrA$^{S226A}$
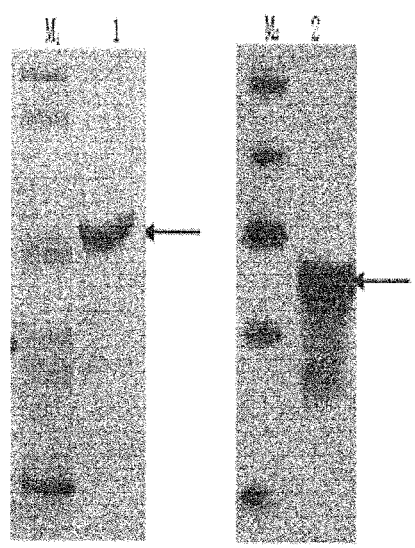
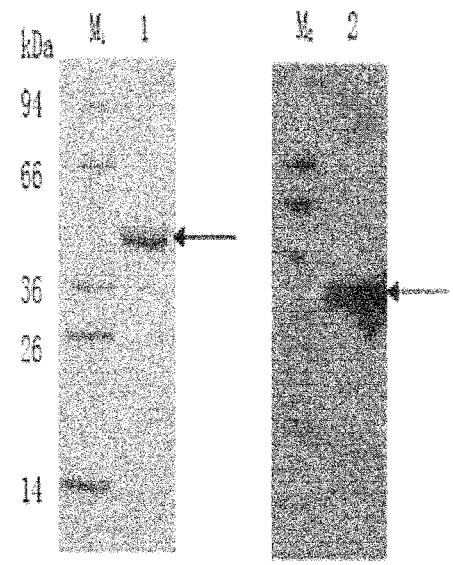
Figure 2A
Figure 2B
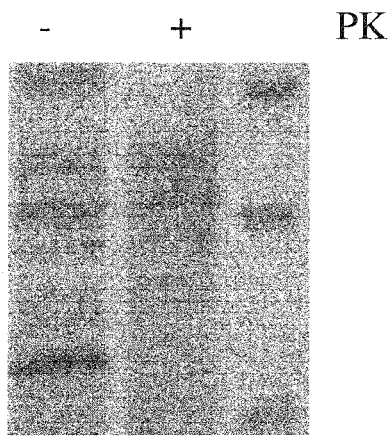
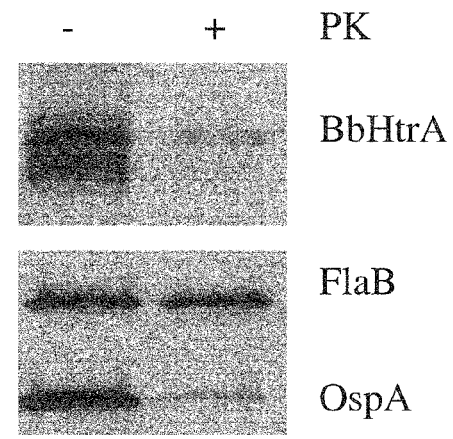

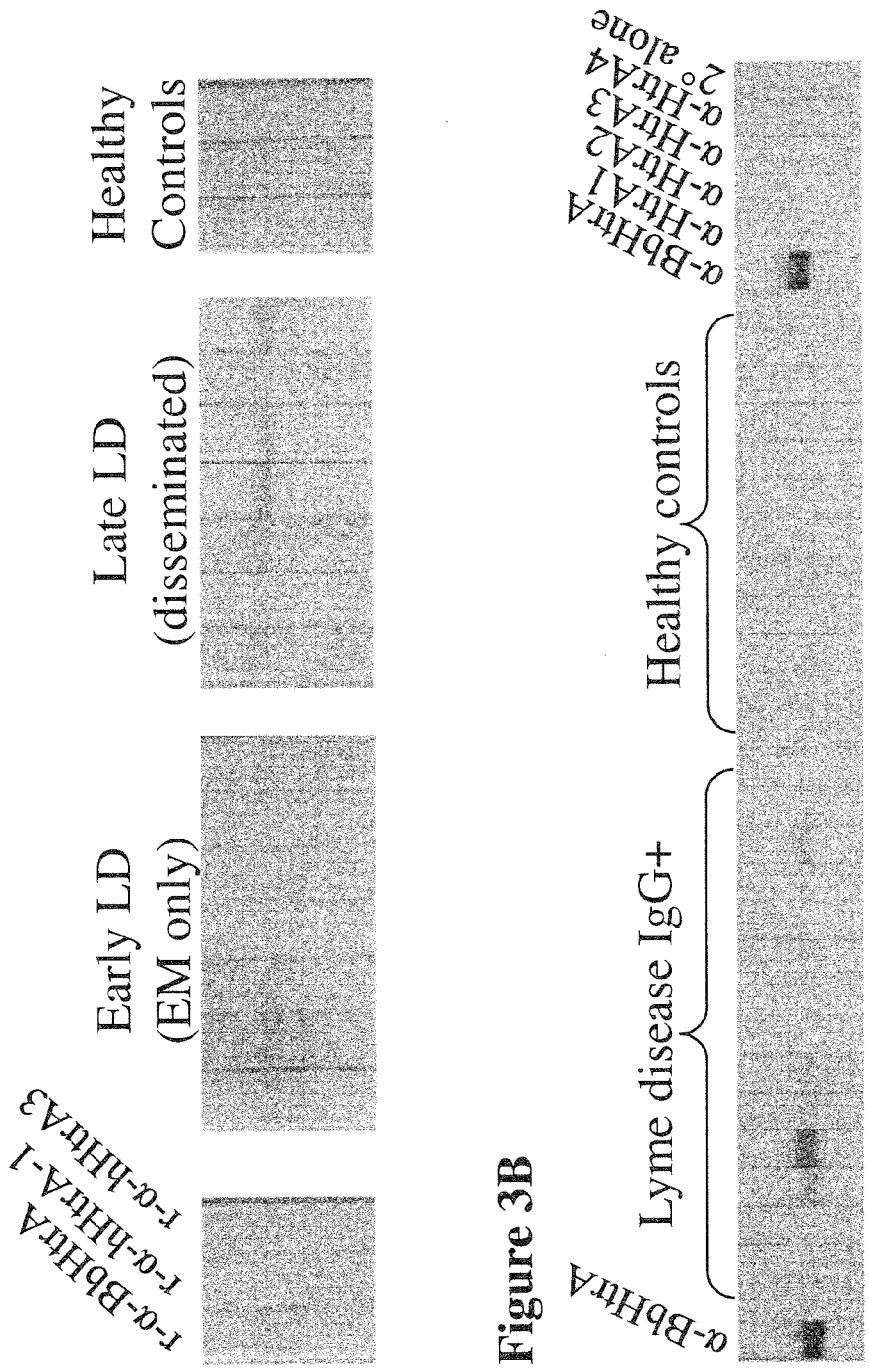

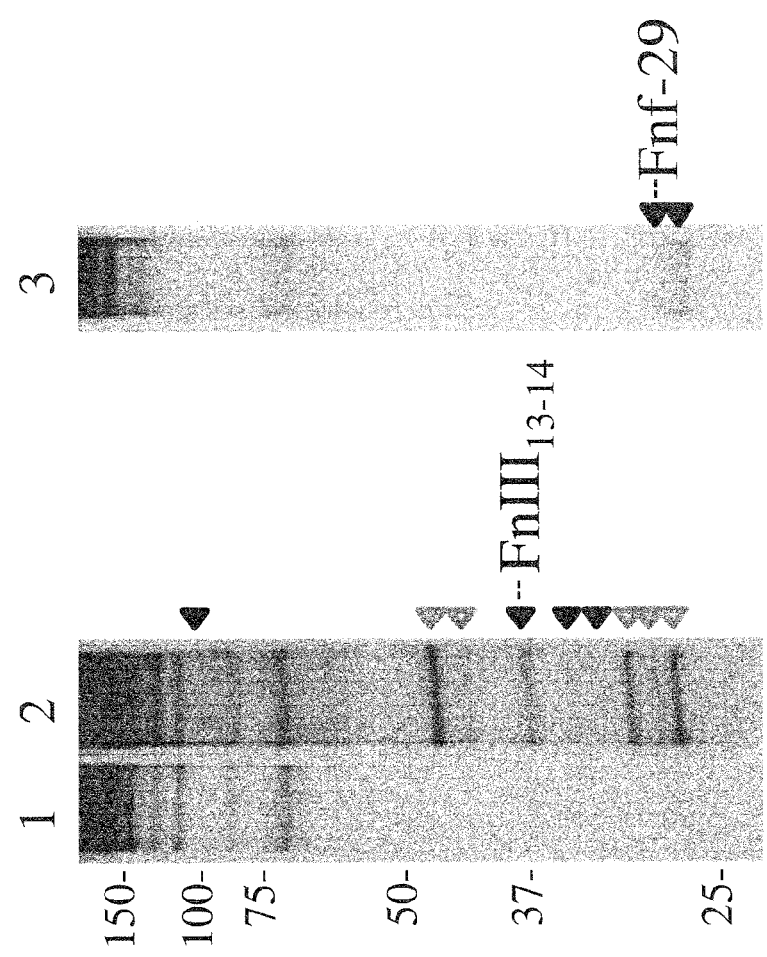

Figure 8B

| Fragment | Tryptic peptide | Amino acids | Region |
|---|---|---|---|
| 100kD | (R)VPGTSTSATLGLTR(G) | 2240-2256 | C' terminal Fibrin & heparin binding |
| | (K)IYLYTLNDNAR(S) | 1971-1983 | |
| 37kD | (R)RPGGEPSPEGTTGQSYNQYSQR(Y) | 2425-2448 | FnIII$_{13}$ |
| | (R)VPGTSTSATLGLTR(G) | 2240-2256 | |
| | (R)TKTETITGFQVDAVPANGQTPIQR(T) | 1926-1951 | |
| 33kD | (R)RPGGEPSPEGTTGQSYNQYSQR(Y) | 2425-2448 | |
| | (R)VPGTSTSATLGLTR(G) | 2240-2256 | |
| 29kD | (R)HTSVQTTSSGSGPFTDVR(A) | 272-291 | N' terminal Fibrin & heparin binding |
| | (R)TYLGNALVCTCYGGSR(G) | 67-84 | |
| 27kD | (R)GNLLQCLCTGNGR(G) | 252-266 | |
| | (R)TYLGNALVCTCYGGSR(G) | 67-84 | |

Figure 9B

| Pos Control | C5a | CD40 Ligand | G-CSF | GM-CSF | GROα (CXCL1) | I-309 (CCL1) | sICAM-1 (CD54) | IFN-g | Pos Control |
|---|---|---|---|---|---|---|---|---|---|
| | IL-1a | IL-1β | IL-1ra | IL-2 | IL-4 | IL-5 | IL-6 | IL-8 (CXCL8) | |
| | IL-10 | IL-12 p70 | IL-13 | IL-16 | IL-17 | IL-17E | IL-23 | IL-27 | |
| | IL-32a | CXCL10 | CXCL11 | MCP-1 (CCL2) | MIF | CCL3 | CCL4 | Serpin E1 | |
| Pos Control | RANTES (CCL5) | CXCL12 | TNF-a | sTREM-1 | | | | | Neg Control |

Identified N' sequence

← XEEKDNTVRAL = Mature N'
* ← FFDMPEFDSERK

*
** ← XEEKDNTVRAL
* ← FFDMPEFDSERK

```
             ▼
BbHtrA  SFPIPFFFFDMPEFDSERKSNWAGSGVIIG
EcDegQ  PEEFKKFFGDDLPDQPAQPFEGLGSGVIIN
           :  ** *      :. :   : ******.
```

Figure 13 Alignment of Bovine Decorin (P21793, SEQ ID NO:415) and Human Decorin (P07585, SEQ ID NO:420)

```
MKATIIFLLVAQVSWAGPFQQKGLFDFMLEDEASSGIPEEHFPEVPEIEPMGPVCPFRCQ     60   P21793
MKATIILLLLAQVSWAGPFQQRGLFDFMLEDEASSGIPEEHFPEVPDDR-DFEPSLGPVCPFRCQ 59   P07585
*****:*::*************::***********************   . ********

CHLRVVQCSDLGLEKVPKDLPPDTALLDLQNNKITEIKDGDFKNLKNLHTLILINNKISK    120   P21793
CHLRVVQCSDLGLDKVPKDLPPDTTLLDLQNNKITEIKDGDFKNLKNLHALILVNNKISK    119   P07585
*************:*********:********************* :*:**:******

ISPGAFAPLVKLERLYLSNQLKELPEKMPKTLQELRVHENEITKVRKSVFNGLNQMIVV    180   P21793
VSPGAFTPLVKLERLYLSRNQLKELPEKMPKTLQELRAHENEITKVRKVTFNGLNQMIVI    179   P07585
:*****:***********::*************** .*********** .**********:

ELGTNPLKSSGIENGAFQGMKKLSYIRIADTNITTIPQGLPPSLTELHLDGNKITKVDAA    240   P21793
ELGTNPLKSSGIENGAFQGMKKLSYIRIADTNITSIPQGLPPSLTELHLDGNKISRVDAA    239   P07585
******************************** :**************** .:***

SLKGLNNLAKIGLSFNSISAVDNGSLANTPHLRELHLNNNKLVKVPGGLADHKYIQVVYL    300   P21793
SLKGLNNLAKIGLSFNSISAVDNGSLANTPHLRELHLDNNKLTRVPGGLAEHKYIQVVYL    299   P07585
************************************ :****. :******:*********

HNNNISAIGSNDFCPPGYNTKKASYSGVSLFSNPVQYWEIQPSTFRCVYVRAAVQLGNYK    360   P21793
HNNNISVVGSSDFCPPGHNTKKASYSGVSLFSNPVQYWEIQPSTFRCVYVRSAIQLGNYK    359   P07585
******. *.:*****:**************************::*:*******
```

Figure 14 Alignment of Bovine Biglycan (P21809, SEQ ID NO:416) and Human Biglycan (P21810, SEQ ID NO:421)

```
MWPLWPLAALLALSQALPFEQKAFWDFTLDDGLPMLNDEEASGAETTSGIPDLDSLPPTY      60  P21809
MWPLMRLVSLLALSQALPFEQRGFWDFTLDDGPFMMNDEEASGAD-TSGVLDPDSVTPTY     59  P21810
***** *.:********* ******:.**********:: *** .  ***: . *** :  ***

SAMCPFGCHCHLRVVQCSDLGLKAVPKEISPDTTLLDLQNNDISELRKDDFKGLQHLYAL     120 P21809
SAMCPFGCHCHLRVVQCSDLGLKSVPKEISPDTTLLDLQNNDISELRKDDFKGLQHLYAL     119 P21810
***********************:************************************

VLVNNKISKIHEKAFSPLRKLQKLYISKNHLVEIPPNLPSSLVELRIHDNRIRKVPKGVF     180 P21809
VLVNNKISKIHEKAFSPLRKLQKLYISKNHLVEIPPNLPSSLVELRIHDNRIRKVPKGVF     179 P21810
************************************************************

SGLRNMNCIEMGGNPLENSGFEPGAFDGLKLNYLRISEAKLTGIPKDLPETLNELHLDHN     240 P21809
SGLRNMNCIEMGGNPLENSGFEPGAFDGLKLNYLRISEAKLTGIPKDLPETLNELHLDHN     239 P21810
************************************************************

KIQAIELEDLLRYSKLYRLGLGHNQIRMIENGSLSFLPTLRELHLDNNKLSRVPAGLPDL     300 P21809
KIQAIELEDLLRYSKLYRLGLGHNQIRMIENGSLSFLPTLRELHLDNNKLARVPSGLPDL     299 P21810
*************************************************: ***.******

KLLQVVYLHTNNITKVGVNDFCPVGFGRVKRAYYNGISLFNNPVPYWEVQPATFRCVTDRL   360 P21809
KLLQVVYLHSNNITKVGVNDFCPMGFGVKRAYYNGISLFNNPVPYWEVQPATFRCVTDRL    359 P21810
*********:*************:***.************************************

AIQFGNYKK    369  P21809    PGS1_BOVIN
AIQFGNYKK    368  P21810    PGS1_HUMAN
*********
```

Figure 15 Alignment of Bovine Fibromodulin (P13605, SEQ ID NO:417) and Human Fibromodulin (Q06828, SEQ ID NO:422)

```
MQWASILLAGLCSLSWAQYEEDSHWWFQFLRNQQSTYDDPYDPYEPYEPYPYGGEEG    60    P13605
MQWTSLLLAGLFSLSQAAYEDDPHWWFHYLRSQQSTYDPYDPYETYEPYPYGVDEG    60    Q06828
****:*:.****   ***.****:* .******:::**.*****.*******  :**.

PAYAYGSPPQPEPRDCPQECDCPPNFPTAMYCDNRNLKYLPFVPSRMKYVVYFQNNQISSI    120   P13605
PAYTYGSPSPPDPRDCPQECDCPPNFPTAMYCDNRNLKYLPFVPSRMKYVVYFQNNQITSI    120   Q06828
***:****. *:*******************************************:**

QEGVFDNATGLLWIALHGNQITSDKVGKKVFSKLRHLERLYLDHNNLTRIPSPLPRSLRE    180   P13605
QEGVFDNATGLLWIALHGNQITSDKVGRKVFSKLRHLERLYLDHNNLTRMPGPLPRSLRE    180   Q06828
***************************:********************:. *******

LHLDHNQISRVPNNALEGLENLTALYLHHNEIQEVGSSMKGLRSLILLDLSYNHLRKVPD    240   P13605
LHLDHNQISRVPNNALEGLENLTALYLQHNEIQEVGSSMRGLRSLILLDLSYNHLRKVPD    240   Q06828
***************************:**********:********************

GLPSALEQLYLEHNNVFSVPDSYFRGSPKLLYVRLSHNSLTNNGLASNTFNSSSLLELDL    300   P13605
GLPSALEQLYMEHNNVYTVPDSYFRGAPKLLYVRLSHNSLTNNGLASNTFNSSSLLELDL    300   Q06828
**********:**** .********.*********************************

SYNQLQKIPPVSTNLENLYLQGNRINEFSISSFCTVVDVMNFSKLQVLRLDGNEIKRSAM    360   P13605
SYNQLQKIPPVNTNLENLYLQGNRINEFSISSFCTVVDVVNFSKLQVLRLDGNEIKRSAM    360   Q06828
***********.***************************:*******************

PADAPLCLRLASLIEI    376    P13605    FMOD_BOVIN
PADAPLCLRLASLIEI    376    Q06828    FMOD_HUMAN
****************
```

Figure 16 Alignment of Bovine COMP (P49747, SEQ ID NO:418) and Human COMP (P35445, SEQ ID NO:423)

```
MVPDTACVLLITLAALGASGGQSPLGSDLGPQMLRELQETNAALQDVRELLRQQVREIT        60    P49747
MVLAAARVLLTLAALGASGGQGMPLGGDLGPQMLRELQETNAALQDVRDLLRQQVKEIT        60    P35445
**:*  ********:****:*********************:**********:***

FLKNTVMECDACGMQQSVRIGLPSVRPLLHCAPGECFPGVACIQTESGARCGPCPAGFTG      120    P49747
FLKNTVMECDACGMQPAR-TPKLTVRPLSQCSPGFCFPGVACTETANGARCGPCPEGFTG      119    P35445
***************  :  *  ****  :*:*** ******  *:*********:****

NGSHCTDVNECNAHPCFPRVRCINTSPGFRCEACPPGYSGPTHQGVGLAFAKANKQVCTD      180    P49747
NGSHCADVNECTAHPCFPRVRCINTSPGFRCEACPGFSGPTHEGVGLAFAKANKQVCTD      179    P35445
*****:****.***********************  :****:***************

INECETGQHNCVPNSVCINTRGSFQCGPCQPGFVGDQASGCQRRAQRFCPDGSPSECHEH      240    P49747
INECETGQHNCVPNSVCVNTVGSFQCGPCQPGFVGDQASGCRRRPRFQRFCPDGTPSPCHEK     239    P35445
*****************:** ********************:* *:* ******:**  **:

ADCVLERDGSRSCVCAVGWAGNGILCGRDTDLDGFPDEKLRCPERQCRKDNCVTVPNSGQ      300    P49747
ADCVLERDGSRSCVCAVGWAGNGLICGRDIDLDGFPDEKLRCSERQCRKDNCVTVPNSGQ      299    P35445
***********************:****  ***********:****************

EDVDRDGIGDACDPDADGDGVPNEKDNCPLVRNPDQRNTDEDKWGDACDMCRSQKNDDQK      360    P49747
EDVDQDGIGDACDPDADGDGVLNEKDNCPLVRNPDQRNTDGDKWGDACDNCRSQKNDDQK      359    P35445
****:****************  **************   ******* **********
```

Figure 16 Continued

```
DTDQDGRGDACDDDIDGDRIRMQADNCPRVPNSDQKDSDGDEIGDACDNCPQKSNPDQAD    420  P49747
DTDKDGRGDACDDDIDGDRIRNPVDNCPRVPNSDQKDIDGDVGDACDNCPQKSNADQRD    419  P35445
*** ******************.********.  *:**** ****.***:**.**:*

VDHDFVGDACDSDQDQDGDGHQDSRDNCFTVPNSAQEDSDHDGGGDACDDDDMDGVPDS    480  P49747
VDHDFVGDACDSDQDQDGDGHQDSKDNCFTVPNSAQDSDHDGQGDACDDDDNDGVPDS    479  P35445
*********************:*********:*****.***********:******

RDNCRLVPNEGQEDADRDGVGDVCQDDFDADKVVDKIDVCPENAEVTLIDERAFQTVVLD    540  P49747
RDNCRLVPNEGQEDMDRDGVGDACQGDFDADKVVDKIDVCPENAEVTLIDERAFQTVVLD    539  P35445
**************.*******.**.***********************************

PEGDAQIDPNWVLNQGREIVQTMNSDPGLAVGYTAFNGVDFEGTFHVNTVTDDDYAGFI    600  P49747
PEGDAQIDPNWVLNQGMEIVQTMNSDPGLAVGYTAFNGVDFEGTFHVNIAIDDDYAGFI    599  P35445
****************.*****************************  : ********

FGYQDSSSFYVMWKQMEQTYWQANPFRAVAEPGIQLKAVKSSTGPGEQLRNALMHTGDT    660  P49747
FGYQDSSSFYVMWKQMEQTYWQANPFRAVAEPGIQLKAVKSSTGPGEQLRNALMHTGDI    659  P35445
***********************************************************:

ESQVRLLMKDPRNVGWKDKRSYRWFLQHRPQVGYIRVRFYEGPELVADSNVVLDITMRGG    720  P49747
ASQVRLLMKDPRNVGWKDKTSYRWFLQHRPQVGYIRVRFYEGPELVADSNVVLDITTMRGG    719  P35445
 *****************.*****************************:*****

RLGVFCFSQENIINANLRYRCNDTIPEDYETHQLRQA    757  P49747  COMP_HUMAN
RLGVFCFSQENIINANLRYRCNDTIPEDYEAQRLLQA    756  P35445  COMP_BOVIN
***************************** ::* **
```

Figure 17 Alignment of Bovine Aggrecan (P13608, SEQ ID NO:419) and Human Aggrecan (P16112, SEQ ID NO:424)

```
MTTLLLVFVTLRVITAAISVEVSEPDNSLSVSTPEPSPLRVLLGSSLTIPCYFIDPMHPV    60   P13608
MTTLLWFVTLRVITAAVTVETSDHDNSLSVSTPQPSPLRVLLGTSLTIPCYFIDPMHPV    60   P16112
*****:*************:.*:*:****************:*********************

TTAPSTAPLAPRIKWSRISKEKEVLLVATEGRVRVNSAYQDKVTLPNYPAIPSDATLEI    120  P13608
TTAPSTAPLAPRIKWSRVSKEKEVLLVATEGRVRVNSAYQDKVSLPNYPAIPSDATLEV    120  P16112
*****************:************************:***************:

QNMRSNDSGILRCEVMHGIEDSQATLEVVKGIVFHYRAISTRYTLDFDRAQRACLQNSA    180  P13608
QSLRSNDSGVYRCEVMHGIEDSEATLEVVKGIVFHYRAISTRYTLDFDRAQRACLQNSA    180  P16112
*.:*****.: *********** *****************************************

IIATPEQLQAAYEDGFHQCDAGWLADQTVRYPIHTPREGCYGDKDEFPGVRTYGIRDTNE    240  P13608
IIATPEQLQAAYEDGFHQCDAGWLADQTVRYPIHTPREGCYGDKDEFPGVRTYGIRDTNE    240  P16112
************************************************************

TYDVYCFAEMEGEVFYATSPEKFTFQEAANECRRLGARLATTGQLYLAWQGGMDMCSAG    300  P13608
TYDVYCFAEMEGEVFYATSPEKFTFQEAANECRRLGARLATTGHVYLAWQAGMDMCSAG    300  P16112
******************************************::******.********

WLADRSVRYPISKARPNCGGNLLGVRTVYLHANQTGYPDPSSRYDAICYTGEDFVDIPES    360  P13608
WLADRSVRYPISKARPNCGGNLLGVRTVYHANQTGYPDPSSRYDAICYTGEDFVDIPEN    360  P16112
****************************:*********************************.

FFGVGGEEDITIQTVTWPDVELPLPRNITEGEARGSVILTAKPDFEVSPTAPEPEEPFTF    420  P13608
FFGVGGEEDITVQTVTWPDMELPLPRNITEGEARGSVILTVKPIEEVSPSPLEPEEPFTF    420  P16112
***********:*******:********************.**:****.. *********
```

Figure 17 Continued

```
VPEVRATAFPEVENRTEEATRPWAFPRESTPGLGAPTAFTSEDLVVQVTLAPGAAEVPGQ  480  P13608
APEIGATAFAEVENETGEATRPWGFP----TPGLGPATAFTSEDLVVQVTA------VPGQ  471  P16112
.**: ****. *  *******.**   ***** ************** *******

PRLPGGVFHYRPGSSRYSLTFEEAKQACLRTGAIIASPEQLQAAYEAGYEQCDAGWLQD  540  P13608
PHLPGGVFHYRPGPTRYSLTFEEAQQACPGTGAVIASPEQLQAAYEAGYEQCDAGWLRD  531  P16112
*:************ :************ ***.**:*********************:*

QTVRYPIVSPRTPCVGDKDSSPGVRTYGVRPPSETYDVCYVDRLEGEVFEATRLEQFTF  600  P13608
QTVRYPIVSPRTPCVGDKDSSPGVRTYGVRPSTETYDVCYCFVDRLEGEVFEATRLEQFTF  591  P16112
***************************** ******* ******************

WEAQEFCESQNATLATTGQLYAAWSRGLDKCYAGWLADGSLRYPIVTPRPACGGDKPGVR  660  P13608
QEALEFCESHNAT--ATTGQLYAAWSRGLDKCYAGWLADGSLRYPIVTPRPACGGDKPGVR  650  P16112
 **:****:***  **********************************************

TVYLYPNQTGLLDPLSRHHAFCFRGVSAAPSPEEEEGSAPTAGPDVEEWMVTQVGPGVAA  720  P13608
TVYLYPNQTGLPDPLSRHHAFCFRGISAVPSPGEEEGGTPTSPSGVEEWIVTQVVPGVAA  710  P16112
*********** ************:**.*** ***    *. .* ****:**** *****

VPIGEETTA-------IPGFTVEPENKTEWELAYTPAGTLPLPGIPPTWPPTGEATEEH  772  P13608
VPVEEETTAVPSGETTAILEFTTEPENQTEWEPAYTPVGTSPLPGILPTWPPTGAETEES  770  P16112
**:  ****        * *:*****:***. ****.**  ****:********* ***:

TEGPSATEVPSASEKPFPSEEPFPEEEPFPSEKPFPPEELFPSEKPFPSEEPFP  832  P13608
TEGPSATEVPSASEEPSPSEVPFFSEEPSPSEE-------------PFP  806  P16112
*************:* .***:** ****.****             ***
```

Figure 17 Continued

```
SEKPFPPEELFPSEKPIPSEEPFPSEEPFPSEKPFPPEEPFPSEKPIPSEEPFPSEKPFP      892   P13608
SVRPFPSVELFPSEEPFPSKEP---------------------------------SP       830   P16112
*  :**** ********: *: :*:*

SEEPFPSEEPSTLSAPVPSRTELPSSGEVSGVPEISGDFTGSGEISGHLDFSGQPSGESA     952   P13608
SEEPSASEEPYTPSPPEPSWTELPSSGEESGAPDVSGDFTGSGDVSGHLDFSGQLSGDRA     890   P16112
****  *  *  *  * ** *****: : :********:;;******  **:: *

SGLPSEDLDSSGLTSTVGSGLPVESGLPSGEEERITWTSAPKVDRLPSGGEGPE--VSGV    1010   P13608
SGLPSGDLDSSGLTSTVGSSGLTVESGLPSGEEERIEWPSTPTVGELPSGAEILEGSASGV    950   P16112
****.******.*****:****: :**** . *

EDISGLPSGGEVH---------------LEISASGVEDISGLPSGGEV-                1043   P13608
GDLSGLPSGEVLETSASGVGDLSGLPSGEVLETTAPGVEDISGLPSGEVLETTAPGVEDI    1010   P16112
 *:******:*   :

------HLEISASGVEDLSRIPSGEGPEISASGVEDISGLPSGEVLETTAPGVEDISGL    1083   P13608
SGLPSGEVLETTAPGVEDISGLPSGEVLETTAPGVEDISGLPSGEVLETTAPGVEDISGI    1070   P16112
        ** :*  ***************

----HLEISASGVEDLSRIPSGEGPEISASGVEDISGLPSGEG-------SGVEDLIGLPSG    1120   P13608
PSGEVLETAAPGVEDISGLPSGEVLETAAPGVEDISGLPSGEVLETAAPGVEDISGLPSG    1130   P16112
     ** :* ****;:****** *.:*

EGPEVSASGVEDLSRLPSGEGPEVSASGVEDLSGLPSGEGPEVSVSGVEDLS--------    1172   P13608
EVLETAAPGVEDISGLPSGEVLETAAPGVEDISGLPSGEVLETAAPGVEDISGLPSGEVL    1190   P16112
*    . :* ****;:******;:******  *. :.: *
```

Figure 17 Continued

```
            ---------RLPSGEGPEVSASGVEDLSRLPSGEGPEISVSGVEDISILPSGEGPEVS  1221  P13608
ETAAPGVEDISGLPSGEVLETAAPGVEDISGLPSGEVLETAAPGVEDISGLPSGEVLETA  1250  P16112
                                    *.:.*  *****:* *****  ****

ASGVEDLSV-----------------------------HLEISTSG              1244  P13608
APGVEDISGLPSGEVLETAAPGVEDISGLPSGEVLETTAPGVEEISGLPSGEVLETTAPG  1310  P16112
*  ****:**                             **  ::  *

VEDLSVLPSGEGHLETSSGVEDISRLPSGEGPEVSASGVEDLSVLPSGEDHLEISASGVE  1304  P13608
VDEISGLPSGEVLETTAPGVEEISGLPSGEVLETSAVGDLSGLPSGGEVLEISVSGVE    1370  P16112
*: :.*  ****  *   *:  ****:*,  **** :  ****   : ****:  .  ****

DLGVLPSGEDHLEISASGVEDISRLPSGEGPEVSASGVEDLSVLPSGEGHLEISASGVED  1364  P13608
DISGLPSGE-VVETSASGIEDVSELPSGEVLETSASGVEDLSRLPSGEEVLEISASGFGD  1429  P16112
*:.  ******  . ***:*:  **  ****.  ** ****:* :****:.  **:*****.

LSRLPSGGEDHLETSASGVGDLSGLPSGREGLEISASGAGDLSGLTSGKEDLTGSASGAL  1424  P13608
LSGVPSGGEGLETSASEVGTDLSGLPSGREGLETSASGAEDLSGLPSGKEDLVGSASGDL  1489  P16112
**.  ****.  ** ****  *.*******.***:**.***.***  :*****  *****:

DLGRIPSVTLGSGQAPEASGLPSGFSGEYSGVDLESGPSSGLPDFSGLPSGFPTVSLVDT  1484  P13608
DLGKLPSGTLGSGQAPETSGLPSGFSGEYSGVDLGSGPPSGLPDFSGLPSGFPTVSLVDS  1549  P16112
***: **..*******:*********:** .*** .***  *********:

TLVEVVTATTAGELEGRGTIDISGAGETSGLPFSELDISGGASGLSSGAELSGQASGSPD  1544  P13608
TLVEVVTASTASTAELEGRGTIGISGAGEISGLPSSELDISGRASGLPSGTELSGQASGSPD  1609  P16112
********: **:******* :******:****. ****** :*** ::********:
```

Figure 17 Continued

```
ISGETSGLFGVSGQPSGFPDISGETSGLLEVSGQPSGFYGEISGVTELSGLASGQPEISG  1604  P13608
VSGEIPGLFGVSGQPSGFPDTSGETS------------------GVTELSGLSSGQPGVSG  1652  P16112
:.***  *************.*****  .****            :******.:.**:.*

EASGILSGLGPPEGITDLSGEAPGIPDLSGQPSGLPEESGTASGIPDLVSSAVSGSGESS  1664  P13608
EASGVLYGTSQPFGITDLSGETSGVPDLSGQPSGLPGESGATSGVPDLVSGTTSGSGESS  1712  P16112
****:*  . ******** :**:***************  .:*****.:*.:.*******

GITFVDTSLVEVTPTTFKEEEGLGSVELSGLPSGELGVSGTSGLADVSGLSSGAIDSSGF  1724  P13608
GITFVDTSLVEVAPTTFKEEEGLGSVELSGLPSGEADLSGKSGMVDVSGQFSGTVDSSGF  1772  P16112
************:***************************  :**  *.*.  *.  .  :*.****

TSQPPEFSGLPSCVTEVSGEASGAESGSSLPSGAYDSSGLPSGFPTVSFVDRTLVESVTQ  1784  P13608
TSQTPEESGLPSGIAEVSGESSRAEIGSSLPSGAYYGSGTPSSFPTVSLVDRTLVESVTQ  1832  P16112
***.**:******  . **** :*  .  :* ***********  .  .* .:**:***.************

APTAQEAGEGPSGILELSGAPSGAPDMSGDHLGSLDQSGLVEPSGEPASTPYFSGD       1844  P13608
APTAQEAGEGPSGILELSGAHSGAPDMSGEHSGFLDLSGLQSGLIEPSGEPPGTPYFSGD  1892  P16112
********************:********:*  .*  **  ***  . ***:********  . :******

FSGTTDVSGESSAATSTSGEASGLPEVTLITSELVEGVTEPTVSQELGQRPPVTYTPQLF  1904  P13608
FASTTNVSGESSVAMGTSGEASGLPEVTLITSELVEFVEGVTEPTISQELGQRPPVTHTPQLE  1952  P16112
*:*.*  ******.* .*:************:*** .***********:**********:****

ESSGEASASG---DVPRFPGSSVEVSSVPESSGETSAYPEAEVGASAAPEASGGASGSP   1960  P13608
ESSGKVSTAGDISGATPVLPGSGVEVSSVPESSVPESSSETSAYPEAGFGASAAPEASREDSGSP  2012  P16112
****  .  . *  .:.*       . :******.******:* ***********:****
```

Figure 17 Continued

```
NLSETTSTFHEADLEGTSGLGVSGSPSAFPEGPTEGLATPEVSGESTTAFDVSVEASGSP  2020  P13608
DLSETTSAFHEANLERSSGLGVSGSTLFQEGEA--SAAPEVSGESTTTSDVGTEAPGLP   2070  P16112
:****:;*****.::*****************   .  *:.****..**..**

SATPLASGDRTDTSGDLSGHTSGLDIVISTTIPESEWTQQTQRPAEARLEIESSSPVHSG  2080  P13608
SATPTASGDRTEISGDLSGHTSQLGVVISTSIPESEWTQQTQRPAETHLEIESSSLLYSG  2130  P16112
****:******::********.:**.:**:*****************:****::.:**

EESQTADTATSPTDASIPASAGGTDDSEATT-TDIDECLSSPCLNGATCVDAIDSFTCLC  2139  P13608
EETHTVETATSPTDASIPASPEWKRESESTAAAPARSCAEEPCCA-GTCKETEGHVICLC  2189  P16112
**::. :*********** :.**** .  * . .**. *     ***:.  .  :***

LPSYQGDVCEIQ-KLCEEGWTKFQGHCYRHFPDRATWVDAESQCRKQQSHLSSIVTPEEQ  2198  P13608
PPGYTGEHCNIDQEVCEEGWNKYQGHCYRHFPDRETWVDAERRCREQQSHLSSIVTPEEQ  2249  P16112
 *.*.*::*:* :****:*.*:*********:****** :***:*************

EFVNNAQDYQWIGLNDKTIEGDFRWSDGHSLQFENWRPNQPDNFFATGEDCVVMIWHEK  2258  P13608
EFVNNAQDYQWIGLNDRTIEGDFRWSDGHPMQFENWRPNQPDNFFAAGEDCVVMIWHEK  2309  P16112
***************:************. :*************:************

GEWNDVPCNYQLPFTCKKGTVACGEPPVEHARIFGQKKDRYEINALVRYQCTEGFIQGH  2318  P13608
GEWNDVPCNYHLPFTCKKGTVACGEPPVEHARTFGQKKDRYEINSLVRYQCTEGFVQRH  2369  P16112
**********:*******************.************:*********:* *

VPTIRCQPSGHWEEPRITCTDPATYKRRLQKRSSRPLRRSHPSTAH  2364  P13608
MPTIRCQPSGHWEEPRITCTDATTYKRRLQKRSSRHPRRSRPSTAH  2415  P16112
:********************.*:***********. **:*****

PGCA_BOVIN
PGCA_HUMAN
```

US 9,383,360 B2

COMPOSITIONS AND METHODS RELATING TO LYME DISEASE

REFERENCE TO RELATED APPLICATION

This application claims priority from U.S. Provisional Patent Application Ser. No. 61/588,820, filed Jan. 20, 2012, the entire content of which is incorporated herein by reference.

FIELD OF THE INVENTION

Generally described herein are compositions and methods of the present invention relating to detection, diagnosis and/or treatment of Lyme disease, also known as Lyme borreliosis. Specifically described are compositions and methods of the present invention relating to *B. burgdorferi* HtrA sensu lato (BbHtrA) protease activity, its substrates, cleavage products, biological effects and use in detection, diagnosis and/or treatment of Lyme disease.

BACKGROUND OF THE INVENTION

In 2011, over 32,000 cases of confirmed or probable Lyme disease were reported to the Centers for Disease Control and Prevention making Lyme disease the most common tick-borne infectious disease in the United States. Lyme disease is also the most common infection transmitted by ticks in Europe and is increasingly a public health problem in Canada and temperate regions of Asia. The causative agent is the bacterium *Borrelia burgdorferi* sensu lato which is transmitted to mammals through the bite of infected ticks.

A complicating factor in diagnosis of Lyme disease is the difficulty of detecting active infection with the causative agent of Lyme disease, particularly in cases where symptoms are present long after potential exposure to infected ticks.

There is a continuing need for compositions and methods for aiding in the detection and diagnosis of Lyme disease in a subject. There is a continuing need for compositions and methods for treatment and/or prevention of Lyme disease.

SUMMARY OF THE INVENTION

Methods of aiding in the diagnosis, assessment and/or treatment of Lyme disease are provided according to aspects of the present invention which include assaying a first sample obtained from a subject having, or suspected of having, Lyme disease for one or more peptides produced by proteolytic activity of *Borrelia burgdorferi* sensu lato HtrA on at least one host protein substrate, to produce an assay result wherein detection of the one or more peptides is indicative of an active *Borrelia burgdorferi* sensu lato infection in the subject.

According to aspects of the present invention, the one or more peptides is selected from the group consisting of: one or more peptides of: SEQ ID NO:33-69 and 163-414, wherein each of the peptides of SEQ ID NO: 33-69 and 163-414 has 5 amino acids closest to the amino terminus and having 1, 2, 3, 4, 5, 6, 7, 8, 9, 10, 11, 12, 13, 14, 15, 16, 17, 18, 19, 20, 21, 22, 23, 24, 25, 26, 27 or 28 additional amino acids; a homologue or variant of one or more peptides of SEQ ID NO: 33-69 and 163-414, the homolog or variant having at least 95% identity to at least one of the peptides of SEQ ID NO: 33-69 and 163-414; a fragment of the one or more peptides of SEQ ID NO: 33-69 and 163-414, the fragment having at least the 5 amino acids closest to the amino terminus; a fragment of the one or more peptides of SEQ ID NO: 33-69 and 163-414, the fragment having at least the 5 amino acids closest to the amino terminus and at least 1, 2, 3, 4, 5, 6, 7, 8, 9, 10, 11, 12, 13, 14, 15, 16, 17, 18, 19, 20, 21, 22, 23, 24, 25, 26, 27 or 28 additional of the amino acids; and a combination of any two or more thereof.

According to aspects of the present invention, the one or more peptides is a cleavage product of *Borrelia burgdorferi* sensu lato HtrA protease activity on a substrate having a cleavage site having SEQ ID NO:70-162, or a homolog or variant having at least 95% identity to a cleavage site having SEQ ID NO:70-162 wherein *Borrelia burgdorferi* sensu lato HtrA has protease activity to cleave at the homolog or variant site.

According to aspects of the present invention, the one or more peptides is selected from the group consisting of: SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69; a homologue or variant of one or more peptides of SEQ ID NO: 52-69, the homolog or variant having at least 95% identity to at least one of the peptides of SEQ ID NO: 52-69; and a combination of any two or more thereof.

According to aspects of the present invention, the one or more peptides is selected from the group consisting of: SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51; a homologue or variant of one or more peptides of SEQ ID NO: 33-51, the homolog or variant having at least 95% identity to at least one of the peptides of SEQ ID NO: 33-51; and a combination of any two or more thereof.

According to aspects of the present invention, the one or more peptides is selected from the group consisting of: one or more peptides of SEQ ID NO:163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413 and 414, wherein each of the peptides of SEQ ID NO: 163-414 has 5 amino acids closest to the amino terminus and having 1, 2, 3, 4, 5, 6, 7, 8, 9, 10, 11, 12, 13, 14, 15, 16, 17, 18, 19, 20, 21, 22, 23, 24, 25, 26, 27 or 28 additional amino acids; a homologue or variant of one or more peptides of SEQ ID NO: 163-414, the homolog or variant having at least 95% identity to at least one of the peptides of SEQ ID NO: 163-414; a fragment of the one or more peptides of SEQ ID NO: 163-414, the fragment having at least the 5 amino acids closest to the amino terminus; a fragment of the one or more peptides of SEQ ID NO: 163-414, the fragment having at least the 5 amino acids closest to the amino terminus and at least 1, 2, 3, 4, 5, 6, 7, 8, 9, 10, 11, 12, 13, 14, 15, 16, 17, 18, 19, 20, 21, 22, 23, 24, 25, 26, 27 or 28 additional of the amino acids; and a combination of any two or more thereof.

Methods of aiding in the diagnosis, assessment and/or treatment of Lyme disease are provided according to aspects of the present invention which include assaying a first sample obtained from a subject having, or suspected of having, Lyme disease for one or more peptides produced by proteolytic activity of *Borrelia burgdorferi* sensu lato HtrA on at least one host protein substrate, to produce an assay result wherein detection of the one or more peptides is indicative of an active *Borrelia burgdorferi* sensu lato infection in the subject; and assaying a second sample obtained from the subject having, or suspected of having, Lyme disease to detect at least one inflammatory cytokine or chemokine selected from: CXCL1, CCL1, sICAM-1, IL-6, IL-8, CCL2, and CCL5, wherein detection of the one or more peptides in combination with an increase in CXCL1, CCL1, sICAM-1, IL-6, IL-8, CCL2, and CCL5 compared to a standard is indicative of an active *Borrelia burgdorferi* sensu lato infection in the subject. The first sample and second sample are each independently selected from: whole blood, plasma, urine, serum, cerebrospinal fluid, synovial fluid and/or a biopsy sample, wherein the biopsy sample is skin or joint tissue. The first and second samples may be the same or different sample type. The second sample may be a portion of the first sample.

Methods of aiding in the diagnosis, assessment and/or treatment of Lyme disease are provided according to aspects of the present invention which include assaying a first sample obtained from a subject having, or suspected of having, Lyme disease for one or more peptides produced by proteolytic activity of *Borrelia burgdorferi* sensu lato HtrA on at least one host protein substrate, to produce an assay result wherein detection of the one or more peptides is indicative of an active *Borrelia burgdorferi* sensu lato infection in the subject; and assaying a second sample obtained from the subject having, or suspected of having, Lyme disease for 1, 2, 3, 4, 5 6 or 7 inflammatory cytokines and chemokines selected from: CXCL1, CCL1, sICAM-1, IL-6, IL-8, CCL2, and CCL5; and assaying the second sample obtained from the subject having, or suspected of having, Lyme disease for least one inflammatory cytokine or chemokine selected from: C5a, CD40 ligand, G-CSF, GM-CSF, IL-1a, IL-1b, IL-ra, IL-2, IL-4, IL-5, IL-10, IL-12p70, IL-13, IL-16, IL-17, IL-17E, IL-23, IL-27, IL-32a, CXCL10, CXCL11, MIF, CCL3, CCL4 and Serpin E1; wherein an increase in 1, 2, 3, 4, 5 6 or 7 of CXCL1, CCL1, sICAM-1, IL-6, IL-8, CCL2, and CCL5 compared to a standard and substantially no increase in the at least one inflammatory cytokine or chemokine selected from: C5a, CD40 ligand, G-CSF, GM-CSF, IFN-g, IL-1a, IL-1b, IL-ra, IL-2, IL-4, IL-5, IL-10, IL-12p70, IL-13, IL-16, IL-17, IL-17E, IL-23, IL-27, IL-32a, CXCL10, CXCL11, MIF, CCL3, CCL4 and Serpin E1 compared to a standard, is indicative of an active *Borrelia burgdorferi* sensu lato infection in the subject. The first sample and second sample are each independently selected from: whole blood, plasma, urine, serum, cerebrospinal fluid; synovial fluid and/or a biopsy sample, wherein the biopsy sample is skin or joint tissue. The first and second samples may be the same or different sample type. The second sample may be a portion of the first sample.

Methods of aiding in the diagnosis, assessment and/or treatment of Lyme disease are provided according to aspects of the present invention which include assaying a first sample obtained from a subject having, or suspected of having, Lyme disease for one or more peptides produced by proteolytic activity of *Borrelia burgdorferi* sensu lato HtrA on at least one host protein substrate, to produce an assay result wherein detection of the one or more peptides is indicative of an active *Borrelia burgdorferi* sensu lato infection in the subject; and assaying a further sample obtained from a subject having, or suspected of having, Lyme disease for one or more peptides produced by proteolytic activity of *Borrelia burgdorferi* sensu lato HtrA on at least one host protein substrate, the further sample obtained from the subject at a later time than the first sample, wherein detection of the one or more peptides is indicative of an active *Borrelia burgdorferi* sensu lato infection in the subject. The first sample and further sample are each independently selected from: whole blood, plasma, urine, serum, cerebrospinal fluid, synovial fluid and/or a biopsy sample, wherein the biopsy sample is skin or joint tissue. The first and further samples may be the same or different sample type. In a preferred aspect of the invention, the first and further samples are of the same sample type.

Methods of aiding in the diagnosis, assessment and/or treatment of Lyme disease are provided according to aspects of the present invention which include assaying a first sample obtained from a subject having, or suspected of having, Lyme disease for one or more peptides produced by proteolytic activity of *Borrelia burgdorferi* sensu lato HtrA on at least one host protein substrate, to produce an assay result wherein detection of the one or more peptides is indicative of an active *Borrelia burgdorferi* sensu lato infection in the subject; assaying a further sample obtained from a subject having, or suspected of having, Lyme disease for one or more peptides produced by proteolytic activity of *Borrelia burgdorferi* sensu lato HtrA on at least one host protein substrate, the further sample obtained from the subject at a later time than the first sample, wherein detection of the one or more peptides is indicative of an active *Borrelia burgdorferi* sensu lato infection in the subject; and assaying a second sample obtained from the subject having, or suspected of having, Lyme disease to detect at least one inflammatory cytokine or chemokine selected from: CXCL1, CCL1, sICAM-1, IL-6, IL-8, CCL2, and CCL5, wherein detection of the one or more peptides in combination with an increase in CXCL1, CCL1, sICAM-1, IL-6, IL-8, CCL2, and CCL5 compared to a standard is indicative of an active *Borrelia burgdorferi* sensu lato infection in the subject. The first sample, second sample and further sample are each independently selected from: whole blood, plasma, urine, serum, cerebrospinal fluid, synovial fluid and/or a biopsy sample, wherein the biopsy sample is skin or joint tissue. The first, second and further samples may be the same or different sample type. In a preferred aspect of the invention, the first and further samples are of the same sample type.

Methods of aiding in the diagnosis, assessment and/or treatment of Lyme disease are provided according to aspects of the present invention which include assaying a first sample obtained from a subject having, or suspected of having, Lyme disease for one or more peptides produced by proteolytic activity of *Borrelia burgdorferi* sensu lato HtrA on at least one host protein substrate, to produce an assay result wherein detection of the one or more peptides is indicative of an active *Borrelia burgdorferi* sensu lato infection in the subject; assaying a further sample obtained from a subject having, or suspected of having, Lyme disease for one or more peptides produced by proteolytic activity of *Borrelia burgdorferi* sensu lato HtrA on at least one host protein substrate, the further sample obtained from the subject at a later time than the first sample, wherein detection of the one or more peptides is indicative of an active *Borrelia burgdorferi* sensu lato infection in the subject; and assaying a second sample obtained from the subject having, or suspected of having, Lyme disease for 1, 2, 3, 4, 5 6 or 7 inflammatory cytokines and chemokines selected from: CXCL1, CCL1, sICAM-1, IL-6, IL-8, CCL2, and CCL5; and assaying the second sample obtained from the subject having, or suspected of having, Lyme disease for least one inflammatory cytokine or chemokine selected from: C5a, CD40 ligand, G-CSF, GM-CSF, IFN-g, IL-1a, IL-1b, IL-ra, IL-2, IL-4, IL-5, IL-10, IL-12p70, IL-13, IL-16, IL-17, IL-17E, IL-23, IL-27, IL-32a, CXCL10, CXCL11, MIF, CCL3, CCL4 and Serpin E1; wherein an increase in 1, 2, 3, 4, 5 6 or 7 of CXCL1, CCL1, sICAM-1, IL-6, IL-8, CCL2, and CCL5 compared to a standard and substantially no increase in the at least one inflammatory cytokine or chemokine selected from: C5a, CD40 ligand, G-CSF, GM-CSF, IFN-g, IL-1a, IL-1b, IL-ra, IL-2, IL-4, IL-5, IL-10, IL-12p70, IL-13, IL-16, IL-17, IL-17E, IL-23, IL-27, IL-32a, CXCL10, CXCL11, MIF, CCL3, CCL4 and Serpin E1 compared to a standard, is indicative of an active *Borrelia burgdorferi* sensu lato infection in the subject. The first sample, second sample and further sample are each independently selected from: whole blood, plasma, urine, serum, cerebrospinal fluid, synovial fluid and/or a biopsy sample, wherein the biopsy sample is skin or joint tissue. The first, second and further samples may be the same or different sample type. In a preferred aspect of the invention, the first and further samples are of the same sample type.

Methods of aiding in the diagnosis, assessment and/or treatment of Lyme disease are provided according to aspects of the present invention which include assaying a first sample obtained from a subject having, or suspected of having, Lyme disease for one or more peptides produced by proteolytic activity of *Borrelia burgdorferi* sensu lato HtrA on at least one host protein substrate, to produce an assay result wherein detection of the one or more peptides is indicative of an active *Borrelia burgdorferi* sensu lato infection in the subject; assaying a further sample obtained from a subject having, or suspected of having, Lyme disease for one or more peptides produced by proteolytic activity of *Borrelia burgdorferi* sensu lato HtrA on at least one host protein substrate, the further sample obtained from the subject at a later time than the first sample, wherein detection of the one or more peptides is indicative of an active *Borrelia burgdorferi* sensu lato infection in the subject; assaying a second sample obtained from the subject having, or suspected of having, Lyme disease to detect at least one inflammatory cytokine or chemokine selected from: CXCL1, CCL1, sICAM-1, IL-6, IL-8, CCL2, and CCL5, wherein detection of the one or more peptides in combination with an increase in CXCL1, CCL1, sICAM-1, IL-6, IL-8, CCL2, and CCL5 compared to a standard is indicative of an active *Borrelia burgdorferi* sensu lato infection in the subject; and assaying a further second sample obtained from the subject having, or suspected of having, Lyme disease to detect at least one inflammatory cytokine or chemokine selected from: CXCL1, CCL1, sICAM-1, IL-6, IL-8, CCL2, and CCL5, the further second sample obtained from the subject at a later time than the second sample, wherein detection of the one or more peptides in combination with an increase in CXCL1, CCL1, sICAM-1, IL-6, IL-8, CCL2, and CCL5 compared to a standard is indicative of an active *Borrelia burgdorferi* sensu lato infection in the subject. The first sample, second sample, further sample and second further sample are each independently selected from: whole blood, plasma, urine, serum, cerebrospinal fluid, synovial fluid and/or a biopsy sample, wherein the biopsy sample is skin or joint tissue. The first, second, further sample and second further sample may be the same or different sample type. In a preferred aspect of the invention, the first and further samples are of the same sample type.

Methods of aiding in the diagnosis, assessment and/or treatment of Lyme disease are provided according to aspects of the present invention which include assaying a first sample obtained from a subject having, or suspected of having, Lyme disease for one or more peptides produced by proteolytic activity of *Borrelia burgdorferi* sensu lato HtrA on at least one host protein substrate, to produce an assay result wherein detection of the one or more peptides is indicative of an active *Borrelia burgdorferi* sensu lato infection in the subject; assaying a further sample obtained from a subject having, or suspected of having, Lyme disease for one or more peptides produced by proteolytic activity of *Borrelia burgdorferi* sensu lato HtrA on at least one host protein substrate, the further sample obtained from the subject at a later time than the first sample, wherein detection of the one or more peptides is indicative of an active *Borrelia burgdorferi* sensu lato infection in the subject; assaying a second sample obtained from the subject having, or suspected of having, Lyme disease for 1, 2, 3, 4, 5 6 or 7 inflammatory cytokines and chemokines selected from: CXCL1, CCL1, sICAM-1, IL-6, IL-8, CCL2, and CCL5; and assaying the second sample obtained from the subject having, or suspected of having, Lyme disease for least one inflammatory cytokine or chemokine selected from: C5a, CD40 ligand, G-CSF, GM-CSF, IFN-g, IL-1a, IL-1b, IL-ra, IL-2, IL-4, IL-5, IL-10, IL-12p70, IL-13, IL-16, IL-17, IL-17E, IL-23, IL-27, IL-32a, CXCL10, CXCL11, MIF, CCL3, CCL4 and Serpin E1; wherein an increase in 1, 2, 3, 4, 5 6 or 7 of CXCL1, CCL1, sICAM-1, IL-6, IL-8, CCL2, and CCL5 compared to a standard and substantially no increase in the at least one inflammatory cytokine or chemokine selected from: C5a, CD40 ligand, G-CSF, GM-CSF, IFN-g, IL-1a, IL-1b, IL-ra, IL-2, IL-4, IL-5, IL-10, IL-12p70, IL-13, IL-16, IL-17, IL-17E, IL-23, IL-27, IL-32a, CXCL10, CXCL11, MIF, CCL3, CCL4 and Serpin E1 compared to a standard, indicative of an active *Borrelia burgdorferi* sensu lato infection in the subject; and assaying the further second sample obtained from the subject having, or suspected of having, Lyme disease for least one inflammatory cytokine or chemokine selected from: C5a, CD40 ligand, G-CSF, GM-CSF, IL-1a, IL-1b, IL-ra, IL-2, IL-4, IL-5, IL-10, IL-12p70, IL-13, IL-16, IL-17, IL-17E, IL-23, IL-27, IL-32a, CXCL10, CXCL11, MIF, CCL3, CCL4 and Serpin E1; the further second sample obtained from the subject at a later time than the second sample, wherein an increase in 1, 2, 3, 4, 5 6 or 7 of CXCL1, CCL1, sICAM-1, IL-6, IL-8, CCL2, and CCL5 compared to a standard and substantially no increase in the at least one inflammatory cytokine or chemokine selected from: C5a, CD40 ligand, G-CSF, GM-CSF, IFN-g, IL-1a, IL-1b, IL-ra, IL-2, IL-4, IL-5, IL-10, IL-12p70, IL-13, IL-16, IL-17, IL-17E, IL-23, IL-27, IL-32a, CXCL10, CXCL11, MIF, CCL3, CCL4 and Serpin E1 compared to a standard, is indicative of an active *Borrelia burgdorferi* sensu lato infection in the subject. The first sample, second sample, further sample and second further sample are each independently selected from: whole blood, plasma, urine, serum, cerebrospinal fluid, synovial fluid and/or a biopsy sample, wherein the biopsy sample is skin or joint tissue. The first, second, further sample and second further sample may be the same or different sample type. In a preferred aspect of the invention, the first and further samples are of the same sample type.

According to aspects of methods of the present invention, assay for the one or more peptides produced by proteolytic activity of *Borrelia burgdorferi* sensu lato HtrA on at least one host protein substrate comprises an immunoassay and/or mass spectrometry.

Methods according to aspects of the present invention are provided for aiding in the diagnosis, assessment and/or treatment of Lyme disease include detecting a host antibody specific for a peptide produced by proteolytic activity of *Borrelia burgdorferi* sensu lato HtrA on a host protein substrate in a sample obtained from a subject suspected of having Lyme disease.

Methods according to aspects of the present invention are provided for screening for an inhibitor of *Borrelia burgdorferi* sensu lato HtrA in-vitro, which include contacting a *Borrelia burgdorferi* sensu lato HtrA protein with a test agent under conditions that promote protease activity of the *Borrelia burgdorferi* sensu lato HtrA protein; and assaying to detect an effect of the test agent to decrease protease activity of the *Borrelia burgdorferi* sensu lato HtrA protein compared to a standard, thereby identifying the test agent as an inhibitor of *Borrelia burgdorferi* sensu lato HtrA. In a preferred option, the *Borrelia burgdorferi* sensu lato HtrA protein is expressed in-vitro.

Methods according to aspects of the present invention are provided for in-vivo screening for an inhibitor of a *Borrelia burgdorferi* sensu lato HtrA protein which include expressing the *Borrelia burgdorferi* sensu lato HtrA protein in a non-human organism; contacting the *Borrelia burgdorferi* sensu lato HtrA protein with a test agent under conditions that promote protease activity of the *Borrelia burgdorferi* sensu lato HtrA protein; and assaying to detect an effect of the test agent to decrease protease activity of the *Borrelia burgdorferi* sensu lato HtrA protein compared to a standard, thereby identifying the test agent as an inhibitor of *Borrelia burgdorferi* sensu lato HtrA. According to aspects of the present invention, the non-human organism is infected with *Borrelia burgdorferi* sensu lato.

Methods according to aspects of the present invention are provided for treating Lyme disease in a subject in need thereof, which include administering a therapeutically effective dose of an inhibitor of protease activity of a *Borrelia burgdorferi* sensu lato HtrA to the subject.

Methods according to aspects of the present invention are provided for treating Lyme disease in a subject in need thereof, which include administering to the subject a therapeutically effective dose of an inhibitor of protease activity of a *Borrelia burgdorferi* sensu lato HtrA, wherein the inhibitor is an inhibitor listed in Table I.

Methods according to aspects of the present invention are provided for producing a detectable immune response in a subject, including administering an amount of inactive *Borrelia burgdorferi* sensu lato HtrA or an immunogenic fragment thereof to a subject to produce a detectable immune response to *Borrelia burgdorferi* sensu lato HtrA in the subject.

Isolated antibodies specific for *Borrelia burgdorferi* sensu lato HtrA are provided according to aspects of the present invention.

Isolated antibodies which specifically recognizes a peptide produced by proteolytic activity of *Borrelia burgdorferi* sensu lato HtrA on a substrate are provided according to aspects of the present invention.

Isolated antibodies which specifically recognize a peptide produced by proteolytic activity of *Borrelia burgdorferi* sensu lato HtrA on a substrate selected from aggrecan, fibronectin, biglycan, decorin, brevican, neurocan, versican, COMP, fibromodulin, E-cadherin or a protein having a *Borrelia burgdorferi* sensu lato HtrA cleavage site selected from SEQ ID NO:70-162 are provided according to aspects of the present invention. Isolated antibodies which specifically recognize a peptide produced by proteolytic activity of *Borrelia burgdorferi* sensu lato HtrA on a substrate selected from aggrecan, fibronectin, biglycan, decorin, brevican, neurocan, versican, COMP, fibromodulin, and E-cadherin are provided according to aspects of the present invention.

Methods of aiding in the diagnosis, assessment and/or treatment of Lyme disease, are provided according to the present invention which include assaying a sample obtained from a subject having, or suspected of having, Lyme disease to detect at least one inflammatory cytokine or chemokine selected from: CXCL1, CCL1, sICAM-1, IL-6, IL-8, CCL2, and CCL5, wherein detection of an increase in at least one inflammatory cytokine or chemokine selected from: CXCL1, CCL1, sICAM-1, IL-6, IL-8, CCL2, and CCL5, compared to a standard is indicative of an active *Borrelia burgdorferi* sensu lato infection in the subject.

Methods of aiding in the diagnosis, assessment and/or treatment of Lyme disease, are provided according to the present invention which include assaying a sample obtained from a subject having, or suspected of having, Lyme disease to detect at 2, 3, 4, 5, 6 or 7 inflammatory cytokines or chemokines selected from: CXCL1, CCL1, sICAM-1, IL-6, IL-8, CCL2, and CCL5, wherein detection of an increase in 2, 3, 4, 5, 6 or 7 inflammatory cytokine or chemokine selected from: CXCL1, CCL1, sICAM-1, IL-6, IL-8, CCL2, and CCL5, compared to a standard is indicative of an active *Borrelia burgdorferi* sensu lato infection in the subject.

Methods of aiding in the diagnosis, assessment and/or treatment of Lyme disease, are provided according to the present invention which include assaying a sample obtained from a subject having, or suspected of having, Lyme disease to detect an increase in 2, 3, 4, 5, 6 or 7 of CXCL1, CCL1, sICAM-1, IL-6, IL-8, CCL2, and CCL5 combined with substantially no increase in at least 1 of C5a, CD40 ligand, G-CSF, GM-CSF, IFN-g, IL-1a, IL-1b, IL-ra, IL-2, IL-4, IL-5, IL-10, IL-12p70, IL-13, IL-16, IL-17, IL-17E, IL-23, IL-27, IL-32a, CXCL10, CXCL11, CCL3, CCL4 and Serpin E1 compared to a standard is indicative of an active *Borrelia burgdorferi* sensu lato infection in the subject.

Methods of aiding in the diagnosis, assessment and/or treatment of Lyme disease, are provided according to the present invention which include assaying a sample obtained from a subject having, or suspected of having, Lyme disease to detect an antibody which specifically binds to *Borrelia burgdorferi* sensu lato HtrA protease or a fragment thereof in a sample obtained from a subject having, or suspected of having, Lyme disease.

Methods of aiding in the diagnosis, assessment and/or treatment of Lyme disease, are provided according to the present invention which include assaying a sample obtained from a subject having, or suspected of having, Lyme disease to detect a *Borrelia burgdorferi* sensu lato HtrA protease and/or a nucleic acid encoding *Borrelia burgdorferi* sensu lato HtrA protease in a sample obtained from a subject having, or suspected of having, Lyme disease.

Methods of aiding in the diagnosis, assessment and/or treatment of Lyme disease are provided according to the present invention which include assaying a sample obtained from a subject having, or suspected of having, Lyme disease for proteolytic activity of *Borrelia burgdorferi* sensu lato HtrA to detect the presence of *Borrelia burgdorferi* sensu lato HtrA, wherein presence of *Borrelia burgdorferi* sensu lato HtrA is indicative of *Borrelia burgdorferi* sensu lato active infection of the subject.

Methods of aiding in the diagnosis, assessment and/or treatment of Lyme disease are provided according to the present invention which include assaying a sample obtained from a subject having, or suspected of having, Lyme disease for proteolytic activity of *Borrelia burgdorferi* sensu lato HtrA to detect the presence of *Borrelia burgdorferi* sensu lato HtrA, wherein the assaying comprises contacting the sample with a substrate for *Borrelia burgdorferi* sensu lato HtrA and determining whether the substrate is cleaved by proteolytic activity of *Borrelia burgdorferi* sensu lato HtrA and wherein presence of *Borrelia burgdorferi* sensu lato HtrA is indicative of *Borrelia burgdorferi* sensu lato active infection of the subject.

Methods of aiding in the diagnosis, assessment and/or treatment of Lyme disease are provided according to the present invention which include assaying a sample obtained from a subject having, or suspected of having, Lyme disease for proteolytic activity of *Borrelia burgdorferi* sensu lato HtrA to detect the presence of *Borrelia burgdorferi* sensu lato HtrA, wherein the assaying comprises contacting the sample with a substrate for *Borrelia burgdorferi* sensu lato HtrA wherein the substrate is selected from the group consisting of: casein, aggrecan, decorin, biglycan, brevican, neurocan, versican, fibronectin, fibromodulin, cartilage oligomeric matrix protein and E-cadherin and determining whether the substrate is cleaved by proteolytic activity of *Borrelia burgdorferi* sensu lato HtrA and wherein presence of *Borrelia burgdorferi* sensu lato HtrA is indicative of *Borrelia burgdorferi* sensu lato active infection of the subject.

Methods of aiding in the diagnosis, assessment and/or treatment of Lyme disease are provided according to the present invention which include assaying a sample obtained from a subject having, or suspected of having, Lyme disease for proteolytic activity of *Borrelia burgdorferi* sensu lato HtrA to detect the presence of *Borrelia burgdorferi* sensu lato HtrA, wherein the assaying comprises contacting the sample with a substrate for *Borrelia burgdorferi* sensu lato HtrA, wherein the substrate comprises a *Borrelia burgdorferi* sensu lato HtrA cleavage site selected from SEQ ID NO:70-162, a homologue or variant thereof, and determining whether the substrate is cleaved by proteolytic activity of *Borrelia burgdorferi* sensu lato HtrA and wherein presence of *Borrelia burgdorferi* sensu lato HtrA is indicative of *Borrelia burgdorferi* sensu lato active infection of the subject.

Commercial packages of the invention are described herein.

BRIEF DESCRIPTION OF THE DRAWINGS

FIG. 1A is an image showing BbHtrA (3 µg) as visualized by Coomassie stain (left panel) and as visualized by anti-His tag Western blot (right panel);

FIG. 1B shows BbHtrA$^{S226A}$ (2 µg) as visualized by Coomassie stain (left panel) and as visualized by anti-His tag Western blot (right panel);

FIG. 2A is an image showing equivalent protein loading for gel electrophoresis;

FIG. 2B is an image of results of a Western blot of the proteins shown in FIG. 2B showing loss of surface protein signal (OspA), retention of internal protein signal (FlaB) and diminished BbHtrA signal;

FIG. 3A is an image showing results of Western blot analysis to detect anti-BbHtrA antibodies in serum samples from human subjects having early or late Lyme disease and from healthy human control subjects;

FIG. 3B is an image showing results of Western blot analysis to detect anti-BbHtrA IgG+ antibodies in serum samples from human subjects having Lyme disease and from healthy human control subjects;

FIG. 8A is an image showing SDS-PAGE analysis of BbHtrA degradation of fibronectin;

FIG. 8B is a table showing results of tandem LC MS/MS analysis of BbHtrA degradation of fibronectin;

FIG. 9B is a key to show the identity of cytokines identified in the cytokine analyses shown in FIG. 9A and in FIG. 10;

FIG. 13 shows alignment of amino acid sequences of bovine and human decorin;

FIG. 14 shows alignment of amino acid sequences of bovine and human biglycan;

FIG. 15 shows alignment of amino acid sequences of bovine and human fibromodulin;

FIG. 16 shows alignment of amino acid sequences of bovine and human cartilage oligomeric matrix protein (COMP); and FIG. 17 shows alignment of amino acid sequences of bovine and human aggrecan.

DETAILED DESCRIPTION OF THE INVENTION

Figure 4A:
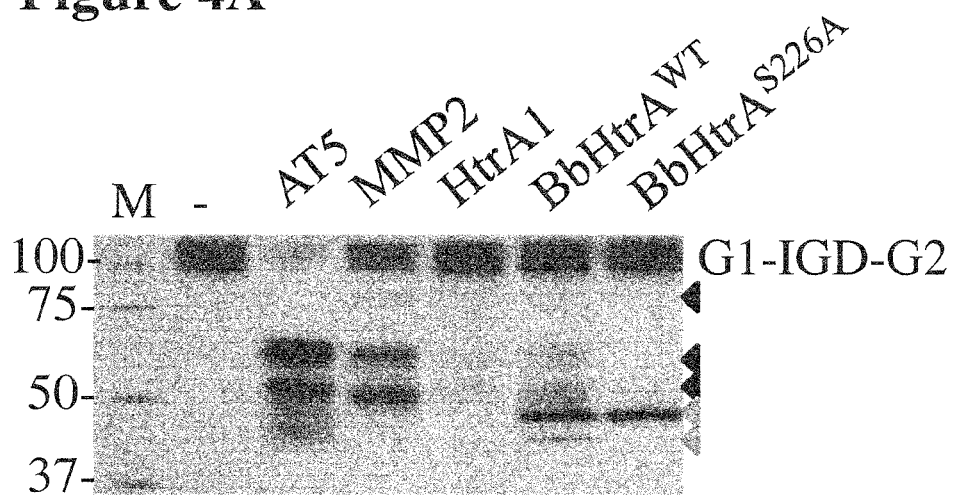
FIG. 4A is an image showing results of SDS-PAGE analysis showing that BbHtrA cleaves recombinant human aggrecan (G1-IGD-G2 domains) within the IGD.

Compositions and methods for aiding in the detection and diagnosis of Lyme disease in a subject are provided according to the present invention. Compositions and methods for treatment and/or prevention of Lyme disease in a subject in need thereof are provided according to the present invention.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; Engelke, D. R., RNA Interference (RNAi): Nuts and Bolts of RNAi Technology, DNA Press LLC, Eagleville, Pa., 2003; Herdewijn, P. (Ed.), Oligonucleotide Synthesis: Methods and Applications, Methods in Molecular Biology, Humana Press, 2004; A. Nagy, M. Gertsenstein, K. Vintersten, R. Behringer, Manipulating the Mouse Embryo: A Laboratory Manual, 3rd edition, Cold Spring Harbor Laboratory Press; Dec. 15, 2002, ISBN-10: 0879695919; Kursad Turksen (Ed.), Embryonic stem cells: methods and protocols in Methods Mol Biol. 2002; 185, Humana Press; Current Protocols in Stem Cell Biology, ISBN: 9780470151808.

The singular terms "a," "an," and "the" are not intended to be limiting and include plural referents unless explicitly state or the context clearly indicates otherwise.

It has been reported that that *Borrelia burgdorferi* do not produce proteases capable of damaging host proteins, Radolf, J. D., et al., Nature Reviews Microbial. online 9 Jan. 2012; Smith, B. G., et al., J Am Acad. Orthop. Surg., 2011, 19(2): 91-100; Guyard, C., et al., Molec. Microbial. 2006, 60 (3), 710-722; Klempner, M. S., et al., J. Infect. Dis., 1995, 171 (5):1258-1265; Coleman, J. L. et al., Infect. Immun., 63(7): 2478-2484, 1995. Unexpectedly, a protease activity capable of cleaving host proteins has been identified and characterized as *B. burgdorferi* HtrA sensu lato (BbHtrA), a member of the high temperature requirement factor A protease/chaperone family, by the present inventors as described herein. *B. burgdorferi* sensu lato HtrA is found by the present inventors to degrade extracellular matrix proteins, such as, but not limited to, aggrecan, biglycan, decorin, fibronectin, brevican, neurocan, versican, fibromodulin, cartilage oligomeric matrix protein (COMP) and e-cadherin. BbHtrA stimulates the release of numerous cytokines and chemokines in the infected host. BbHtrA protease activity may contribute to the various pathologies associated with Lyme disease, particularly Lyme arthritis.

Methods of Aiding in the Diagnosis of Lyme Disease

Methods of aiding in the diagnosis of Lyme disease are provided according to the present invention.

Lyme disease, also known as Lyme borreliosis, is caused by bacteria transmitted to mammals through the bite of infected *Ixodes* ticks.

*Borrelia burgdorferi, Borrelia garinii* and *Borrelia afzelii* cause Lyme disease in Eurasia and *Borrelia burgdorferi* causes Lyme disease in the United States and Canada. *B. garinii* has been found in pelagic bird colonies off the coast of North America, so there may be potential for infection by this agent in North America. The three Lyme disease agents *Borrelia burgdorferi, Borrelia garinii* and *Borrelia afzelii* are referred to as *Borrelia burgdorferi* sensu lato, that is, "in the broad sense." The North American genospecies *Borrelia burgdorferi* is called *Borrelia burgdorferi* sensu stricto, "in the strict sense."

Lyme disease is characterized by three stages: 1) early localized Lyme disease; 2) early disseminated Lyme disease; and 3) late disseminated Lyme disease.

A subject may be suspected of having Lyme disease where symptoms are consistent with those of Lyme disease and where an *Ixodes* tick bite is known or may have occurred. A characteristic rash called erythema migrans occurs in 70-80% of Lyme disease patients at the site of an infected tick bite.

Early localized Lyme disease is characterized by erythema migrans. Early disseminated Lyme disease typically occurs days to weeks after the initial bite by an infected tick and possible signs include secondary erythema migrans, early neuroborreliosis (cranial nerve palsy, meningitis, or radiculoneuropathy) or, uncommonly, Lyme carditis (atrioventricular node conduction block). Non-specific symptoms such as malaise, fever, headache, and muscle and joint pains may be present. Late disseminated Lyme disease occurs months to years after the initial bite by an infected tick. The most common manifestation of late disseminated Lyme disease in North America is Lyme arthritis, which is characterized by intermittent attacks in large joints, particularly the knees. Rarely, late neuroborreliosis develops, with manifestations including encephalopathy, encephalomyelitis, and/or peripheral neuropathy. Wormser, G. P., et al. Clin Infect Dis 2006; 43:1089-1134.

Lyme arthritis is a late manifestation of Lyme disease affecting up to 60% of untreated patients in the United States. Ten percent of patients treated with antibiotics continue to suffer from recurrent bouts of Lyme arthritis, Steere, A. C. and L. Glickstein, Nat Rev Immunol, 2004. 4(2): p. 143-52. Cartilage loss and subsequent bone destruction which are features of osteoarthritis and rheumatoid arthritis also occur in advanced cases of Lyme arthritis, Lawson, J. P. et al., Radiology, 1985, 154(1):37-43. Lyme arthritis develops when the bacteria invade joint tissue, most commonly the knee, and trigger inflammation as part of a strong host immune response. Despite this vigorous immune response, *Borrelia* are able to persist in joints which are thought to be a protective niche for the bacteria due to limited perfusion, Liang, F. T., et al., Am J Pathol, 2004, 165(3):977-85.

In the early localized stage of Lyme disease, direct detection of *Borrelia burgdorferi* can sometimes be achieved by bacterial culture or PCR from a skin sample obtained at the site of the erythema migrans rash. In early disseminated infection, direct detection of *Borrelia burgdorferi* can sometimes be achieved by bacterial culture or PCR of blood can be successful. However, in later stages of Lyme disease the bacteria are difficult to detect.

*Borrelia burgdorferi* sensu lato, which cause Lyme disease, are found by the present inventors to have a serine protease activity, termed herein "*Borrelia burgdorferi* sensu lato HtrA protease activity." Methods of aiding in the diagnosis of Lyme disease are provided according to the present invention which include detecting one or more peptides produced by *Borrelia burgdorferi* sensu lato HtrA protease activity on at least one host protein substrate in a sample obtained from a subject having or suspected of having Lyme disease.

Methods of aiding in the diagnosis of Lyme disease are provided according to the present invention which include detecting one or more peptides produced by *Borrelia burgdorferi* sensu lato HtrA protease activity on a host extracellular matrix protein. As disclosed herein aggrecan, biglycan, decorin, fibronectin, brevican, neurocan, versican, fibromodulin, COMP and e-cadherin are substrates for *Borrelia* burgdorferi sensu lato HtrA. According to aspects of methods of the present invention, one or more peptides produced by proteolytic activity of Borrelia burgdorferi sensu lato HtrA on a host extracellular matrix protein such as, but not limited to, aggrecan, biglycan, decorin, fibronectin, brevican, neurocan, versican, fibromodulin, COMP and e-cadherin may be assayed in a sample obtained from a subject having or suspected of having Lyme disease according to methods of the invention.

The term "subject" is used herein to refer to a human subject and can also refer to a mammalian subject capable of infection by Borrelia burgdorferi sensu lato, including, but not limited to, non-human primates rodents and dogs.

A sample which is assayed for one or more peptides produced by proteolytic activity of Borrelia burgdorferi sensu lato HtrA on at least one host protein substrate is any sample type containing the peptide or peptides to be assayed, such as, but not limited to whole blood, plasma, serum, urine, cerebrospinal fluid, synovial fluid and/or a biopsy sample, such as a skin biopsy or an arthroscopic biopsy sample of joint tissue.

Detection of peptides produced by proteolytic activity of Borrelia burgdorferi sensu lato HtrA on at least one host protein substrate can be accomplished by qualitative and/or quantitative assays including, but not limited to, immunoassay and mass spectrometry.

Assays according to the present invention optionally and preferably compare the assay result to a standard.

Standards are well-known in the art and the standard used can be any appropriate standard. In one example, a standard for use in assay of one or more Borrelia burgdorferi sensu lato HtrA cleavage products is an amount of one or more Borrelia burgdorferi sensu lato HtrA cleavage products of the present invention present in a comparable control sample from a control subject. In a further example, a standard for use in assay of one or more inflammatory cytokines and chemokines is an amount of one or more inflammatory cytokines and chemokines selected from: CXCL1, CCL1, sICAM-1, IL-6, IL-8, CCL2, and CCL5 and one or more inflammatory cytokines and chemokines selected from selected from: C5a, CD40 ligand, G-CSF, GM-CSF, IFN-g, IL-1a, IL-1b, TL-ra, IL-2, IL-4, IL-5, IL-10, IL-12p70, IL-13, IL-16, IL-17, IL-17E, IL-23, IL-27, IL-32a, CXCL10, CXCL11, MIF, CCL3, CCL4 and Serpin E1, present in a comparable control sample from a control subject. Control samples may be obtained from one or more subjects who do not have a Borrelia burgdorferi sensu lato infection, for example. A preferred control sample is a comparable control sample obtained from one or more subjects residing in an area where Borrelia burgdorferi sensu lato is not endemic. Travel histories may be obtained from potential control subjects living in areas where Borrelia burgdorferi sensu lato is not endemic to identify potential control subjects who have visited areas where Borrelia burgdorferi sensu lato is endemic and such persons are eliminated as control subjects. The types of subjects with other diseases commonly confused with Lyme disease where no Borrelia burgdorferi sensu lato infection is present and which would be suitable for a comparator population has been defined by the Clinical Laboratory Standards Institute as described in Barbour A G et al., Western Blot Assay for Antibodies to Borrelia burgdorferi: Approved Guideline M34-A, 2000, Clinical Laboratory Standards, Institute, Wayne Pa. A standard in an assay of Borrelia burgdorferi sensu lato HtrA cleavage products may be a reference level of one or more Borrelia burgdorferi sensu lato HtrA cleavage products of the present invention determined in a sample of an individual control subject or in a population of control subjects. A standard in an assay of indicated cytokines and/or chemokines may be a reference level of the indicated cytokines and/or chemokines determined in a sample of an individual control subject or in a population of control subjects. A standard may be such a reference level stored in a print or electronic medium for recall and comparison to an assay result.

A standard in an assay of Borrelia burgdorferi sensu lato HtrA cleavage products can be an amount of one or more Borrelia burgdorferi sensu lato HtrA cleavage products of the present invention present in a comparable sample obtained from the same subject at a different time. For example, a standard can be an amount of one or more Borrelia burgdorferi sensu lato HtrA cleavage products of the present invention present in a comparable sample obtained from the same subject at an earlier time. A first sample can be obtained from an individual subject at a first time to obtain a subject-specific baseline level of the one or more Borrelia burgdorferi sensu lato HtrA cleavage products of the present invention in the first sample. A second sample can be obtained from the individual subject at a second time and assayed for one or more Borrelia burgdorferi sensu lato HtrA cleavage products of the present invention to monitor differences in the levels of the one or more Borrelia burgdorferi sensu lato HtrA cleavage products of the present invention compared to the first sample, thereby monitoring Lyme disease in the subject. Additional samples can be obtained from the subject at additional time points and assayed for one or more Borrelia burgdorferi sensu lato HtrA cleavage products to monitor differences in the levels of the corresponding Borrelia burgdorferi sensu lato HtrA cleavage products of the present invention compared to the first sample, second sample or other samples, thereby monitoring Lyme disease in the subject.

A standard can be an average level of one or more Borrelia burgdorferi sensu lato HtrA cleavage products of the present invention present in comparable samples of one or more populations. The "average level" is determined by assay of the one or more Borrelia burgdorferi sensu lato HtrA cleavage products of the present invention in comparable samples obtained from each member of the population. The term "comparable sample" is used to indicate that the samples are of the same type. For example, each of the comparable samples is a serum sample. In a further example, each of the comparable samples is a biopsy sample. In a further example, each of the comparable samples is a synovial fluid sample. In a further example, each of the comparable samples is a whole blood, plasma, serum, urine, cerebrospinal fluid, joint tissue or skin sample.

A difference detected in levels of one or more Borrelia burgdorferi sensu lato HtrA cleavage products of the present invention compared to a standard can be an increase or decrease in level of the one or more Borrelia burgdorferi sensu lato HtrA cleavage products. A difference detected in levels of one or more Borrelia burgdorferi sensu lato HtrA cleavage products of the present invention compared to a standard can be a detectable level of the one or more Borrelia burgdorferi sensu lato HtrA cleavage products where the Borrelia burgdorferi sensu lato HtrA cleavage products are undetectable in the standard. A difference detected in levels of one or more Borrelia burgdorferi sensu lato HtrA cleavage products of the present invention compared to a standard can be an undetectable level of the one or more Borrelia burgdorferi sensu lato HtrA cleavage products where the Borrelia burgdorferi sensu lato HtrA cleavage products are detectable in the standard.

A standard in an assay of cytokines and/or chemokines can be an amount of the indicated cytokines and/or chemokines in a comparable sample obtained from the same subject at a different time. For example, a standard can be an amount of one or more cytokines and/or chemokines present in a comparable sample obtained from the same subject at an earlier time. A first sample can be obtained from an individual subject at a first time to obtain a subject-specific baseline level of the one or more cytokines and/or chemokines in the first sample. A second sample can be obtained from the individual subject at a second time and assayed for one or more cytokines and/or chemokines to monitor differences in the levels of the one or more cytokines and/or chemokines compared to the first sample, thereby monitoring Lyme disease in the subject. Additional samples can be obtained from the subject at additional time points and assayed for one or more cytokines and/or chemokines to monitor differences in the levels of the corresponding cytokines and/or chemokines compared to the first sample, second sample or other samples, thereby monitoring Lyme disease in the subject.

A standard can be an average level of one or more cytokines and/or chemokines present in comparable samples of one or more populations. The "average level" is determined by assay of the one or more cytokines and/or chemokines in comparable samples obtained from each member of the population. The term "comparable sample" is used to indicate that the samples are of the same type. For example, each of the comparable samples is a serum sample. In a further example, each of the comparable samples is a biopsy sample. In a further example, each of the comparable samples is a synovial fluid sample. In a further example, each of the comparable samples is a whole blood, plasma, serum, urine, cerebrospinal fluid, joint tissue or skin sample.

A difference detected in levels of one or more cytokines and/or chemokines compared to a standard can be an increase or decrease in level of the one or more cytokines and/or chemokines. A difference detected in levels of one or more cytokines and/or chemokines compared to a standard can be a detectable level of the one or more cytokines and/or chemokines where the cytokines and/or chemokines are undetectable in the standard. A difference detected in levels of one or more cytokines and/or chemokines compared to a standard can be an undetectable level of the one or more cytokines and/or chemokines where the cytokines and/or chemokines are detectable in the standard.

Assay results can be analyzed using statistical analysis by any of various methods, exemplified by parametric or non-parametric tests, analysis of variance, analysis of covariance, logistic regression for multivariate analysis, Fisher's exact test, the chi-square test, Student's T-test, the Mann-Whitney test, Wilcoxon signed ranks test, McNemar test, Friedman test and Page's L trend test. These and other statistical tests are well-known in the art as detailed in Hicks, C M, Research Methods for Clinical Therapists: Applied Project Design and Analysis, Churchill Livingstone; 5th Ed., 2009; and Freund, R J et al., Statistical Methods, Academic Press; 3rd Ed., 2010.

Immunoassays are well-known in the art and include, but are not limited to, enzyme-linked immunosorbent assay (ELISA), antigen capture, flow cytometry, immunoblot, immunoprecipitation, immunodiffusion, immunocytochemistry, radioimmunoassay, and combinations of any of these. Immunoassays for both qualitative and quantitative assay of a sample are described in detail in standard references, illustratively including Wild, D., The Immunoassay Handbook, 3rd Ed., Elsevier Science, 2005; Gosling, J. P., Imunoassays: A Practical Approach, Practical Approach Series, Oxford University Press, 2005; E. Harlow and D. Lane, Antibodies: A Laboratory Manual, Cold Spring Harbor Laboratory Press, 1988; F. Breitling and S. Dübel, Recombinant Antibodies, John Wiley & Sons, New York, 1999; H. Zola, Monoclonal Antibodies: Preparation and Use of Monoclonal Antibodies and Engineered Antibody Derivatives, Basics: From Background to Bench, BIOS Scientific Publishers, 2000; B. K. C. Lo, Antibody Engineering: Methods and Protocols, Methods in Molecular Biology, Humana Press, 2003; F. M. Ausubel et al., Eds., Short Protocols in Molecular Biology, Current Protocols, Wiley, 2002; Ormerod, M. G., Flow Cytometry: a practical approach, Oxford University Press, 2000; and Givan, A. L., Flow Cytometry: first principles, Wiley, New York, 2001.

In particular embodiments, an assay for one or more peptides includes use of a mass spectrometry technique. For example, a peptide can be ionized using an ionization method such as electrospray ionization (ESI), matrix-assisted laser desorption/ionization (MALDI) or surface enhanced laser desorption/ionization (SELDI). Mass analysis is conducted using, for example, time-of-flight (TOF) mass spectrometry or Fourier transform ion cyclotron resonance mass spectrometry. Mass spectrometry techniques are known in the art and exemplary detailed descriptions of methods for protein and/or peptide assay are found in Li J., et al., Clin Chem., 48(8): 1296-304, 2002; Hortin, G. L., Clinical Chemistry 52: 1223-1237, 2006; Hortin, G. L., Clinical Chemistry 52: 1223-1237, 2006; A. L. Burlingame, et al. (Eds.), Mass Spectrometry in Biology and Medicine, Humana Press, 2000; and D. M. Desiderio, Mass Spectrometry of Peptides, CRC Press, 1990.

A peptide contained in a sample from a subject is optionally purified for assay according to a method of the present invention.

The term "purified" in the context of a sample refers to separation of a desired material in the sample from at least one other component present in the sample.

In particular embodiments, a peptide or peptides is optionally substantially purified from the sample to produce a substantially purified sample for use in an inventive assay. The term "substantially purified" refers to a desired material separated from other substances naturally present in a sample obtained from the subject so that the desired material makes up at least about 1-100% of the mass, by weight, such as about 1%, 5%, 10%, 25%, 50% 75% or greater than about 75% of the mass, by weight, of the substantially purified sample.

Sample purification is achieved by techniques illustratively including electrophoretic methods such as gel electrophoresis and 2-D gel electrophoresis; chromatography methods such as HPLC, ion exchange chromatography, affinity chromatography, size exclusion chromatography, thin layer and paper chromatography. It is appreciated that electrophoresis and chromatographic methods can also be used to separate a peptide or peptides from other components in a sample in the course of performing an assay, as in, for example separation of proteins in immunoblot assays. Enrichment (initial purification) may be achieved by centrifugation and/or differential extraction using polar or non-polar solvents.

Peptides which may be detected in a sample obtained from a subject having or suspected of having Lyme disease according to methods of the present invention are specific products of cleavage by *Borrelia burgdorferi* sensu lato HtrA protease activity, i.e. *Borrelia burgdorferi* sensu lato HtrA cleavage products.

The term "*Borrelia burgdorferi* sensu lato HtrA cleavage product" encompasses, but is not limited to, *Borrelia burgdorferi* sensu lato HtrA cleavage products identified herein as SEQ ID NO:33-69 and 70-414.

*Borrelia burgdorferi* sensu lato HtrA cleavage products of decorin include those identified herein as SEQ ID NO:33-37; SEQ ID NO:52-55 and SEQ ID NO:315-364.

Methods according to aspects of the present invention include assay for *Borrelia burgdorferi* sensu lato HtrA cleavage products of decorin including one or more of: the peptide of SEQ ID NO:33, SEQ ID NO:34, SEQ ID NO:35, SEQ ID NO:36, SEQ ID NO:37, a homologue or variant thereof having at least 95% identity to the reference peptide, or a combination of any two or more thereof.

Methods according to aspects of the present invention include assay for *Borrelia burgdorferi* sensu lato HtrA cleavage products of decorin including one or more of: the peptide of SEQ ID NO:52, SEQ ID NO:53, SEQ ID NO:54, SEQ ID NO:55, a homologue or variant thereof having at least 95% identity to the reference peptide, or a combination of any two or more thereof.

Methods according to aspects of the present invention include assay for *Borrelia burgdorferi* sensu lato HtrA cleavage products of decorin including one or more of: the peptide of SEQ ID NO:315-364, wherein each of the peptides of SEQ ID NO: 315-364 has 5 amino acids closest to the amino terminus and has 1, 2, 3, 4, 5, 6, 7, 8, 9, 10, 11, 12, 13, 14, 15, 16, 17, 18, 19, 20, 21, 22, 23, 24, 25, 26, 27 or 28 additional amino acids; a homologue or variant thereof having at least 95% identity to the reference peptide; a fragment of the one or more peptides of SEQ ID NO: 315-364, the fragment having at least the 5 amino acids closest to the amino terminus; a fragment of the one or more peptides of SEQ ID NO: 315-364, the fragment having at least the 5 amino acids closest to the amino terminus and at least 1, 2, 3, 4, 5, 6, 7, 8, 9, 10, 11, 12, 13, 14, 15, 16, 17, 18, 19, 20, 21, 22, 23, 24, 25, 26, 27 or 28 additional of the amino acids; or a combination of any two or more thereof.

*Borrelia burgdorferi* sensu lato HtrA cleavage products of biglycan include those identified herein as SEQ ID NO:38-40; SEQ ID NO:56-58 and SEQ ID NO:214-263.

Methods according to aspects of the present invention include assay for *Borrelia burgdorferi* sensu lato HtrA cleavage products of biglycan including one or more of: the peptide of SEQ ID NO:38, SEQ ID NO:39, SEQ ID NO:40, a homologue or variant thereof having at least 95% identity to the reference peptide, or a combination of any two or more thereof.

Methods according to aspects of the present invention include assay for *Borrelia burgdorferi* sensu lato HtrA cleavage products of biglycan including one or more of: the peptide of SEQ ID NO:56, SEQ ID NO:57, SEQ ID NO:58, a homologue or variant thereof having at least 95% identity to the reference peptide, or a combination of any two or more thereof.

Methods according to aspects of the present invention include assay for *Borrelia burgdorferi* sensu lato HtrA cleavage products of biglycan including one or more of: the peptide of SEQ ID NO:214-263, wherein each of the peptides of SEQ ID NO:214-263 has 5 amino acids closest to the amino terminus and has 1, 2, 3, 4, 5, 6, 7, 8, 9, 10, 11, 12, 13, 14, 15, 16, 17, 18, 19, 20, 21, 22, 23, 24, 25, 26, 27 or 28 additional amino acids; a homologue or variant thereof having at least 95% identity to the reference peptide; a fragment of the one or more peptides of SEQ ID NO: 214-263, the fragment having at least the 5 amino acids closest to the amino terminus; a fragment of the one or more peptides of SEQ ID NO: 214-263, the fragment having at least the 5 amino acids closest to the amino terminus and at least 1, 2, 3, 4, 5, 6, 7, 8, 9, 10, 11, 12, 13, 14, 15, 16, 17, 18, 19, 20, 21, 22, 23, 24, 25, 26, 27 or 28 additional of the amino acids; or a combination of any two or more thereof.

*Borrelia burgdorferi* sensu lato HtrA cleavage products of aggrecan include those identified herein as SEQ ID NO:41-43; SEQ ID NO:59-61 and SEQ ID NO:163-213.

Methods according to aspects of the present invention include assay for *Borrelia burgdorferi* sensu lato HtrA cleavage products of aggrecan including one or more of: the peptide of SEQ ID NO:41, SEQ ID NO:42, SEQ ID NO:43, a homologue or variant thereof having at least 95% identity to the reference peptide, or a combination of any two or more thereof.

Methods according to aspects of the present invention include assay for *Borrelia burgdorferi* sensu lato HtrA cleavage products of aggrecan including one or more of: the peptide of SEQ ID NO:59, SEQ ID NO:60, SEQ ID NO:61, a homologue or variant thereof having at least 95% identity to the reference peptide, or a combination of any two or more thereof.

Methods according to aspects of the present invention include assay for *Borrelia burgdorferi* sensu lato HtrA cleavage products of aggrecan including one or more of: the peptide of SEQ ID NO:163-213, wherein each of the peptides of SEQ ID NO: 163-213 has 5 amino acids closest to the amino terminus and has 1, 2, 3, 4, 5, 6, 7, 8, 9, 10, 11, 12, 13, 14, 15, 16, 17, 18, 19, 20, 21, 22, 23, 24, 25, 26, 27 or 28 additional amino acids; a homologue or variant thereof having at least 95% identity to the reference peptide; a fragment of the one or more peptides of SEQ ID NO:163-213, the fragment having at least the 5 amino acids closest to the amino terminus; a fragment of the one or more peptides of SEQ ID NO:163-213, the fragment having at least the 5 amino acids closest to the amino terminus and at least 1, 2, 3, 4, 5, 6, 7, 8, 9, 10, 11, 12, 13, 14, 15, 16, 17, 18, 19, 20, 21, 22, 23, 24, 25, 26, 27 or 28 additional of the amino acids; or a combination of any two or more thereof.

*Borrelia burgdorferi* sensu lato HtrA cleavage products of fibromodulin include those identified herein as SEQ ID NO:44-46; SEQ ID NO:62-64 and SEQ ID NO:365-414.

Methods according to aspects of the present invention include assay for *Borrelia burgdorferi* sensu lato HtrA cleavage products of fibromodulin including one or more of: the peptide of SEQ ID NO:44, SEQ ID NO:45, SEQ ID NO:46, a homologue or variant thereof having at least 95% identity to the reference peptide, or a combination of any two or more thereof.

Methods according to aspects of the present invention include assay for *Borrelia burgdorferi* sensu lato HtrA cleavage products of fibromodulin including one or more of: the peptide of SEQ ID NO:62, SEQ ID NO:63, SEQ ID NO:64, a homologue or variant thereof having at least 95% identity to the reference peptide, or a combination of any two or more thereof.

Methods according to aspects of the present invention include assay for *Borrelia burgdorferi* sensu lato HtrA cleavage products of fibromodulin including one or more of: the peptide of SEQ ID NO:365-414, wherein each of the peptides of SEQ ID NO:365-414 has 5 amino acids closest to the amino terminus and has 1, 2, 3, 4, 5, 6, 7, 8, 9, 10, 11, 12, 13, 14, 15, 16, 17, 18, 19, 20, 21, 22, 23, 24, 25, 26, 27 or 28 additional amino acids; a homologue or variant thereof having at least 95% identity to the reference peptide; a fragment of the one or more peptides of SEQ ID NO:365-414, the fragment having at least the 5 amino acids closest to the amino terminus; a fragment of the one or more peptides of SEQ ID NO:365-414, the fragment having at least the 5 amino acids closest to the amino terminus and at least 1, 2, 3, 4, 5, 6, 7, 8, 9, 10, 11, 12, 13, 14, 15, 16, 17, 18, 19, 20, 21, 22, 23, 24, 25, 26, 27 or 28 additional of the amino acids; or a combination of any two or more thereof

*Borrelia burgdorferi* sensu lato HtrA cleavage products of COMP include those identified herein as SEQ ID NO:47-51; SEQ ID NO:65-69 and SEQ ID NO:264-314.

Methods according to aspects of the present invention include assay for *Borrelia burgdorferi* sensu lato HtrA cleavage products of COMP including one or more of: the peptide of SEQ ID NO:47, SEQ ID NO:48, SEQ ID NO:49, SEQ ID NO:50, SEQ ID NO:51, a homologue or variant thereof having at least 95% identity to the reference peptide, or a combination of any two or more thereof.

Methods according to aspects of the present invention include assay for *Borrelia burgdorferi* sensu lato HtrA cleavage products of COMP including one or more of: the peptide of SEQ ID NO:65, SEQ ID NO:66, SEQ ID NO:67, SEQ ID NO:68, SEQ ID NO:69, a homologue or variant thereof having at least 95% identity to the reference peptide, or a combination of any two or more thereof.

Methods according to aspects of the present invention include assay for *Borrelia burgdorferi* sensu lato HtrA cleavage products of COMP including one or more of: the peptide of SEQ ID NO:264-314, wherein each of the peptides of SEQ ID NO: 264-314 has 5 amino acids closest to the amino terminus and has 1, 2, 3, 4, 5, 6, 7, 8, 9, 10, 11, 12, 13, 14, 15, 16, 17, 18, 19, 20, 21, 22, 23, 24, 25, 26, 27 or 28 additional amino acids; a homologue or variant thereof having at least 95% identity to the reference peptide; a fragment of the one or more peptides of SEQ ID NO:264-314, the fragment having at least the 5 amino acids closest to the amino terminus; a fragment of the one or more peptides of SEQ ID NO:264-314, the fragment having at least the 5 amino acids closest to the amino terminus and at least 1, 2, 3, 4, 5, 6, 7, 8, 9, 10, 11, 12, 13, 14, 15, 16, 17, 18, 19, 20, 21, 22, 23, 24, 25, 26, 27 or 28 additional of the amino acids; or a combination of any two or more thereof Methods according to aspects of the present invention include assay for *Borrelia burgdorferi* sensu lato HtrA cleavage products of a protein or peptide substrate having one or more cleavage sites having SEQ ID NO:70-162, a homologue or variant thereof, cleaved by *Borrelia burgdorferi* sensu lato HtrA.

Methods and compositions of the present invention are not limited to particular *Borrelia burgdorferi* sensu lato HtrA cleavage products identified by SEQ ID NO herein and homologues and variants of a reference nucleic acid or protein may be assayed and used according to aspects of the present invention.

Homologues and variants of a *Borrelia burgdorferi* sensu lato HtrA cleavage product described herein include, for example, naturally occurring mutants and *Borrelia burgdorferi* sensu lato HtrA cleavage products derived from orthologues.

Methods of aiding in the diagnosis of Lyme disease are provided according to the present invention which include detecting a *Borrelia burgdorferi* sensu lato HtrA protease, or a fragment thereof, and/or a nucleic acid encoding *Borrelia burgdorferi* sensu lato HtrA protease, or a fragment thereof, in a sample obtained from a subject having, or suspected of having, Lyme disease.

According to aspects of the present invention, detecting a *Borrelia burgdorferi* sensu lato HtrA protease in a sample obtained from a subject includes qualitative and/or quantitative assays including, but not limited to, immunoassay and mass spectrometry. According to aspects of the present invention, detecting a *Borrelia burgdorferi* sensu lato HtrA protease in a, sample obtained from a subject includes qualitative and/or quantitative assays including, but not limited to, antigen capture. Binding agent compositions which bind substantially specifically to *Borrelia burgdorferi* sensu lato HtrA protease are provided according to the present invention along with methods for use of the binding agents to detect *Borrelia burgdorferi* sensu lato HtrA protease in a sample obtained from a subject having, or suspected of having, Lyme disease.

According to aspects of the present invention, detecting a nucleic acid encoding *Borrelia burgdorferi* sensu lato HtrA protease in a sample obtained from a subject includes, but is not limited to, amplification techniques such as, but not limited to, PCR, RT-PCR ligation-mediated PCR and phi-29 PCR; nucleic acid hybridization techniques such as, but not limited to, Northern blot, Southern blot, RNase protection assay, dot blot and in situ hybridization. Nucleic acid assays for both qualitative and quantitative assay of a nucleic acid in a sample are described in detail in standard references, illustratively including J. Sambrook and D. W. Russell, Molecular Cloning: A Laboratory Manual, Cold Spring Harbor Laboratory Press; 3rd Ed., 2001; F. M. Ausubel et al., Eds., Short Protocols in Molecular Biology, Current Protocols, Wiley, 2002; C. W. Dieffenbach et al., PCR Primer: A Laboratory Manual, Cold Spring Harbor Laboratory Press, 2003; and V. Demidov et al., DNA Amplification: Current Technologies and Applications, Taylor & Francis, 2004.

A sample which is assayed to detect a *Borrelia burgdorferi* sensu lato HtrA protease, or a fragment thereof, and/or a nucleic acid encoding *Borrelia burgdorferi* sensu lato HtrA protease, or a fragment thereof, is any sample type containing or suspected of containing the *Borrelia burgdorferi* sensu lato HtrA protease to be assayed, such as, but not limited to whole blood, plasma, serum, urine, cerebrospinal fluid, synovial fluid and/or a biopsy sample, such as skin or an arthroscopic biopsy sample of joint tissue.

Methods of aiding in the diagnosis of Lyme disease are provided according to the present invention which include detecting an antibody which specifically binds to *Borrelia burgdorferi* sensu lato HtrA protease in a sample obtained from a subject having, or suspected of having, Lyme disease. Detecting an antibody which specifically binds to *Borrelia burgdorferi* sensu lato HtrA protease in a sample obtained from a subject having, or suspected of having, Lyme disease includes qualitative and/or quantitative assays including, but not limited to, immunoassay and mass spectrometry.

A sample which is assayed to detect an antibody which specifically binds to *Borrelia burgdorferi* sensu lato HtrA protease is any sample type containing or suspected of containing the antibody or antibodies to be assayed, such as, but not limited to whole blood, plasma, serum, urine, cerebrospinal fluid, synovial fluid and/or a biopsy sample, such as skin or an arthroscopic biopsy sample of joint tissue.

Methods of aiding in the diagnosis of Lyme disease are provided according to the present invention which include detecting an increase in inflammatory cytokines and chemokines in a sample obtained from a subject having, or suspected of having, Lyme disease compared to a control.

It is understood by the ordinarily skilled artisan that detecting an increase in inflammatory cytokines and chemokines refers to detecting an increase in inflammatory cytokines and chemokines as determinable by use of appropriate controls.

Methods of aiding in the diagnosis of Lyme disease are provided according to the present invention which include detecting an increase in one or more of: CXCL1, CCL1, sICAM-1, IL-6, IL-8, CCL5 and CCL2, in a sample obtained from a subject having, or suspected of having, Lyme disease.

Methods of aiding in the diagnosis of Lyme disease are provided according to the present invention which include detecting an increase in at least 2, 3, 4, 5 or 6 inflammatory cytokines and chemokines selected from: CXCL1, CCL1, sICAM-1, IL-6, IL-8, CCL5 and CCL2, in a sample obtained from a subject having, or suspected of having, Lyme disease.

Methods of aiding in the diagnosis of Lyme disease are provided according to the present invention which include detecting an increase in at least 2, 3, 4, 5 or 6 inflammatory cytokines and chemokines selected from: CXCL1, CCL1, sICAM-1, IL-6, IL-8, CCL5 and CCL2, in a sample obtained from a subject having, or suspected of having, Lyme disease and further includes detecting substantially no increase in at least 1 inflammatory cytokine or chemokine selected from: C5a, CD40 ligand, G-CSF, GM-CSF, IL-1a, IL-1b, TL-ra, IL-2, IL-4, IL-5, IL-10, IL-12p70, IL-13, IL-16, IL-17, IL-17E, IL-23, IL-27, IL-32a, CXCL10, CXCL11, CCL3, CCL4 and Serpin E1.

Methods of aiding in the diagnosis of Lyme disease are provided according to the present invention which include detecting an increase in at least 2, 3, 4, 5 or 6 inflammatory cytokines and chemokines selected from: CXCL1, CCL1, sICAM-1, IL-6, IL-8, CCL5 and CCL2, in a sample obtained from a subject having, or suspected of having, Lyme disease and further includes detecting substantially no increase in at least 2, 3, 4, 5, 6, 7, 8, 9, 10, 11, 12, 13, 14, 15, 16, 17, 18, 19, 20, 21, 22, 23, 24, 25, or 26 inflammatory cytokines and chemokines selected from: C5a, CD40 ligand, G-CSF, GM-CSF, IFN-g, IL-1a, IL-1b, TL-ra, IL-2, IL-4, IL-5, IL-10, IL-12p70, IL-13, IL-16, IL-17, IL-17E, IL-23, IL-27, IL-32a, CXCL10, CXCL11, MW, CCL3, CCL4 and Serpin E1.

Inflammatory cytokines and/or chemokines are assayed by qualitative and/or quantitative assays including, but not limited to, immunoassay and mass spectrometry.

Binding agents, such as antibodies, substantially specific for a specified cytokine or chemokine are generated according to well-known methodology or may be obtained commercially.

A sample which is assayed to detect an increase in inflammatory cytokines and chemokines is any sample type containing the inflammatory cytokines and chemokines to be assayed, such as, but not limited to whole blood, plasma, serum, urine, cerebrospinal fluid, synovial fluid and/or a biopsy sample, such as skin or an arthroscopic biopsy sample of joint tissue.

Methods of aiding in the diagnosis of Lyme disease are provided according to the present invention which include detecting an increase in inflammatory cytokines and chemokines in a sample obtained from a subject having, or suspected of having, Lyme disease compared to a control; and detecting one or more $Borrelia$ $burgdorferi$ sensu lato HtrA cleavage products.

Methods of aiding in the diagnosis of Lyme disease are provided according to the present invention which include detecting an increase in one or more of: CXCL1, CCL1, sICAM-1, IL-6, IL-8, CCL5 and CCL2, and detecting one or more $Borrelia$ $burgdorferi$ sensu lato HtrA cleavage products identified herein as SEQ ID NO:33-414, a homologue or variant thereof having at least 95% identity to the reference peptide, a fragment thereof having at least 5, 6, 7, 8, 9, 10, 11, 12, 13, 14, 15, 16, 17, 18, 19, 20, 21, 22, 23, 24, 25, 26, 27, 28, 29, 30, 31, 32, 33 or 34 amino acids, or a combination of any two or more thereof in a sample obtained from a subject having, or suspected of having, Lyme disease.

Methods of aiding in the diagnosis of Lyme disease are provided according to the present invention which include detecting an increase in at least 2, 3, 4, 5 or 6 inflammatory cytokines and chemokines selected from: CXCL1, CCL1, sICAM-1, IL-6, IL-8, CCL5 and CCL2, and detecting one or more $Borrelia$ $burgdorferi$ sensu lato HtrA cleavage products identified herein as SEQ ID NO:33-414, a homologue or variant thereof having at least 95% identity to the reference peptide, a fragment thereof having at least 5, 6, 7, 8, 9, 10, 11, 12, 13, 14, 15, 16, 17, 18, 19, 20, 21, 22, 23, 24, 25, 26, 27, 28, 29, 30, 31, 32, 33 or 34 amino acids, or a combination of any two or more thereof, in a sample obtained from a subject having, or suspected of having, Lyme disease.

Methods of aiding in the diagnosis of Lyme disease are provided according to the present invention which include detecting an increase in at least 2, 3, 4, 5 or 6 inflammatory cytokines and chemokines selected from: CXCL1, CCL1, sICAM-1, IL-6, IL-8, CCL5 and CCL2, detecting substantially no increase in at least 1 inflammatory cytokine or chemokine selected from: C5a, CD40 ligand, G-CSF, GM-CSF, IFN-g, IL-1a, IL-1b, IL-ra, IL-2, IL-4, IL-5, IL-10, IL-12p70, IL-13, IL-16, IL-17, IL-17E, IL-23, IL-27, IL-32a, CXCL10, CXCL11, MIF, CCL3, CCL4 and Serpin E1, and detecting one or more $Borrelia$ $burgdorferi$ sensu lato HtrA cleavage products identified herein as SEQ ID NO:33-414, a homologue or variant thereof having at least 95% identity to the reference peptide, a fragment thereof having at least 5, 6, 7, 8, 9, 10, 11, 12, 13, 14, 15, 16, 17, 18, 19, 20, 21, 22, 23, 24, 25, 26, 27, 28, 29, 30, 31, 32, 33 or 34 amino acids, or a combination of any two or more thereof, in a sample obtained from a subject having, or suspected of having, Lyme disease in a sample obtained from a subject having, or suspected of having, Lyme disease.

Methods of aiding in the diagnosis of Lyme disease are provided according to the present invention which include detecting an increase in at least 2, 3, 4, 5 or 6 inflammatory cytokines and chemokines selected from: CXCL1, CCL1, sICAM-1, IL-6, IL-8, CCL5 and CCL2, detecting substantially no increase in at least 2, 3, 4, 5, 6, 7, 8, 9, 10, 11, 12, 13, 14, 15, 16, 17, 18, 19, 20, 21, 22, 23, 24, 25, or 26 inflammatory cytokines and chemokines selected from: C5a, CD40 ligand, G-CSF, GM-CSF, IFN-g, IL-1a, IL-1b, IL-ra, IL-2, IL-4, IL-5, IL-10, IL12p70, IL-13, IL-16, IL-17, IL-17E, IL-23, IL-27, IL-32a, CXCL10, CXCL11, MIF, CCL3, CCL4 and Serpin E1, and detecting one or more $Borrelia$ $burgdorferi$ sensu lato HtrA cleavage products identified herein as SEQ ID NO:33-414, a homologue or variant thereof having at least 95% identity to the reference peptide, a fragment thereof having at least 5, 6, 7, 8, 9, 10, 11, 12, 13, 14, 15, 16, 17, 18, 19, 20, 21, 22, 23, 24, 25, 26, 27, 28, 29, 30, 31, 32, 33 or 34 amino acids, or a combination of any two or more thereof, in a sample obtained from a subject having, or suspected of having, Lyme disease.

Binding Agents

The term "binding agent" as used herein refers to an agent characterized by substantially specific binding to a specified substance. The phrase "substantially specific" and grammatical equivalents as used herein in reference to binding of a binding agent to a specified substance refers to binding of the binding agent to the specified substance without substantial binding to other substances present in a sample to be assayed for presence of the specified substance. It is understood by the ordinarily skilled artisan that substantially specific binding refers to substantially specific binding as determinable by use of appropriate controls to distinguish it from nonspecific binding.

The term "binding" refers to a physical or chemical interaction between a binding agent and the target. Binding includes, but is not limited to, ionic bonding, non-ionic bonding, covalent bonding, hydrogen bonding, hydrophobic interaction, hydrophilic interaction, and Van der Waals interaction.

Compositions and methods are provided according to the present invention wherein a binding agent is an antibody in particular embodiments. The term "antibody" is used herein in its broadest sense and includes single antibodies and mixtures of antibodies characterized by substantially specific binding to an antigen. An antibody provided according to compositions and methods is illustratively a polyclonal antibody, a monoclonal antibody, a chimeric antibody, a humanized antibody, and/or an antigen binding antibody fragment, for example. The term antibody refers to a standard intact immunoglobulin having four polypeptide chains including two heavy chains (H) and two light chains (L) linked by disulfide bonds in particular embodiments. Antigen binding antibody fragments illustratively include an Fab fragment, an Fab' fragment, an F(ab')2 fragment, an Fd fragment, an Fv fragment, an scFv fragment and a domain antibody (dAb), for example. In addition, the term antibody refers to antibodies of various classes including IgG, IgM, IgA, IgD and IgE, as well as subclasses, illustratively including for example human subclasses IgG1, IgG2, IgG3 and IgG4 and murine subclasses IgG1, IgG2, IgG2a. IgG2b, IgG3 and IgGM, for example.

In particular embodiments, an antibody which is characterized by substantially specific binding has a dissociation constant, Kd, less than about $10^{-7}$M, such as less than about $10^{-8}$M, less than about $10^{-9}$M or less than about $10^{-10}$ M, or less depending on the specific composition. Binding affinity of an antibody can be determined by Scatchard analysis such as described in P. J. Munson and D. Rodbard, Anal. Biochem., 107:220-239, 1980 or by other methods such as Biomolecular Interaction Analysis using plasmon resonance.

An immunogenic fragment is a peptide or protein having about 4-500 amino acids, and in particular embodiments, at least 5 amino acids, or in further embodiments, at least 6, 7, 8, 9, 10, 11, 12, 13, 14, 15, 20, 22, 23, 24, 25, 26, 27, 28, 29, 30, 31, 32, 33, 34, 35, 40, 50, 100, 200, 300, or 400 amino acids.

Peptides and/or proteins used as immunogens may be conjugated to a carrier, such as keyhole limpet hemocyanin or bovine serum albumin. Broadly, an immunogen is administered to an animal in particular methods, such as a rabbit, goat, mouse, rat, sheep or chicken and immunoglobulins produced in the animal are obtained from the animal, and optionally, purified for screening and use.

Antibodies and methods for preparation of antibodies are well-known in the art. Details of methods of antibody generation and screening of generated antibodies for substantially specific binding to an antigen are described in standard references such as E. Harlow and D. Lane, Antibodies: A Laboratory Manual, Cold Spring Harbor Laboratory Press, 1988; F. Breitling and S. Dübel, Recombinant Antibodies, John Wiley & Sons, New York, 1999; H. Zola, Monoclonal Antibodies: Preparation and Use of Monoclonal Antibodies and Engineered Antibody Derivatives, Basics: From Background to Bench, BIOS Scientific Publishers, 2000; and B. K. C. Lo, Antibody Engineering: Methods and Protocols, Methods in Molecular Biology, Humana Press, 2003.

In particular embodiments, monoclonal antibodies and methods including use of monoclonal antibodies are provided by the present invention. Monoclonal antibodies are prepared using techniques known in the art such as described in E. Harlow and D. Lane, Antibodies: A Laboratory Manual, Cold Spring Harbor Laboratory Press, 1988; F. Breitling and S. Dübel, Recombinant Antibodies, John Wiley & Sons, New York, 1999; H. Zola, Monoclonal Antibodies: Preparation and Use of Monoclonal Antibodies and Engineered Antibody Derivatives, Basics: From Background to Bench, BIOS Scientific Publishers, 2000; and B. K. C. Lo, Antibody Engineering: Methods and Protocols, Methods in Molecular Biology, Humana Press, 2003, for example. Monoclonal antibodies according to the present invention and/or used in methods according to the present invention are produced by techniques illustratively including, but not limited to, hybridoma techniques, recombinant nucleic acid methodology and/or isolation from a phage library, for example as described in the above cited references. Monoclonal antibodies are advantageously used in particular embodiments due to the specificity of the binding of monoclonal antibodies which recognize a single epitope.

Particular methods of monoclonal antibody preparation include obtaining spleen cells from an animal immunized with an immunogen and fusing the antibody-secreting lymphocytes with myeloma or transformed cells to obtain a hybridoma cell capable of replicating indefinitely in culture.

Hybridoma cells producing antibodies substantially specific for a biomarker of Lyme disease are provided according to the present invention.

Antibodies obtained are tested for substantially specific binding to the immunogen by methods illustratively including ELISA, Western blot and immunocytochemistry.

A binding agent can be a nucleic acid binding agent. A nucleic acid binding agent, such as, but not limited to, a nucleic acid probe or primer able to hybridize to a target *Borrelia burgdorferi* sensu lato HtrA mRNA or cDNA can be used for detecting and/or quantifying mRNA or cDNA encoding a *Borrelia burgdorferi* sensu lato HtrA protein or a fragment thereof. A nucleic acid probe can be an oligonucleotide of at least 10, 15, 30, 50 or 100 nucleotides in length and sufficient to specifically hybridize under stringent conditions to *Borrelia burgdorferi* sensu lato HtrA nucleic acid such as mRNA or cDNA or complementary sequence thereof. A nucleic acid primer can be an oligonucleotide of at least 10, 15 or 20 nucleotides in length and sufficient to specifically hybridize under stringent conditions to the mRNA or cDNA, or complementary sequence thereof.

A binding agent can be an isolated non-immunoglobulin protein, peptide or nucleic acid which binds to a molecule of interest with substantial specificity. For example, a binding agent is illustratively an aptamer which substantially specifically binds to a *Borrelia burgdorferi* sensu lato HtrA cleavage product. The term "aptamer" refers to a peptide and/or nucleic acid that substantially specifically binds to a specified substance. In the case of a nucleic acid aptamer, the aptamer is characterized by binding interaction with a target other than Watson/Crick base pairing or triple helix binding with a second and/or third nucleic acid. Such binding interaction may include Van der Waals interaction, hydrophobic interaction, hydrogen bonding and/or electrostatic interactions, for example. Similarly, peptide-based aptamers are characterized by specific binding to a target wherein the aptamer is not a naturally occurring ligand for the target. Techniques for identification and generation of peptide and nucleic acid aptamers is known in the art as described, for example, in F. M. Ausubel et al., Eds., Short Protocols in Molecular Biology, Current Protocols, Wiley, 2002; S. Klussman, Ed., The Aptamer Handbook: Functional Oligonucleotides and Their Applications, Wiley, 2006; and J. Sambrook and D. W. Russell, Molecular Cloning: A Laboratory Manual, Cold Spring Harbor Laboratory Press, $3^{rd}$ Ed., 2001.

Binding Agents Specific for Products of *Borrelia burgdorferi* sensu lato HtrA Cleavage of a Substrate Binding agent compositions characterized by substantially specific binding to one or more products of *Borrelia burgdorferi* sensu lato HtrA cleavage of a substrate are provided according to the present invention along with methods for use of the binding agents.

Isolated antibodies characterized by substantially specific binding to a peptide produced by proteolytic activity of *Borrelia burgdorferi* sensu lato HtrA on a substrate are provided according to the present invention.

In particular aspects, antibodies characterized by substantially specific binding to one or more peptides produced by proteolytic activity of *Borrelia burgdorferi* sensu lato HtrA on at least one host protein substrate are used in methods described herein.

A *Borrelia burgdorferi* sensu lato HtrA cleavage product and/or a fragment thereof is used as an immunogen to produce an antibody characterized by substantially specific binding to the *Borrelia burgdorferi* sensu lato HtrA cleavage product. Alternatively, or in combination, full-length *Borrelia burgdorferi* sensu lato HtrA substrate may be used as an immunogen to produce antibodies.

A *Borrelia burgdorferi* sensu lato HtrA cleavage product and/or fragment thereof for use as an immunogen may be obtained by techniques illustratively including isolation from a sample obtained from a subject containing the product or fragment of the product, produced by recombinant techniques or chemically synthesized, for example as described in Harrington, M. G., Methods Enzymol. 182:488-495, 1990; J. Sambrook and D. W. Russell, Molecular Cloning: A Laboratory Manual, Cold Spring Harbor Laboratory Press, $3^{rd}$ Ed., 2001; and Merrifield, JACS, 85:2149-2154, 1963.

According to one embodiment, a *Borrelia burgdorferi* sensu lato HtrA cleavage product used as an immunogen is a *Borrelia burgdorferi* sensu lato HtrA cleavage product of aggrecan, biglycan, decorin, fibronectin, brevican, neurocan, versican, fibromodulin, COMP and/or E-cadherin.

A binding agent provided according to embodiments of the present invention is characterized by substantially specific binding to a peptide produced by proteolytic activity of *Borrelia burgdorferi* sensu lato HtrA on aggrecan, biglycan, decorin, fibronectin, brevican, neurocan, versican, fibromodulin, COMP and/or E-cadherin. In further embodiments, a monoclonal antibody provided according to the present invention binds substantially specifically to a peptide produced by proteolytic activity of *Borrelia burgdorferi* sensu lato HtrA on aggrecan, biglycan, decorin, fibronectin, brevican, neurocan, versican, fibromodulin, COMP and/or E-cadherin and does not bind substantially specifically to uncleaved aggrecan, biglycan, decorin, fibronectin, brevican, neurocan, versican, fibromodulin, COMP and/or E-cadherin, or cleavage fragments of these proteins other than produced by proteolytic activity of *Borrelia burgdorferi* sensu lato HtrA.

For example, a particular monoclonal antibody according to the present invention recognizes a neoepitope at or near the "cleavage site" of a *Borrelia burgdorferi* sensu lato HtrA cleavage product, wherein the neoepitope is not present and/or not antigenic in the uncleaved protein and cleavage fragments other than a *Borrelia burgdorferi* sensu lato HtrA cleavage product or fragment thereof. A *Borrelia burgdorferi* sensu lato HtrA cleavage product or fragment thereof is indicative of Lyme disease according to particular embodiments of the present invention.

Isolated antibodies which specifically bind to a neoepitope of a peptide produced by proteolytic activity of *Borrelia burgdorferi* sensu lato HtrA on a human host protein are provided according to the present invention.

Isolated antibodies which specifically bind to a neoepitope of a peptide produced by proteolytic activity of *Borrelia burgdorferi* sensu lato HtrA on aggrecan, biglycan, decorin, fibronectin, brevican, neurocan, versican, fibromodulin, COMP and/or E-cadherin are provided according to the present invention.

The term "neoepitope" refers to the amino terminal 5-10 amino acid residues of a substrate of *Borrelia burgdorferi* sensu lato HtrA which are exposed subsequent to proteolytic activity.

Commercial packages for aiding in the diagnosis of Lyme disease in a subject are provided according to embodiments of the present invention which include a binding agent characterized by substantially specific binding to a *Borrelia burgdorferi* sensu lato HtrA cleavage product. One or more auxiliary components are optionally included in commercial packages of the present invention, such as, but not limited to, a control reagent, buffer, diluent or a reconstituting agent.

Binding Agents Specific for *Borrelia burgdorferi* Sensu Lato HtrA

Binding agent compositions which bind substantially specifically to *Borrelia burgdorferi* sensu lato HtrA, or a fragment thereof, are provided according to the present invention along with methods for use of the binding agents.

Isolated antibodies which bind substantially specifically to *Borrelia burgdorferi* sensu lato HtrA protease are provided according to the present invention.

In particular aspects, antibodies which bind substantially specifically to *Borrelia burgdorferi* sensu lato HtrA protease are used in methods described herein.

A *Borrelia burgdorferi* sensu lato HtrA protease and/or a fragment thereof is used as an immunogen to produce an antibody specific to the *Borrelia burgdorferi* sensu lato HtrA protease.

A *Borrelia burgdorferi* sensu lato HtrA protease and/or fragment thereof for use as an immunogen may be obtained by techniques illustratively including isolation from a sample obtained from a subject containing the protease or fragment of the protease, produced by recombinant techniques or chemically synthesized.

Commercial packages for aiding in the diagnosis of Lyme disease in a subject are provided according to aspects of the present invention which include a binding agent for substantially specific binding to a *Borrelia burgdorferi* sensu lato HtrA protease. One or more auxiliary components are optionally included in commercial packages of the present invention, such as, but not limited to, a control reagent, buffer, diluent or a reconstituting agent.

According to aspects of the present invention, commercial packages for aiding in the diagnosis, assessment and/or treatment of Lyme disease in a subject are provided according to aspects of the present invention which include: a binding agent, such as an antibody, characterized by substantially specific binding to a *Borrelia burgdorferi* sensu lato HtrA protease; and one or more substrates for *Borrelia burgdorferi* sensu lato HtrA protease.

According to aspects of the present invention, commercial packages for aiding in the diagnosis of Lyme disease in a subject are provided according to aspects of the present invention which include: a binding agent, such as an antibody, for substantially characterized by binding to a *Borrelia burgdorferi* sensu lato HtrA protease; and one or more substrates for *Borrelia burgdorferi* sensu lato HtrA protease including a *Borrelia burgdorferi* sensu lato HtrA protease cleavage sites selected from SEQ ID NO:70-162, such as aggrecan, fibronectin, biglycan, decorin, brevican, neurocan, versican, cartilage oligomeric matrix protein (COMP), fibromodulin, E-cadherin, a fragment or homologue thereof containing one or more *Borrelia burgdorferi* sensu lato HtrA protease cleavage sites selected from SEQ ID NO:70-162.

According to aspects of the present invention, commercial packages for aiding in the diagnosis, assessment and/or treatment of Lyme disease in a subject are provided according to aspects of the present invention which include a binding agent characterized by substantially specific binding to a neoepitope of a *Borrelia burgdorferi* sensu lato HtrA cleavage product.

According to aspects of the present invention, commercial packages for aiding in the diagnosis, assessment and/or treatment of Lyme disease in a subject are provided according to aspects of the present invention which include at least one antibody characterized by substantially specific binding to a neoepitope of a *Borrelia burgdorferi* sensu lato HtrA cleavage product.

According to aspects of the present invention, commercial packages for aiding in the diagnosis, assessment and/or treatment of Lyme disease in a subject are provided according to aspects of the present invention which include two or more antibodies wherein each antibody is characterized by substantially specific binding to a neoepitope of a different *Borrelia burgdorferi* sensu lato HtrA cleavage product. Multiple anti-*Borrelia burgdorferi* sensu lato HtrA cleavage product antibodies are provided according to aspects of inventive commercial packages of the present invention.

Such antibodies are optionally arrayed on a support for multiplex analysis of *Borrelia burgdorferi* sensu lato HtrA cleavage products in a sample obtained from a subject having or suspected of having Lyme disease.

According to further aspects, commercial kits of the present invention include at least one, 2, 3, 4, 5, 6, 7, 8, 9, 10 or more, antibodies characterized by substantially specific binding to a neoepitope of a *Borrelia burgdorferi* sensu lato HtrA cleavage product and one or more antibodies characterized by substantially specific binding to at least one cytokine or chemokine selected from: CXCL1, CCL1, sICAM-1, IL-6, IL-8, CCL2, and CCL5. Commercial kits of the present invention optionally further include at least one cytokine or chemokine selected from: C5a, CD40 ligand, G-CSF, GM-CSF, IFN-g, IL-1a, IL-1b, IL-ra, IL-2, IL-4, IL-5, IL-10, IL-12p70, IL-13, IL-16, IL-17, IL-17E, IL-23, IL-27, IL-32a, CXCL10, CXCL11, CCL3, CCL4 and Serpin E1. Such antibodies are optionally arrayed on a support for multiplex analysis of *Borrelia burgdorferi* sensu lato HtrA cleavage products and chemokines/cytokines in a sample obtained from a subject having or suspected of having Lyme disease.

Amino Acid and Nucleic Acid Sequences

The term "*Borrelia burgdorferi* sensu lato HtrA" encompasses *Borrelia burgdorferi* HtrA identified herein as SEQ ID NO:1, encoded by nucleic acid sequence SEQ ID NO:2; *Borrelia garinii* HtrA identified herein as SEQ ID NO:5, encoded by nucleic acid sequence SEQ ID NO:6; *Borrelia afzelii*. HtrA identified herein as SEQ ID NO:7, encoded by nucleic acid sequence SEQ ID NO:8; *Borrelia burgdorferi* HtrA identified herein as SEQ ID NO:9, encoded by nucleic acid sequence SEQ ID NO:10; *Borrelia garinii* HtrA identified herein as SEQ ID NO:13, encoded by nucleic acid sequence SEQ ID NO:14; *Borrelia afzelii* HtrA identified herein as SEQ ID NO:15, encoded by nucleic acid sequence SEQ ID NO:16; *Borrelia burgdorferi* HtrA identified herein as SEQ ID NO:17, encoded by nucleic acid sequence SEQ ID NO:18; *Borrelia garinii* HtrA identified herein as SEQ ID NO:21, encoded by nucleic acid sequence SEQ ID NO:22; and *Borrelia afzelii* HtrA identified herein as SEQ ID NO:23, encoded by nucleic acid sequence SEQ ID NO:24.

Methods and compositions of the present invention are not limited to particular amino acid and nucleic sequences identified by SEQ ID NO herein and homologues and variants of a reference nucleic acid or protein may be used.

Homologues and variants of a nucleic acid or protein described herein are characterized by conserved functional properties compared to the corresponding nucleic acid or protein.

*Borrelia burgdorferi* HtrA and *Borrelia burgdorferi* sensu lato HtrA encompasses proteins having at least 80%, 85%, 90%, 91%, 92%, 93%, 94%, 95%, 96%, 97%, 98%, 99%, or 100% identity to the protein having the amino acid sequence set forth in SEQ ID NO:1, or a protein encoded by a nucleic acid sequence that hybridizes under high stringency hybridization conditions to the nucleic acid set forth in SEQ ID NO:2 or a complement thereof so long as the protein is characterized by protease function of the protein of SEQ ID NO:1.

*Borrelia garinii* HtrA and *Borrelia burgdorferi* sensu lato HtrA encompasses proteins having at least 80%, 85%, 90%, 91%, 92%, 93%, 94%, 95%, 96%, 97%, 98%, 99%, or 100% identity to the protein having the amino acid sequence set forth in SEQ ID NO:5, or a protein encoded by a nucleic acid sequence that hybridizes under high stringency hybridization conditions to the nucleic acid set forth in SEQ ID NO:6 or a complement thereof so long as the protein is characterized by protease function of the protein of SEQ ID NO:5.

*Borrelia afzelii* HtrA and *Borrelia burgdorferi* sensu lato HtrA encompasses proteins having at least 80%, 85%, 90%, 91%, 92%, 93%, 94%, 95%, 96%, 97%, 98%, 99%, or 100% identity to the protein having the amino acid sequence set forth in SEQ ID NO:7, or a protein encoded by a nucleic acid sequence that hybridizes under high stringency hybridization conditions to the nucleic acid set forth in SEQ ID NO:8 or a complement thereof so long as the protein is characterized by protease function of the protein of SEQ ID NO:7.

*Borrelia burgdorferi* HtrA and *Borrelia burgdorferi* sensu lato HtrA encompasses proteins having at least 80%, 85%, 90%, 91%, 92%, 93%, 94%, 95%, 96%, 97%, 98%, 99%, or 100% identity to the protein having the amino acid sequence set forth in SEQ ID NO:9, or a protein encoded by a nucleic acid sequence that hybridizes under high stringency hybridization conditions to the nucleic acid set forth in SEQ ID NO:10 or a complement thereof so long as the protein is characterized by protease function of the protein of SEQ ID NO:9.

*Borrelia garinii* HtrA and *Borrelia burgdorferi* sensu lato HtrA encompasses proteins having at least 80%, 85%, 90%, 91%, 92%, 93%, 94%, 95%, 96%, 97%, 98%, 99%, or 100% identity to the protein having the amino acid sequence set forth in SEQ ID NO:13, or a protein encoded by a nucleic acid sequence that hybridizes under high stringency hybridization conditions to the nucleic acid set forth in SEQ ID NO:14 or a complement thereof so long as the protein is characterized by protease function of the protein of SEQ ID NO:13.

*Borrelia afzelii* HtrA and *Borrelia burgdorferi* sensu lato HtrA encompasses proteins having at least 80%, 85%, 90%, 91%, 92%, 93%, 94%, 95%, 96%, 97%, 98%, 99%, or 100% identity to the protein having the amino acid sequence set forth in SEQ ID NO:15, or a protein encoded by a nucleic acid sequence that hybridizes under high stringency hybridization conditions to the nucleic acid set forth in SEQ ID NO:16 or a complement thereof so long as the protein is characterized by protease function of the protein of SEQ ID NO:15.

*Borrelia burgdorferi* HtrA and *Borrelia burgdorferi* sensu lato HtrA encompasses proteins having at least 80%, 85%, 90%, 91%, 92%, 93%, 94%, 95%, 96%, 97%, 98%, 99%, or 100% identity to the protein having the amino acid sequence set forth in SEQ ID NO:17, or a protein encoded by a nucleic acid sequence that hybridizes under high stringency hybridization conditions to the nucleic acid set forth in SEQ ID NO:18 or a complement thereof so long as the protein is characterized by protease function of the protein of SEQ ID NO:17.

*Borrelia garinii* HtrA and *Borrelia burgdorferi* sensu lato HtrA encompasses proteins having at least 80%, 85%, 90%, 91%, 92%, 93%, 94%, 95%, 96%, 97%, 98%, 99%, or 100% identity to the protein having the amino acid sequence set forth in SEQ ID NO:21, or a protein encoded by a nucleic acid sequence that hybridizes under high stringency hybridization conditions to the nucleic acid set forth in SEQ ID NO:22 or a complement thereof so long as the protein is characterized by protease function of the protein of SEQ ID NO:21.

*Borrelia afzelii* HtrA and *Borrelia burgdorferi* sensu lato HtrA encompasses proteins having at least 80%, 85%, 90%, 91%, 92%, 93%, 94%, 95%, 96%, 97%, 98%, 99%, or 100% identity to the protein having the amino acid sequence set forth in SEQ ID NO:23, or a protein encoded by a nucleic acid sequence that hybridizes under high stringency hybridization conditions to the nucleic acid set forth in SEQ ID NO:24 or a complement thereof so long as the protein is characterized by protease function of the protein of SEQ ID NO:23.

A "catalytic triad" is at amino acid positions corresponding to 119H, 149D and 226S in the full-length protein, and at amino acid positions 82H, 112D and 189S in the mature protein, lacking a signal peptide. Mutations may be made such that the catalytic triad is 226Ser/119His/149Glu, 226Ser/119His/149His, 226Ser/119Glu/149Asp, 226Ser/119His, 226Ser/149Lys, or 226Ser alone at the indicated corresponding positions or analogous positions in variants or homologs of proteins disclosed herein.

The term "fragment of *Borrelia burgdorferi* sensu lato HtrA" refers to any fragment of a *Borrelia burgdorferi* sensu lato HtrA that is operable in the described method utilizing the fragment, as understood by the ordinarily skilled artisan. A fragment of *Borrelia burgdorferi* sensu lato HtrA is operative in any of the inventive methods described herein utilizing a *Borrelia burgdorferi* sensu lato HtrA.

"*Borrelia burgdorferi* sensu lato HtrA nucleic acid" as used herein refers to an isolated nucleic acid having a sequence that has at least 80%, 85%, 90%, 91%, 92%, 93%, 94%, 95%, 96%, 97%, 98%, or 99% identity to the nucleic acid sequence set forth in SEQ ID NO:2, SEQ ID NO:6, SEQ ID NO:8, SEQ ID NO:10, SEQ ID NO:14, SEQ ID NO:16, SEQ ID NO:18, SEQ ID NO:22, SEQ ID NO:24, or an isolated nucleic acid molecule having a sequence that hybridizes under high stringency hybridization conditions to the nucleic acid set forth in SEQ ID NO:2 SEQ ID NO:6, SEQ ID NO:8, SEQ ID NO:10, SEQ ID NO:14, SEQ ID NO:16, SEQ ID NO:18, SEQ ID NO:22, SEQ ID NO:24; or a complement thereof, so long as the nucleic acid effects the function described in the particular inventive method comprising use of the nucleic acid. A fragment of *Borrelia burgdorferi* sensu lato HtrA nucleic acid is any fragment of a *Borrelia burgdorferi* sensu lato HtrA DNA that is operable in the described method utilizing the fragment, as understood by the ordinarily skilled artisan. A fragment of *Borrelia burgdorferi* sensu lato HtrA DNA is operative in any of the inventive methods described herein utilizing a *Borrelia burgdorferi* sensu lato HtrA nucleic acid.

The terms "complement" and "complementary" refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'. Further, the nucleotide sequence 3'-TCGA- is 100% complementary to a region of the nucleotide sequence 5'-TTAGCTGG-3'.

The terms "hybridization" and "hybridizes" refer to pairing and binding of complementary nucleic acids. Hybridization occurs to varying extents between two nucleic acids depending on factors such as the degree of complementarity of the nucleic acids, the melting temperature, Tm, of the nucleic acids and the stringency of hybridization conditions, as is well known in the art. The term "stringency of hybridization conditions" refers to conditions of temperature, ionic strength, and composition of a hybridization medium with respect to particular common additives such as formamide and Denhardt's solution. Determination of particular hybridization conditions relating to a specified nucleic acid is routine and is well known in the art, for instance, as described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002. High stringency hybridization conditions are those which only allow hybridization of substantially complementary nucleic acids. Typically, nucleic acids having about 85-100% complementarity are considered highly complementary and hybridize under high stringency conditions. Intermediate stringency conditions are exemplified by conditions under which nucleic acids having intermediate complementarity, about 50-84% complementarity, as well as those having a high degree of complementarity, hybridize. In contrast, low stringency hybridization conditions are those in which nucleic acids having a low degree of complementarity hybridize.

The terms "specific hybridization" and "specifically hybridizes" refer to hybridization of a particular nucleic acid to a target nucleic acid without substantial hybridization to nucleic acids other than the target nucleic acid in a sample.

Stringency of hybridization and washing conditions depends on several factors, including the Tm of the probe and target and ionic strength of the hybridization and wash conditions, as is well-known to the skilled artisan. Hybridization and conditions to achieve a desired hybridization stringency are described, for example, in Sambrook et al., Molecular Cloning: A Laboratory Manual, Cold Spring Harbor Laboratory Press, 2001; and Ausubel, F. et al., (Eds.), Short Protocols in Molecular Biology, Wiley, 2002.

High stringency hybridization conditions are known to the ordinarily skilled artisan. An example of high stringency hybridization conditions is hybridization of nucleic acids over about 100 nucleotides in length in a solution containing 6×SSC, 5×Denhardt's solution, 30% formamide, and 100 micrograms/ml denatured salmon sperm at 37° C. overnight followed by washing in a solution of 0.1×SSC and 0.1% SDS at 60° C. for 15 minutes. SSC is 0.15M NaCl/0.015M Na citrate. Denhardt's solution is 0.02% bovine serum albumin/0.02% FICOLL/0.02% polyvinylpyrrolidone. Under highly stringent conditions, SEQ ID No. 2, SEQ ID NO:6 and SEQ ID NO:8 will hybridize to the complement of substantially identical targets and not to unrelated sequences.

Percent identity is determined by comparison of amino acid or nucleic acid sequences, including a reference amino acid or nucleic acid sequence and a putative homologue amino acid or nucleic acid sequence. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). The two sequences compared are generally the same length or nearly the same length.

The determination of percent identity between two sequences can also be accomplished using a mathematical algorithm. Algorithms used for determination of percent identity illustratively include the algorithms of S. Karlin and S. Altshul, PNAS, 90:5873-5877, 1993; T. Smith and M. Waterman, Adv. Appl. Math. 2:482-489, 1981, S. Needleman and C. Wunsch, J. Mol. Biol., 48:443-453, 1970, W. Pearson and D. Lipman, PNAS, 85:2444-2448, 1988 and others incorporated into computerized implementations such as, but not limited to, GAP, BESTFIT, FASTA, TFASTA, and BLAST, for example incorporated in the Wisconsin Genetics Software Package, Genetics Computer Group, 575 Science Drive, Madison, Wis.) and publicly available from the National Center for Biotechnology Information.

A non-limiting example of a mathematical algorithm utilized for the comparison of two sequences is the algorithm of Karlin and Altschul, 1990, PNAS 87:2264-2268, modified as in Karlin and Altschul, 1993, PNAS. 90:5873-5877. Such an algorithm is incorporated into the NBLAST and XBLAST programs of Altschul et al., 1990, J. Mol. Biol. 215:403. BLAST nucleotide searches are performed with the NBLAST nucleotide program parameters set, e.g., for score=100, word length=12 to obtain nucleotide sequences homologous to a nucleic acid molecules of the present invention. BLAST protein searches are performed with the XBLAST program parameters set, e.g., to score 50, word length=3 to obtain amino acid sequences homologous to a protein molecule of the present invention. To obtain gapped alignments for comparison purposes, Gapped BLAST are utilized as described in Altschul et al., 1997, Nucleic Acids Res. 25:3389-3402. Alternatively, PSI BLAST is used to perform an iterated search which detects distant relationships between molecules. When utilizing BLAST, Gapped BLAST, and PSI Blast programs, the default parameters of the respective programs (e.g., of XBLAST and NBLAST) are used. Another preferred, non limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 is used.

The percent identity between two sequences is determined using techniques similar to those described above, with or without allowing gaps. In calculating percent identity, typically only exact matches are counted.

One of skill in the art will recognize that one or more nucleic acid or amino acid mutations can be introduced without altering the functional properties of a given nucleic acid or protein, respectively. Mutations can be introduced using standard molecular biology techniques, such as site-directed mutagenesis and PCR-mediated mutagenesis, to produce variants. For example, one or more amino acid substitutions, additions, or deletions can be made without altering the functional properties of a reference protein. Similarly, one or more nucleic acid substitutions, additions, or deletions can be made without altering the functional properties of a reference nucleic acid sequence.

When comparing a reference protein to a putative homologue, amino acid similarity may be considered in addition to identity of amino acids at corresponding positions in an amino acid sequence. "Amino acid similarity" refers to amino acid identity and conservative amino acid substitutions in a putative homologue compared to the corresponding amino acid positions in a reference protein.

Conservative amino acid substitutions can be made in reference proteins to produce variants.

Conservative amino acid substitutions are art recognized substitutions of one amino acid for another amino acid having similar characteristics. For example, each amino acid may be described as having one or more of the following characteristics: electropositive, electronegative, aliphatic, aromatic, polar, hydrophobic and hydrophilic. A conservative substitution is a substitution of one amino acid having a specified structural or functional characteristic for another amino acid having the same characteristic. Acidic amino acids include aspartate, glutamate; basic amino acids include histidine, lysine, arginine; aliphatic amino acids include isoleucine, leucine and valine; aromatic amino acids include phenylalanine, glycine, tyrosine and tryptophan; polar amino acids include aspartate, glutamate, histidine, lysine, asparagine, glutamine, arginine, serine, threonine and tyrosine; and hydrophobic amino acids include alanine, cysteine, phenylalanine, glycine, isoleucine, leucine, methionine, proline, valine and tryptophan; and conservative substitutions include substitution among amino acids within each group. Amino acids may also be described in terms of relative size; alanine, cysteine, aspartate, glycine, asparagine, proline, threonine, serine, valine are all typically considered to be small.

A variant can include synthetic amino acid analogs, amino acid derivatives and/or non-standard amino acids, illustratively including, without limitation, alpha-aminobutyric acid, citrulline, canavanine, cyanoalanine, diaminobutyric acid, diaminopimelic acid, dihydroxy-phenylalanine, djenkolic acid, homoarginine, hydroxyproline, norleucine, norvaline, 3-phosphoserine, homoserine, 5-hydroxytryptophan, 1-methylhistidine, 3-methylhistidine, and ornithine.

With regard to nucleic acids, it will be appreciated by those of skill in the art that due to the degenerate nature of the genetic code, multiple nucleic acid sequences can encode a particular protein, and that such alternate nucleic acids may be used in compositions and methods of the present invention.

An assay of the present invention can incorporate a support for attachment of a specific binding agent, such as, but not limited to an antibody or probe. A support with attached specific binding agent can be solid or semi-solid and can be any of various materials such as glass, silicon, paper, a synthetic or naturally occurring polymer, such as polystyrene, polycarbonate, polypropylene, PVDF, nylon, cellulose, agarose, dextran, and polyacrylamide or any other material to which a specific binding agent can be stably attached for use in a binding assay. Multiple specific binding agents can be arrayed on such supports for multiplex assays, such as microarrays for example.

Such supports can be in any of a variety of forms and shapes including, but not limited to, microtiter plates, microtiter wells, pins, fibers, beads, magnetic beads, coded beads, slides, silicon chips and membranes such as a nitrocellulose or PVDF membrane. Such supports can further be used to purify a desired target.

A support used can include functional groups for binding to a specific binding agent such as an antibody or neoepitope-containing peptide, including, but not limited to carboxyl, amine, amino, carboxylate, halide, ester, alcohol, carbamide, aldehyde, chloromethyl, sulfur oxide, nitrogen oxide, epoxy and/or tosyl functional groups. Attachment of a specific binding agent to a support is achieved by any of various methods, illustratively including adsorption and chemical bonding. In one example, 1-Ethyl-3-[3-dimethylaminopropyl]carbodiimide hydrochloride, EDC or EDAC chemistry, can be used to attach a specific binding agent to a support. The specific binding agent can be bonded directly or indirectly to the material of the support, for example, via bonding to a coating or linker disposed on the support. Functional groups, modification thereof and attachment of a binding partner to a support are known in the art, for example as described in Fitch, R. M., Polymer Colloids: A Comprehensive Introduction, Academic Press, 1997.

Methods of aiding in the diagnosis, assessment and/or treatment of Lyme disease are provided according to the present invention which include assaying a sample obtained from a subject having, or suspected of having, Lyme disease for proteolytic activity of *Borrelia burgdorferi* sensu lato HtrA to detect the presence of *Borrelia burgdorferi* sensu lato HtrA, wherein presence of *Borrelia burgdorferi* sensu lato HtrA is indicative of *Borrelia burgdorferi* sensu lato active infection of the subject.

Methods of aiding in the diagnosis, assessment and/or treatment of Lyme disease are provided according to the present invention which include assaying a sample obtained from a subject having, or suspected of having, Lyme disease for proteolytic activity of *Borrelia burgdorferi* sensu lato HtrA to detect the presence of *Borrelia burgdorferi* sensu lato HtrA, wherein the assaying comprises contacting the sample with a substrate for *Borrelia burgdorferi* sensu lato HtrA and determining whether the substrate is cleaved by proteolytic activity of *Borrelia burgdorferi* sensu lato HtrA and wherein presence of *Borrelia burgdorferi* sensu lato HtrA is indicative of *Borrelia burgdorferi* sensu lato active infection of the subject.

Methods of aiding in the diagnosis, assessment and/or treatment of Lyme disease are provided according to the present invention which include assaying a sample obtained from a subject having, or suspected of having, Lyme disease for proteolytic activity of *Borrelia burgdorferi* sensu lato HtrA to detect the presence of *Borrelia burgdorferi* sensu lato HtrA, wherein the assaying comprises contacting the sample with a substrate for *Borrelia burgdorferi* sensu lato HtrA wherein the substrate is selected from the group consisting of: casein, aggrecan, decorin, biglycan, brevican, neurocan, versican, fibronectin, fibromodulin, cartilage oligomeric matrix protein and E-cadherin and determining whether the substrate is cleaved by proteolytic activity of *Borrelia burgdorferi* sensu lato HtrA and wherein presence of *Borrelia burgdorferi* sensu lato HtrA is indicative of *Borrelia burgdorferi* sensu lato active infection of the subject.

Methods of aiding in the diagnosis, assessment and/or treatment of Lyme disease are provided according to the present invention which include assaying a sample obtained from a subject having, or suspected of having, Lyme disease for proteolytic activity of *Borrelia burgdorferi* sensu lato HtrA to detect the presence of *Borrelia burgdorferi* sensu lato HtrA, wherein the assaying comprises contacting the sample with a substrate for *Borrelia burgdorferi* sensu lato HtrA, wherein the substrate comprises a *Borrelia burgdorferi* sensu lato HtrA cleavage site selected from SEQ ID NO:70-162, a homologue or variant thereof, and determining whether the substrate is cleaved by proteolytic activity of *Borrelia burgdorferi*سظsensu lato HtrA and wherein presence of *Borrelia burgdorferi* sensu lato HtrA is indicative of *Borrelia burgdorferi* sensu lato active infection of the subject.

A sample is optionally purified to enrich for *Borrelia burgdorferi* sensu lato HtrA.

For example, an antibody of other binding partner substantially specific for *Borrelia burgdorferi*سظsensu lato HtrA is attached to a solid support to capture *Borrelia burgdorferi* sensu lato HtrA.

According to aspects of the present invention, the substrate includes a detectable label.

The term "detectable label" refers to a substance that can be measured and/or observed, visually or by any appropriate method illustratively including spectroscopic, optical, photochemical, biochemical, enzymatic, electrical and/or immunochemical methods of detection, to indicate presence of the label. Non-limiting examples of detectable labels that can be used in conjunction with methods described herein illustratively include a fluorescent moiety, a chemiluminescent moiety, a bioluminescent moiety, a magnetic particle, an enzyme, a substrate, a radioisotope and a chromophore. For example, a detectable label can be a dye, such as a fluorophore, a chromophore, a radioactive moiety or a member of a specific binding pair such as biotin. The term "member of a specific binding pair" refers to a substance that specifically recognizes and interacts with a second substance exemplified by specific binding pairs such as biotin-avidin, biotin-streptavidin, antibody-antigen, and target-aptamer. Non-limiting examples of detectable labels that can be used include fluorescent dyes such as fluorescein and its derivatives, rhodamine and its derivatives, Texas Red, BODIPY dyes including but not limited to BODIPY-FL, BODIPY-TR, BODIPY-TMR, BODIPY-630/650, BODIPY-650/670; 5'carboxy-fluorescein ("FMA"), 6-carboxy-4',5'-dichloro-2',7'-dimethoxyfluorescein, succinimidyl ester ("JOE"), 6-carboxytetramethylrhodamine ("TAMRA"), 6Ncarboxy-X-rhodamine ("ROX"), HEX, TET, IRD40, IRD41, cyanine dyes such as Cyanine 3 and Cyanine 5, and ALEXA dyes, including but not limited to ALEXA-488, ALEXA-532, ALEXA-546, ALEXA-568, and ALEXA-594; chromophores such as horseradish peroxidase, alkaline phosphatase and digoxigenin; and radioactive moieties such as $^{32}P$, $^{35}S$, $^{3}H$, $^{125}I$ or $^{14}C$; and binding partners such as biotin and biotin derivatives. Detection of a detectable label is achieved by any of various well-known methods such as, but not limited to, spectrophotometric and radiometric methods According to aspects of the present invention, the substrate is a chromogenic or flurogenic substrate. A chromogenic or fluorogenic substrate is characterized by attachment of a chemical group attached to the substrate which gives rise to color or fluorescence following cleavage by the protease. The generation of color or fluorescence can be detected spectrophotometrically and is proportional to cleavage of the substrate. Chromogenic moieties are known in the art and include, without limitation, pNA.

Methods of aiding in the diagnosis of Lyme disease are provided according to the present invention which include detecting a host antibody specific for a peptide produced by proteolytic activity of *Borrelia burgdorferi* sensu lato HtrA on a host protein substrate or on *Borrelia burgdorferi* sensu lato HtrA itself in a sample obtained from a subject suspected of having Lyme disease.

Detecting a host antibody specific for a peptide produced by proteolytic activity of *Borrelia burgdorferi* sensu lato HtrA in a sample obtained from a subject having, or suspected of having, Lyme disease includes qualitative and/or quantitative assays including, but not limited to, immunoassay and mass spectrometry.

A sample which is assayed to detect a host antibody specific for a peptide produced by proteolytic activity of *Borrelia burgdorferi* sensu lato HtrA is any sample type containing or suspected of containing the antibody or antibodies to be assayed, such as, but not limited to whole blood, plasma, serum, urine, cerebrospinal fluid, synovial fluid and/or a biopsy sample, such as skin or an arthroscopic biopsy sample of joint tissue.

One or more peptides containing a neoepitope produced by proteolytic activity of *Borrelia burgdorferi* sensu lato HtrA on a host substrate may be included in an assay to detect host antibodies which specifically bind to the neoepitope. One or more aggrecan, biglycan, decorin, fibronectin, brevican, neurocan, versican, fibromodulin, COMP and/or E-cadherin peptides containing a neoepitope produced by proteolytic activity of *Borrelia burgdorferi* sensu lato HtrA on a host substrate may be included in an assay to detect host antibodies which specifically bind to the neoepitope according to aspects of the present invention. The term "neoepitope" refers to the amino terminal 5-10 amino acid residues of a substrate of *Borrelia burgdorferi* sensu lato HtrA which are exposed subsequent to proteolytic activity. One or more aggrecan, biglycan, decorin, fibronectin, brevican, neurocan, versican, fibromodulin, COMP and/or E-cadherin peptides of SEQ ID NO:33-69 and 162-414 each of which contains a neoepitope produced by proteolytic activity of *Borrelia burgdorferi* sensu lato HtrA on a host substrate may be included in an assay to detect host antibodies which specifically bind to the neoepitope according to aspects of the present invention. Such peptides are optionally arrayed on a support for multiplex analysis to detect host antibodies in a sample obtained from a subject having or suspected of having Lyme disease. Peptides and proteins described herein may be prepared by any of various methods such as isolation from natural sources, isolation from an in-vitro cleavage reaction, recombinant production or chemical synthetic techniques.

According to aspects of the present invention, commercial packages for aiding in the diagnosis, assessment and/or treatment of Lyme disease in a subject are provided according to aspects of the present invention which include one or more peptides containing a neoepitope produced by proteolytic activity of *Borrelia burgdorferi* sensu lato HtrA on a host substrate may be included in an commercial package for use to detect host antibodies which specifically bind to the neoepitope. The host may be a subject having or suspected of having Lyme disease. Alternatively, the host may be an immunized subject. Multiple peptides containing a neoepitope produced by proteolytic activity of *Borrelia burgdorferi* sensu lato HtrA on a host substrate are provided according to aspects of inventive commercial packages of the present invention. Such peptides are optionally arrayed on a support for multiplex analysis of host antibodies substantially specific for one or more of the peptides. According to further aspects, commercial kits of the present invention include at least one, 2, 3, 4, 5, 6, 7, 8, 9, 10 or more, peptides of aggrecan, biglycan, decorin, fibronectin, brevican, neurocan, versican, fibromodulin, COMP and/or E-cadherin which are *Borrelia burgdorferi* sensu lato HtrA cleavage products containing a neoepitope. According to further aspects, commercial kits of the present invention include at least one, 2, 3, 4, 5, 6, 7, 8, 9, 10 or more, peptides of aggrecan, biglycan, decorin, fibronectin, brevican, neurocan, versican, fibromodulin, COMP and/or E-cadherin peptides of SEQ ID NO:33-69 and 162-414 each of which contains a neoepitope produced by proteolytic activity of *Borrelia burgdorferi* sensu lato HtrA. Peptides included in commercial packages according to aspects of the present invention are optionally arrayed on a support. One or more auxiliary components are optionally included in commercial packages of the present invention, such as, but not limited to, a control reagent, buffer, diluent or a reconstituting agent.

Protease Inhibitors

Methods of screening for an inhibitor of *Borrelia burgdorferi* sensu lato protease activity are provided according to the present invention.

Methods of screening for an inhibitor of *Borrelia burgdorferi* sensu lato protease activity are provided according to the present invention which include contacting a *Borrelia burgdorferi* sensu lato HtrA protein with a test agent under conditions that promote protease activity of the *Borrelia burgdorferi* sensu lato HtrA protein and detecting an effect of the test agent to decrease protease activity of the *Borrelia burgdorferi* sensu lato HtrA protein, thereby identifying the test agent as an inhibitor of *Borrelia burgdorferi* sensu lato HtrA protease activity.

The term "test agent" encompasses compounds; small molecules; biochemicals; and biological agents such as proteins, peptides, cytokines, antibodies, and fragments thereof.

Conditions that promote protease activity as described in any of the inventive methods provided herein are well known in the art, including such conditions described in the references provided herein, and otherwise described or illustrated herein.

An assay used in methods of identifying an inhibitor herein may have any of various formats, including, but not limited to, cell-based and array assays. An array assay refers to an ordered array of one or more materials, such as an arrangement of addressable regions including putative inhibitors, for example.

The *Borrelia burgdorferi* sensu lato HtrA protein is optionally expressed by recombinant methodology for use in methods for screening for an inhibitor of *Borrelia burgdorferi* sensu lato HtrA. The expressed protein may be produced in a cell or in a cell-free expression system. For example, the nucleic acid sequence of SEQ ID NO:2 is expressed to produce recombinant *Borrelia burgdorferi* sensu lato HtrA for use in methods for screening for an inhibitor of *Borrelia burgdorferi* sensu lato HtrA The expressed recombinant *Borrelia burgdorferi* sensu lato HtrA is contacted with a test agent under conditions that promote protease activity and the effects of the test agent on protease activity are detected and compared to appropriate controls. Detection of a specific decrease in protease activity due to the test agent identifies an inhibitor of *Borrelia burgdorferi* sensu lato HtrA protease activity. The expressed protein is optionally isolated from cells in which it is expressed. Alternatively, the assay may include cells expressing the *Borrelia burgdorferi* sensu lato HtrA.

Exemplary putative inhibitors of *Borrelia burgdorferi* sensu lato HtrA protease activity include, but are not limited to, those described in Table I.

TABLE I

| Inhibitor common or chemical name | Systematic name |
|---|---|
| Elaspol, Sivelestat, ONO 5046 | N-{2-[({4-[(2,2-dimethylpropanoyl)oxy]phenyl}sulfonyl)amino]benzoyl}glycine |
| Midesteine, MR-889 | N-[(Tetrahydro-2-oxothiophen)-3-yl]-2-[[(thiophen-2-yl)carbonyl]thio]propionamide |
| AE-3763 | 1-[N-[2-[3-(Carboxymethyl)-2-oxoimidazolidin-1-yl]acetyl]-L-valyl-L-prolinamide N-[3,3,3-trifluoro-1(S)-isopropyl-2-oxopropyl]amide |
| ONO-6818 | 2-(5-amino-6-oxo-2-phenyl-1,6-dihydropyrimidin-1-yl)-N-[(1R,2R)-1-(5-tert-butyl-1,3,4-oxadiazol-2-yl)-1-hydroxy-3-methylbutan-2-yl]acetamide |
| Nafamostat | 4-[(Aminoiminomethyl)amino]-benzoic acid 6-(aminoiminomethyl)-2-naphthalenyl ester dimethanesulfonate ester dimethanesulfonate |
| Camostat mesilate | 4-Guanidinobenzoic acid 4-[[[(dimethylcarbamoyl)methoxy]carbonyl]methyl]phenyl•methanesulfonic acid |
| AK-968/40385474, MolPort-019-779-730, STK958229, AKOS003924934 | [3-[(E)-[[2-[(6-ethoxy-1,3-benzothiazol-2-yl)sulfanyl]acetyl]hydrazinylidene]methyl]phenyl] 4-iodo-2-methylpyrazole-3-carboxylate |
| ASN 05116187, MolPort-000-061-068 | 2-{[1-(4-acetamidophenyl)-1,2,3,4-tetrazol-5-yl]sulfanyl}-N-(6-ethoxy-1,3-benzothiazol-2-yl)acetamide |
| ASN 04363098, MolPort-000-040-886, SMR000123570 AC1MKUQN ASN 04363098 Opreal_023656 Opreal_263722 MLS000122916 MLS002536593 HMS2414H15 ZINC06512029 AKOS000710916 | 2-[5-(4-Diethylsulfamoyl-phenyl)-[1,3,4]oxadiazol-2-ylsulfanyl]-N-(3,5-dimethoxy-phenyl)-acetamide |
| ASN 05343143, MolPort-000-068-903 | N-(6-ethoxybenzothiazol-2-yl)-2-[[5-(4-methylsulfonylaminophenyl)-1,3,4-oxadiazol-2-yl]sulfanyl]ethanamide |
| ASN 04363145, MolPort-000-040-916 | Ethyl 2-[[2-[[5-[4-(diethylsulfamoyl)phenyl]-1,3,4-oxadiazol-2-yl]sulfanyl]acetyl]amino]-4,5-dimethylthiophene-3-carboxylate |
| BAS 01074227, | 2-(2,4-Dihydroxyphenyl)-3-{[(Z)-(2-hydroxy-4-oxo-2,5-cyclohexadien-1-ylidene)methyl]amino}-2,3-dihydro-4(1H)-quinazolinone |
| ASN 03776561, MolPort-000-027-875 | 1-(3-chlorophenyl)-3-[2-(morpholin-4-yl)ethyl]-3-({7-oxo-2H,3H,6H-[1,4]dioxino[2,3-g]quinolin-8-yl}methyl)thiourea |
| MolPort-001-670-311 | 3-[(1E)-({2-[(6-ethoxy-1,3-benzothiazol-2-yl)sulfanyl]acetamido}imino)methyl]phenyl 4-iodo-1-methyl-1H-pyrazole-5-carboxylate |
| Ulinastatin, UTI, Bikunin, Uristatin, Ulinastatin, AMBP, EDC1, HI30, ITIL, IATIL, ITILC, Urinary Trypsin Inhibitor | AVLPQEEEGSGGGQLVTEVTKKEDSCQLGYSAGPCMGMTSRYFY NGTSMACETFQYGGCMGNGNNFVTEKECLQTCRTVAACNLPIVR GPCRAFIQLWAFDAVKGKCVLFPYGGCQGNGNKFYSEKECREYC GVPGDGDEELL (SEQ ID NO: 425) |
| Bowman-Birk inhibitor, Soybean trypsin inhibitor | MPSTWGAAGGGLKLGRTGNSNCPVTVLQDYSEIFRGTPVKFSIPGI SPGIIFTGTPLEIEFAEKPYCAESSKWVAFVDNEIQKACVGIGGPEG HPGQQTFSGTFSIQKYKFGYKLVFCITGSGTCLDIGRFDAKNGEGG RRLNLTEHEAFDIVFIEASKVDGIIKSVV (SEQ ID NO: 426) |

Additional exemplary putative inhibitors of *Borrelia burgdorferi* sensu lato HtrA protease activity include, but are not limited to, those described in Abbente, G. et al., Medicinal Chem. 1:71-104, 2005.

Recombinant Expression of Proteins and Nucleic Acids

The term “expressed” refers to transcription of a nucleic acid sequence to produce a corresponding mRNA and/or translation of the mRNA to produce the corresponding protein. Expression constructs can be generated recombinantly or synthetically or by DNA synthesis using well-known methodology to express a desired nucleic acid and/or protein. The term "expression construct" is used herein to refer to a double-stranded recombinant DNA molecule containing a nucleic acid sequence desired to be expressed and containing appropriate regulatory elements necessary or desirable for the transcription of the operably linked nucleic acid sequence in vitro or in vivo. The term "recombinant" is used to indicate a nucleic acid construct in which two or more nucleic acids are linked and which are not found linked in nature. The term "nucleic acid" as used herein refers to RNA or DNA molecules having more than one nucleotide in any form including single-stranded, double-stranded, oligonucleotide or polynucleotide. The term "nucleotide sequence" is used to refer to the ordering of nucleotides in an oligonucleotide or polynucleotide in a single-stranded form of nucleic acid.

An expression construct is introduced into a cell using well-known methodology, such as, but not limited to, by introduction of a vector containing the expression construct into the cell. A "vector" is a nucleic acid molecule that transfers an inserted nucleic acid molecule into and/or between host cells, becoming self-replicating. The term includes vectors that function primarily for insertion of a nucleic acid molecule into a cell, replication of vectors that function primarily for the replication of nucleic acid, and expression vectors that function for transcription and/or translation of the DNA or RNA. Also included are vectors that provide more than one of the above functions.

Vectors include plasmids, viruses, BACs, YACs, and the like. Particular viral vectors illustratively include those derived from adenovirus, adeno-associated virus and lentivirus.

The term "regulatory element" as used herein refers to a nucleotide sequence which controls some aspect of the expression of an operably linked nucleic acid sequence. Exemplary regulatory elements illustratively include an enhancer, an internal ribosome entry site (IRES), an intron; an origin of replication, a polyadenylation signal (pA), a promoter, a transcription termination sequence, and an upstream regulatory domain, which contribute to the replication, transcription, post-transcriptional processing of a nucleic acid sequence. Those of ordinary skill in the art are capable of selecting and using these and other regulatory elements in an expression construct with no more than routine experimentation.

The term "signal peptide" refers to a protein, typically about 3-60 amino acids in length, that directs localization of a second protein to which the signal peptide is operably linked to a particular location within a cell. A nucleic acid encoding a signal peptide may be included in an expression construct and may encode a signal peptide operably linked to the naturally occurring protein or may be an exogenous signal peptide. Signal peptides and their use are well-known in the art.

The term "operably linked" as used herein refers to a nucleic acid in functional relationship with a second nucleic acid. The term "operably linked" encompasses functional connection of two or more nucleic acid molecules, such as an oligonucleotide or polynucleotide to be transcribed and a regulatory element such as a promoter or an enhancer element, which allows transcription of the oligonucleotide or polynucleotide to be transcribed.

The term "promoter" as used herein refers to a DNA sequence operably linked to a nucleic acid sequence to be transcribed such as a nucleic acid sequence encoding a desired molecule. A promoter is generally positioned upstream of a nucleic acid sequence to be transcribed and provides a site for specific binding by RNA polymerase and other transcription factors. In specific embodiments, a promoter is generally positioned upstream of the nucleic acid sequence transcribed to produce the desired molecule, and provides a site for specific binding by RNA polymerase and other transcription factors.

In addition to a promoter, one or more enhancer sequences may be included such as, but not limited to, cytomegalovirus (CMV) early enhancer element and an SV40 enhancer element. Additional included sequences are an intron sequence such as the beta globin intron or a generic intron, a transcription termination sequence, and an mRNA polyadenylation (pA) sequence such as, but not limited to SV40-pA, beta-globin-pA, the human growth hormone (hGH) pA and SCF-pA. The term "polyA" or "p(A)" or "pA" refers to nucleic acid sequences that signal for transcription termination and mRNA polyadenylation. A polyA sequence is characterized by the hexanucleotide motif AAUAAA. Commonly used polyadenylation signals are the SV40 pA, the human growth hormone (hGH) pA, the beta-actin pA, and beta-globin pA. The sequences can range in length from 32 to 450 bp. Multiple pA signals may be used.

Method for In-Vivo Screening for an Inhibitor of a *Borrelia burgdorferi* sensu lato HtrA Protease Activity Methods for in-vivo screening for an inhibitor of a *Borrelia burgdorferi* sensu lato HtrA protease activity are provided according to the present invention which include expressing the *Borrelia burgdorferi* sensu lato HtrA protein in a non-human organism; contacting the *Borrelia burgdorferi* sensu lato HtrA protein with a test agent under conditions that promote protease activity of the *Borrelia burgdorferi* sensu lato HtrA protein; and detecting a specific effect of the test agent to decrease protease activity of the *Borrelia burgdorferi* sensu lato HtrA protein, thereby identifying the test agent as an inhibitor of *Borrelia burgdorferi* sensu lato HtrA Assays for inhibitor activity described herein are optionally performed using a transgenic non-human animal, such as a transgenic mouse modified to express *Borrelia burgdorferi* sensu lato HtrA, for example to test efficacy and specificity of inhibitor compounds.

Any of various methods can be used to introduce a transgene into a non-human animal to assay for inhibitors. Such techniques are well-known in the art and include, but are not limited to, pronuclear microinjection, viral infection and transformation of embryonic stem cells and iPS cells. Methods for generating transgenic animals that can be used include, but are not limited to, those described in J. P. Sundberg and T. Ichiki, Eds., Genetically Engineered Mice Handbook, CRC Press; 2006; M. H. Hofker and J. van Deursen, Eds., Transgenic Mouse Methods and Protocols, Humana Press, 2002; A. L. Joyner, Gene Targeting: A Practical Approach, Oxford University Press, 2000; Manipulating the Mouse Embryo: A Laboratory Manual, 3rd edition, Cold Spring Harbor Laboratory Press; 2002, ISBN-10: 0879695919; K. Turksen (Ed.), Embryonic stem cells: methods and protocols in Methods Mol Biol. 2002; 185, Humana Press; Current Protocols in Stem Cell Biology, ISBN: 978047015180; Meyer et al. PNAS USA, vol. 107 (34), 15022-15026; U.S. Pat. Nos. 5,994,618 and 6,891,082; and Pinkert, C. A., Transgenic Animal Technology, A Laboratory Handbook, $2^{nd}$ ed., Academic Press, 2002.

Assays for inhibitor activity described herein are optionally performed using a non-human animal infected with *Borrelia burgdorferi* sensu lato, for example to test efficacy and specificity of inhibitor compounds.

Methods and pharmaceutical compositions for treating Lyme disease in a subject in need thereof are provided according to the present invention.

Pharmaceutical compositions according to embodiments of the present invention include a pharmaceutically acceptable carrier. The term "pharmaceutically acceptable carrier" refers to a carrier which is substantially non-toxic to a subject and substantially inert to the active agent. A pharmaceutically acceptable carrier is a solid, liquid or gel in form and is typically sterile and pyrogen free.

Methods of treating Lyme disease in a subject in need thereof are provided according to the present invention which include administering a therapeutically effective dose of an inhibitor of protease activity of a *Borrelia burgdorferi* sensu lato HtrA to the subject.

Methods and compositions of the present invention can be used for prophylaxis as well as amelioration of signs and/or symptoms of Lyme disease. The terms "treating" and "treatment" used to refer to treatment of Lyme disease in a subject include: preventing, inhibiting or ameliorating Lyme disease in the subject, such as slowing progression of Lyme disease and/or reducing or ameliorating a sign or symptom of Lyme disease.

Methods of diagnosis, assessment and/or treating a subject according to aspects of the present invention including assay of a sample obtained from a subject having or suspected of having Lyme disease and detection of one or more *Borrelia burgdorferi* sensu lato HtrA cleavage product and/or one or more cytokines and chemokines indicative of active *Borrelia burgdorferi* sensu lato infection according to methods of the present invention optionally includes treating a subject having Lyme disease or at risk of having Lyme disease by administration of a therapeutically effective amount of an antibiotic effective to kill or inhibit *Borrelia burgdorferi* sensu lato. Examples of such antibiotics include but are not limited to amoxicillin, cefotaxime, ceftriaxone, cefuroxime, doxycycline, erythromycin, penicillin and tetracycline.

Antibiotics that can be used in treatment are described, for example, in Goodman et al., Goodman and Gilman's The Pharmacological Basis of Therapeutics, 8th Ed., Macmillan Publishing Co., 1990. Guidelines for the antibiotic treatment of Lyme disease are found in Wormser G P, et al., Clin. Infect. Dis. 2006; 43:1089-134; and Halperin, J. J. et al., Neurology, 2007, 69(1):91-102.

A therapeutically effective amount of a vaccine composition or a composition including an inhibitor of *Borrelia burgdorferi* sensu lato HtrA protease activity of the present invention is an amount which has a beneficial effect in a subject being treated.

Pharmaceutical compositions suitable for delivery of an inhibitor of *Borrelia burgdorferi* sensu lato HtrA protease activity to a subject may be prepared in various forms illustratively including physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers include water, ethanol, polyols such as propylene glycol, polyethylene glycol, glycerol, and the like, suitable mixtures thereof; vegetable oils such as olive oil; and injectable organic esters such as ethyloleate. Proper fluidity can be maintained, for example, by the use of a coating such as lecithin, by the maintenance of the required particle size in the case of dispersions, and by the use of surfactants, such as sodium lauryl sulfate. Additional components illustratively including a buffer, a solvent, or a diluent may be included.

Such formulations are administered by a suitable route including parenteral and oral administration. Administration may include systemic or local injection, and particularly intraarticular or intravenous injection.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and substances similar in nature.

Prolonged delivery of an injectable pharmaceutical form can be brought about by the use of agents delaying absorption, for example, aluminum monostearate and gelatin.

Solid dosage forms for oral administration include capsules, tablets, pills, powders, and granules. In such solid dosage forms, one or more inhibitors of *Borrelia burgdorferi* sensu lato HtrA protease activity is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, plant starches such as potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, glycerol monostearate, and glycols (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also include a buffering agent.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include a pharmaceutically acceptable carrier formulated as an emulsion, solution, suspension, syrup, or elixir. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to an inhibitor of *Borrelia burgdorferi* sensu lato HtrA protease activity, may contain suspending agents, as for example, ethoxylated isostearyl alcohols, polyoxyethylene sorbitol and sorbitol esters, microcrystalline cellulose, aluminum metahydroxide, bentonite, agar-agar or tragacanth, or mixtures of these substances, and the like.

In particular aspects, compositions of the present invention are formulated for topical application, for example to the site of a tick bite. In further particular aspects, compositions of the present invention are formulated for topical application and are characterized by less than 10% absorption of an active ingredient in the composition into the system of an individual treated topically. In still further particular aspects, compositions of the present invention are formulated for topical application and are characterized by less than 9%, 8%, 7%, 6%, 5%, 4%, 3%, 2%, 1% absorption of an active ingredient in the composition into the system of an individual treated topically. Absorption into the system of an individual can be measured by any of various methods, particularly assay for the active ingredient, a metabolite and/or a breakdown product of the active ingredient in a sample obtained from an individual treated with the topical formulation. For example, a blood, plasma or serum sample can be assayed for presence of the active ingredient, a metabolite of the active ingredient and/or a breakdown product of the active ingredient.

A topical formulation can be an ointment, lotion, cream or gel in particular aspects. Topical dosage forms such as ointment, lotion, cream or gel bases are described in Remington: The Science and Practice of Pharmacy, 21st Ed., Lippincott Williams & Wilkins, 2006, p. 880-882 and p. 886-888; and in Allen, L. V. et al., Ansel's Pharmaceutical Dosage Forms and Drug Delivery Systems, 8th Ed., Lippincott Williams & Wilkins, 2005, p. 277-297.

Pharmaceutically acceptable carriers and formulation of pharmaceutical compositions are known in the art, illustratively including, but not limited to, as described in Remington: The Science and Practice of Pharmacy, 21st Ed., Lippincott, Williams & Wilkins, Philadelphia, Pa., 2006; and Allen, L. V. et al., Ansel's Pharmaceutical Dosage Forms and Drug Delivery Systems, 8th Ed., Lippincott, Williams & Wilkins, Philadelphia, Pa., 2005.

A pharmaceutical composition according to the present invention is suitable for administration to a subject by a variety of systemic and/or local routes including, but not limited to, intravenous, intraarticular, intramuscular, subcutaneous, intraperitoneal, oral, otic, rectal, vaginal, topical, parenteral, pulmonary, ocular, nasal, and mucosal.

An inhibitor of *Borrelia burgdorferi* sensu lato HtrA protease activity may be administered acutely or chronically. For example, a composition as described herein may be administered as a unitary dose or in multiple doses over a relatively limited period of time, such as seconds-hours. In a further embodiment, administration may include multiple doses administered over a period of days-years, such as for extended treatment of Lyme disease.

A therapeutically effective amount of a pharmaceutical composition according to the present invention will vary depending on the particular pharmaceutical composition used, the severity of the condition to be treated, the species of the subject, the age and sex of the subject and the general physical characteristics of the subject to be treated. One of skill in the art could determine a therapeutically effective amount in view of these and other considerations typical in medical practice. In general it is contemplated that a therapeutically effective amount would be in the range of about 0.001 mg/kg-100 mg/kg body weight, optionally in the range of about 0.01-10 mg/kg, and further optionally in the range of about 0.1-5 mg/kg. Further, dosage may be adjusted depending on whether treatment is to be acute or continuing.

Inhibitors of *Borrelia burgdorferi* sensu lato HtrA protease activity are optionally formulated to achieve lipid-solubility and/or aqueous-solubility.

In particular aspects, a pharmaceutically acceptable carrier is a particulate carrier such as lipid particles including liposomes, micelles, unilamellar or mulitlamellar vesicles; polymer particles such as hydrogel particles, polyglycolic acid particles or polylactic acid particles; inorganic particles such as calcium phosphate particles such as described in for example U.S. Pat. No. 5,648,097; and inorganic/organic particulate carriers such as described for example in U.S. Pat. No. 6,630,486.

A particulate pharmaceutically acceptable carrier can be selected from among a lipid particle; a polymer particle; an inorganic particle; and an inorganic/organic particle. A mixture of particle types can also be included as a particulate pharmaceutically acceptable carrier.

A particulate carrier is typically formulated such that particles have an average particle size in the range of about 1 nm-10 microns. In particular aspects, a particulate carrier is formulated such that particles have an average particle size in the range of about 1 nm-100 nm.

Combination Treatments

Combinations of therapeutic agents are administered according to embodiments of the present invention. For example, an inhibitor of *Borrelia burgdorferi* sensu lato HtrA protease activity and at least one additional therapeutic agent are administered to a subject to treat Lyme disease in a subject in need thereof.

The term "additional therapeutic agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues which is a biologically, physiologically, or pharmacologically active substance (or substances) that acts locally or systemically in a subject.

Additional therapeutic agents included in aspects of methods and compositions of the present invention include, but are not limited to, antibiotics, analgesics, antipyretics, antidepressants, antipsychotics, antihistamines, anti-osteoporosis agents, anti-osteonecrosis agents, antiinflammatory agents, anxiolytics, chemotherapeutic agents, diuretics, growth factors, hormones, non-steroidal antiinflammatory agents, steroids and vasoactive agents.

Combination therapies utilizing one or more inhibitors of *Borrelia burgdorferi* sensu lato HtrA protease activity and one or more additional therapeutic agents may show synergistic effects, e.g., a greater therapeutic effect than would be observed using either the one or more inhibitors of *Borrelia burgdorferi* sensu lato HtrA protease activity or one or more additional therapeutic agents alone as a monotherapy.

According to aspects, combination therapies include: (1) pharmaceutical compositions that include one or more inhibitors of *Borrelia burgdorferi* sensu lato HtrA protease activity in combination with one or more additional therapeutic agents; and (2) co-administration of one or more inhibitors of *Borrelia burgdorferi* sensu lato HtrA protease activity of the present invention with one or more additional therapeutic agents wherein the one or more inhibitors of *Borrelia burgdorferi* sensu lato HtrA protease activity and the one or more additional therapeutic agents have not been formulated in the same composition. When using separate formulations, the one or more inhibitors of *Borrelia burgdorferi* sensu lato HtrA protease activity may be administered at the same time, intermittent times, staggered times, prior to, subsequent to, or combinations thereof, with reference to the administration of the one or more additional therapeutic agents.

Combination treatments can allow for reduced effective dosage and increased therapeutic index of the one or more inhibitors of *Borrelia burgdorferi* sensu lato HtrA protease activity and the one or more additional therapeutic agents used in methods of the present invention.

According to embodiments, a method of treating a subject having Lyme disease or at risk of having Lyme disease includes administration of a therapeutically effective amount of one or more inhibitors of *Borrelia burgdorferi* sensu lato HtrA protease activity and further includes a therapeutically effective amount of an antibiotic effective to kill or inhibit *Borrelia burgdorferi* sensu lato. Examples of such antibiotics include but are not limited to amoxicillin, cefotaxime, ceftriaxone, cefuroxime, doxycycline, erythromycin, penicillin and tetracycline.

Antibiotics are described, for example, in Goodman et al., Goodman and Gilman's The Pharmacological Basis of Therapeutics, 8th Ed., Macmillan Publishing Co., 1990. Guidelines for the antibiotic treatment of Lyme disease are found in Wormser G P, et al., Clin. Infect. Dis. 2006; 43:1089-134.

Commercial Packages for treatment

Commercial packages are provided according to aspects of the present invention for treating Lyme disease in a subject in need thereof, including an inhibitor of *Borrelia burgdorferi* sensu lato HtrA protease activity. One or more auxiliary components are optionally included in commercial packages of the present invention, such as a pharmaceutically acceptable carrier exemplified by, but not limited to, a buffer, diluent or a reconstituting agent. An adjunct therapeutic is optionally included in commercial packages of the present invention, such as an antibiotic.

Vaccine Methods and Compositions

Methods for producing a detectable immune response in a subject are provided according to the present invention.

Methods for producing a detectable immune response in a subject are provided according to the present invention which include administering an amount of proteolytically inactive *Borrelia burgdorferi* sensu lato HtrA and/or an immunogenic fragment of *Borrelia burgdorferi* sensu lato HtrA to a subject to produce a detectable immune response to *Borrelia burgdorferi* sensu lato HtrA in the subject.

*Borrelia burgdorferi* sensu lato HtrA is rendered proteolytically inactive by any of various inactivation methods, illustratively including, but not limited to, denaturation by heat and/or chemical treatment such as cross-linking or use of a proteolytically inactive mutant protein, such as, but not limited to BbHtrA$^{S226A}$.

Administration of a vaccine composition according to a method of the present invention includes administration of one or more doses of a vaccine composition to a subject at one time in particular embodiments. Alternatively, two or more doses of a vaccine composition are administered at time intervals of weeks-years. A suitable schedule for administration of vaccine composition doses depends on several factors including age and health status of the subject, type of vaccine composition used and route of administration, for example. One of skill in the art is able to readily determine a dose and schedule of administration to be administered to a particular subject.

Vaccines and methods for their use to induce active immunity and protection against Lyme disease in a subject are provided according to the present invention.

In particular embodiments, vaccine compositions for enhancing immunological protection against Lyme disease in a subject are provided according to the present invention which includes *Borrelia burgdorferi* sensu lato HtrA and/or an immunogenic fragment thereof admixed with a pharmaceutically acceptable carrier.

The term "vaccine composition" is used herein to refer to a composition including proteolytically inactive *Borrelia burgdorferi* sensu lato HtrA and/or an immunogenic fragment thereof capable of inducing an immune response in a subject inoculated with the vaccine composition.

A vaccine composition of the present invention may be in any form suitable for administration to a subject.

A vaccine composition is administered by any suitable route of administration including oral and parenteral such as intradermal, intramuscular, mucosal, nasal, or subcutaneous routes of administration.

For example, a vaccine composition for parenteral administration may be formulated as an injectable liquid including proteolytically inactive *Borrelia burgdorferi* sensu lato HtrA and/or an immunogenic fragment thereof and a pharmaceutically acceptable carrier. Examples of suitable aqueous and nonaqueous carriers include water, ethanol, polyols such as propylene glycol, polyethylene glycol, glycerol, and the like, suitable mixtures thereof; vegetable oils such as olive oil; and injectable organic esters such as ethyloleate. Proper fluidity can be maintained, for example, by the use of a coating such as lecithin, by the maintenance of a desirable particle size in the case of dispersions, and/or by the use of a surfactant, such as sodium lauryl sulfate. A stabilizer is optionally included such as, for example, sucrose, EDTA, EGTA, and an antioxidant.

A solid dosage form for administration or for suspension in a liquid prior to administration illustratively includes capsules, tablets, powders, and granules. In such solid dosage forms, proteolytically inactive *Borrelia burgdorferi* sensu lato HtrA and/or an immunogenic fragment thereof is admixed with at least one carrier illustratively including a buffer such as, for example, sodium citrate or an alkali metal phosphate illustratively including sodium phosphates, potassium phosphates and calcium phosphates; a filler such as, for example, starch, lactose, sucrose, glucose, mannitol, and silicic acid; a binder such as, for example, carboxymethylcellulose, alignates, gelatin, polyvinylpyrrolidone, sucrose, and acacia; a humectant such as, for example, glycerol; a disintegrating agent such as, for example, agar-agar, calcium carbonate, plant starches such as potato or tapioca starch, alginic acid, certain complex silicates, and sodium carbonate; a solution retarder such as, for example, paraffin; an absorption accelerator such as, for example, a quaternary ammonium compound; a wetting agent such as, for example, cetyl alcohol, glycerol monostearate, and a glycol; an adsorbent such as, for example, kaolin and bentonite; a lubricant such as, for example, talc, calcium stearate, magnesium stearate, a solid polyethylene glycol or sodium lauryl sulfate; a preservative such as an antibacterial agent and an antifungal agent, including for example, sorbic acid, gentamycin and phenol; and a stabilizer such as, for example, sucrose, EDTA, EGTA, and an antioxidant.

Solid dosage forms optionally include a coating such as an enteric coating. The enteric coating is typically a polymeric material. Preferred enteric coating materials have the characteristics of being bioerodible, gradually hydrolyzable and/or gradually water-soluble polymers. The amount of coating material applied to a solid dosage generally dictates the time interval between ingestion and drug release. A coating is applied having a thickness such that the entire coating does not dissolve in the gastrointestinal fluids at pH below 3 associated with stomach acids, yet dissolves above pH 3 in the small intestine environment. It is expected that any anionic polymer exhibiting a pH-dependent solubility profile is readily used as an enteric coating in the practice of the present invention to achieve delivery of the active agent to the lower gastrointestinal tract. The selection of the specific enteric coating material depends on properties such as resistance to disintegration in the stomach; impermeability to gastric fluids and active agent diffusion while in the stomach; ability to dissipate at the target intestine site; physical and chemical stability during storage; non-toxicity; and ease of application.

Suitable enteric coating materials illustratively include cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, preferably formed from acrylic acid, methacrylic acid, methyl acrylate, ammonium methylacrylate, ethyl acrylate, methyl methacrylate and/or ethyl; vinyl polymers and copolymers such as polyvinyl pyrrolidone, polyvinyl acetate, polyvinylacetate phthalate, vinylacetate crotonic acid copolymer, and ethylene-vinyl acetate copolymers; shellac; and combinations thereof. A particular enteric coating material includes acrylic acid polymers and copolymers described for example U.S. Pat. No. 6,136,345.

The enteric coating optionally contains a plasticizer to prevent the formation of pores and cracks that allow the penetration of the gastric fluids into the solid dosage form. Suitable plasticizers illustratively include, triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, a coating composed of an anionic carboxylic acrylic polymer typically contains approximately 10% to 25% by weight of a plasticizer, particularly dibutyl phthalate, polyethylene glycol, triethyl citrate and triacetin. The coating can also contain other coating excipients such as detackifiers, antifoaming agents, lubricants (e.g., magnesium stearate), and stabilizers (e.g. hydroxypropylcellulose, acids or bases) to solubilize or disperse the coating material, and to improve coating performance and the coated product.

Liquid dosage forms for oral administration include inactivated *Borrelia burgdorferi* sensu lato HtrA and/or an immunogenic fragment thereof and a pharmaceutically acceptable carrier formulated as an emulsion, solution, suspension, syrup, or elixir. A liquid dosage form of a vaccine composition of the present invention may include a wetting agent, an emulsifying agent, a suspending agent, a sweetener, a flavoring, or a perfuming agent.

Detailed information concerning customary ingredients, equipment and processes for preparing dosage forms is found in Pharmaceutical Dosage Forms: Tablets, eds. H. A. Lieberman et al., New York: Marcel Dekker, Inc., 1989; and in L. V. Allen, Jr. et al., Ansel's Pharmaceutical Dosage Forms and Drug Delivery Systems, 8th Ed., Philadelphia, Pa.: Lippincott, Williams & Wilkins, 2004, throughout and in chapter 16; A. R. Gennaro, Remington: The Science and Practice of Pharmacy, Lippincott Williams & Wilkins, 21st ed., 2005, particularly chapter 89; and J. G. Hardman et al., Goodman & Gilman's The Pharmacological Basis of Therapeutics, McGraw-Hill Professional, 10th ed., 2001.

An adjuvant is optionally included in a vaccine composition according to embodiments of the present invention. Adjuvants are known in the art and illustratively include Freund's adjuvant, aluminum hydroxide, aluminum phosphate, aluminum oxide, saponin, dextrans such as DEAE-dextran, vegetable oils such as peanut oil, olive oil, and/or vitamin E acetate, mineral oil, bacterial lipopolysaccharides, peptidoglycans, polylactides, CpG containing oligonucleotides and proteoglycans.

In particular aspects, a vaccine composition includes a particulate carrier adjuvant such as lipid particles including liposomes, micelles, unilamellar or mulitlamellar vesicles; polymer particles such as hydrogel particles, polyglycolic acid particles or polylactic acid particles such as poly(lactic-co-glycolic acid) microspheres and other carriers described in Hanes, J. et al., Adv. Drug. Delivery Rev., 28:97-119, 1997; inorganic particles such as calcium phosphate particles such as described in for example U.S. Pat. No. 5,648,097; and inorganic/organic particulate carriers such as described for example in U.S. Pat. No. 6,630,486.

Induction of an immunological response in a subject can be determined by any of various techniques known in the art, illustratively including detection of anti-*Borrelia burgdorferi* sensu lato HtrA antibodies, measurement of anti-*Borrelia burgdorferi* sensu lato HtrA antibody titer and/or lymphocyte proliferation assay. Signs and symptoms of Lyme disease may be monitored to detect induction of an immunological response to administration of a vaccine composition of the present invention in a subject. For example, induction of an immunological response is detected by preventing or reducing skin, neural, cardiac, and/or arthritic abnormalities characteristic of Lyme disease in a subject.

Embodiments of inventive compositions and methods are illustrated in the following examples. These examples are provided for illustrative purposes and are not considered limitations on the scope of inventive compositions and methods.

EXAMPLES

Example 1

BbHtrA and BbHtrA$^{S226A}$

BbHtrA contains a 37 amino acid signal sequence, the cleavage of which results in a mature protein of 437 amino acids with an amino terminus beginning at amino acid $^{38}$Glu. BbHtrA is homologous to other DegP/HtrA proteases and sequence alignment indicates that BbHtrA serine 226 is part of the catalytic triad (His119, Asp149, and Ser226). Mutation of Ser226 to alanine is expected to abolish proteolytic activity. Wild type BbHtrA and BbHtrA$^{S226A}$ full length genes were codon optimized for expression in *E. coli*, synthesized, sequenced, and cloned into pUC57. For protein production, the sequence for the mature proteins (amino acids 38-474) were sub-cloned into expression vectors using the following primers:

```
Forward:
                                        (SEQ ID NO: 25)
CTTTAAGAAGGAGATATACATATGGAAGAAAAAGATAACACCGTG;

Reverse:
                                        (SEQ ID NO: 26)
ATACAGCTGTGCGGCCGCAAGCTTTCATTAGTGATGGTGATGGTGAT

GAA.
```

FIG. 1A shows BbHtrA (3 μg) shows as visualized by Coomassie stain (left panel) and anti-His tag Western (right panel). FIG. 1B shows BbHtrA$^{S226A}$ (2 µg) as visualized by Coomassie stain (left panel) and anti-His tag Western (right panel). BbHtrA and BbHtrA$^{S226A}$ were purified from the soluble cellular fraction by application to a nickel column and eluted with imidazole. Preparations were then further purified by size exclusion chromatography and dialyzed into a storage buffer (TBS, 10% glycerol). ProteoSpin endotoxin removal kits (Norgen) were used, per the product insert, to reduce the lipopolysaccharide (LPS) in the recombinant proteins. Proteins were aliquoted and stored at −80° C. until use.

Example 2

Polyclonal Rabbit and Mouse Anti-BbHtrA Antibodies

Rabbit and mouse polyclonal anti-BbHtrA antibodies, directed against a BbHtrA KLH-conjugated peptide (306-VSAAIIASLYPGSPAVKSG-324) (SEQ ID NO:27), were generated for detection of BbHtrA.

Example 3

BbHtrA is accessible to proteinase K in *B. burgdorferi*

Protease accessibility studies on intact spirochetes were used to examine the exposure of BbHtrA to proteinase K. *B. burgdorferi* (strain B31) was cultured in complete BSK II medium to early log phase ($4.5 \times 10^6$/ml) and harvested by centrifugation at 2,000×g for 20 min. *Borrelia* were washed to remove media components, and resuspended in phosphate buffered saline (PBS) containing 5 mM MgCl$_2$. The sample was divided equally, half was incubated with proteinase K (20 µg, Qiagen) and the other half was stored on ice. After 40 minutes, the reaction was stopped by addition of a protease inhibitor cocktail (HALT, Pierce) and incubated for an additional 5 min. The cells were pelleted, washed with PBS/Mg$^{2+}$ to remove excess proteinase K and resuspended in non-reducing SDS-PAGE sample buffer and ~$1 \times 10^8$ *Borrelia* were loaded per lane in pre-cast Tris-glycine gels (BioRad). Proteins separated by electrophoresis were transferred to a nitrocellulose membrane which was stained to reveal total protein (FIG. 2A). After total protein stain removal, the membrane was blocked (Starting Block, Pierce) and then probed with antibodies for a known surface protein (anti-OspA, H5332, 1 µg/ml) and a periplasmic internal protein (anti-FlaB, H9724, 0.025 µg/ml). Unbound primary antibody was removed by washing with TBS Tween. An appropriate alkaline phosphatase labeled secondary antibody (5 ng/ml) was applied for sixty minutes after which the membrane was washed to remove unbound antibody. A chemiluminescent phosphatase substrate was applied to enable visualization of the antibody complexes and images were captured with a chemiluminescence imaging system (BioRad). The membrane was stripped of antibodies (Restore, Pierce) and reprobed overnight with polyclonal rabbit anti-BbHtrA (0.2 µg/ml) followed by an appropriate secondary antibody (KPL, alkaline phosphatase-conjugated, 50 ng/ml) (FIG. 2B). All antibodies were diluted in Starting Block (Pierce). Signals were detected by chemiluminescence. As expected, the signal for OspA was greatly diminished and that of FlaB was retained after exposure to the protease. The BbHtrA signal was greatly diminished upon treatment, indicating that part of the cellular pool was accessible to proteinase K and part was protected by intracellular localization.

FIG. 2A shows total protein stain demonstrating equivalent loading levels and the efficacy of the proteinase K (PK) treatment. FIG. 2B is an image of a Western blot showing loss of surface protein signal (OspA), retention of internal protein signal (FlaB) and diminished BbHtrA signal.

Example 4

BbHtrA is Expressed During Infection of Humans and is an Immunogenic Protein

Western blot strips of purified recombinant BbHtrA were probed with sera from the CDC Lyme disease reference panel and demonstrate that antibodies against this protease are generated during infection of humans (FIGS. 3A and 3B). Recombinant BbHtrA (FIG. 3A) or BbHtrA$^{S226A}$ (FIG. 3B) was electrophoretically separated in precast Tris-HCl gels (BioRad). BbHtrA degrades itself, resulting in more than one band in FIG. 3A, whereas a single band was observed when the mutant protease was used (FIG. 3B). Protein was transferred to a nitrocellulose membrane (BioRad) (100 Volts, 60 minutes) and the membrane was blocked (Starting Block, Pierce) for 60 minutes. The membrane was cut into strips which was probed with anti-borrelial antibodies from human sera (1:100, CDC Lyme disease reference panel or 1:250, ViraMed diagnostic kit positive control sera, 60 minutes) or control sera from healthy blood donors living in U.S. regions non-endemic for Lyme disease, washed with TBS-Tween to remove excess primary antibody, and incubated with alkaline phosphatase conjugated goat anti-human antibody (1:6,000, ViraMed, 60 minutes, room temperature). Protein/antibody complexes were visualized by the addition of colorimetric alkaline phosphatase substrate (BCIP/NBT, BioRad). Given the similarity of BbHtrA to HtrA1 (~33% identity, ~54% similarity) and to lesser degrees to HtrAs 2-4, strips were also probed with commercially available rabbit polyclonal anti-HtrAs 1-4, all of which were negative (FIGS. 3A and 3B). Rabbit polyclonal antibody against a BbHtrA peptide served as a positive control.

Example 5

Proteolysis Assays

For proteolysis assays described in Examples herein, purified protein substrates (200-600 nM) and proteases (100-150 nM) were diluted in assay buffer (50 mM HEPES, pH 7.4, 5 mM CaCl$_2$) and incubated overnight at 37° C. Samples were boiled for 4 minutes to inactivate the proteases. Proteoglycans were deglycosylated by overnight incubation at 37° C. with 0.01 U chondroitinase ABC (Seikagaku). Reactions were stopped by the addition of SDS/PAGE sample buffer, boiled for 4 minutes, and electrophoresed on pre-cast Tris-glycine gels (BioRad). Reaction products were visualized by silver staining.

Example 6

BbHtrA Degrades Recombinant and Full Length Aggrecan

Figure 4B:
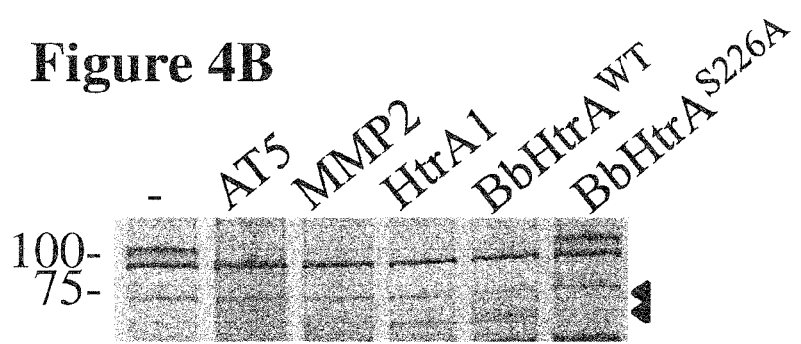
FIG. 4B is an image showing results of SDS-PAGE analysis showing that BbHtrA cleaves native, fully glycosylated aggrecan.
Figure 4C:
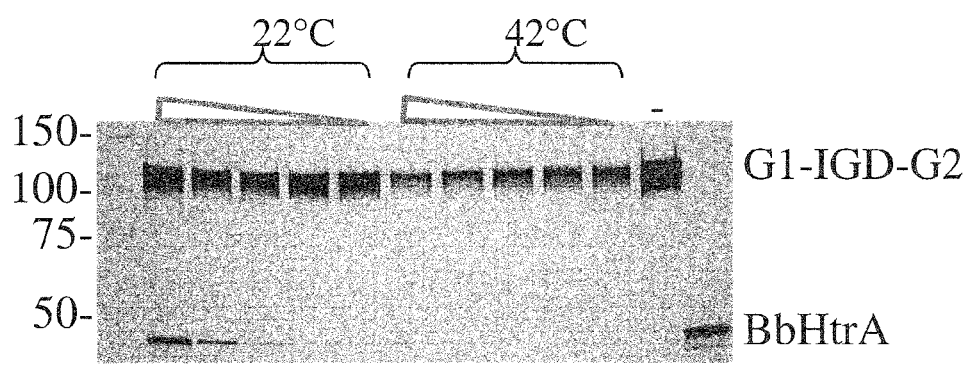
FIG. 4C is an image showing results of SDS-PAGE analysis showing a temperature and dose dependent increase in BbHtrA activity against recombinant aggrecan.

Purified ECM components were incubated with wild type BbHtrA or the inactive mutant BbHtrA$^{S226A}$ (FIGS. 4A-4C). BbHtrA cleaved recombinant human aggrecan (G1-IGD-G2 domains) within the IGD (FIG. 4A). Cleavage of recombinant aggrecan generated three high molecular weight proteolytic fragments which migrated at ~110 kd, ~60 kd and ~50 kd. These fragments were dependent on the presence of proteolytically active BbHtrA as incubation of recombinant aggrecan (FIG. 4A, lane 1) alone or with the inactive mutant (FIG. 4A, lane 6) failed to generate these fragments.

BbHtrA also degraded native, fully glycosylated aggrecan (FIG. 4B, lane 5). Again, this degradation required BbHtrA catalytic activity (FIG. 4B, lane 6). The BbHtrA-generated aggrecan fragments appear to be a doublet, unlike those generated by HtrA1.

BbHtrA shows a temperature dependent increase in activity against recombinant aggrecan (FIG. 4C). There is a concentration dependency. Increased aggrecan degradation is observed upon incubation with increasing concentrations of BbHtrA (FIG. 4C).

BbHtrA degrades itself after proteolysis (FIG. 4A, lane 5, ~43 kD band; FIG. 8, lane 1, gray arrows). The cleavage site was identified between $^{80}$Phe-Phe$^{81}$.

FIG. 4 shows images of SDS-PAGE analyses FIG. 4A shows degradation of recombinant human aggrecan. Aggrecan was incubated with: lane 1, buffer alone; lane 2, ADAMTS-5; lane 3, MMP2; lane 4, HtrA1; lane 5, BbHtrA; and 6, BbHtrA$^{S226A}$. Digestion products were separated by SDS-PAGE and silver stained. Black arrows, cleavage products; gray arrows, protease. FIG. 4B shows degradation of native bovine aggrecan. The numbering is the same as in FIG. 4A. Black arrow, cleavage products. FIG. 4C shows BbHtrA proteolytic activity is increased at elevated temperatures and is concentration dependent.

Example 7

BbHtrA Degrades Extracellular Matrix Proteins

Figure 5:
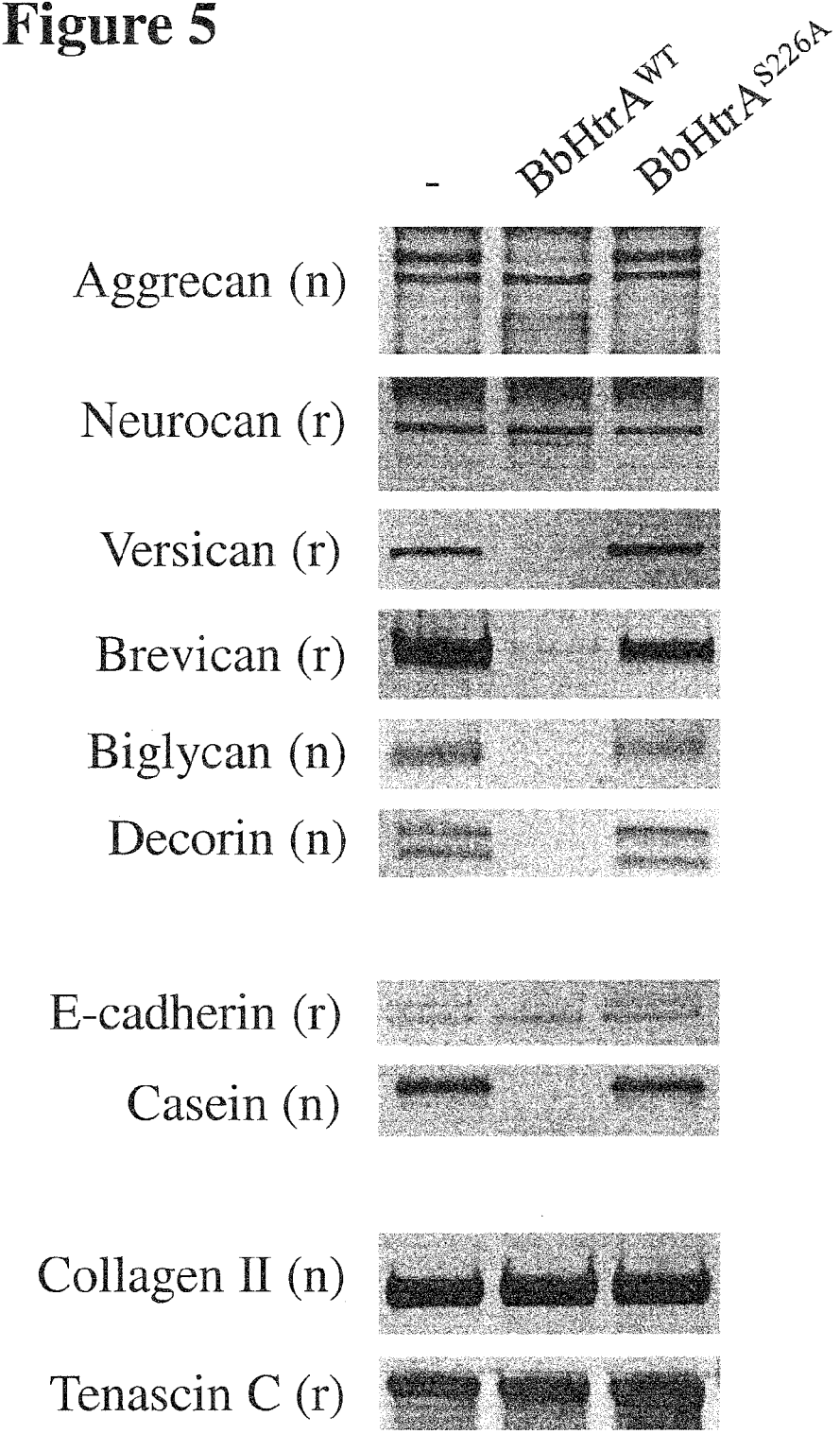
FIG. 5 is an image of SDS-PAGE analysis showing that BbHtrA specifically degrades aggrecan, e-cadherin, brevican, neurocan, versican, biglycan and decorin.

Purified proteins were incubated with BbHtrA or BbHtrA$^{S226A}$ as described herein. HtrA (also known as DegP) proteases belong to the family of serine proteases which contain a highly reactive serine residue in their active site. This serine (Ser210 in DegP) is part of the canonical His-Ser-Asp catalytic triad and mutation of the catalytic serine abolishes proteolytic activity (Skorko-Glonek et al., 1995). In BbHtrA, residues His119, Ser226 and Asp149 form the catalytic triad and mutation of serine 226 to alanine abolished proteolytic activity as expected (FIG. 5).

Reaction products were separated by SDS-PAGE and silver stained. Native collagen II and recombinant tenascin C were not degraded by BbHtrA indicating selectivity for proteoglycans, E-cadherin and fibronectin. FIG. 5 is an image of SDS-PAGE analysis showing that BbHtrA degrades aggrecan, neurocan, versican, brevican, biglycan, decorin, E-cadherin, and casein.

TABLE II

Table II summarizes BbHtrA protease assays using various substrates.

| Substrate | Source | Proteolytic activity |
| --- | --- | --- |
| Proteoglycans | | |
| Aggrecan | nB, rH | + |
| Brevican | rH | + |
| Neurocan | rH | + |
| Versican | rH | + |
| Decorin | nB, rH | + |
| Biglycan | nB, rH | + |
| Other ECM Components | | |
| Plasma fibronectin | nH | + |
| E-cadherin | rH | + |
| Casein | nB | + |
| Collagen type II | nH | ND |
| Laminin LAMB I | nH | ND |
| Tenascin C | nH | ND |
| TGF-β3 | rH | ND | nB = native bovine;
rH = recombinant human;
nH = native human;
ND = degradation not detected Example 8

Figure 6A:
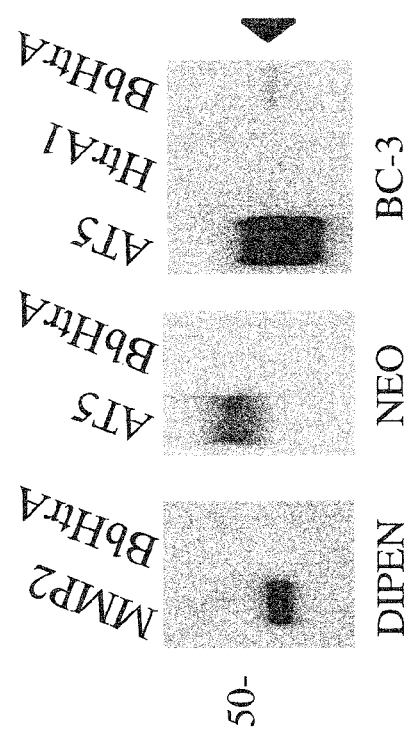
FIG. 6A is an image showing Western blot analysis of BbHtrA-generated aggrecan fragments recognized by monoclonal antibody BC-3.
Figure 6B:
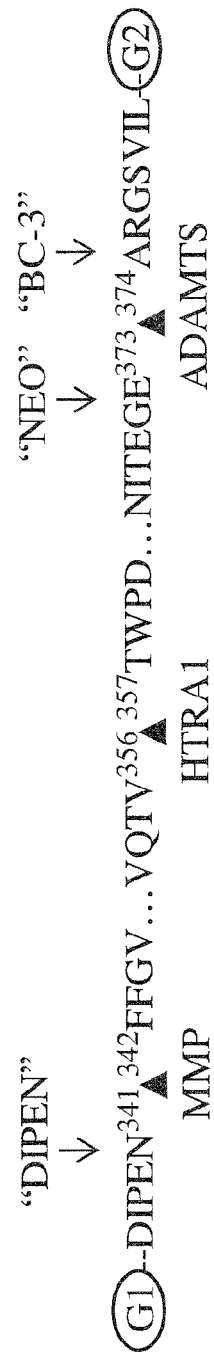
FIG. 6B is a schematic showing the proteolytic sites within the IGD and the epitopes for the antibodies raised against the neoepitopes.

Identification of BbHtrA Cleavage Sites within Aggrecan Using Amino Terminal Sequence Analysis and Western Blotting Cleavage within the aggrecan IGD by ADAMTS-5, MMP-2 and HtrA1 is very specific and, consequently, monoclonal antibodies to the newly exposed termini ("neoepitopes") have been developed. Currently, neoepitope antibodies are commercially available to detect the activity of aggrecanases and MMPs (FIG. 6A). Given the similarity in the sizes of the aggrecan fragments, BbHtrA reaction products were probed with three of these antibodies. To examine cleavage at the MMP site, the reaction products were also probed with the DIPEN neoepitope antibody. Cleavage at DIPEN$^{342}$ (SEQ ID NO:28); was not detected (FIG. 6B). The amino terminus at the aggrecanase site ($^{374}$ARGS, SEQ ID NO:29) was weakly identified by the BC-3 antibody in the BbHtrA-generated degradation products (FIG. 6B). The carboxyl terminal neoepitope ($^{373}$NITEGE, SEQ ID NO:30) was not detected (FIG. 6B). BbHtrA may cleave at $^{356}$VQTV (SEQ ID NO:31) releasing the peptide fragment 357-373 containing the NITEGE (SEQ ID NO:30) neoepitope.

FIG. 6A is an image showing Western blot analysis of BbHtrA-generated recombinant aggrecan fragments recognized by monoclonal antibody BC-3, indicating cleavage between amino acids 373 and 374 within the aggrecan IGD.

FIG. 6B is a schematic showing the proteolytic sites within the IGD and the epitopes for the antibodies raised against the neoepitopes.

Figure 7A:
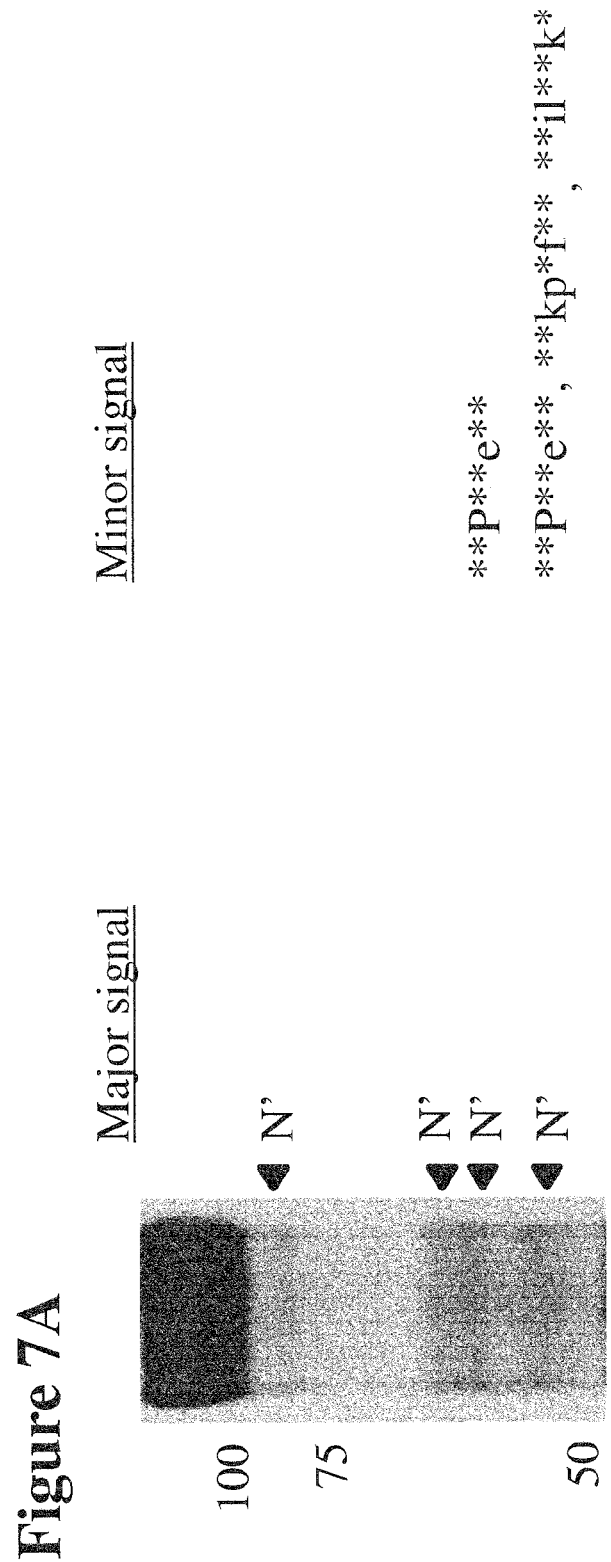
FIG. 7A shows major and minor peptides identified by Edman degradation of the BbHtrA-generated aggrecan fragments.
Figure 7B:
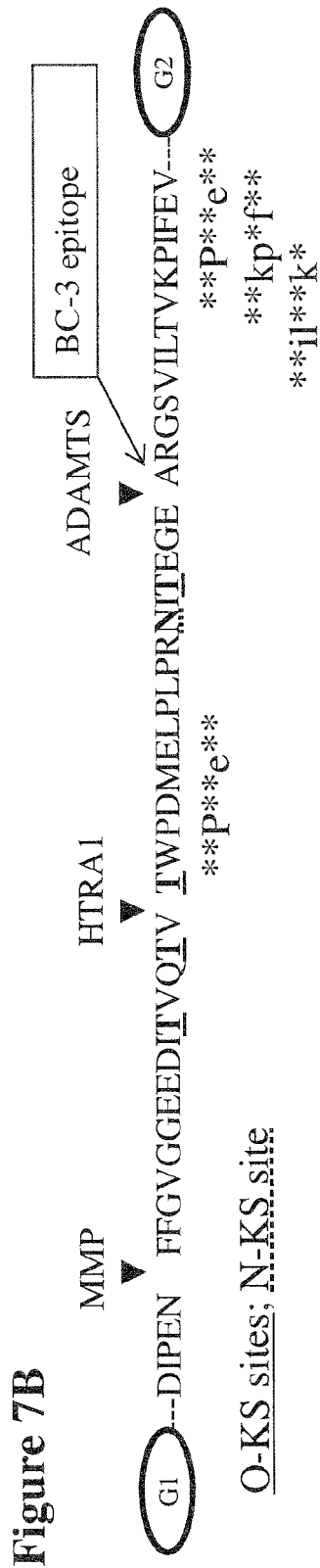
FIG. 7B is a schematic diagram of the pathologic proteolytic cleavage sites within the aggrecan IGD showing possible location of BbHtrA-generated minor signals.

Amino terminal sequence analysis of the reaction products was performed. For Edman degradation and N-terminal sequencing, following SDS-PAGE and electroblotting onto PVDF membranes, the protein bands visualized with Coomassie Brilliant Blue were sequenced using model cLC-Procise sequencer (Applied Biosystems, Foster City, Calif.) applying manufacturer's PVDF chemistry cycles. The N-terminal sequences were identified for the main PTH signal that was assigned against the known template protein sequence. The major signals detected for all products were consistent with the amino terminus of recombinant aggrecan ($^{20}$VETS-DHDNSLS, SEQ ID NO:32) (FIG. 7A). Several minor signals were identified in the band detected by the BC-3 antibody (FIG. 7B) which is consistent with cleavage at or near the aggrecanase site (FIG. 7B). Additionally, minor signals in the ~60 kD band could be consistent with cleavage at the HtrA1 site (FIG. 7B).

The abundance of recombinant aggrecan amino terminal fragments reflects processive degradation of substrates from their carboxyl terminus. However, the very reproducible and characteristic bands generated by BbHtrA suggest that the protease cleaves a minimum of two distinct points within the IGD and then releases the substrate. The protease may be halted by variable post-translational modifications of the aggrecan IGD. In support of this hypothesis, there are potential O-linked keratan sulfate attachment sites very near the proteolytic sites (FIG. 7B) and, at least in calf and steer aggrecan, ⅔ of these are modified with KS Hering, T. M., et al., Arch Biochem Biophys, 1997. 345(2): 259-70. There is 100% inter-species conservation of Asn$^{368}$ at the aggrecanase site and glycosylation at Asn$^{368}$ has a proposed regulatory role for aggrecanases Miwa, H. E., et al., Biochim Biophys Acta, 2009. 1790(3): 161-72.

BbHtrA is not a purely processive protease. BbHtrA cleaves aggrecan internally at the $^{374}$ARGS aggrecanase site and processively from the carboxyl terminus until it reaches distinct points within the IGD.

FIG. 7A shows major and minor amino acid residues identified by Edman degradation of the aggrecan fragments. * indicates that no amino acid could be assigned to that position.

FIG. 7B is a schematic diagram of the pathologic proteolytic cleavage sites within the aggrecan IGD showing possible location of BbHtrA-generated minor signals.

Example 9

Identification of BbHtrA-Generated Fibronectin Fragments Using Mass Spectrometry BbHtrA generates pro-inflammatory amino terminal (Fnf-29) and carboxyl terminal ($FnIII_{13-14}$) fibronectin fragments. BbHtrA degradation of fibronectin yielded distinct product bands. Fibronectin was incubated with BbHtrA overnight (FIG. 8A, lane 1) or for 96 hours (FIG. 8A, lane 3). Reaction products were separated electrophoretically, and the bands were excised and analyzed by tandem LC MS/MS, FIG. 8B.

For mass spectrometry analysis, peptides are purified and concentrated using an on-line enrichment column (Agilent Zorbax C18, 5 µm, 5×0.3 mm). Subsequent chromatographic separation is performed on a reverse phase nanospray column (Agilent 1100 nanoHPLC, Zorbax C18, 5 µm, 75 µm ID×150 mm column) using a 42 minute linear gradient from 25%-55% buffer B (90% ACN, 0.1% formic acid) at a flow rate of 300 nanoliters/min. Peptides are eluted directly into the mass spectrometer (Thermo Scientific LTQ linear ion trap) and spectra are collected over a m/z range of 200-2000 Da using a dynamic exclusion limit of 2 MS/MS spectra of a given peptide mass for 30 s (exclusion duration of 90 s). Compound lists of the resulting spectra were generated using Bioworks 3.0 software (Thermo Scientific) with an intensity threshold of 5,000 and 1 scan/group. MS/MS spectra are searched against the appropriate protein database using the Mascot database search engine (version 2.1).

The majority of the fibronectin tryptic peptides identified map to the carboxyl terminus and, with prolonged incubation amino terminal fragments were also observed. The most abundant carboxyl terminal fragment (~37 kD) yielded fragments that span from fibronectin type three repeat 13 ($FnIII_{13}$) to the terminus.

FIGS. 8A and 8B show results indicating that BbHtrA degradation of fibronectin generates amino terminal Fnf-29, and carboxyl terminal $FnIII_{13-14}$. FIG. 8A shows an image of an SDS-PAGE analysis of an experiment in which fibronectin was incubated with: lane 1, BbHtrA 15 hours; lane 2, fibronectin alone; lane 3, BbHtrA 96 hours. Black arrows indicate proteolytic fragments; gray arrows indicate BbHtrA. FIG. 8B is a table showing BbHtrA-generated fibronectin fragments identified by mass spectrometry. All peptides had peptide identity scores of greater than 95% yielding a 100% protein identity.

Example 10

BbHtrA Induces Inflammatory Cytokine and Chemokine Expression in Cultured Chondrocytes Chondrocyte aggregate cultures are used which form an extensive extracellular matrix with components characteristic of articular cartilage including aggrecan and type II collagen as described in Welter, J. et al, BioTechniques, 2007, 42(6): 732-737; and Solchaga, L. A. et al., Chondrogenic Differentiation of Bone Marrow-Derived Mesenchymal Stem Cells: Tips and Tricks, 2011, 698:253-278.

To form the chondrocyte aggregate cultures, $1 \times 10^6$ human mesenchymal stem cells (passage one, Lonza, catalog #PT-2501) were plated in a T150 flask (Corning) and cultured in growth media: mesenchymal stem cell basal media (MSCBM, Lonza, #PT-3238), mesenchymal growth supplements (SingleQuots, Lonza, #PT-4105), and 5 ng/ml recombinant human fetal growth factor (Shenandoah Biotechnology). When confluent, cells were trypsin-released (0.5% trypsin EDTA, Gibco), expanded to two T150 flasks and fed with growth media every three days. When confluent, cells were harvested, resuspended in fresh growth media containing 5% DMSO and aliquots of $1 \times 10^6$ cells were cryopreserved in liquid nitrogen.

Human mesenchymal stem cells were used to promote chondrogenesis and chondrocyte aggregate formation for use in these studies. Two vials of passage three cryopreserved cells were thawed, plated in growth media in two T150 flasks and then expanded to six T150 flasks as above. Cells were harvested (0.5% trypsin EDTA, Gibco), pooled, enumerated and induced to chondrogenic differentiation as follows. Cells were resuspended in defined chondrocyte differentiation media: high glucose DMEM (Gibco), 50 µg/ml ascorbic acid-2-phosphate (Sigma), 39.3 ng/ml dexamethasone (Sigma), 40 m/ml L-proline (Sigma), ITS+Premix (BD Biosciences), 10 ng/ml transforming growth factor β-3 (Shenandoah Biotechnology) and 30 µg/ml gentamicin sulfate+15 ng/ml amphotericin-B (GA-1000, Lonza, #PT-4504E). High density aggregates were obtained by plating, on average, $3 \times 10^5$ cells per well in a conical bottom 96 well plate (Thermo Scientific), pelleting by centrifugation (5 minutes at 600 g), and incubation at 37° C. and 5% $CO_2$. Pellets formed coherent spherical aggregates by day two of culture. After seven days, wide bore tips were used to transfer aggregates to V-bottom 96 well plates (Corning). Aggregates were maintained in differentiation media at 37° C. and 5% $CO_2$ for 3-5 weeks and fed every two days until experimentation.

For chondrocyte cytokine induction assays, 24 hours prior to experimentation, dexamethasone containing media was removed, aggregates were rinsed with DPBS (Gibco) and dexamethasone-free differentiation media was added. For experimentation, aggregates were transferred to 24 well plates (24 aggregates per condition), spent media was removed and fresh warmed dexamethasone-free media containing samples was added. Aggregates were then incubated at 37° C. and 5% $CO_2$ for two days.

Figure 9A:
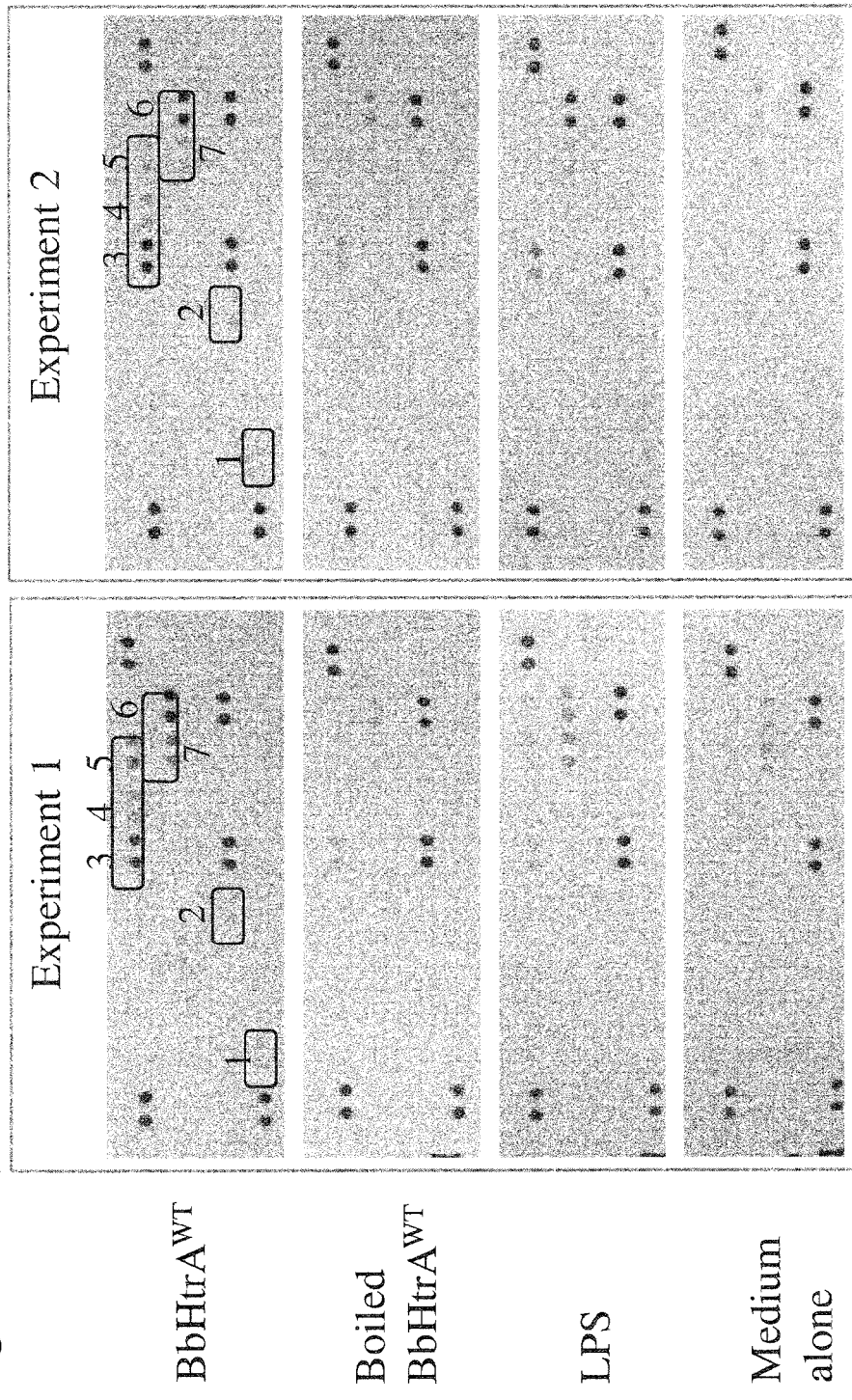
FIG. 9A is an image of a dot immunoblot analysis of cytokines induced in chondrocytes upon stimulation with BbHtrA, heat-denatured BbHtrA, lipopolysaccharide, or medium alone.
Figure 10:
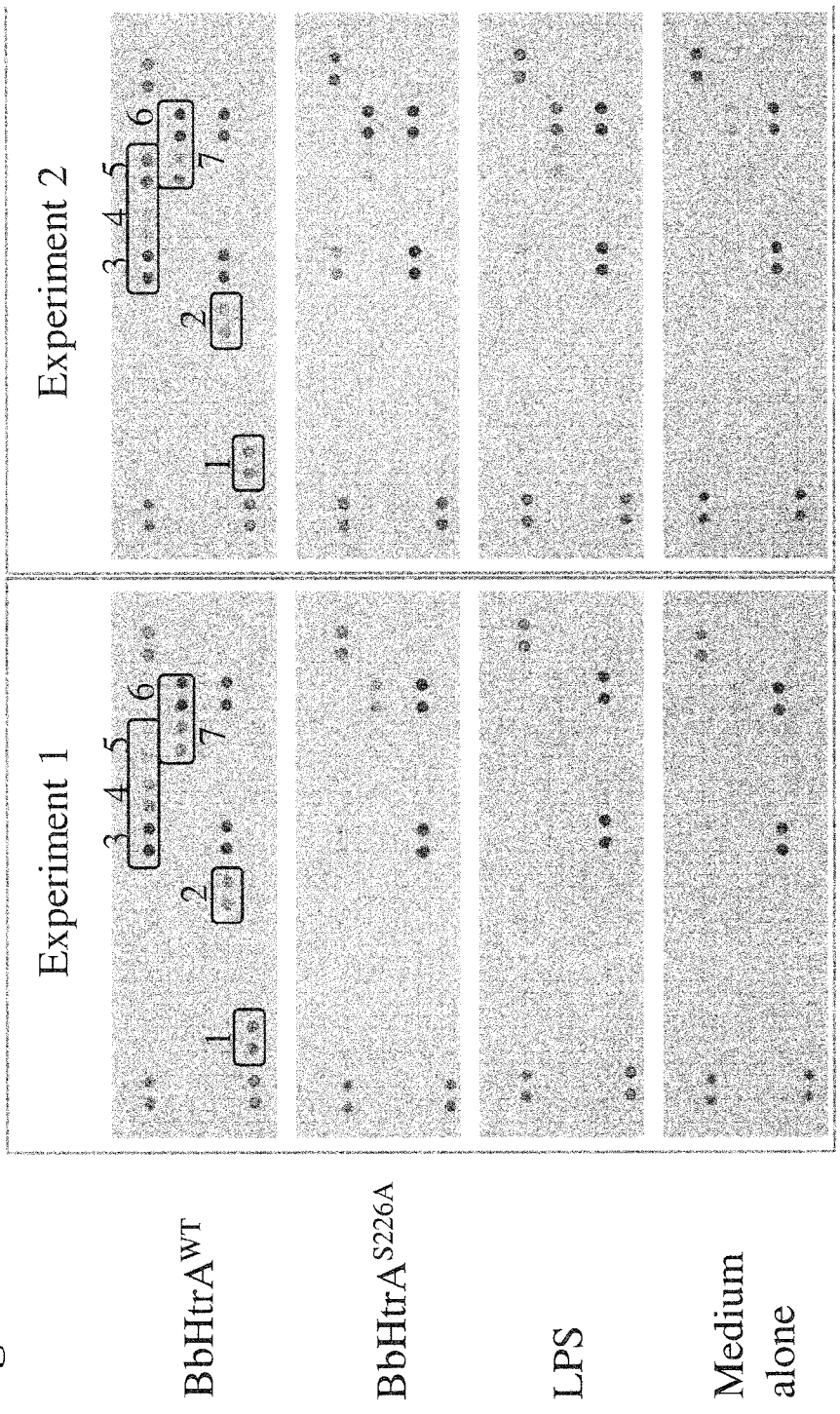
FIG. 10 is an image of a dot immunoblot analysis of cytokines induced in chondrocytes upon stimulation with BbHtrA, BbHtrA$^{S226A}$, lipopolysaccharide or medium alone.

Recombinant BbHtrA or $BbHtrA^{S226A}$ was added to culture medium and incubated with chondrocyte aggregate cultures. BbHtrA and $BbHtrA^{S226A}$ were purified using an *E. coli* system and was expected to contain endotoxin which would have a stimulatory effect on the chondrocytes. To control for endotoxin contamination (lipopolysaccharide, LPS), an endotoxin removal kit (Noragen) was used to remove the bulk of LPS from recombinant BbHtrAs. The relative toxicity of the amount remaining in the BbHtrA and $BbHtrA^{S226A}$ samples was determined by a chromogenic Limulus Amoebocyte Lysate (LAL) method (Lonza, Walkersville, Md.). Prior to addition to aggregates, LPS (44 ng, 200 EU), $BbHtrA^{WT}$ (20 µg, 27.9 EU LPS) and $BbHtrA^{S226A}$ (20 µs, 1.99 EU LPS) were incubated in 1 mg/ml polymyxin B sulfate (Sigma) on ice for 30 min with occasional mixing. Warmed dexamethasone-free medium was then added to each test condition to a final volume of 1 ml. Control aggregates were maintained in untreated medium also containing polymyxin B sulfate. The final concentration for all test conditions was 60 µg/ml polymyxin B sulfate. For chondrocyte cytokine induction, equivalent numbers of aggregates per test condition were transferred to individual wells of 24 well plates, spent medium was removed and 1 ml freshly warmed dexamethasone-free medium containing test components was added. Aggregates were incubated at 37° C. and 5% $CO_2$ for 48 hours. (FIGS. 9A-9B and FIG. 10).

Proteome Profiler Cytokine Arrays (R&D Systems, #ARY005) were used to detect 32 cytokines released in response to various conditions and were performed per product inserts. Briefly, spent media from chondrocyte assays was immediately diluted 1:5 in assay buffer containing biotinylated cytokine detection antibodies and incubated at room temperature for 60 minutes. The capture antibodies are spotted in duplicate on nitrocellulose membranes which were blocked with supplied buffer for 60 minutes. The samples were added to the blocked membranes and incubated overnight at 4° C. with mixing. After washing to remove unbound cytokines, membranes were incubated with 0.05 μg/ml phosphatase-labeled streptavidin (IPL) for 30 minutes. After washing to remove unbound streptavidin, precipitating phosphatase substrate (BioRad) was added. Membranes were developed simultaneously to control for development time. Pixel densities for each spot on a membrane were measured, the averaged background values from the negative controls for that membrane were subtracted and then the duplicate values for a particular cytokine were averaged.

Comparison of BbHtrA, Heat-denatured BbHtrA and LPS-induced Cytokine Responses. Initial experiments compared BbHtrA, heat denatured BbHtrA and LPS (FIG. 9A). The medium alone condition demonstrated that chondrocytes constitutively expressed cytokines MIF and Serpin E1 and very low levels of several others. LPS induced TLR4-mediated release of the cytokines CXCL1, IL-6 and IL-8 and very low levels of CCL5. BbHtrA, like LPS, stimulated release of CXCL1, IL-6, IL-8 and CCL5. Unlike LPS, however, CCL2 and sICAM-1 were also released in response to BbHtrA. The level of LPS used in these experiments was 7-fold greater than the residual LPS in recombinant BbHtrA, yet many of the cytokine signals were stronger from the BbHtrA treated chondrocytes and two were unique to the response to BbHtrA. The requirement of BbHtrA proteolytic activity for these responses was demonstrated by the near loss of all induced signals upon heat denaturation of BbHtrA. Cytokines were determined to be released in response to BbHtrA if the signals were greater than that seen in the control condition and greatly diminished by heat denaturation of BbHtrA. Six inflammatory cytokines and chemokines were stimulated in response to BbHtrA; CXCL1, CCL1, sICAM-1, IL-6, IL-8 and CCL2. A guide to the identities of the signals detected by the proteome profiler are shown in FIG. 9B.

Comparison of BbHtrA, BbHtrAS226A and LPS-induced Cytokine Responses. To examine the impact of BbHtrA proteolytic activity on the observed responses, additional experiments compared BbHtrA$^{WT}$, BbHtrA$^{S226A}$, LPS and medium alone (FIG. 10). Results were very similar to the previous experiments (FIG. 9A). Inter-assay variability was observed in the strength of the responses although the cytokines induced were consistent. Chondrocytes released CCL5, CCL2, CXCL1, CCL1, sICAM-1, IL-6 and IL-8 in response to BbHtrA. Results with BbHtrA$^{S226A}$ demonstrated that catalytic activity was required for most of these responses. BbHtrA$^{S226A}$ stimulated release of IL-8 and CXCL1 which may suggest direct BbHtrA interaction with surface receptors or the displacement of a receptor agonist from the ECM. IL6, IL8 and low levels of CXCL1 were observed upon LPS stimulation of TLR4. Cytokines CXCL1, CCL1, sICAM-1, IL-6, IL-8, CCL2, and CCL5 were elevated in response to BbHtrA protease compared with BbHtrA inactivated by heat (FIG. 9A) or mutation of its active site (FIG. 10). Pixel densities of each of the cytokines induced by BbHtrA and controls are shown in Table III

TABLE III

Table III shows results of cytokine assays

| Cytokine | Condition | Mean | StdDev | N |
|---|---|---|---|---|
| RANTES/CCL5 | Medium | 0.246 | 0.053 | 6 |
| | BbHtrA | 0.736 | 0.393 | 8 |
| | BbHtrA$^{S226A}$ | 0.265 | 0.056 | 6 |
| | LPS | 0.365 | 0.084 | 6 |
| MCP-1/CCL2 | Medium | 0.055 | 0.031 | 6 |
| | BbHtrA | 0.452 | 0.275 | 8 |
| | BbHtrA$^{S226A}$ | 0.050 | 0.041 | 6 |
| | LPS | 0.082 | 0.028 | 6 |
| GROα/CXCL1 | Medium | 0.174 | 0.044 | 6 |
| | BbHtrA | 1.349 | 0.095 | 8 |
| | BbHtrA$^{S226A}$ | 0.647 | 0.251 | 6 |
| | LPS | 0.631 | 0.431 | 6 |
| I-309/CCL1 | Medium | 0.123 | 0.033 | 6 |
| | BbHtrA | 0.535 | 0.138 | 8 |
| | BbHtrA$^{S226A}$ | 0.163 | 0.017 | 6 |
| | LPS | 0.132 | 0.037 | 6 |
| sICAM-1/CD54 | Medium | 0.173 | 0.035 | 6 |
| | BbHtrA | 0.890 | 0.598 | 8 |
| | BbHtrA$^{S226A}$ | 0.257 | 0.070 | 6 |
| | LPS | 0.166 | 0.022 | 6 |
| IL-8 | Medium | 0.402 | 0.089 | 6 |
| | BbHtrA | 1.581 | 0.126 | 8 |
| | BbHtrA$^{S226A}$ | 1.187 | 0.422 | 6 |
| | LPS | 1.063 | 0.667 | 6 |
| IL-6 | Medium | 0.253 | 0.041 | 6 |
| | BbHtrA | 0.627 | 0.310 | 8 |
| | BbHtrA$^{S226A}$ | 0.309 | 0.147 | 6 |
| | LPS | 0.353 | 0.199 | 6 |
| Positive control | Medium | 1.392 | 0.181 | 18 |
| | BbHtrA | 1.438 | 0.118 | 24 |
| | BbHtrA$^{S226A}$ | 1.406 | 0.138 | 18 |
| | LPS | 1.298 | 0.135 | 18 |

Example 11

Figures 11A, 11B:
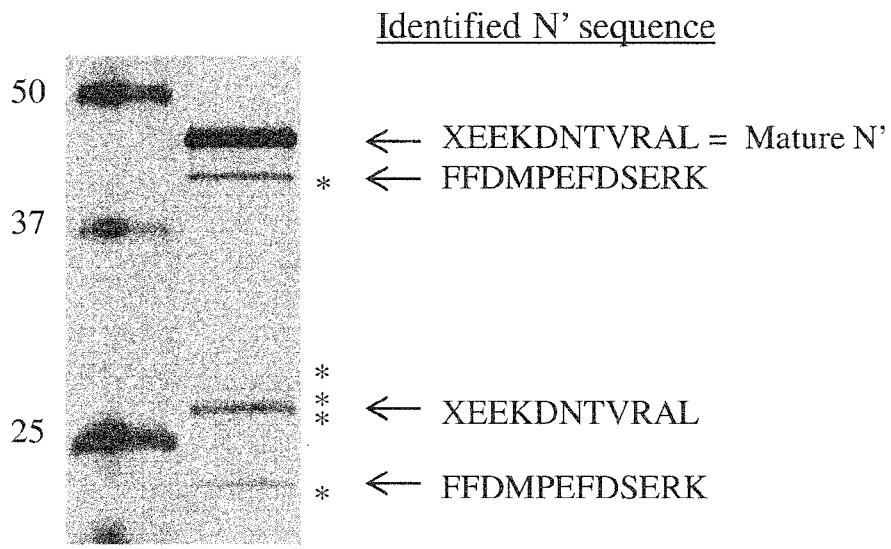
FIG. 11A is an image of a silver stain of an SDS-PAGE gel of BbHtrA self-digestion products showing the location of amino terminal signals obtained by Edman degradation.
FIG. 11B shows a ClustalW alignment of BbHtrA and *E. coli* DegQ showing conserved paired phenylalanines at the site of BbHtrA self digestion.

BbHtrA undergoes partial self-degradation generating a lower molecular weight form of the protease often referred to the short-form and designated by an 's' preceding the protease name. FIG. 11A shows a silver stain of self-digested BbHtrA electrophoretically separated by SDS-PAGE. Amino terminal sequence analysis by Edman degradation of the ~43 kD band established that s-BbHtrA arises from self-cleavage between $^{80}$Phe-Phe$^{81}$ (FIG. 11A). This cleavage removes 43 residues from the mature protein (amino acids 38-80) resulting in a predicted ~5 kD mass change which is consistent with the observed changes in the protein bands. It is likely that the ~23 and ~28 kD bands result from consistent C' processing of the protein. In addition to s-BbHtrA, other self-degradation products are observed in FIG. 11A. Mass spectrometric analysis identified additional self-cleavage sites between $^{313}$Ser-Leu$^{314}$, $^{334}$Val-Asn$^{335}$, $^{385}$Ser-Ser$^{386}$, and $^{416}$Val-Val$^{417}$. * indicates BbHtrA self-cleavage products.

Comparison of the BbHtrA sequence aligned with that of E. coli DegQ (FIG. 11B) demonstrates that these paired phenylalanines are conserved. FIG. 11B shows a ClustalW alignment of BbHtrA and E. coli DegQ showing conserved paired phenylalanines.

Example 12

Survey of Species of Borrelia for Presence of Borrelia burgdorferi sensu lato HtrA Proteolytic activity was studied by zymography of lysates of the prototype strains of each of the major genospecies of Borrelia that cause Lyme disease. Borrelia burgdorferi (passage 4, non-clonal, infectious strain B31), Borrelia garinii (unknown passage, infectious strain FR-20047) and Borrelia

*afzelii* (unknown passage, infectious strain ACA-1) were grown in Barbour-Stoenner-Kelly media (BSK II) supplemented with 6% rabbit serum at 37° C. Borrelial lysates (~1×10$^8$ *B. garinii, B. afzelii*; ~5×10$^7$ *B. burgdorferi*) and recombinant BbHtrA proteins (1 μg) were subjected to SDS-PAGE electrophoresis using 12% β-casein Zymogram Ready Gels (Bio-Rad). Following electrophoresis, the gels were renatured in 2.5% Triton X-100 (Sigma) for 60 min at 37° C. with a buffer change at 15 min. The gels were developed in Zymogram Development Buffer (BioRad) for 40 h at 37° C. with a buffer change at 15 min. Gels were stained (0.5% Coomassie Brilliant Blue R-250, 40% methanol, 10% glacial acetic acid) for 60 min at room temperature and then destained (40% methanol, 10% glacial acetic acid).

Figure 12A:
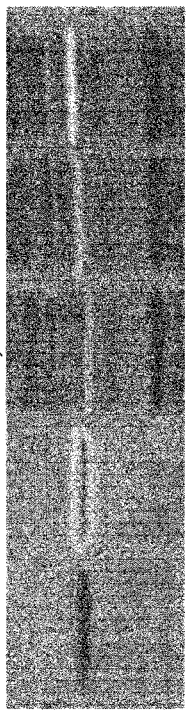
FIG. 12A is an image of a β-casein zymogram of the indicated lysates and recombinant proteins.
Figure 12B:
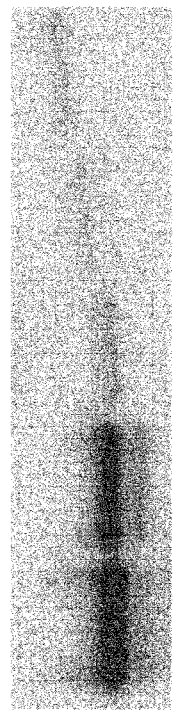
FIG. 12B is an image of a Western blot of the same lysates and recombinant proteins used in the image of FIG. 12A immunostained with polyclonal anti-BbHtrA.
Figure 12C:
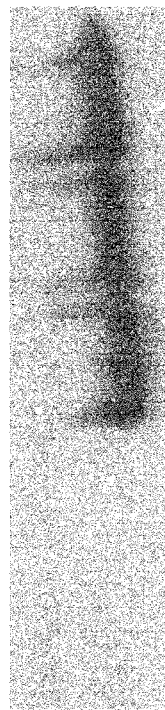
FIG. 12C is an image of a control for the Western blot of FIG. 12B immunostained with monoclonal anti-FlaB.
Figure 12D:
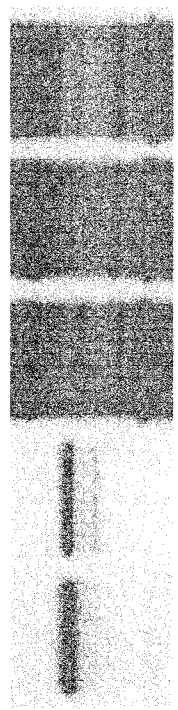
FIG. 12D is an image of a Coomassie stained gel of lysates and recombinant proteins used in FIGS. 12A-C.

Recombinant BbHtrA was proteolytically active against β-casein as evidenced by clearing around the protein band whereas BbHtrA$^{S226A}$ was not (FIG. 12A, lanes 1 and 2). Within the lysates, proteases displaying caseinolytic activity migrated at positions similar to the recombinant BbHtrA bands (FIG. 12A, lanes 3-5). All three species contained Western blot bands reactive with anti-BbHtrA peptide IgG antibodies (FIG. 12B), which likely represent the HtrA homologs. Black arrowhead indicates recombinant BbHtrA$^{WT}$ self-degradation product. FIG. 12C demonstrates the relative loading of the samples by immunoblot probed with anti-flagellar protein antibody (FlaB). Total protein was stained with silver (FIG. 12D). *B. burgdorferi* sensu stricto, *B. garinii*, and *B. afzelii* each possess an active HtrA.

Example 13

Mass Spectrometry of Fibronectin Fragments

In-gel reduced, alkylated, and trypsin digested peptides were purified and concentrated using an on-line enrichment column (Agilent Zorbax C18, 5 μm, 5×0.3 mm). Subsequent chromatographic separation was performed on a reverse phase nanospray column (Agilent 1100 nano HPLC, Zorbax C18, 5 μm, 75 μm ID×150 mm column) using a 42 min linear gradient from 25%-55% buffer B (90% ACN, 0.1% formic acid) at a flow rate of 300 nanoliters/min. Peptides were eluted directly into the mass spectrometer (Thermo Scientific LTQ linear ion trap) and spectra were collected over a m/z range of 200-2000 Da using a dynamic exclusion limit of 2 MS/MS spectra of a given peptide mass for 30 s (exclusion duration of 90 s). Compound lists of the resulting spectra were generated using Bioworks 3.0 software (Thermo Scientific) with an intensity threshold of 5,000 and 1 scan/group. MS/MS spectra were searched against the International Protein Index (IPI) human database (56,555 sequence entries) using the Mascot database search engine (version 2.2.1). The following parameters were employed in the database searches: peptide mass tolerance of 2 Da, fragment ion mass tolerance of 1.5 Da, fully tryptic digestion allowing for 1 missed cleavage, variable modification of methionine oxidation, and a fixed modification of cysteine carbamidomethylation. Protein identifications from all samples were combined using probabilistic protein identification algorithms implemented in Scaffold software (Proteome Software, Portland, Oreg.). Peptide and protein probability thresholds of 95% and 95%, respectively, were applied to the results (2.2% FDR as calculated by Scaffold based on probability statistics). A minimum of 2 unique peptides were required for protein identification. Proteins containing shared peptides are grouped by Scaffold to satisfy the laws of parsimony. Manual validation of MS/MS spectra was performed for all protein identifications above these thresholds that were based on one or two peptides. Criteria for manual validation included the following: 1) The peptide must be identified by all three search engines (Sequest, Mascot, and X! Tandem); 2) there must be a minimum of 80% coverage of theoretical y or b ions (at least 5 in consecutive order); 3) there must be an absence of prominent unassigned peaks greater than 5% of the maximum intensity; and 4) indicative residue specific fragmentation, such as intense ions N-terminal to proline and immediately C-terminal to aspartate and glutamate, were used as additional parameters of confirmation.

Example 14

Mass Spectrometry of Proteolysis Assays

Protease reactions were resuspended in 50 uL 0.1% formic acid (EMD, Gibbstown, N.J.) in 3% acetonitrile (Fisher Scientific) and transferred into sample vials. Liquid chromatography was carried out using an Agilent 1200 series HPLC equipped with a capillary pump and a nano pump (Agilent, Santa Clara, Calif.). Eluted peptides were analyzed on an Agilent quadrupole time of flight system (QTOF, model 6510) mass spectrometer with an HPLC-chip interface. A long HPLC chip was used with a 40-nL enrichment column and a 75-um×150-mm analytical column combined on a single chip. Buffer A for the nano pump consisted of 0.1% formic acid in HPLC grade water; buffer B contained 90% acetonitrile, 10% HPLC grade water, and 0.1% formic acid. The buffer for the capillary pump contained 3% acetonitrile, 97% HPLC grade water, and 0.1% formic acid. QTOF parameters were as follows: voltage, 1920; drying gas, 5 L/min; temperature, 350° C.; m/z (mass to charge ratio) range (ms), 300 to 1600; m/z range (ms/ms), 50 to 2200; precursor ions, 4; active exclusion, yes; and scan rate, ultra (26,000 m/z per second). Gradient conditions for the nano pump were as follows: 3% B from 0 to 1 minute, from 15% B to 40% B between minutes 1 to 7, 100% B from minutes 7.1 to 11, and 3% B from 11.1 to 18.1 minutes. A total of 4 uL of the resuspended protease reactions were injected onto the enrichment column for concentration/purification. The chip cube was switched to redirect the flow from the nano pump to elute the enrichment column onto the analytical column from 0 to 50 minutes. Flow rates were 0.45 uL/min for the nano pump and 4 uL/min for the capillary pump. All samples were run in duplicate. Standards were run at the beginning of each day and at the end of a set of analyses for quality control purposes. Raw data were extracted and analyzed by using the Spectrum Mill database searching program (Rev A.03.03.080 SR1; Agilent, Santa Clara, Calif.). Peak picking was performed within Spectrum Mill with the following parameters: MH$^+$ between 200 and 4000 Da, a maximum charge state of 7 was allowed (z≤7), and the program was directed to attempt to find a precursor charge state. During searching, the following parameters were applied: searches were performed with the Swiss-Prot Bovine database (Release 2010_11 of 2 Nov. 10 of UniProtKB/Swiss-Prot contains 522019 sequence entries, comprising 184241293 amino acids abstracted from 192744 references), oxidized methionine and deamidated asparagine as variable modifications, no enzyme search, precursor mass tolerance of 30 PPM, product mass tolerance 60 PPM, maximum ambiguous precursor charge of 4, and dynamic peak thresholding. Data were evaluated and protein identifications were considered significant if the following confidence thresholds were met: minimum of 2 peptides per protein, protein score >20, individual peptide scores of at least 10, and Scored Percent Intensity (SPI) of at least 70%. A reverse (random) database search was simultaneously conducted, and manual inspection of spectra was used to validate the match of the spectrum to the predicted peptide fragmentation pattern.

Peptides found are listed in Table IV.

TABLE IV

| SEQ ID NO | Bovine Substrate/ Uniprot ID | Amino-terminal amino acid | BbHtrA-generated Peptides | Measured (Da) | Matched (Da) |
|---|---|---|---|---|---|
| SEQ ID NO: 33 | Decorin/ P21793 | 72 | GLEKVPKDLPPDTALLDLQNNKITEI | 719.40 | 2874.58 |
| SEQ ID NO: 34 | Decorin/ P21793 | 179 | VVELGTNPLKS | 578.83 | 1156.66 |
| SEQ ID NO: 35 | Decorin/ P21793 | 179 | VVELGTNPLKSSGIENGAFQGMKKLS | 676.86 | 2704.43 |
| SEQ ID NO: 36 | Decorin/ P21793 | 179 | VVELGTNPLKSSGIENGAFQGMKKLSYIRI | 813.44 | 3249.77 |
| SEQ ID NO: 37 | Decorin/ P21793 | 179 | VVELGTNPLKSSGIENGAFQGMKKL | 655.10 | 2617.40 |
| SEQ ID NO: 38 | Biglycan/ P21809 | 296 | GLPDLKLL | 434.78 | 868.55 |
| SEQ ID NO: 39 | Biglycan/ P21809 | 296 | GLPDLKLLQV | 548.34 | 1095.68 |
| SEQ ID NO: 40 | Biglycan/ P21809 | 296 | GLPDLKLLQVV | 597.88 | 1194.75 |
| SEQ ID NO: 41 | Aggrecan/ P13608 | 105 | TLPNYPAIPSDA | 629.82 | 1258.63 |
| SEQ ID NO: 42 | Aggrecan/ P13608 | 105 | TLPNYPAIPSDATLEI | 857.95 | 1714.89 |
| SEQ ID NO: 43 | Aggrecan/ P13608 | 202 | GWLADQTVRYPI | 709.88 | 1418.74 |
| SEQ ID NO: 44 | Fibromodulin/ P13605 | 319 | YLQGNRINEFSI | 727.38 | 1453.74 |
| SEQ ID NO: 45 | Fibromodulin/ P13605 | 336 | VVDVMNFSKLQV | 689.88 | 1378.74 |
| SEQ ID NO: 46 | Fibromodulin/ P13605 | 337 | VDVMNFSKLQV | 640.34 | 1279.67 |
| SEQ ID NO: 47 | COMP/ P35445 | 611 | VMWKQMEQT | 590.78 | 1180.55 |
| SEQ ID NO: 48 | COMP/ P35445 | 612 | MWKQMEQTYWQA | 815.36 | 1629.72 |
| SEQ ID NO: 49 | COMP/ P35445 | 612 | MWKQMEQTYWQANPFRA | 739.01 | 2215.02 |
| SEQ ID NO: 50 | COMP/ P35445 | 654 | WHTGDTASQV | 551.25 | 1101.50 |
| SEQ ID NO: 51 | COMP/ P35445 | 654 | WHTGDTASQVRL | 457.57 | 1370.68 |

Both human and bovine substrates were degraded by BbHtrA (Table II). Mass spectrometry data (Table IV) were generated using native, fully glycosylated bovine substrates. Sequence alignments demonstrate the high degree of sequence conservation at the observed cleavage sites indicating cleavage will occur at these sites within the human substrates. Cleavage will also occur at the homologous positions within the human substrates (Table V) based on analysis of 93 known BbHtrA cleavage sites to generate a model of BbHtrA substrate characteristics. Corresponding peptides of the corresponding human proteins are listed in Table V.

TABLE V

| SEQ ID NO | Human Substrate/ Uniprot ID | Amino-terminal amino acid | Human peptides at positions analogous to BbHtrA-generated bovine peptides in Table III |
|---|---|---|---|
| SEQ ID NO: 52 | Decorin/ P07585 | 71 | GLDKVPKDLPPDTTLLDLQNNKITEI |
| SEQ ID NO: 53 | Decorin/ P07585 | 178 | VIELGTNPLKS |

TABLE V-continued

| SEQ ID NO | Human Substrate/ Uniprot ID | Amino-terminal amino acid | Human peptides at positions analogous to BbHtrA-generated bovine peptides in Table III |
|---|---|---|---|
| SEQ ID NO: 54 | Decorin/ P07585 | 178 | VIELGTNPLKSSGIENGAFQGMKKLS |
| SEQ ID NO: 55 | Decorin/ P07585 | 178 | VIELGTNPLKSSGIEnGAFQGMKKLSYIRI |
| SEQ ID NO: 56 | Biglycan/ P21810 | 295 | GLPDLKLL |
| SEQ ID NO: 57 | Biglycan/ P21810 | 295 | GLPDLKLLQV |
| SEQ ID NO: 58 | Biglycan/ P21810 | 295 | GLPDLKLLQVV |
| SEQ ID NO: 59 | Aggrecan/ P16112 | 105 | SLPNYPAIPSDA |
| SEQ ID NO: 60 | Aggrecan/ P16112 | 105 | SLPNYPAIPSDATLEV |
| SEQ ID NO: 61 | Aggrecan/ P16112 | 202 | GWLADQTVRYPI |
| SEQ ID NO: 62 | Fibromodulin/ Q06828 | 319 | YLQGNRINEFSI |
| SEQ ID NO: 63 | Fibromodulin/ Q06828 | 336 | VVDVVNFSKLQV |
| SEQ ID NO: 64 | Fibromodulin/ Q06828 | 337 | VDVVNFSKLQV |
| SEQ ID NO: 65 | COMP/ P49747 | 612 | VMWKQMEQT |
| SEQ ID NO: 66 | COMP/ P49747 | 613 | MWKQMEQTYWQA |
| SEQ ID NO: 67 | COMP/ P49747 | 613 | MWKQMEQTYWQANPFRA |
| SEQ ID NO: 68 | COMP/ P49747 | 655 | WHTGDTESQV |
| SEQ ID NO: 69 | COMP/ P49747 | 655 | WHTGDTESQVRL |

A list of empirically derived BbHtrA protease cleavage sites is presented in Table VI. Each listed cleavage site is represented by the generic formula (P4P3P2P1)×P1'P2'P3'P4' where P4, P3, P2 and P1 represent the ordered sequence of the four amino acids on the side of the BbHtrA protease cleavage site closer to the N-terminal of the full-length protein and P1', P2', P3' and P4' represent the ordered sequence of the four amino acids on the side of the BbHtrA protease cleavage site closer to the C-terminal of the full-length protein. Protease cleavage breaks molecular bonds between amino acids P1 and P1', represented as "x" to generate fragments of the full-length protein, wherein one fragment has the amino acid sequence P4P3P2P1 at the C-terminus and the second fragment has the amino acid sequence P1'P2'P3'P4' at the N-terminus. Parentheses are provided around the amino acid sequence P4P3P2P1 in Table VI solely to aid in visualization of these cleavage sites. These cleavage sites are depicted in isolation from the larger context of the proteins in which they are found. As will be recognized by those of skill in the art, conservative amino acid substitutions may be made in these cleavage sites without affecting the ability of BbHtrA to cleave at the sites.

TABLE VI

| SEQ ID NO | (P4P3P2P1) × P1'P2'P3'P4' |
|---|---|
| SEQ ID NO: 70 | (AFQT)VVLD |
| SEQ ID NO: 71 | (AIEL)EDLL |
| SEQ ID NO: 72 | (AKLT)GIPK |
| SEQ ID NO: 73 | (AVKS)STGP |
| SEQ ID NO: 74 | (CIEM)GGNP |
| SEQ ID NO: 75 | (CSDL)GLEK |
| SEQ ID NO: 76 | (CVYV)RAAV |
| SEQ ID NO: 77 | (DIKA)QLNL |
| SEQ ID NO: 78 | (DTNI)TTIP |
| SEQ ID NO: 79 | (FCTV)VDVM |
| SEQ ID NO: 80 | (FEPG)AFDG |
| SEQ ID NO: 81 | (FQTV)VLDP |
| SEQ ID NO: 82 | (FRAV)AEPG |
| SEQ ID NO: 83 | (FRCV)TDRL |
| SEQ ID NO: 84 | (FYVV)MWKQ |
| SEQ ID NO: 85 | (GISL)FNNP |
| SEQ ID NO: 86 | (GLKL)NYLR |
| SEQ ID NO: 87 | (GLPS)ALEQ |
| SEQ ID NO: 88 | (GVVV)DYID |
| SEQ ID NO: 89 | (HEKA)FSPL |
| SEQ ID NO: 90 | (HLYA)LVLV |
| SEQ ID NO: 91 | (HNNV)FSVP |
| SEQ ID NO: 92 | (IEMG)GNPL |
| SEQ ID NO: 93 | (IHQL)YLDS |
| SEQ ID NO: 94 | (IIAS)LYPG |
| SEQ ID NO: 95 | (IMKV)NGVS |

TABLE VI-continued

| SEQ ID NO | (P4P3P2P1) × P1'P2'P3'P4' |
|---|---|
| SEQ ID NO: 96 | (IPFF)FEDM |
| SEQ ID NO: 97 | (IQEV)GSSM |
| SEQ ID NO: 98 | (ISEA)KLTG |
| SEQ ID NO: 99 | (ISKI)SPGA |
| SEQ ID NO: 100 | (ISLF)NNPV |
| SEQ ID NO: 101 | (ISPG)AFAP |
| SEQ ID NO: 102 | (IVQT)MNSD |
| SEQ ID NO: 103 | (KDKT)SYRW |
| SEQ ID NO: 104 | (KELS)SSKM |
| SEQ ID NO: 105 | (KGVV)VDYI |
| SEQ ID NO: 106 | (KIQA)IELE |
| SEQ ID NO: 107 | (KLQV)LRLD |
| SEQ ID NO: 108 | (KLYI)SKNH |
| SEQ ID NO: 109 | (KVDA)ASLK |
| SEQ ID NO: 110 | (LENL)YLQG |
| SEQ ID NO: 111 | (LENS)GFEP |
| SEQ ID NO: 112 | (LILI)NNKI |
| SEQ ID NO: 113 | (LKAV)KSST |
| SEQ ID NO: 114 | (LPPS)LTEL |
| SEQ ID NO: 115 | (LQNS)AIIA |
| SEQ ID NO: 116 | (LRNA)LWHT |
| SEQ ID NO: 117 | (MCSA)GWLA |
| SEQ ID NO: 118 | (MEQT)YWQA |
| SEQ ID NO: 119 | (MKKL)SYIR |
| SEQ ID NO: 120 | (MNCI)EMGG |

TABLE VI-continued

| SEQ ID NO | (P4P3P2P1) × P1'P2'P3'P4' |
|---|---|
| SEQ ID NO: 121 | (NGIS)LFNN |
| SEQ ID NO: 122 | (NHLV)EIPP |
| SEQ ID NO: 123 | (NKLS)RVPA |
| SEQ ID NO: 124 | (NLPS)SLVE |
| SEQ ID NO: 125 | (NNKI)SKIS |
| SEQ ID NO: 126 | (NNKL)SRVP |
| SEQ ID NO: 127 | (NQMI)VVEL |
| SEQ ID NO: 128 | (NQTG)LLDP |
| SEQ ID NO: 129 | (NRNL)KYLP |
| SEQ ID NO: 130 | (NWVV)LNQG |
| SEQ ID NO: 131 | (PDTA)LLDL |
| SEQ ID NO: 132 | (PDTT)LLDL |
| SEQ ID NO: 133 | (PFRA)VAEP |
| SEQ ID NO: 134 | (PNWV)VLNQ |
| SEQ ID NO: 135 | (PSRM)KYVY |
| SEQ ID NO: 136 | (PVST)NLEN |
| SEQ ID NO: 137 | (QCDA)GWLA |
| SEQ ID NO: 138 | (QDKV)TLPN |
| SEQ ID NO: 139 | (QLKA)VKSS |
| SEQ ID NO: 140 | (QTVV)LDPE |
| SEQ ID NO: 141 | (RNAL)WHTG |
| SEQ ID NO: 142 | (RNWI)KGVV |
| SEQ ID NO: 143 | (RSLI)LLDL |
| SEQ ID NO: 144 | (RVPA)GLPD |
| SEQ ID NO: 145 | (SFCT)VVDV |
| SEQ ID NO: 146 | (SFYV)VMWK |

TABLE VI-continued

| SEQ ID NO | (P4P3P2P1) × P1'P2'P3'P4' |
|---|---|
| SEQ ID NO: 147 | (SKNH)LVEI |
| SEQ ID NO: 148 | (SKSV)SNLR |
| SEQ ID NO: 149 | (SLSV)SIPE |
| SEQ ID NO: 150 | (SPGA)FAPL |
| SEQ ID NO: 151 | (TKKA)SYSG |
| SEQ ID NO: 152 | (TSYI)SDFY |
| SEQ ID NO: 153 | (VFYA)TSPE |
| SEQ ID NO: 154 | (VKRA)YYNG |
| SEQ ID NO: 155 | (VVDV)MNFS |
| SEQ ID NO: 156 | (VVEL)GTNP |
| SEQ ID NO: 157 | (YIRV)RFYE |
| SEQ ID NO: 158 | (YLRI)SEAK |
| SEQ ID NO: 159 | (YNGI)SLEN |
| SEQ ID NO: 160 | (YSGV)SLFS |
| SEQ ID NO: 161 | (YVRA)AVQL |

TABLE VI-continued

| SEQ ID NO | (P4P3P2P1) × P1'P2'P3'P4' |
|---|---|
| SEQ ID NO: 162 | (YWQA)NPFR |

Example 15

BbHtrA Cleavage Sites within Human Aggrecan, Biglycan, Decorin, Cartilage Oligomeric Matrix Protein and Fibromodulin SitePrediction, an internet-based protease cleavage site prediction tool, described in detail in Verspurten, J., et al., Trends Biochem Sci, 2009, 34(7):319-23, was used to predict BbHtrA cleavage sites in human aggrecan (Table VII), human biglycan (Table VIII), human cartilage oligomeric matrix protein (Table IX), human decorin (Table X) and human fibromodulin (Table XI). Ninety-three unique BbHtrA cleavage sites, identified by mass spectrometry from BbHtrA self-degradation and bovine aggrecan, biglycan, decorin, cartilage oligomeric matrix protein, were used as the training data-set to analyze BbHtrA substrate cleavage motifs, see Table VI. For each of the 93 sites, eight amino acids (four on either side of the cut site; generically described as (P4P3P2P1)× P1'P2'P3'P4' as indicated above,) were entered into the SitePrediction 'known sites' input box. UniProt identifier codes for human aggrecan, biglycan, decorin, cartilage oligomeric matrix protein and fibromodulin were entered into the 'substrate' input box. SitePrediction default parameters (0.1 penalty and BLOSUM62 amino acid substitution sequence alignment matrix) were used to predict 50 cleavage sites for each candidate human protein. The plot of true positive versus the false positive values (ROC curve) for the known BbHtra P sites yielded an area under the curve (AUC) of 0.945.

Example 16

Table VII lists predicted BbHtrA-generated peptides of Human Aggrecan (Uniprot Identifier P16112).

TABLE VII

| SEQ ID NO | Amino-Terminal Amino Acid | Predicted Human Aggrecan (Uniprot Identifier P16112) Peptides |
|---|---|---|
| SEQ ID NO: 163 | 31 | VSIPQPSPLRVLLGTSLTIPCYFIDPMHPVTTAP |
| SEQ ID NO: 164 | 32 | SIPQPSPLRVLLGTSLTIPCYFIDPMHPVTTAPS |
| SEQ ID NO: 165 | 86 | LLVATEGRVRVNSAYQDKVSLPNYPAIPSDATLE |
| SEQ ID NO: 166 | 105 | SLPNYPAIPSDATLEVQSLRSNDSGVYRCEVMHG |
| SEQ ID NO: 167 | 117 | TLEVQSLRSNDSGVYRCEVMHGIEDSEATLEVVV |
| SEQ ID NO: 168 | 191 | AYEDGFHQCDAGWLADQTVRYPIHTPREGCYGDK |
| SEQ ID NO: 169 | 202 | GWLADQTVRYPIHTPREGCYGDKDEFPGVRTYGI |
| SEQ ID NO: 170 | 259 | TSPEKFTFQEAANECRRLGARLATTGHVYLAWQA |
| SEQ ID NO: 171 | 300 | GWLADRSVRYPISKARPNCGGNLLGVRTVYVHAN |
| SEQ ID NO: 172 | 336 | GYPDPSSRYDAICYTGEDFVDIPENFFGVGGEED |
| SEQ ID NO: 173 | 408 | SPSPLEPEEPPFTFAPEIGATAFAEVENETGEATR |
| SEQ ID NO: 174 | 516 | AYEAGYEQCDAGWLRDQTVRYPIVSPRTPCVGDK |

TABLE VII-continued

| SEQ ID NO | Amino-Terminal Amino Acid | Predicted Human Aggrecan (Uniprot Identifier P16112) Peptides |
|---|---|---|
| SEQ ID NO: 175 | 624 | GWLADGSLRYPIVTPRPACGGDKPGVRTVYLYPN |
| SEQ ID NO: 176 | 660 | GLPDPLSRHHAFCFRGISAVPSPGEEEGGTPTSP |
| SEQ ID NO: 177 | 891 | SGLPSGDLDSSGLTSTVGSGLTVESGLPSGDEER |
| SEQ ID NO: 178 | 916 | GLPSGDEERIEWPSTPTVGELPSGAEILEGSASG |
| SEQ ID NO: 179 | 920 | GDEERIEWPSTPTVGELPSGAEILEGSASGVGDL |
| SEQ ID NO: 180 | 955 | GLPSGEVLETSASGVGDLSGLPSGEVLETTAPGV |
| SEQ ID NO: 181 | 974 | GLPSGEVLETSASGVGDLSGLPSGEVLETTAPGV |
| SEQ ID NO: 182 | 1296 | SGLPSGEVLETTAPGVDEISGLPSGEVLETTAPG |
| SEQ ID NO: 183 | 1334 | SGLPSGEVLETTAPGVDEISGLPSGEVLETTAPG |
| SEQ ID NO: 184 | 1354 | GLPSGEVLETSASGVGDLSGLPSGEVLETTAPGV |
| SEQ ID NO: 185 | 1365 | SVSGVEDISGLPSGEVVETSASGIEDVSELPSGE |
| SEQ ID NO: 186 | 1368 | GVEDISGLPSGEVVETSASGIEDVSELPSGEGLE |
| SEQ ID NO: 187 | 1392 | SELPSGEGLETSASGVEDLSRLPSGEEVLEISAS |
| SEQ ID NO: 188 | 1448 | GTDLSGLPSGREGLETSASGAEDLSGLPSGKEDL |
| SEQ ID NO: 189 | 1453 | GLPSGREGLETSASGAEDLSGLPSGKEDLVGSAS |
| SEQ ID NO: 190 | 1497 | GTLGSGQAPETSGLPSGFSGEYSGVDLGSGPPSG |
| SEQ ID NO: 191 | 1509 | GLPSGFSGEYSGVDLGSGPPSGLPDFSGLPSGFP |
| SEQ ID NO: 192 | 1530 | GLPDFSGLPSGFPTVSLVDSTLVEVVTASTASEL |
| SEQ ID NO: 193 | 1545 | SLVDSTLVEVVTASTASELEGRGTIGISGAGEIS |
| SEQ ID NO: 194 | 1550 | TLVEVVTASTASELEGRGTIGISGAGEISGLPSS |
| SEQ ID NO: 195 | 1561 | SELEGRGTIGISGAGEISGLPSSELDISGRASGL |
| SEQ ID NO: 196 | 1593 | GLPSGTELSGQASGSPDVSGEIPGLFGVSGQPSG |
| SEQ ID NO: 197 | 1597 | GTELSGQASGSPDVSGEIPGLFGVSGQPSGFPDT |
| SEQ ID NO: 198 | 1686 | GLPGFSGATSGVPDLVSGTTSGSGESSGITFVDT |
| SEQ ID NO: 199 | 1720 | SLVEVAPTTFKEEEGLGSVELSGLPSGEADLSGK |
| SEQ ID NO: 200 | 1741 | SGLPSGEADLSGKSGMVDVSGQFSGTVDSSGFTS |
| SEQ ID NO: 201 | 1742 | GLPSGEADLSGKSGMVDVSGQFSGTVDSSGFTSQ |
| SEQ ID NO: 202 | 1820 | SLVDSTLVEVVTASTASELEGRGTIGISGAGEIS |
| SEQ ID NO: 203 | 1875 | GLIEPSGEPPGTPYFSGDFASTTNVSGESSVAMG |
| SEQ ID NO: 204 | 1881 | GEPPGTPYFSGDFASTTNVSGESSVAMGTSGEAS |
| SEQ ID NO: 205 | 1915 | GLPEVTLITSEFVEGVTEPTISQELGQRPPVTHT |
| SEQ ID NO: 206 | 1979 | SSVPESSSETSAYPEAGFGASAAPEASREDSGSP |
| SEQ ID NO: 207 | 1980 | SVPESSSETSAYPEAGFGASAAPEASREDSGSPD |
| SEQ ID NO: 208 | 1990 | AYPEAGFGASAAPEASREDSGSPDLSETTSAFHE |
| SEQ ID NO: 209 | 2030 | SGLGVSGSTLTFQEGEASAAPEVSGESTTTSDVG |
| SEQ ID NO: 210 | 2101 | SIPESEWTQQTQRPAETHLEIESSSLLYSGEETH |
| SEQ ID NO: 211 | 2125 | SLLYSGEETHTVETATSPTDASIPASPEWKRESE |

TABLE VII-continued

| SEQ ID NO | Amino-Terminal Amino Acid | Predicted Human Aggrecan (Uniprot Identifier P16112) Peptides |
|---|---|---|
| SEQ ID NO: 212 | 2127 | LYSGEETHTVETATSPTDASIPASPEWKRESEST |
| SEQ ID NO: 213 | 2244 | VTPEEQEFVNNNAQDYQWIGLNDRTIEGDFRWSD |

Table VIII lists predicted BbHtrA-generated peptides of Human Biglycan (Uniprot Identifier P21810)

TABLE VIII

| SEQ ID NO | Amino-Terminal Amino Acid | Predicted Human Biglycan (Uniprot Identifier P21810) Peptides |
|---|---|---|
| SEQ ID NO: 214 | 8 | VSLLALSQALPFEQRGFWDFTLDDGPFMMNDEEA |
| SEQ ID NO: 215 | 10 | LLALSQALPFEQRGFWDFTLDDGPFMMNDEEASG |
| SEQ ID NO: 216 | 11 | LALSQALPFEQRGFWDFTLDDGPFMMNDEEASGA |
| SEQ ID NO: 217 | 12 | ALSQALPFEQRGFWDFTLDDGPFMMNDEEASGAD |
| SEQ ID NO: 218 | 13 | LSQALPFEQRGFWDFTLDDGPFMMNDEEASGADT |
| SEQ ID NO: 219 | 17 | LPFEQRGFWDFTLDDGPFMMNDEEASGADTSGVL |
| SEQ ID NO: 220 | 48 | GVLDPDSVTPTYSAMCPFGCHCHLRVVQCSDLGL |
| SEQ ID NO: 221 | 49 | VLDPDSVTPTYSAMCPFGCHCHLRVVQCSDLGLK |
| SEQ ID NO: 222 | 50 | LDPDSVTPTYSAMCPFGCHCHLRVVQCSDLGLKS |
| SEQ ID NO: 223 | 80 | GLKSVPKEISPDTTLLDLQNNDISELRKDDFKGL |
| SEQ ID NO: 224 | 94 | LLDLQNNDISELRKDDFKGLQHLYALVLVNNKIS |
| SEQ ID NO: 225 | 103 | SELRKDDFKGLQHLYALVLVNNKISKIHEKAFSP |
| SEQ ID NO: 226 | 119 | LVLVNNKISKIHEKAFSPLRKLQKLYISKNHLVE |
| SEQ ID NO: 227 | 122 | VNNKISKIHEKAFSPLRKLQKLYISKNHLVEIPP |
| SEQ ID NO: 228 | 123 | NNKISKIHEKAFSPLRKLQKLYISKNHLVEIPPN |
| SEQ ID NO: 229 | 127 | SKIHEKAFSPLRKLQKLYISKNHLVEIPPNLPSS |
| SEQ ID NO: 230 | 134 | FSPLRKLQKLYISKNHLVEIPPNLPSSLVELRIH |
| SEQ ID NO: 231 | 146 | SKNHLVEIPPNLPSSLVELRIHDNRIRKVPKGVF |
| SEQ ID NO: 232 | 152 | EIPPNLPSSLVELRIHDNRIRKVPKGVFSGLRNM |
| SEQ ID NO: 233 | 160 | SLVELRIHDNRIRKVPKGVFSGLRNMNCIEMGGN |
| SEQ ID NO: 234 | 161 | LVELRIHDNRIRKVPKGVFSGLRNMNCIEMGGNP |
| SEQ ID NO: 235 | 162 | VELRIHDNRIRKVPKGVFSGLRNMNCIEMGGNPL |
| SEQ ID NO: 236 | 163 | ELRIHDNRIRKVPKGVFSGLRNMNCIEMGGNPLE |
| SEQ ID NO: 237 | 179 | FSGLRNMNCIEMGGNPLENSGFEPGAFDGLKLNY |
| SEQ ID NO: 238 | 192 | GNPLENSGFEPGAFDGLKLNYLRISEAKLTGIPK |
| SEQ ID NO: 239 | 199 | GFEPGAFDGLKLNYLRISEAKLTGIPKDLPETLN |
| SEQ ID NO: 240 | 204 | AFDGLKLNYLRISEAKLTGIPKDLPETLNELHLD |
| SEQ ID NO: 241 | 211 | NYLRISEAKLTGIPKDLPETLNELHLDHNKIQAI |
| SEQ ID NO: 242 | 216 | SEAKLTGIPKDLPETLNELHLDHNKIQAIELEDL |
| SEQ ID NO: 243 | 219 | KLTGIPKDLPETLNELHLDHNKIQAIELEDLLRY |

TABLE VIII-continued

| SEQ ID NO | Amino-Terminal Amino Acid | Predicted Human Biglycan (Uniprot Identifier P21810) Peptides |
|---|---|---|
| SEQ ID NO: 244 | 222 | GIPKDLPETLNELHLDHNKIQAIELEDLLRYSKL |
| SEQ ID NO: 245 | 231 | LNELHLDHNKIQAIELEDLLRYSKLYRLGLGHNQ |
| SEQ ID NO: 246 | 244 | IELEDLLRYSKLYRLGLGHNQIRMIENGSLSFLP |
| SEQ ID NO: 247 | 245 | ELEDLLRYSKLYRLGLGHNQIRMIENGSLSFLPT |
| SEQ ID NO: 248 | 247 | EDLLRYSKLYRLGLGHNQIRMIENGSLSFLPTLR |
| SEQ ID NO: 249 | 256 | YRLGLGHNQIRMIENGSLSFLPTLRELHLDNNKL |
| SEQ ID NO: 250 | 274 | SFLPTLRELHLDNNKLARVPSGLPDKLLQVVYL |
| SEQ ID NO: 251 | 275 | FLPTLRELHLDNNKLARVPSGLPDKLLQVVYLH |
| SEQ ID NO: 252 | 279 | LRELHLDNNKLARVPSGLPDKLLQVVYLHSNNI |
| SEQ ID NO: 253 | 290 | ARVPSGLPDKLLQVVYLHSNNITKVGVNDFCPM |
| SEQ ID NO: 254 | 291 | RVPSGLPDKLLQVVYLHSNNITKVGVNDFCPMG |
| SEQ ID NO: 255 | 295 | GLPDKLLQVVYLHSNNITKVGVNDFCPMGFGVK |
| SEQ ID NO: 256 | 305 | VYLHSNNITKVGVNDFCPMGFGVKRAYYNGISLF |
| SEQ ID NO: 257 | 313 | TKVGVNDFCPMGFGVKRAYYNGISLFNNPVPYWE |
| SEQ ID NO: 258 | 316 | GVNDFCPMGFGVKRAYYNGISLFNNPVPYWEVQP |
| SEQ ID NO: 259 | 331 | YYNGISLFNNPVPYWEVQPATFRCVTDRLAIQFG |
| SEQ ID NO: 260 | 336 | SLFNNPVPYWEVQPATFRCVTDRLAIQFGNYKK |
| SEQ ID NO: 261 | 338 | FNNPVPYWEVQPATFRCVTDRLAIQFGNYKK |
| SEQ ID NO: 262 | 339 | NNPVPYWEVQPATFRCVTDRLAIQFGNYKK |
| SEQ ID NO: 263 | 356 | TDRLAIQFGNYKK |

Table IX lists predicted BbHtrA-generated peptides; Cartilage oligomeric matrix protein (COMP, Uniprot Identifier P49747)

TABLE IX

| SEQ ID NO | Amino-Terminal Amino Acid | Predicted BbHtrA-Generated Peptides; Cartilage oligomeric matrix protein (COMP, Uniprot Identifier P49747) |
|---|---|---|
| SEQ ID NO: 264 | 10 | LLTLAALGASGQGQSPLGSDLGPQMLRELQETNA |
| SEQ ID NO: 265 | 11 | LTLAALGASGQGQSPLGSDLGPQMLRELQETNAA |
| SEQ ID NO: 266 | 13 | LAALGASGQGQSPLGSDLGPQMLRELQETNAALQ |
| SEQ ID NO: 267 | 14 | AALGASGQGQSPLGSDLGPQMLRELQETNAALQD |
| SEQ ID NO: 268 | 15 | ALGASGQGQSPLGSDLGPQMLRELQETNAALQDV |
| SEQ ID NO: 269 | 19 | SGQGQSPLGSDLGPQMLRELQETNAALQDVRELL |
| SEQ ID NO: 270 | 27 | GSDLGPQMLRELQETNAALQDVRELLRQQVREIT |
| SEQ ID NO: 271 | 28 | SDLGPQMLRELQETNAALQDVRELLRQQVREITF |
| SEQ ID NO: 272 | 29 | DLGPQMLRELQETNAALQDVRELLRQQVREITFL |
| SEQ ID NO: 273 | 49 | RELLRQQVREITFLKNTVMECDACGMQQSVRTGL |
| SEQ ID NO: 274 | 60 | TFLKNTVMECDACGMQQSVRTGLPSVRPLLHCAP |

TABLE IX-continued

Predicted BbHtrA-Generated Peptides; Cartilage oligomeric matrix protein (COMP, Uniprot Identifier P49747)

| SEQ ID NO | Amino-Terminal Amino Acid | Sequence |
|---|---|---|
| SEQ ID NO: 275 | 81 | GLPSVRPLLHCAPGFCFPGVACIQTESGARCGPC |
| SEQ ID NO: 276 | 85 | VRPLLHCAPGFCFPGVACIQTESGARCGPCPAGF |
| SEQ ID NO: 277 | 117 | GFTGNGSHCTDVNECNAHPCFPRVRCINTSPGFR |
| SEQ ID NO: 278 | 258 | GWAGNGILCGRDTDLDGFPDEKLRCPERQCRKDN |
| SEQ ID NO: 279 | 294 | TVPNSGQEDVDRDGIGDACDPDADGDGVPNEKDN |
| SEQ ID NO: 280 | 331 | VRNPDQRNTDEDKWGDACDNCRSQKNDDQKDTDQ |
| SEQ ID NO: 281 | 332 | RNPDQRNTDEDKWGDACDNCRSQKNDDQKDTDQD |
| SEQ ID NO: 282 | 487 | VPNPGQEDADRDGVGDVCQDDFDADKVVDKIDVC |
| SEQ ID NO: 283 | 514 | VDKIDVCPENAEVTLTDFRAFQTVVLDPEGDAQI |
| SEQ ID NO: 284 | 525 | EVTLTDFRAFQTVVLDPEGDAQIDPNWVVLNQGR |
| SEQ ID NO: 285 | 537 | VVLDPEGDAQIDPNWVVLNQGREIVQTMNSDPGL |
| SEQ ID NO: 286 | 538 | VLDPEGDAQIDPNWVVLNQGREIVQTMNSDPGLA |
| SEQ ID NO: 287 | 539 | LDPEGDAQIDPNWVVLNQGREIVQTMNSDPGLAV |
| SEQ ID NO: 288 | 553 | VLNQGREIVQTMNSDPGLAVGYTAFNGVDFEGTF |
| SEQ ID NO: 289 | 554 | LNQGREIVQTMNSDPGLAVGYTAFNGVDFEGTFH |
| SEQ ID NO: 290 | 564 | MNSDPGLAVGYTAFNGVDFEGTFHVNTVTDDDYA |
| SEQ ID NO: 291 | 565 | NSDPGLAVGYTAFNGVDFEGTFHVNTVTDDDYAG |
| SEQ ID NO: 292 | 570 | LAVGYTAFNGVDFEGTFHVNTVTDDDYAGFIFGY |
| SEQ ID NO: 293 | 573 | GYTAFNGVDFEGTFHVNTVTDDDYAGFIFGYQDS |
| SEQ ID NO: 294 | 581 | DFEGTFHVNTVTDDDYAGFIFGYQDSSSFYVVMW |
| SEQ ID NO: 295 | 591 | VTDDDYAGFIFGYQDSSSFYVVMWKMEQTYWQA |
| SEQ ID NO: 296 | 592 | TDDDYAGFIFGYQDSSSFYVVMWKMEQTYWQAN |
| SEQ ID NO: 297 | 611 | VVMWKMEQTYWQANPFRAVAEPGIQLKAVKSST |
| SEQ ID NO: 298 | 612 | VMWKMEQTYWQANPFRAVAEPGIQLKAVKSSTG |
| SEQ ID NO: 299 | 621 | YWQANPFRAVAEPGIQLKAVKSSTGPGEQLRNAL |
| SEQ ID NO: 300 | 630 | VAEPGIQLKAVKSSTGPGEQLRNALWHTGDTESQ |
| SEQ ID NO: 301 | 631 | AEPGIQLKAVKSSTGPGEQLRNALWHTGDTESQV |
| SEQ ID NO: 302 | 638 | KAVKSSTGPGEQLRNALWHTGDTESQVRLLWKDP |
| SEQ ID NO: 303 | 640 | VKSSTGPGEQLRNALWHTGDTESQVRLLWKDPRN |
| SEQ ID NO: 304 | 641 | KSSTGPGEQLRNALWHTGDTESQVRLLWKDPRNV |
| SEQ ID NO: 305 | 643 | STGPGEQLRNALWHTGDTESQVRLLWKDPRNVGW |
| SEQ ID NO: 306 | 644 | TGPGEQLRNALWHTGDTESQVRLLWKDPRNVGWK |
| SEQ ID NO: 307 | 654 | LWHTGDTESQVRLLWKDPRNVGWKDKKSYRWFLQ |
| SEQ ID NO: 308 | 667 | LWKDPRNVGWKDKKSYRWFLQHRPQVGYIRVRFY |
| SEQ ID NO: 309 | 675 | GWKDKKSYRWFLQHRPQVGYIRVRFYEGPELVAD |
| SEQ ID NO: 310 | 693 | GYIRVRFYEGPELVADSNVVLDTTMRGGRLGVFC |
| SEQ ID NO: 311 | 698 | RFYEGPELVADSNVVLDTTMRGGRLGVFCFSQEN |

TABLE IX-continued

| SEQ ID NO | Amino-Terminal Amino Acid | Predicted BbHtrA-Generated Peptides; Cartilage oligomeric matrix protein (COMP, Uniprot Identifier P49747) |
|---|---|---|
| SEQ ID NO: 312 | 707 | ADSNVVLDTTMRGGRLGVFCFSQENIIWANLRYR |
| SEQ ID NO: 313 | 712 | VLDTTMRGGRLGVFCFSQENIIWANLRYRCNDTI |
| SEQ ID NO: 314 | 713 | LDTTMRGGRLGVFCFSQENIIWANLRYRCNDTIP |

Table X lists predicted BbHtrA-generated peptides; Human Decorin (Uniprot Identifier P07585)

TABLE X

| SEQ ID NO | Amino-Terminal Amino Acid | Predicted BbHtrA-Generated Peptides; Human Decorin (Uniprot Identifier P07585) |
|---|---|---|
| SEQ ID NO: 315 | 7 | LLLLAQVSWAGPFQQRGLFDFMLEDEASGIGPEV |
| SEQ ID NO: 316 | 9 | LLAQVSWAGPFQQRGLFDFMLEDEASGIGPEVPD |
| SEQ ID NO: 317 | 10 | LAQVSWAGPFQQRGLFDFMLEDEASGIGPEVPDD |
| SEQ ID NO: 318 | 50 | LGPVCPFRCQCHLRVVQCSDLGLDKVPKDLPPDT |
| SEQ ID NO: 319 | 71 | GLDKVPKDLPPDTTLLDLQNNKITEIKDGDFKNL |
| SEQ ID NO: 320 | 85 | LLDLQNNKITEIKDGDFKNLKNLHALILVNNKIS |
| SEQ ID NO: 321 | 94 | TEIKDGDFKNLKNLHALILVNNKISKVSPGAFTP |
| SEQ ID NO: 322 | 105 | KNLHALILVNNKISKVSPGAFTPLVKLERLYLSK |
| SEQ ID NO: 323 | 114 | NNKISKVSPGAFTPLVKLERLYLSKNQLKELPEK |
| SEQ ID NO: 324 | 118 | SKVSPGAFTPLVKLERLYLSKNQLKELPEKMPKT |
| SEQ ID NO: 325 | 119 | KVSPGAFTPLVKLERLYLSKNQLKELPEKMPKTL |
| SEQ ID NO: 326 | 121 | SPGAFTPLVKLERLYLSKNQLKELPEKMPKTLQE |
| SEQ ID NO: 327 | 124 | AFTPLVKLERLYLSKNQLKELPEKMPKTLQELRA |
| SEQ ID NO: 328 | 125 | FTPLVKLERLYLSKNQLKELPEKMPKTLQELRAH |
| SEQ ID NO: 329 | 135 | YLSKNQLKELPEKMPKTLQELRAHENEITKVRKV |
| SEQ ID NO: 330 | 137 | SKNQLKELPEKMPKTLQELRAHENEITKVRKVTF |
| SEQ ID NO: 331 | 142 | KELPEKMPKTLQELRAHENEITKVRKVTFNGLNQ |
| SEQ ID NO: 332 | 169 | TFNGLNQMIVIELGTNPLKSSGIENGAFQGMKKL |
| SEQ ID NO: 333 | 178 | VIELGTNPLKSSGIENGAFQGMKKLSYIRIADTN |
| SEQ ID NO: 334 | 182 | GTNPLKSSGIENGAFQGMKKLSYIRIADTNITSI |
| SEQ ID NO: 335 | 183 | TNPLKSSGIENGAFQGMKKLSYIRIADTNITSIP |
| SEQ ID NO: 336 | 189 | SGIENGAFQGMKKLSYIRIADTNITSIPQGLPPS |
| SEQ ID NO: 337 | 190 | GIENGAFQGMKKLSYIRIADTNITSIPQGLPPSL |
| SEQ ID NO: 338 | 195 | AFQGMKKLSYIRIADTNITSIPQGLPPSLTELHL |
| SEQ ID NO: 339 | 203 | SYIRIADTNITSIPQGLPPSLTELHLDGNKISRV |
| SEQ ID NO: 340 | 223 | LTELHLDGNKISRVDAASLKGLNNLAKLGLSFNS |
| SEQ ID NO: 341 | 234 | SRVDAASLKGLNNLAKLGLSFNSISAVDNGSLAN |
| SEQ ID NO: 342 | 239 | ASLKGLNNLAKLGLSFNSISAVDNGSLANTPHLR |
| SEQ ID NO: 343 | 240 | SLKGLNNLAKLGLSFNSISAVDNGSLANTPHLRE |

TABLE X-continued

| SEQ ID NO | Amino-Terminal Amino Acid | Predicted BbHtrA-Generated Peptides; Human Decorin (Uniprot Identifier P07585) |
|---|---|---|
| SEQ ID NO: 344 | 244 | LNNLAKLGLSFNSISAVDNGSLANTPHLRELHLD |
| SEQ ID NO: 345 | 245 | NNLAKLGLSFNSISAVDNGSLANTPHLRELHLDN |
| SEQ ID NO: 346 | 248 | AKLGLSFNSISAVDNGSLANTPHLRELHLDNNKL |
| SEQ ID NO: 347 | 249 | KLGLSFNSISAVDNGSLANTPHLRELHLDNNKLT |
| SEQ ID NO: 348 | 253 | SFNSISAVDNGSLANTPHLRELHLDNNKLTRVPG |
| SEQ ID NO: 349 | 258 | SAVDNGSLANTPHLRELHLDNNKLTRVPGGLAEH |
| SEQ ID NO: 350 | 260 | VDNGSLANTPHLRELHLDNNKLTRVPGGLAEHKY |
| SEQ ID NO: 351 | 266 | ANTPHLRELHLDNNKLTRVPGGLAEHKYIQVVYL |
| SEQ ID NO: 352 | 282 | TRVPGGLAEHKYIQVVYLHNNNISVVGSSDFCPP |
| SEQ ID NO: 353 | 283 | RVPGGLAEHKYIQVVYLHNNNISVVGSSDFCPPG |
| SEQ ID NO: 354 | 287 | GLAEHKYIQVVYLHNNNISVVGSSDFCPPGHNTK |
| SEQ ID NO: 355 | 297 | VYLHNNNISVVGSSDFCPPGHNTKKASYSGVSLF |
| SEQ ID NO: 356 | 305 | SVVGSSDFCPPGHNTKKASYSGVSLFSNPVQYWE |
| SEQ ID NO: 357 | 307 | VGSSDFCPPGHNTKKASYSGVSLFSNPVQYWEIQ |
| SEQ ID NO: 358 | 308 | GSSDFCPPGHNTKKASYSGVSLFSNPVQYWEIQP |
| SEQ ID NO: 359 | 323 | SYSGVSLFSNPVQYWEIQPSTFRCVYVRSAIQLG |
| SEQ ID NO: 360 | 326 | GVSLFSNPVQYWEIQPSTFRCVYVRSAIQLGNYK |
| SEQ ID NO: 361 | 328 | SLFSNPVQYWEIQPSTFRCVYVRSAIQLGNYK |
| SEQ ID NO: 362 | 330 | FSNPVQYWEIQPSTFRCVYVRSAIQLGNYK |
| SEQ ID NO: 363 | 331 | SNPVQYWEIQPSTFRCVYVRSAIQLGNYK |
| SEQ ID NO: 364 | 352 | AIQLGNYK |

Table XI lists predicted BbHtrA-generated peptides; Human Fibromodulin (Uniprot Identifier O068281.

TABLE XI

| SEQ ID NO | Amino-Terminal Amino Acid | Predicted BbHtrA-Generated Peptides; Human Fibromodulin (Uniprot Identifier Q06828) |
|---|---|---|
| SEQ ID NO: 365 | 5 | SLLLLAGLFSLSQAQYEDDPHWWFHYLRSQQSTY |
| SEQ ID NO: 366 | 6 | LLLLAGLFSLSQAQYEDDPHWWFHYLRSQQSTYY |
| SEQ ID NO: 367 | 8 | LLAGLFSLSQAQYEDDPHWWFHYLRSQQSTYYDP |
| SEQ ID NO: 368 | 9 | LAGLFSLSQAQYEDDPHWWFHYLRSQQSTYYDPY |
| SEQ ID NO: 369 | 11 | GLFSLSQAQYEDDPHWWFHYLRSQQSTYYDPYDP |
| SEQ ID NO: 370 | 12 | LFSLSQAQYEDDPHWWFHYLRSQQSTYYDPYDPY |
| SEQ ID NO: 371 | 38 | YYDPYDPYPYETYEPYPYGVDEGPAYTYGSPSPP |
| SEQ ID NO: 372 | 98 | KYLPFVPSRMKYVYFQNNQITSIQEGVFDNATGL |
| SEQ ID NO: 373 | 118 | TSIQEGVFDNATGLLWIALHGNQITSDKVGRKVF |
| SEQ ID NO: 374 | 124 | VFDNATGLLWIALHGNQITSDKVGRKVFSKLRHL |

TABLE XI-continued

| SEQ ID NO | Amino-Terminal Amino Acid | Predicted BbHtrA-Generated Peptides; Human Fibromodulin (Uniprot Identifier Q06828) |
|---|---|---|
| SEQ ID NO: 375 | 129 | TGLLWIALHGNQITSDKVGRKVFSKLRHLERLYL |
| SEQ ID NO: 376 | 151 | FSKLRHLERLYLDHNNLTRMPGPLPRSLRELHLD |
| SEQ ID NO: 377 | 161 | YLDHNNLTRMPGPLPRSLRELHLDHNQISRVPNN |
| SEQ ID NO: 378 | 169 | RMPGPLPRSLRELHLDHNQISRVPNNALEGLENL |
| SEQ ID NO: 379 | 178 | LRELHLDHNQISRVPNNALEGLENLTALYLQHNE |
| SEQ ID NO: 380 | 189 | SRVPNNALEGLENLTALYLQHNEIQEVGSSMRGL |
| SEQ ID NO: 381 | 196 | LEGLENLTALYLQHNEIQEVGSSMRGLRSLILLD |
| SEQ ID NO: 382 | 205 | LYLQHNEIQEVGSSMRGLRSLILLDLSYNHLRKV |
| SEQ ID NO: 383 | 216 | GSSMRGLRSLILLDLSYNHLRKVPDGLPSALEQL |
| SEQ ID NO: 384 | 225 | LILLDLSYNHLRKVPDGLPSALEQLYMEHNNVYT |
| SEQ ID NO: 385 | 227 | LLDLSYNHLRKVPDGLPSALEQLYMEHNNVYTVP |
| SEQ ID NO: 386 | 231 | SYNHLRKVPDGLPSALEQLYMEHNNVYTVPDSYF |
| SEQ ID NO: 387 | 245 | ALEQLYMEHNNVYTVPDSYFRGAPKLLYVRLSHN |
| SEQ ID NO: 388 | 246 | LEQLYMEHNNVYTVPDSYFRGAPKLLYVRLSHNS |
| SEQ ID NO: 389 | 257 | YTVPDSYFRGAPKLLYVRLSHNSLTNNGLASNTF |
| SEQ ID NO: 390 | 259 | VPDSYFRGAPKLLYVRLSHNSLTNNGLASNTFNS |
| SEQ ID NO: 391 | 271 | LYVRLSHNSLTNNGLASNTFNSSSLLELDLSYNQ |
| SEQ ID NO: 392 | 274 | RLSHNSLTNNGLASNTFNSSSLLELDLSYNQLQK |
| SEQ ID NO: 393 | 276 | SHNSLTNNGLASNTFNSSSLLELDLSYNQLQKIP |
| SEQ ID NO: 394 | 281 | TNNGLASNTFNSSSLLELDLSYNQLQKIPPVNTN |
| SEQ ID NO: 395 | 282 | NNGLASNTFNSSSLLELDLSYNQLQKIPPVNTNL |
| SEQ ID NO: 396 | 290 | FNSSSLLELDLSYNQLQKIPPVNTNLENLYLQGN |
| SEQ ID NO: 397 | 293 | SSLLELDLSYNQLQKIPPVNTNLENLYLQGNRIN |
| SEQ ID NO: 398 | 294 | SLLELDLSYNQLQKIPPVNTNLENLYLQGNRINE |
| SEQ ID NO: 399 | 295 | LLELDLSYNQLQKIPPVNTNLENLYLQGNRINEF |
| SEQ ID NO: 400 | 296 | LELDLSYNQLQKIPPVNTNLENLYLQGNRINEFS |
| SEQ ID NO: 401 | 297 | ELDLSYNQLQKIPPVNTNLENLYLQGNRINEFSI |
| SEQ ID NO: 402 | 302 | YNQLQKIPPVNTNLENLYLQGNRINEFSISSFCT |
| SEQ ID NO: 403 | 312 | NTNLENLYLQGNRINEFSISSFCTVVDVVNFSKL |
| SEQ ID NO: 404 | 314 | NLENLYLQGNRINEFSISSFCTVVDVVNFSKLQV |
| SEQ ID NO: 405 | 319 | YLQGNRINEFSISSFCTVVDVVNFSKLQVLRLDG |
| SEQ ID NO: 406 | 336 | VVDVVNFSKLQVLRLDGNEIKRSAMPADAPLCLR |
| SEQ ID NO: 407 | 337 | VDVVNFSKLQVLRLDGNEIKRSAMPADAPLCLRL |
| SEQ ID NO: 408 | 340 | VNFSKLQVLRLDGNEIKRSAMPADAPLCLRLASL |
| SEQ ID NO: 409 | 346 | QVLRLDGNEIKRSAMPADAPLCLRLASLIEI |
| SEQ ID NO: 410 | 348 | LRLDGNEIKRSAMPADAPLCLRLASLIEI |
| SEQ ID NO: 411 | 349 | RLDGNEIKRSAMPADAPLCLRLASLIEI |
| SEQ ID NO: 412 | 359 | AMPADAPLCLRLASLIEI |

TABLE XI-continued

| SEQ ID NO | Amino-Terminal Amino Acid | Predicted BbHtrA-Generated Peptides; Human Fibromodulin (Uniprot Identifier Q06828) |
|---|---|---|
| SEQ ID NO: 413 | 371 | ASLIEI |
| SEQ ID NO: 414 | 372 | SLIEI |

Example 17

Enzyme Linked Immunosorbent Assay (ELISA) for BbHtrA-Generated Protein Fragments (Biomarkers) from Mammalian Samples An exemplary ELISA is described here but other formulations embodying these principles also may be used, including multiplex ELISAs. Microtiter plate wells are coated with 100 µL of up to 20 µg/mL capture antibody (a monoclonal or polyclonal antibody (or a mixture of antibodies directed against several substrates) specifically immunoreactive with a BbHtrA substrate including, but not limited to, brevican, neurocan, versican, E-cadherin decorin, biglycan, fibromodulin, cartilage oligomeric matrix protein, and/or aggrecan in 0.1M bicarbonate buffer, pH 9.2, covered, and held at 4° C. for 16-18 h. Coating buffers may vary in type and pH, wash solutions may vary in constituents such as salt and detergent, or blocking agents may be vary to include reagents such as dry milk powder. Wells are washed 5 times in 100 mM phosphate buffer, 150 mM NaCl, and 0.05% Tween 20 to remove unbound capture antibodies, followed by the addition of 300 µL of blocking buffer containing 100 mM phosphate buffer, 150 mM NaCl and 0.2% BSA per well. The plates are incubated for 1 h at RT with rotation (150 rpm) followed by 5 washes with 100 mM phosphate buffer, 150 mM NaCl. 100 µL of each sample (whole blood, plasma, serum, urine, synovial fluid, cerebrospinal fluid) diluted in 100 mM phosphate buffer, 150 mM NaCl and 0.2% BSA is added to duplicate wells, and plates are incubated for 1 h at RT or 16 h at 4° C. with rotation. Wells are washed with 100 mM phosphate buffer, 150 mM NaCl, and 0.05% Tween 20 to remove unbound antigens, and then 100 µL per well of up to 10 µg/mL detection antibody in 150 mM NaCl and 0.2% BSA is added and incubated 1 h at RT with rotation. Detection antibodies include monoclonal antibodies conjugated with a detectable label such as horse radish peroxidase (HRP) or alkaline phosphatase (AP), but not limited to these enzymes, that are specifically immunoreactive with the BbHtrA-generated candidate substrate protein terminus which is exposed after BbHtrA digestion of a candidate substrate protein including, but not limited to, brevican, neurocan, versican, E-cadherin decorin, biglycan, fibromodulin, cartilage oligomeric matrix protein, and/or aggrecan Wells are washed with 100 mM phosphate buffer, 150 mM NaCl, and 0.05% Tween 20 to remove unbound detection antibody. Biomarker-detection antibody complexes are detected by the addition of 100 µL per well of 2 mg/mL p-nitrophenyl phosphate (for AP labeled detection antibodies) or 3,5,3',5'-tetramethylbenzidine (for HRP labeled detection antibodies). The reaction is stopped by the addition of 100 µL per well of 0.75M NaOH (for AP) or 2M $H_2SO_4$ (for HRP) and a spectrophotometer is used to measure the optical density of wells at 405 nm (for AP) or 450 nm (for HRP). Quantitation of biomarker levels in samples is achieved by comparing values obtained from samples with those generated by a standard curve of serial dilutions of known concentrations of BbHtrA-generated biomarkers diluted in control uninfected body fluid. Values from subject samples are then compared to samples from healthy individuals and patients with other diseases.

Example 18

Enzyme Linked Immunosorbent Assay (ELISA) for BbHtrA-Induced Cytokines from Mammalian Samples An exemplary ELISA is described here but other formulations embodying these principles also may be used, including multiplex ELISAs. Microtiter plate wells are coated with 100 µL of up to 20 µg/mL capture antibody (a monoclonal or polyclonal antibody (or a mixture of antibodies directed against several substrates) specifically immunoreactive with a BbHtrA-induced cytokine including, but not limited to CXCL1, CCL1, CCL2, CCL5, sICAM-1, IL-6, IL-8 in 0.1M bicarbonate buffer, pH 9.2, covered, and held at 4° C. for 16-18 h. Coating buffers may vary in type and pH, wash solutions may vary in constituents such as salt and detergent, or blocking agents may be vary to include reagents such as dry milk powder. Wells are washed 5 times in 100 mM phosphate buffer, 150 mM NaCl, and 0.05% Tween 20 to remove unbound capture antibodies, followed by the addition of 300 µL of blocking buffer containing 100 mM phosphate buffer, 150 mM NaCl and 0.2% BSA per well. The plates are incubated for 1 h at RT with rotation (150 rpm) followed by 5 washes with 100 mM phosphate buffer, 150 mM NaCl. 100 µL of each sample (whole blood, plasma, serum, urine, synovial fluid, cerebrospinal fluid) diluted in 100 mM phosphate buffer, 150 mM NaCl and 0.2% BSA is added to duplicate wells, and plates are incubated for 1 h at RT or 16 h at 4° C. with rotation. Wells are washed with 100 mM phosphate buffer, 150 mM NaCl, and 0.05% Tween 20 to remove unbound antigens, and then 100 µL per well of up to 10 µg/mL detection antibody in 150 mM NaCl and 0.2% BSA is added and incubated 1 h at RT with rotation. Detection antibodies include monoclonal antibodies conjugated with a detectable label such as horse radish peroxidase (HRP) or alkaline phosphatase (AP), but not limited to these enzymes, that are specifically immunoreactive with a BbHtrA-induced cytokine including but not limited to CXCL1, CCL1, CCL2, CCL5, sICAM-1, IL-6, IL-8. Wells are washed with 100 mM phosphate buffer, 150 mM NaCl, and 0.05% Tween 20 to remove unbound detection antibody. Cytokine-detection antibody complexes are detected by the addition of 100 µL per well of 2 mg/mL p-nitrophenyl phosphate (for AP labeled detection antibodies) or 3,5,3',5'-tetramethylbenzidine (for HRP labeled detection antibodies). The reaction is stopped by the addition of 100 µL per well of 0.75M NaOH (for AP) or 2M $H_2SO_4$ (for HRP) and a spectrophotometer is used to measure the optical density of wells at 405 nm (for AP) or 450 nm (for HRP). Quantitation of cytokine levels in samples is achieved by comparing values obtained from samples with those generated by a standard curve of serial dilutions of known concentrations of BbHtrA-induced bytokines diluted in control uninfected body fluid. Values from subject samples are then compared to samples from healthy individuals and patients with other diseases.

BbHtrA-generated protein fragment biomarkers and BbHtrA-induced cytokines optionally can be measured independently or at the same time in microplate, membrane, or glass-based microarray immunoassays or multi-plex bead based immunoassay.

Example 19

Assay for Activity of BbHtrA Isolated from Mammalian Samples

An exemplary activity assay is described here but other formulations embodying these principles also may be used. Microtiter plates or magnetic beads are coated with 100 µL of up to 20 µg/mL capture antibody (a monoclonal or polyclonal antibody) specifically immunoreactive with *Borrelia burgdorferi* sensu lato BbHtrA. in 0.1M bicarbonate buffer, pH 9.2, covered, and held at 4° C. for 16-18 h. Coating buffers may vary in type and pH, wash solutions may vary in constituents such as salt and detergent, or blocking agents may be vary to include reagents such as dry milk powder. Wells are washed 5 times in 100 mM phosphate buffer, 150 mM NaCl, and 0.05% Tween 20 to remove unbound capture antibodies, followed by the addition of 300 µL of blocking buffer containing 100 mM phosphate buffer, 150 mM NaCl and 0.2% BSA per well. Capture antibodies are adsorbed for 1 h at RT with rotation (150 rpm) followed by 5 washes with 100 mM phosphate buffer, 150 mM NaCl. BbHtrA isolation/enrichment: 100 µL or an appropriate volume of each sample (whole blood, plasma, serum, synovial fluid, cerebrospinal fluid) or control (serial dilutions of recombinant BbHtrA) diluted in 100 mM phosphate buffer, 150 mM NaCl and 0.2% BSA is added in duplicate and samples are incubated for 1 h at RT or 16 h at 4° C. with rotation. Wells are washed with 100 mM phosphate buffer, 150 mM NaCl, and 0.05% Tween 20 to remove unbound antigens. BbHtrA substrate is then added including but not limited to fluorescein isothiocyanate-labeled casein (FITC-casein) or para-nitro-aniline (pNA) labeled chromogenic DPMFKLV-pNA. Alternatively, a substrate composed of an FITC- or pNA-labeled peptide from a BbHtrA substrate including, but not limited to, aggrecan, decorin, biglycan, brevican, neurocan, versican, fibronectin, fibromodulin, cartilage oligomeric matrix protein, and/or E-cadherin is added. Labeled substrates are incubated with isolated BbHtrA and incubated for 1 h at RT or 16 h at 4° C. with rotation to allow for substrate degradation. Presence of BbHtrA is indicated by BbHtrA cleavage of these substrates which generates a measurable fluorescent or colorometric signal detectable by fluorimetry or spectrophotometry. Alternatively, reactions are subjected to mass spectrometry to identify BbHtrA-generated degradation products. Quantitation of BbHtrA activity in samples is achieved by comparing values obtained from samples with those generated by a standard curve of serial dilutions of known concentrations of recombinant BbHtrA. Values from subject samples are then compared to samples from healthy individuals and patients with other diseases.

Example 20

Mass Spectrometric Analysis of Mammalian Samples

Prior to mass spectrometric analysis, a sample obtained from a subject having, or suspected of having, Lyme disease and intended for mass spectrometric analysis is optionally and preferably subjected to immunodepletion chromatography to remove high abundance materials, such as serum proteins. Alternatively, reverse phase chromatography is used to isolate peptides present in the sample. For absolute quantitation, samples are spiked with known concentrations of an appropriate internal standard. Mass spectrometric analysis of the subject sample is then performed, for example as described in Examples 13 and 14.

Example 21

In this example, peptides of SEQ IDs 52-69 are synthesized using standard peptide synthesis methodology. The peptides are conjugated to a carrier protein such as BSA, MBP or KLH for use in production of antibodies which specifically recognize the amino terminal 5-10 amino acid residues of these peptides, a "neo-epitope."

Peptide-carrier protein fusions are used to immunize mice for antibody production and purification using standard methods known to those skilled in the art. Hybridoma cells are screened for those which specifically recognize the amino terminal 5-10 amino acid residues. Clones producing monoclonal antibodies specifically recognizing BbHtrA-generated neo-epitopes are identified by competition ELISAs and meet the following criteria: recognition of the BbHtrA-generated amino terminus, lack of recognition of the intact substrate or a peptide spanning the cleavage site or truncations thereof and lack of recognition of the carrier protein. Standard methods are used to obtain large quantities of the purified monoclonal anti-neo-epitope antibodies specific for BbHtrA-generated peptides.

Monoclonal Antibody Production

Female specific-pathogen-free inbred C57BL/6 mice can be used at 5 to 6 weeks of age. Upon arrival the mice are quarantined for 2 weeks and acclimated to a 12-hour light/dark cycle. Animals are housed in ventilated microisolator cages under environmentally controlled conditions. The animal rooms are monitored for specific pathogens through a disease surveillance and a sentinel animal program. Food and water are provided ad libitum.

Mice are immunized with a BbHtrA cleavage product conjugated to a carrier protein such as Keyhole Limpet Hemocyanin by subcutaneous or intraperitoneal injection. Booster injections of the antigen are given biweekly and titers can be checked using blood drawn from the tail vein. The spleens are removed aseptically for hybridoma production days to weeks after antigen injection.

Cell viability of exponentially growing myeloma cells is checked microscopically prior to use and the myeloma cultures are split at an appropriate time prior to the fusion to ensure mitotically active cells.

Hybridomas are produced using standard polyethyleneglycol-based cell fusion techniques. Cell cultures can be maintained in Dulbecco's Modified Eagle Medium, supplemented with 1 mM pyruvate, 100 units/mL penicillin, 100 µg/mL streptomycin and 0.292 mg/mL L-glutamine, 100 µM sodium hypoxanthine, 16 µM thymidine and 10% fetal calf serum and 100 units/mL IL-6.

After about seven days, culture fluid is recovered from each well and screened for BbHtrA cleavage product-reactive IgG, such as by ELISA.

Sequences

SEQ ID NO:1 *Borrelia burgdorferi* HtrA (BB0104, BbHtrA) amino acid sequence, Catalytic triad is at amino acid positions 119H, 149D and 226S.

MEKKFFSGFLLSFLALSIGFFIGMHYLASNRSNIVFAEEKDNTVRALQDS
FREVSKKILPSSVEVHATGVIKQSFPIPFFFFDMPEFDSERKSNWAGSGV
IIGRDSQKKSLFYVVTNSHVVDKATELEVVSYDKKKHKAKLIGKDEKKDI
ALISFESDDATIKVADLGDSDKLEIGDWVMAVGSPFQFSFTVTAGIVSGL
QRSANPNLQSRNLFIQTDAAINRGNSGGPLVNIKGEVIGINAWIASNSGG
NIGLGFAIPVNNIKSTVDFFLKGKKIESAWLGISFYPLKTRDSEVLKSLG
VESNDVSAAIIASLYPGSPAVKSGLRAGDIIMKVNGVSMSVFQDVTSYIS
DFYAGEKVNVEILRGNVKKNIEIVLAVRPKDKELSSSKMLPGFVVYPLVE
DIKAQLNLRNWIKGVVVDYIDKNLASNIKMKSGDVILSVNSKSVSNLREF
YDALEVGKNTYKILRGNDSFKITF

SEQ ID NO:2 *Borrelia burgdorferi* HtrA (BB0104, BbHtrA) nucleic acid sequence

CTAAAATGTAATTTTAAAAGAATCGTTTCCTCTCAAAATTTTATAAGTAT
TTTTTCCAACCTCAAGAGCATCATAAAATTCTCTTAAATTAGAAACACTT
TTTGAATTTACAGAAAGAATTACATCTCCTGATTTCATTTTAATATTTGA
TGCTAAATTTTTATCAATATAATCAACAACAACACCTTTAATCCAATTTC
TTAAATTAAGCTGAGCTTTAATATCCTCAACCAATGGATACACAACAAAG
CCTGGAAGCATCTTTGAAGAAGAAAGCTCTTTATCCTTAGGTCTAACAGC
AAGAACAATCTCAATATTTTTTTTGACATTGCCTCTTAAGATTTCTACAT
TTACTTTCTCACCAGCATAAAAATCACTAATATATGATGTAACATCTTGA
AAAACGCTCATGGAAACCCCATTAACCTTCATAATAATATCCCCTGCCCT
AAGCCCTGATTTAACAGCGGGTGAACCCGGATAAAGAGAAGCAATAATTG
CAGCTGAAACATCATTACTTTCAACCCCTAAGCTTTTTAGCACCTCAGAA
TCTCTTGTCTTTAGCGGATAAAAAGAAATTCCAAGCCAAGCCGATTCAAT
TTTTTTACCTTTAAGGAAAAAATCTACAGTGCTTTTAATATTGTTAACAG
GAATTGCAAAACCCAACCCAATATTTCCGCCAGAATTTGAAGCTATCCAA
GCATTAATTCCAATAACCTCGCCCTTTATATTTACAAGAGGACCACCTGA
ATTACCCCTGTTGATTGCAGCATCGGTTTGAATAAACAGATTCCTTGATT
GCAAATTAGGATTTGCAGAACGTTGCAATCCACTTACAATACCTGCTGTA
ACTGTAAAACTAAATTGAAAAGGGCTGCCCACTGCCATAACCCAATCACC
TATTTCAAGCTTATCACTATCTCCAAGATCAGCTACTTTAATAGTTGCGT
CATCACTTTCAAAGCTAATAAGGGCAATATCCTTTTTTTCATCTTTGCCA
ATTAACTTAGCCTTGTGCTTTTTTTTATCATAAGATACAACTTCAAGTTC
AGTTGCCTTATCTACCACATGACTATTCGTAACCACATAAAATAATGATT
TTTTTTGAGAATCTCTACCAATTATTACTCCAGACCCCGCCCAATTGCTT
TTTCTCTCAGAATCAAATTCTGGCATATCAAAAAGAAAAATGGAATAGG
AAAACTCTGCTTGATTACCCCTGTTGCATGAACTTCCACAGATGATGGTA
AAATTTTCTTGGAAACCTCTCTAAAAGAATCTTGTAAGGCTCGTACGGTA
TTGTCCTTTTCTTCTGCAAAAACAATGTTGCTTCTATTAGAAGCTAAATA

ATGCATCCCAATAAAAAATCCAATACTCAAAGCCAAAAAACTAAGAAGAA
ATCCAGAAAAAAACTTTTTTTCCAC

SEQ ID NO:3 *Borrelia burgdorferi* HtrA (BB0104, BbHtrA$^{S226A}$) amino acid sequence. Mutation site S→A is at position 226. In this sequence the signal peptide is amino acids 1-37 and the mature protein is amino acid 38-474.

MEKKFFSGFLLSFLALSIGFFIGMHYLASNRSNIVFAEEKDNTVRALQDS
FREVSKKILPSSVEVHATGVIKQSFPIPFFFFDMPEFDSERKSNWAGSGV
IIGRDSQKKSLFYVVTNSHVVDKATELEVVSYDKKKHKAKLIGKDEKKDI
ALISFESDDATIKVADLGDSDKLEIGDWVMAVGSPFQFSFTVTAGIVSGL
QRSANPNLQSRNLFIQTDAAINRGNAGGPLVNIKGEVIGINAWIASNSGG
NIGLGFAIPVNNIKSTVDFFLKGKKIESAWLGISFYPLKTRDSEVLKSLG
VESNDVSAAIIASLYPGSPAVKSGLRAGDIIMKVNGVSMSVFQDVTSYIS
DFYAGEKVNVEILRGNVKKNIEIVLAVRPKDKELSSSKMLPGFVVYPLVE
DIKAQLNLRNWIKGVVVDYIDKNLASNIKMKSGDVILSVNSKSVSNLREF
YDALEVGKNTYKILRGNDSFKITF

SEQ ID NO:4 *Borrelia burgdorferi* HtrA (BB0104, BbHtrA$^{S226A}$) nucleic acid sequence CTAAAATGTAATTTTAAAAGAATCGTTTCCTCTCAAAATTTTATAAGTAT
TTTTTCCAACCTCAAGAGCATCATAAAATTCTCTTAAATTAGAAACACTT
TTTGAATTTACAGAAAGAATTACATCTCCTGATTTCATTTTAATATTTGA
TGCTAAATTTTTATCAATATAATCAACAACAACACCTTTAATCCAATTTC
TTAAATTAAGCTGAGCTTTAATATCCTCAACCAATGGATACACAACAAAG
CCTGGAAGCATCTTTGAAGAAGAAAGCTCTTTATCCTTAGGTCTAACAGC
AAGAACAATCTCAATATTTTTTTTGACATTGCCTCTTAAGATTTCTACAT
TTACTTTCTCACCAGCATAAAAATCACTAATATATGATGTAACATCTTGA
AAAACGCTCATGGAAACCCCATTAACCTTCATAATAATATCCCCTGCCCT
AAGCCCTGATTTAACAGCGGGTGAACCCGGATAAAGAGAAGCAATAATTG
CAGCTGAAACATCATTACTTTCAACCCCTAAGCTTTTTAGCACCTCAGAA
TCTCTTGTCTTTAGCGGATAAAAAGAAATTCCAAGCCAAGCCGATTCAAT
TTTTTTACCTTTAAGGAAAAAATCTACAGTGCTTTTAATATTGTTAACAG
GAATTGCAAAACCCAACCCAATATTTCCGCCAGAATTTGAAGCTATCCAA
GCATTAATTCCAATAACCTCGCCCTTTATATTTACAAGAGGACCACCTGC
ATTACCCCTGTTGATTGCAGCATCGGTTTGAATAAACAGATTCCTTGATT
GCAAATTAGGATTTGCAGAACGTTGCAATCCACTTACAATACCTGCTGTA
ACTGTAAAACTAAATTGAAAAGGGCTGCCCACTGCCATAACCCAATCACC
TATTTCAAGCTTATCACTATCTCCAAGATCAGCTACTTTAATAGTTGCGT
CATCACTTTCAAAGCTAATAAGGGCAATATCCTTTTTTTCATCTTTGCCA
ATTAACTTAGCCTTGTGCTTTTTTTTATCATAAGATACAACTTCAAGTTC
AGTTGCCTTATCTACCACATGACTATTCGTAACCACATAAAATAATGATT TTTTTTGAGAATCTCTACCAATTATTACTCCAGACCCCGCCCAATTGCTT
TTTCTCTCAGAATCAAATTCTGGCATATCAAAAAAGAAAAATGGAATAGG
AAAACTCTGCTTGATTACCCCTGTTGCATGAACTTCCACAGATGATGGTA
AAATTTTCTTGGAAACCTCTCTAAAAGAATCTTGTAAGGCTCGTACGGTA
TTGTCCTTTTCTTCTGCAAAAACAATGTTGCTTCTATTAGAAGCTAAATA
ATGCATCCCAATAAAAAATCCAATACTCAAAGCCAAAAAACTAAGAAGAA
ATCCAGAAAAAAACTTTTTTTCCAC SEQ ID NO:5 *Borrelia garinii* HtrA (BG0105) amino acid sequence MEKKFFSGFILSFLALGIGFFIGMHYLDSNRSNIVFAEEKDNTVQALQDS
FREVSKKILSSSVEVHATGVIKQSFPIPFFFFDMPEFDSERKSNWAGSGV
IIGRDSQKKSLFYVVTNSHVVDKATELEVVSYDKKKHKAKLIGKDEKKDI
ALISFESDDATIKVADLGDSDKLEIGDWVMAVGSPFQFSFTVTAGIVSGL
QRSANPNLQSRNLFIQTDAAINRGNSGGPLVNIKGEVIGINAWIASNSGG
NIGLGFAIPVNNIKSTVDFFLKGKKIESAWLGISFYPLKTRDSEVLKSLG
VEGKDVSAAIIASLYPGSPAVKSGLKAGDIIVKVNGVSMSVFQDVTSYIS
DFYAGEKVNVEILRGNVKKNIEIVLAVRPKDKELSSSKMLPGFIVYPLVE
DIKAQLNLRNWIKGVVVDYIDKNLASNIKMKSGDVILSVNSQSVSNLREF
YDALKIGKNTYKILRGNDSFKISF SEQ ID NO:6 *Borrelia garinii* HtrA (BG0105) nucleic acid sequence CTAAAACGAAATTTTAAAAGAATCATTTCCTCTTAAAATTTTATAAGTAT
TTTTTCCAATCTTAAGAGCATCATAAAATTCTCTTAAATTAGAAACACTT
TGTGAATTTACAGAAAGAATCACATCTCCTGATTTCATCTTAATATTTGA
TGCTAAATTTTTATCAATATAATCAACAACAACGCCTTTAATCCAATTTC
TTAAATTAAGCTGAGCTTTAATATCCTCAACTAATGGATACACAATAAAA
CCTGGAAGCATTTTGGAAGAAGAAAGTTCTTTATCCTTAGGTCTAACAGC
AAGAACAATCTCAATATTTTTTTGACATTACCTCTTAAAATTTCTACAT
TTACTTTCTCACCAGCATAAAAATCGCTAATATATGATGTAACATCTTGA
AAAACACTCATAGAAACCCATTAACCTTAACAATAATATCGCCTGCTTT
AAGCCCTGACTTAACGGCAGGTGAACCTGGATAAAGAGAGGCAATAATTG
CAGCTGAAACATCCTTACCTTCAACTCCTAAGCTTTTTAGTACTTCAGAA
TCTCTTGTCTTTAAAGGATAAAAGAAATTCCAAGCCATGCTGATTCAAT
TTTTTTACCTTTAAGAAAAAATCTACAGTACTTTTAATATTATTAACAG
GAATTGCAAAACCTAACCCAATATTTCCTCCAGAATTTGAAGCTATCCAA
GCATTAATTCCAATAACTTCACCTTTTATATTTACAAGAGGACCGCCTGA
ATTACCTCTGTTGATTGCAGCATCAGTTTGAATAAATAAATTCCTTGATT
GTAAATTAGGATTTGCAGAGCGTTGTAATCCACTTACAATACCTGCTGTA
ACTGTAAAACTAAATTGAAAAGGACTACCTACTGCCATAACCCAATCACC
TATTTCAAGCTTATCACTATCTCCAAGATCAGCTACTTTAATAGTTGCAT
CATCACTTTCAAAGCTAATAAGAGCAATATCTTTTTTTTCATCTTTGCCA
ATTAACTTAGCCTTGTGCTTTTTTTTATCATAAGACACAACTTCAAGTTC
AGTTGCCTTATCTACTACATGACTATTTGTAACCACATAAAATAATGATT
TTTTTTGAGAATCCCTACCAATTATTACTCCAGACCCTGCCCAATTGCTT
TTTCTCTCAGAATCAAATTCTGGCATATCAAAAAAGAAAAATGGAATAGG
AAAACTCTGTTTAATTACCCCGGTTGCATGAACTTCTACGGACGATGATA
AAATTTTCTTGGAAACTTCCCTAAAAGAATCTTGTAAGGCTTGTACTGTA
TTGTCTTTTCTTCTGCAAAAACAATATTGCTTCTATTAGAATCTAAGTA
ATGCATTCCAATAAAAAAACCAATACCTAAAGCCAAAAAACTGAGAATAA
ATCCAGAAAAAACTTTTTTTCCAC SEQ ID NO:7 *Borrelia afzelii* HtrA (BafACA1_0105) amino acid sequence MEKKFFSGFILSFLALGIGFFIGMHYLDSNRSNIVFAEEKGNTVQTLQDS
FREVSKKILPSSVEVHATGVIKQSFPIPFFFFDMPEFDSERKSNWAGSGV
IIGRDSKNKSLFYVVTNSHVVDKATELEVVSYDKKKHKAKLIGKDEKKDI
ALISFESDDATIKVADLGDSDKLEIGDWVMAVGSPFQFSFTVTAGIVSGL
QRSANPNLQSRNLFIQTDAAINRGNSGGPLVNTKGEVIGINAWIASNSGG
NIGLGFAIPVNNIKSTVDFFLKGKKIESAWLGISFYPLKTRDPEVLKSLG
VEGDDVPAAIIASLYPGSPAIKSGLRAGDIIVKVNGVPMSVFQDVTSYIS
DFYAGEKINVEILRGNVKKNIEIILAVRPKDKELSSSKMFPGFVVYPLVE
DIKAQLNLRNWTKGVVVDYIDKNLASNIKMKSGDVILSVNSKSVSNLREF
YDALEIGKNTYNILRGNDSFKISF SEQ ID NO:8 *Borrelia afzelii* HtrA (BafACA1_0105) nucleic acid sequence CTAAAACGAAATTTTAAAAGAATCGTTTCCTCTTAAAATGTTATAAGTAT
TTTTTCCAATCTCAAGAGCATCATAAAATTCTCTTAAATTAGAAACACTT
TTTGAATTTACAGAAAGAATTACATCTCCTGATTTCATCTTAATATTTGA
TGCTAAATTTTTATCAATATAATCAACAACAACGCCTTTAGTCCAATTTC
TTAAATTAAGCTGAGCTTTAATATCTTCAACTAATGGATACACAACAAAA
CCTGGAAACATTTTTGAAGAAGAAAGCTCTTTGTCCTTGGGTCTAACAGC
AAGAATAATCTCAATATTCTTTTTAACATTACCTCTTAAAATTTCTACAT
TGATTTCTCACCAGCATAAAAATCGCTAATATATGATGTAACGTCTTGA
AAAACACTCATGGGAACTCCATTAACCTTCACAATAATGTCTCCCGCTCT
AAGCCCTGACTTAATAGCAGGTGAACCTGGATAAAGAGAAGCAATAATTG
CAGCTGGAACATCATCACCTTCAACCCCAAGCTTTTTAGCACTTCAGGA
TCTCTTGTCTTTAATGGGTAAAAGAAATTCCAAGCCATGCTGATTCAAT
TTTTTTACCTTTAAGGAAAAAATCTACGGTACTTTTAATATTGTTAACAG
GAATTGCAAAACCTAACCCAATATTTCCACCAGAATTTGAAGCTATCCAA
GCATTAATCCCAATAACTTCACCTTTTGTATTTACAAGAGGTCCACCTGA -continued
ATTACCTCTATTGATTGCAGCATCAGTTTGAATAAATAAATTTCTTGATT

GTAAATTAGGATTTGCAGAACGTTGCAATCCACTTACAATACCTGCTGTA

ACTGTAAAACTAAATTGAAAAGGGCTACCTACCGCCATAACCCAATCACC

TATTTCAAGCTTATCACTATCCCCAAGATCAGCCACTTTAATAGTTGCAT

CATCACTTTCAAAGCTAATAAGCGCAATATCCTTTTTTTCATCTTTGCCA

ATTAACTTAGCCTTATGCTTTTCTTATCATAAGATACAACTTCAAGTTC

AGTTGCCTTATCTACTACATGACTATTGGTAACTACATAAAATAATGATT

TATTTTTGGAATCTCTACCAATTATTACTCCAGACCCTGCCCAATTGCTT

TTTCTCTCAGAATCAAATTCTGGCATATCAAAAAAGAAAAATGGAATAGG

AAAACTCTGCTTAATTACCCCTGTTGCATGAACTTCTACAGATGATGGTA

AAATTTTCTTGGAAACTTCTCTAAAAGAGTCTTGCAAGGTTTGTACTGTA

TTACCCTTTTCTTCTGCAAAAACAATGTTACTTCTATTAGAATCTAAATA

ATGCATCCCAATAAAAAACCCAATACCCAAAGCTAAAAGCTAAGAATAA

ATCCAGAAAAAAACTTTTTTTCCAC

SEQ ID NO:9 *Borrelia burgdorferi* HtrA (BB0104, BbHtrA) amino acid sequence without signal peptide, Catalytic triad is at amino acid positions corresponding to 119H, 149D and 226S in the full-length protein; here Catalytic triad is at amino acid positions 82H, 112D and 189S.

EEKDNTVRALQDSFREVSKKILPSSVEVHATGVIKQSFPIPFFFFDMPEF

DSERKSNWAGSGVIIGRDSQKKSLFYVVTNSHVVDKATELEVVSYDKKKH

KAKLIGKDEKKDIALISFESDDATIKVADLGDSDKLEIGDWVMAVGSPFQ

FSFTVTAGIVSGLQRSANPNLQSRNLFIQTDAAINRGNSGGPLVNIKGEV

IGINAWIASNSGGNIGLGFAIPVNNIKSTVDFFLKGKKIESAWLGISFYP

LKTRDSEVLKSLGVESNDVSAAIIASLYPGSPAVKSGLRAGDIIMKVNGV

SMSVFQDVTSYISDFYAGEKVNVEILRGNVKKNIEIVLAVRPKDKELSSS

KMLPGFVVYPLVEDIKAQLNLRNWIKGVVVDYIDKNLASNIKMKSGDVIL

SVNSKSVSNLREFYDALEVGKNTYKILRGNDSFKITF

SEQ ID NO:10 *Borrelia burgdorferi* HtrA (BB0104, BbHtrA) nucleic acid sequence without signal peptide

CTAAAATGTAATTTTAAAAGAATCGTTTCCTCTCAAAATTTTATAAGTAT

TTTTTCCAACCTCAAGAGCATCATAAAATTCTCTTAAATTAGAAACACTT

TTTGAATTTACAGAAAGAATTACATCTCCTGATTTCATTTTAATATTTGA

TGCTAAATTTTTATCAATATAATCAACAACAACACCTTTAATCCAATTTC

TTAAATTAAGCTGAGCTTTAATATCCTCAACCAATGGATACACAACAAAG

CCTGGAAGCATCTTTGAAGAAGAAAGCTCTTTATCCTTAGGTCTAACAGC

AAGAACAATCTCAATATTTTTTTGACATTGCCTCTTAAGATTTCTACAT

TTACTTTCTCACCAGCATAAAAATCACTAATATATGATGTAACATCTTGA

AAAACGCTCATGGAAACCCCATTAACCTTCATAATAATATCCCCTGCCCT

AAGCCCTGATTTAACAGCGGGTGAACCCGGATAAAGAGAAGCAATAATTG

CAGCTGAAACATCATTACTTTCAACCCCTAAGCTTTTTAGCACCTCAGAA

TCTCTTGTCTTTAGCGGATAAAAAGAAATTCCAAGCCAAGCCGATTCAAT

TTTTTTACCTTTAAGGAAAAAATCTACAGTGCTTTTAATATTGTTAACAG

GAATTGCAAAACCCAACCCAATATTTCCGCCAGAATTTGAAGCTATCCAA

GCATTAATTCCAATAACCTCGCCCTTTATATTTACAAGAGGACCACCTGA

ATTACCCCTGTTGATTGCAGCATCGGTTTGAATAAACAGATTCCTTGATT

GCAAATTAGGATTTGCAGAACGTTGCAATCCACTTACAATACCTGCTGTA

ACTGTAAAACTAAATTGAAAAGGGCTGCCCACTGCCATAACCCAATCACC

TATTTCAAGCTTATCACTATCTCCAAGATCAGCTACTTTAATAGTTGCGT

CATCACTTTCAAAGCTAATAAGGGCAATATCCTTTTTTTCATCTTTGCCA

ATTAACTTAGCCTTGTGCTTTTTTTTATCATAAGATACAACTTCAAGTTC

AGTTGCCTTATCTACCACATGACTATTCGTAACCACATAAAATAATGATT

TTTTTTGAGAATCTCTACCAATTATTACTCCAGACCCCGCCCAATTGCTT

TTTCTCTCAGAATCAAATTCTGGCATATCAAAAAGAAAATGGAATAGG

AAAACTCTGCTTGATTACCCCGTTGCATGAACTTCCACAGATGATGGTA

AAATTTTCTTGGAAACCTCTCTAAAAGAATCTTGTAAGGCTCGTACGGTA

TTGTCCTTTTCTTC

SEQ ID NO:11 *Borrelia burgdorferi* HtrA (BB0104, BbHtrA$^{S226A}$) amino acid sequence without signal peptide. Mutation site S→A is at position 189, analogous to position 226 in the full-length protein.

EEKDNTVRALQDSFREVSKKILPSSVEVHATGVIKQSFPIPFFFFDMPEF

DSERKSNWAGSGVIIGRDSQKKSLFYVVTNSHVVDKATELEVVSYDKKKH

KAKLIGKDEKKDIALISFESDDATIKVADLGDSDKLEIGDWVMAVGSPFQ

FSFTVTAGIVSGLQRSANPNLQSRNLFIQTDAAINRGNAGGPLVNIKGEV

IGINAWIASNSGGNIGLGFAIPVNNIKSTVDFFLKGKKIESAWLGISFYP

LKTRDSEVLKSLGVESNDVSAAIIASLYPGSPAVKSGLRAGDIIMKVNGV

SMSVFQDVTSYISDFYAGEKVNVEILRGNVKKNIEIVLAVRPKDKELSSS

KMLPGFVVYPLVEDIKAQLNLRNWIKGVVVDYIDKNLASNIKMKSGDVIL

SVNSKSVSNLREFYDALEVGKNTYKILRGNDSFKITF

SEQ ID NO:12 *Borrelia burgdorferi* HtrA (BB0104, BbHtrA$^{S226A}$) nucleic acid sequence without signal peptide

CTAAAATGTAATTTTAAAAGAATCGTTTCCTCTCAAAATTTTATAAGTAT

TTTTTCCAACCTCAAGAGCATCATAAAATTCTCTTAAATTAGAAACACTT

TTTGAATTTACAGAAAGAATTACATCTCCTGATTTCATTTTAATATTTGA

TGCTAAATTTTTATCAATATAATCAACAACAACACCTTTAATCCAATTTC

TTAAATTAAGCTGAGCTTTAATATCCTCAACCAATGGATACACAACAAAG

CCTGGAAGCATCTTTGAAGAAGAAAGCTCTTTATCCTTAGGTCTAACAGC

AAGAACAATCTCAATATTTTTTTGACATTGCCTCTTAAGATTTCTACAT

TTACTTTCTCACCAGCATAAAAATCACTAATATATGATGTAACATCTTGA

AAAACGCTCATGGAAACCCCATTAACCTTCATAATAATATCCCCTGCCCT

```
AAGCCCTGATTTAACAGCGGGTGAACCCGGATAAAGAGAAGCAATAATTG

CAGCTGAAACATCATTACTTTCAACCCCTAAGCTTTTTAGCACCTCAGAA

TCTCTTGTCTTTAGCGGATAAAAAGAAATTCCAAGCCAAGCCGATTCAAT

TTTTTTACCTTTAAGGAAAAAATCTACAGTGCTTTTAATATTGTTAACAG

GAATTGCAAAACCCAACCCAATATTTCCGCCAGAATTTGAAGCTATCCAA

GCATTAATTCCAATAACCTCGCCCTTTATATTTACAAGAGGACCACCTGC

ATTACCCCTGTTGATTGCAGCATCGGTTTGAATAAACAGATTCCTTGATT

GCAAATTAGGATTTGCAGAACGTTGCAATCCACTTACAATACCTGCTGTA

ACTGTAAAACTAAATTGAAAAGGGCTGCCCACTGCCATAACCCAATCACC

TATTTCAAGCTTATCACTATCTCCAAGATCAGCTACTTTAATAGTTGCGT

CATCACTTTCAAAGCTAATAAGGGCAATATCCTTTTTTTCATCTTTGCCA

ATTAACTTAGCCTTGTGCTTTTTTTTATCATAAGATACAACTTCAAGTTC

AGTTGCCTTATCTACCACATGACTATTCGTAACCACATAAAATAATGATT

TTTTTTGAGAATCTCTACCAATTATTACTCCAGACCCCGCCCAATTGCTT

TTTCTCTCAGAATCAAATTCTGGCATATCAAAAAGAAAAATGGAATAGG

AAAACTCTGCTTGATTACCCCTGTTGCATGAACTTCCACAGATGATGGTA

AAATTTTCTTGGAAACCTCTCTAAAAGAATCTTGTAAGGCTCGTACGGTA

TTGTCCTTTTCTTC
```

SEQ ID NO:13 *Borrelia garinii* HtrA (BG0105) amino acid sequence without signal peptide

```
EEKDNTVQALQDSFREVSKKILSSSVEVHATGVIKQSFPIPFFFFDMPEF

DSERKSNWAGSGVIIGRDSQKKSLFYVVTNSHVVDKATELEVVSYDKKKH

KAKLIGKDEKKDIALISFESDDATIKVADLGDSDKLEIGDWVMAVGSPFQ

FSFTVTAGIVSGLQRSANPNLQSRNLFIQTDAAINRGNSGGPLVNIKGEV

IGINAWIASNSGGNIGLGFAIPVNNIKSTVDFFLKGKKIESAWLGISFYP

LKTRDSEVLKSLGVEGKDVSAAIIASLYPGSPAVKSGLKAGDIIVKVNGV

SMSVFQDVTSYISDFYAGEKVNVEILRGNVKKNIEIVLAVRPKDKELSSS

KMLPGFIVYPLVEDIKAQLNLRNWIKGVVVDYIDKNLASNIKMKSGDVIL

SVNSQSVSNLREFYDALKIGKNTYKILRGNDSFKISF
```

SEQ ID NO:14 *Borrelia garinii* HtrA (BG0105) nucleic acid sequence encoding the protein without the signal peptide

```
CTAAAACGAAATTTTAAAAGAATCATTTCCTCTTAAAATTTTATAAGTAT

TTTTTCCAATCTTAAGAGCATCATAAAATTCTCTTAAATTAGAAACACTT

TGTGAATTTACAGAAAGAATCACATCTCCTGATTTCATCTTAATATTTGA

TGCTAAATTTTATCAATATAATCAACAACAACGCCTTTAATCCAATTTC

TTAAATTAAGCTGAGCTTTAATATCCTCAACTAATGGATACACAATAAAA

CCTGGAAGCATTTTGGAAGAAGAAAGTTCTTTATCCTTAGGTCTAACAGC

AAGAACAATCTCAATATTTTTTTGACATTACCTCTTAAAATTTCTACAT

TTACTTTCTCACCAGCATAAAAATCGCTAATATATGATGTAACATCTTGA

AAAACACTCATAGAAACCCCATTAACCTTAACAATAATATCGCCTGCTTT
```

```
AAGCCCTGACTTAACGGCAGGTGAACCTGGATAAAGAGAGGCAATAATTG

CAGCTGAAACATCCTTACCTTCAACTCCTAAGCTTTTTAGTACTTCAGAA

TCTCTTGTCTTTAAAGGATAAAAAGAAATTCCAAGCCATGCTGATTCAAT

TTTTTTACCTTTAAGAAAAAAATCTACAGTACTTTTAATATTATTAACAG

GAATTGCAAAACCTAACCCAATATTTCCTCCAGAATTTGAAGCTATCCAA

GCATTAATTCCAATAACTTCACCTTTATATTTACAAGAGGACCGCCTGA

ATTACCTCTGTTGATTGCAGCATCAGTTTGAATAAATAAATTCCTTGATT

GTAAATTAGGATTTGCAGAGCGTTGTAATCCACTTACAATACCTGCTGTA

ACTGTAAAACTAAATTGAAAAGGACTACCTACTGCCATAACCCAATCACC

TATTTCAAGCTTATCACTATCTCCAAGATCAGCTACTTTAATAGTTGCAT

CATCACTTTCAAAGCTAATAAGAGCAATATCTTTTTTTCATCTTTGCCA

ATTAACTTAGCCTTGTGCTTTTTTTTATCATAAGACACAACTTCAAGTTC

AGTTGCCTTATCTACTACATGACTATTTGTAACCACATAAAATAATGATT

TTTTTTGAGAATCCCTACCAATTATTACTCCAGACCCTGCCCAATTGCTT

TTTCTCTCAGAATCAAATTCTGGCATATCAAAAAAGAAAAATGGAATAGG

AAAACTCTGTTTAATTACCCCGGTTGCATGAACTTCTACGGACGATGATA

AAATTTTCTTGGAAACTTCCCTAAAAGAATCTTGTAAGGCTTGTACTGTA

TTGTCTTTTCTTC
```

SEQ ID NO:15 *Borrelia afzelii* HtrA (BafACA1_0105) amino acid sequence without signal peptide

```
EEKGNTVQTLQDSFREVSKKILPSSVEVHATGVIKQSFPIPFFFFDMPEF

DSERKSNWAGSGVIIGRDSKNKSLFYVVTNSHVVDKATELEVVSYDKKKH

KAKLIGKDEKKDIALISFESDDATIKVADLGDSDKLEIGDWVMAVGSPFQ

FSFTVTAGIVSGLQRSANPNLQSRNLFIQTDAAINRGNSGGPLVNTKGEV

IGINAWIASNSGGNIGLGFAIPVNNIKSTVDFFLKGKKIESAWLGISFYP

LKTRDPEVLKSLGVEGDDVPAAIIASLYPGSPAIKSGLRAGDIIVKVNGV

PMSVFQDVTSYISDFYAGEKINVEILRGNVKKNIEIILAVRPKDKELSSS

KMFPGFVVYPLVEDIKAQLNLRNWTKGVVVDYIDKNLASNIKMKSGDVIL

SVNSKSVSNLREFYDALEIGKNTYNILRGNDSFKISF
```

SEQ ID NO:16 *Borrelia afzelii* HtrA (BafACA1_0105) nucleic acid sequence without signal peptide

```
CTAAAACGAAATTTTAAAAGAATCGTTTCCTCTTAAAATGTTATAAGTAT

TTTTTCCAATCTCAAGAGCATCATAAAATTCTCTTAAATTAGAAACACTT

TTTGAATTTACAGAAAGAATTACATCTCCTGATTTCATCTTAATATTTGA

TGCTAAATTTTATCAATATAATCAACAACAACGCCTTTAGTCCAATTTC

TTAAATTAAGCTGAGCTTTAATATCTTCAACTAATGGATACACAACAAAA

CCTGGAAACATTTTTGAAGAAGAAAGCTCTTTGTCCTTGGGTCTAACAGC

AAGAATAATCTCAATATTCTTTTTAACATTACCTCTTAAAATTTCTACAT

TGATTTTCTCACCAGCATAAAAATCGCTAATATATGATGTAACGTCTTGA
```

```
AAAACACTCATGGGAACTCCATTAACCTTCACAATAATGTCTCCCGCTCT

AAGCCCTGACTTAATAGCAGGTGAACCTGGATAAAGAGAAGCAATAATTG

CAGCTGGAACATCATCACCTTCAACCCCCAAGCTTTTTAGCACTTCAGGA

TCTCTTGTCTTTAATGGGTAAAAAGAAATTCCAAGCCATGCTGATTCAAT

TTTTTTACCTTTAAGGAAAAAATCTACGGTACTTTTAATATTGTTAACAG

GAATTGCAAAACCTAACCCAATATTTCCACCAGAATTTGAAGCTATCCAA

GCATTAATCCCAATAACTTCACCTTTTGTATTTACAAGAGGTCCACCTGA

ATTACCTCTATTGATTGCAGCATCAGTTTGAATAAATAAATTTCTTGATT

GTAAATTAGGATTTGCAGAACGTTGCAATCCACTTACAATACCTGCTGTA

ACTGTAAAACTAAATTGAAAAGGGCTACCTACCGCCATAACCCAATCACC

TATTTCAAGCTTATCACTATCCCCAAGATCAGCCACTTTAATAGTTGCAT

CATCACTTTCAAAGCTAATAAGCGCAATATCCTTTTTTTCATCTTTGCCA

ATTAACTTAGCCTTATGCTTTTCTTATCATAAGATACAACTTCAAGTTC

AGTTGCCTTATCTACTACATGACTATTGGTAACTACATAAAATAATGATT

TATTTTTGGAATCTCTACCAATTATTACTCCAGACCCTGCCCAATTGCTT

TTTCTCTCAGAATCAAATTCTGGCATATCAAAAAAGAAAAATGGAATAGG

AAAACTCTGCTTAATTACCCCTGTTGCATGAACTTCTACAGATGATGGTA

AAATTTTCTTGGAAACTTCTCTAAAAGAGTCTTGCAAGGTTTGTACTGTA

TTACCCTTTTCTTC
```

SEQ ID NO:17 *Borrelia burgdorferi* HtrA (BB0104, BbHtrA) amino acid sequence without signal peptide, without the PDZ2 domain, Catalytic triad is at amino acid positions corresponding to 119H, 149D and 226S in the full-length protein, here Catalytic triad is at amino acid positions 82H, 112D and 189S.

```
EEKDNTVRALQDSFREVSKKILPSSVEVHATGVIKQSFPIPFFFFDMPEF

DSERKSNWAGSGVIIGRDSQKKSLFYVVTNSHVVDKATELEVVSYDKKKH

KAKLIGKDEKKDIALISFESDDATIKVADLGDSDKLEIGDWVMAVGSPFQ

FSFTVTAGIVSGLQRSANPNLQSRNLFIQTDAAINRGNSGGPLVNIKGEV

IGINAWIASNSGGNIGLGFAIPVNNIKSTVDFFLKGKKIESAWLGISFYP

LKTRDSEVLKSLGVESNDVSAAIIASLYPGSPAVKSGLRAGDIIMKVNGV

SMSVFQDVTSYISDFYAGEKVNVEILRGNVKKNIEI
```

SEQ ID NO:18 *Borrelia burgdorferi* HtrA (BB0104, BbHtrA) nucleic acid sequence encoding the protein without the signal peptide and without the PDZ2 domain.

```
AATCTCAATATTTTTTTGACATTGCCTCTTAAGATTTCTACATTTACTT

TCTCACCAGCATAAAAATCACTAATATATGATGTAACATCTTGAAAAACG

CTCATGGAAACCCCATTAACCTTCATAATAATATCCCCTGCCCTAAGCCC

TGATTTAACAGCGGGTGAACCCGGATAAAGAGAAGCAATAATTGCAGCTG

AAACATCATTACTTTCAACCCCTAAGCTTTTTAGCACCTCAGAATCTCTT

GTCTTTAGCGGATAAAAGAAATTCCAAGCCAAGCCGATTCAATTTTTTT

ACCTTTAAGGAAAAAATCTACAGTGCTTTTAATATTGTTAACAGGAATTG

CAAAACCCAACCCAATATTTCCGCCAGAATTTGAAGCTATCCAAGCATTA

ATTCCAATAACCTCGCCCTTTATATTTACAAGAGGACCACCTGAATTACC

CCTGTTGATTGCAGCATCGGTTTGAATAAACAGATTCCTTGATTGCAAAT

TAGGATTTGCAGAACGTTGCAATCCACTTACAATACCTGCTGTAACTGTA

AAACTAAATTGAAAAGGGCTGCCCACTGCCATAACCCAATCACCTATTTC

AAGCTTATCACTATCTCCAAGATCAGCTACTTTAATAGTTGCGTCATCAC

TTTCAAAGCTAATAAGGGCAATATCCTTTTTTTCATCTTTGCCAATTAAC

TTAGCCTTGTGCTTTTTTTATCATAAGATACAACTTCAAGTTCAGTTGC

CTTATCTACCACATGACTATTCGTAACCACATAAAATAATGATTTTTTTT

GAGAATCTCTACCAATTATTACTCCAGACCCCGCCCAATTGCTTTTTCTC

TCAGAATCAAATTCTGGCATATCAAAAAAGAAAAATGGAATAGGAAAACT

CTGCTTGATTACCCCTGTTGCATGAACTTCCACAGATGATGGTAAAATTT

TCTTGGAAACCTCTCTAAAAGAATCTTGTAAGGCTCGTACGGTATTGTCC

TTTTCTTC
```

SEQ ID NO:19 *Borrelia burgdorferi* HtrA (BB0104, BbHtrA$^{S226A}$) amino acid sequence without signal peptide, without PDZ2. Mutation site S→A is at position 189, analogous to position 226 in the full-length protein.

```
EEKDNTVRALQDSFREVSKKILPSSVEVHATGVIKQSFPIPFFFFDMPEF

DSERKSNWAGSGVIIGRDSQKKSLFYVVTNSHVVDKATELEVVSYDKKKH

KAKLIGKDEKKDIALISFESDDATIKVADLGDSDKLEIGDWVMAVGSPFQ

FSFTVTAGIVSGLQRSANPNLQSRNLFIQTDAAINRGNAGGPLVNIKGEV

IGINAWIASNSGGNIGLGFAIPVNNIKSTVDFFLKGKKIESAWLGISFYP

LKTRDSEVLKSLGVESNDVSAAIIASLYPGSPAVKSGLRAGDIIMKVNGV

SMSVFQDVTSYISDFYAGEKVNVEILRGNVKKNIEI
```

SEQ ID NO:20 *Borrelia burgdorferi* HtrA (BB0104, BbHtrA$^{S226A}$) nucleic acid sequence encoding the protein without the signal peptide and without the PDZ2 domain.

```
AATCTCAATATTTTTTTGACATTGCCTCTTAAGATTTCTACATTTACTT

TCTCACCAGCATAAAAATCACTAATATATGATGTAACATCTTGAAAAACG

CTCATGGAAACCCCATTAACCTTCATAATAATATCCCCTGCCCTAAGCCC

TGATTTAACAGCGGGTGAACCCGGATAAAGAGAAGCAATAATTGCAGCTG

AAACATCATTACTTTCAACCCCTAAGCTTTTTAGCACCTCAGAATCTCTT

GTCTTTAGCGGATAAAAGAAATTCCAAGCCAAGCCGATTCAATTTTTTT

ACCTTTAAGGAAAAAATCTACAGTGCTTTTAATATTGTTAACAGGAATTG

CAAAACCCAACCCAATATTTCCGCCAGAATTTGAAGCTATCCAAGCATTA

ATTCCAATAACCTCGCCCTTTATATTTACAAGAGGACCACCTGCATTACC

CCTGTTGATTGCAGCATCGGTTTGAATAAACAGATTCCTTGATTGCAAAT

TAGGATTTGCAGAACGTTGCAATCCACTTACAATACCTGCTGTAACTGTA

AAACTAAATTGAAAAGGGCTGCCCACTGCCATAACCCAATCACCTATTTC

AAGCTTATCACTATCTCCAAGATCAGCTACTTTAATAGTTGCGTCATCAC
```

-continued

TTTCAAAGCTAATAAGGGCAATATCCTTTTTTTCATCTTTGCCAATTAAC

TTAGCCTTGTGCTTTTTTTATCATAAGATACAACTTCAAGTTCAGTTGC

CTTATCTACCACATGACTATTCGTAACCACATAAAATAATGATTTTTTTT

GAGAATCTCTACCAATTATTACTCCAGACCCCGCCCAATTGCTTTTTCTC

TCAGAATCAAATTCTGGCATATCAAAAAGAAAAATGGAATAGGAAAACT

CTGCTTGATTACCCCTGTTGCATGAACTTCCACAGATGATGGTAAAATTT

TCTTGGAAACCTCTCTAAAAGAATCTTGTAAGGCTCGTACGGTATTGTCC

TTTTCTTC

SEQ ID NO:21 *Borrelia garinii* HtrA (BG0105) amino acid sequence without the signal peptide and without the PDZ2 domain.

EEKDNTVQALQDSFREVSKKILSSSVEVHATGVIKQSFPIPFFFFDMPEF

DSERKSNWAGSGVIIGRDSQKKSLFYVVTNSHVVDKATELEVVSYDKKKH

KAKLIGKDEKKDIALISFESDDATIKVADLGDSDKLEIGDWVMAVGSPFQ

FSFTVTAGIVSGLQRSANPNLQSRNLFIQTDAAINRGNSGGPLVNIKGEV

IGINAWIASNSGGNIGLGFAIPVNNIKSTVDFFLKGKKIESAWLGISFYP

LKTRDSEVLKSLGVEGKDVSAAIIASLYPGSPAVKSGLKAGDIIVKVNGV

SMSVFQDVTSYISDFYAGEKVNVEILRGNVKKNIEI

SEQ ID NO:22 *Borrelia garinii* HtrA (BG0105) nucleic acid sequence, encoding the protein without the signal peptide and without the PDZ2 domain.

AATCTCAATATTTTTTTGACATTACCTCTTAAAATTTCTACATTTACTT

TCTCACCAGCATAAAAATCGCTAATATATGATGTAACATCTTGAAAAACA

CTCATAGAAACCCCATTAACCTTAACAATAATATCGCCTGCTTTAAGCCC

TGACTTAACGGCAGGTGAACCTGGATAAAGAGAGGCAATAATTGCAGCTG

AAACATCCTTACCTTCAACTCCTAAGCTTTTTAGTACTTCAGAATCTCTT

GTCTTTAAAGGATAAAAGAAATTCCAAGCCATGCTGATTCAATTTTTTT

ACCTTTAAGAAAAAAATCTACAGTACTTTTAATATTATTAACAGGAATTG

CAAAACCTAACCCAATATTTCCTCCAGAATTTGAAGCTATCCAAGCATTA

ATTCCAATAACTTCACCTTTTATATTTACAAGAGGACCGCCTGAATTACC

TCTGTTGATTGCAGCATCAGTTTGAATAAATAAATTCCTTGATTGTAAAT

TAGGATTTGCAGAGCGTTGTAATCCACTTACAATACCTGCTGTAACTGTA

AAACTAAATTGAAAAGGACTACCTACTGCCATAACCCAATCACCTATTTC

AAGCTTATCACTATCTCCAAGATCAGCTACTTTAATAGTTGCATCATCAC

TTTCAAAGCTAATAAGAGCAATATCTTTTTTTTCATCTTTGCCAATTAAC

TTAGCCTTGTGCTTTTTTTATCATAAGACACAACTTCAAGTTCAGTTGC

CTTATCTACTACATGACTATTTGTAACCACATAAAATAATGATTTTTTTT

GAGAATCCCTACCAATTATTACTCCAGACCCTGCCCAATTGCTTTTTCTC

TCAGAATCAAATTCTGGCATATCAAAAAGAAAAATGGAATAGGAAAACT

CTGTTTAATTACCCCGGTTGCATGAACTTCTACGGACGATGATAAAATTT

TCTTGGAAACTTCCCTAAAAGAATCTTGTAAGGCTTGTACTGTATTGTCT

TTTTCTTC

SEQ ID NO:23 *Borrelia afzelii* HtrA (BafACA1_0105) amino acid sequence without signal peptide, without the PDZ2 domain.

EEKGNTVQTLQDSFREVSKKILPSSVEVHATGVIKQSFPIPFFFFDMPEF

DSERKSNWAGSGVIIGRDSKNKSLFYVVTNSHVVDKATELEVVSYDKKKH

KAKLIGKDEKKDIALISFESDDATIKVADLGDSDKLEIGDWVMAVGSPFQ

FSFTVTAGIVSGLQRSANPNLQSRNLFIQTDAAINRGNSGGPLVNTKGEV

IGINAWIASNSGGNIGLGFAIPVNNIKSTVDFFLKGKKIESAWLGISFYP

LKTRDPEVLKSLGVEGDDVPAAIIASLYPGSPAIKSGLRAGDIIVKVNGV

PMSVFQDVTSYISDFYAGEKINVEILRGNVKKNIEI

SEQ ID NO:24 *Borrelia afzelii* HtrA (BafACA1_0105) nucleic acid sequence without signal peptide, without the PDZ2 domain.

AATCTCAATATTCTTTTTAACATTACCTCTTAAAATTTCTACATTGATTT

TCTCACCAGCATAAAAATCGCTAATATATGATGTAACGTCTTGAAAAACA

CTCATGGGAACTCCATTAACCTTCACAATAATGTCTCCCGCTCTAAGCCC

TGACTTAATAGCAGGTGAACCTGGATAAAGAGAAGCAATAATTGCAGCTG

GAACATCATCACCTTCAACCCCCAAGCTTTTTAGCACTTCAGGATCTCTT

GTCTTTAATGGGTAAAAAGAAATTCCAAGCCATGCTGATTCAATTTTTTT

ACCTTTAAGGAAAAAATCTACGGTACTTTTAATATTGTTAACAGGAATTG

CAAAACCTAACCCAATATTTCCACCAGAATTTGAAGCTATCCAAGCATTA

ATCCCAATAACTTCACCTTTTGTATTTACAAGAGGTCCACCTGAATTACC

TCTATTGATTGCAGCATCAGTTTGAATAAATAAATTTCTTGATTGTAAAT

TAGGATTTGCAGAACGTTGCAATCCACTTACAATACCTGCTGTAACTGTA

AAACTAAATTGAAAAGGGCTACCTACCGCCATAACCCAATCACCTATTTC

AAGCTTATCACTATCCCCAAGATCAGCCACTTTAATAGTTGCATCATCAC

TTTCAAAGCTAATAAGCGCAATATCCTTTTTTTCATCTTTGCCAATTAAC

TTAGCCTTATGCTTTTTCTTATCATAAGATACAACTTCAAGTTCAGTTGC

CTTATCTACTACATGACTATTGGTAACTACATAAAATAATGATTTATTTT

TGGAATCTCTACCAATTATTACTCCAGACCCTGCCCAATTGCTTTTCTC

TCAGAATCAAATTCTGGCATATCAAAAAGAAAAATGGAATAGGAAAACT

CTGCTTAATTACCCCTGTTGCATGAACTTCTACAGATGATGGTAAAATTT

TCTTGGAAACTTCTCTAAAAGAGTCTTGCAAGGTTTGTACTGTATTACCC

TTTTCTTC

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A method of aiding in the diagnosis of Lyme disease, comprising: assaying a first sample obtained from a subject having, or suspected of having, Lyme disease for one or more peptides selected from the group consisting of: peptides of SEQ ID NOs: 56, 59, 60, 61, 62, 63, 64, 66 and the product of cleavage at cleavage sites 108 and 124, produced by proteolytic activity of *Borrelia burgdorferi* sensu lato HtrA on at least one host protein substrate, to produce an assay result wherein detection of the one or more peptides is indicative of an active *Borrelia burgdorferi* sensu lato infection in the subject.

2. The method of claim 1, further comprising:

assaying a second sample obtained from the subject having, or suspected of having, Lyme disease to detect at least one inflammatory cytokine or chemokine selected from: CXCL1, CCL1, sICAM-1, IL-6, IL-8, CCL2, and CCL5, wherein detection of the one or more peptides in combination with an increase in CXCL1, CCL1, sICAM-1, IL-6, IL-8, CCL2, and CCL5 compared to a standard is indicative of an active *Borrelia burgdorferi* sensu lato infection in the subject.

3. The method of claim 1, further comprising: assaying a further sample obtained from a subject having, or suspected of having, Lyme disease for one or more of the peptides.

4. The method of claim 1, wherein the first sample is selected from: whole blood, plasma, serum, urine, cerebrospinal fluid, synovial fluid and/or a biopsy sample, wherein the biopsy sample is skin or joint tissue.

5. The method of claim 2, wherein the second sample is selected from: whole blood, plasma, serum, urine, cerebrospinal fluid, synovial fluid and/or a biopsy sample, wherein the biopsy sample is skin or joint tissue.

6. The method of claim 1, wherein detecting the one or more peptides produced by proteolytic activity of *Borrelia burgdorferi* sensu lato HtrA on at least one host protein substrate comprises an immunoassay and/or mass spectrometry.

7. A commercial package for aiding in the diagnosis of Lyme disease in a subject comprising:

a reagent selected from the group consisting of: one or more peptides selected from the group consisting of: peptides of SEQ ID NOs: 56, 59, 60, 61, 62, 63, 64, 66 and the product of cleavage at cleavage sites 108 and 124, containing a neoepitope produced by proteolytic activity of *Borrelia burgdorferi* sensu lato HtrA on a host substrate; and one or more substrates for *Borrelia burgdorferi* sensu lato HtrA protease.

8. The commercial package of claim 7, wherein the one or more substrates is selected from the group consisting of: one or more substrates for *Borrelia burgdorferi* sensu lato HtrA protease selected from the group consisting of: aggrecan, fibronectin, biglycan, cartilage oligomeric matrix protein (COMP).

9. The commercial package of claim 7 wherein the one or more peptides are arrayed on a support.

10. The method of claim 3, wherein the further sample is selected from: whole blood, plasma, serum, urine, cerebrospinal fluid, synovial fluid and/or a biopsy sample, wherein the biopsy sample is skin or joint tissue.

* * * * *

SEQUENCE LISTING

<160> NUMBER OF SEQ ID NOS: 426

<210> SEQ ID NO 1
<211> LENGTH: 474
<212> TYPE: PRT
<213> ORGANISM: Borrelia burgdorferi

<400> SEQUENCE: 1

Met Glu Lys Lys Phe Phe Ser Gly Phe Leu Leu Ser Phe Leu Ala Leu
1               5                   10                  15

Ser Ile Gly Phe Phe Ile Gly Met His Tyr Leu Ala Ser Asn Arg Ser
            20                  25                  30

Asn Ile Val Phe Ala Glu Glu Lys Asp Asn Thr Val Arg Ala Leu Gln
        35                  40                  45

Asp Ser Phe Arg Glu Val Ser Lys Lys Ile Leu Pro Ser Ser Val Glu
    50                  55                  60

Val His Ala Thr Gly Val Ile Lys Gln Ser Phe Pro Ile Pro Phe Phe
65                  70                  75                  80

Phe Phe Asp Met Pro Glu Phe Asp Ser Glu Arg Lys Ser Asn Trp Ala
                85                  90                  95

Gly Ser Gly Val Ile Ile Gly Arg Asp Ser Gln Lys Lys Ser Leu Phe
            100                 105                 110

Tyr Val Val Thr Asn Ser His Val Val Asp Lys Ala Thr Glu Leu Glu
        115                 120                 125

Val Val Ser Tyr Asp Lys Lys Lys His Lys Ala Lys Leu Ile Gly Lys
    130                 135                 140

Asp Glu Lys Lys Asp Ile Ala Leu Ile Ser Phe Glu Ser Asp Asp Ala
145                 150                 155                 160

Thr Ile Lys Val Ala Asp Leu Gly Asp Ser Asp Lys Leu Glu Ile Gly
                165                 170                 175

Asp Trp Val Met Ala Val Gly Ser Pro Phe Gln Phe Ser Phe Thr Val
            180                 185                 190

Thr Ala Gly Ile Val Ser Gly Leu Gln Arg Ser Ala Asn Pro Asn Leu
        195                 200                 205

Gln Ser Arg Asn Leu Phe Ile Gln Thr Asp Ala Ala Ile Asn Arg Gly
    210                 215                 220

Asn Ser Gly Gly Pro Leu Val Asn Ile Lys Gly Glu Val Ile Gly Ile
225                 230                 235                 240

Asn Ala Trp Ile Ala Ser Asn Ser Gly Gly Asn Ile Gly Leu Gly Phe
                245                 250                 255

Ala Ile Pro Val Asn Asn Ile Lys Ser Thr Val Asp Phe Phe Leu Lys
            260                 265                 270

Gly Lys Lys Ile Glu Ser Ala Trp Leu Gly Ile Ser Phe Tyr Pro Leu
        275                 280                 285

Lys Thr Arg Asp Ser Glu Val Leu Lys Ser Leu Gly Val Glu Ser Asn
    290                 295                 300

Asp Val Ser Ala Ala Ile Ile Ala Ser Leu Tyr Pro Gly Ser Pro Ala
305                 310                 315                 320

Val Lys Ser Gly Leu Arg Ala Gly Asp Ile Ile Met Lys Val Asn Gly
                325                 330                 335

Val Ser Met Ser Val Phe Gln Asp Val Thr Ser Tyr Ile Ser Asp Phe
            340                 345                 350

Tyr Ala Gly Glu Lys Val Asn Val Glu Ile Leu Arg Gly Asn Val Lys
        355                 360                 365

```
Lys Asn Ile Glu Ile Val Leu Ala Val Arg Pro Lys Asp Lys Glu Leu
        370                 375                 380

Ser Ser Ser Lys Met Leu Pro Gly Phe Val Val Tyr Pro Leu Val Glu
385                 390                 395                 400

Asp Ile Lys Ala Gln Leu Asn Leu Arg Asn Trp Ile Lys Gly Val Val
                405                 410                 415

Val Asp Tyr Ile Asp Lys Asn Leu Ala Ser Asn Ile Lys Met Lys Ser
                420                 425                 430

Gly Asp Val Ile Leu Ser Val Asn Ser Lys Ser Val Ser Asn Leu Arg
                435                 440                 445

Glu Phe Tyr Asp Ala Leu Glu Val Gly Lys Asn Thr Tyr Lys Ile Leu
        450                 455                 460

Arg Gly Asn Asp Ser Phe Lys Ile Thr Phe
465                 470

<210> SEQ ID NO 2
<211> LENGTH: 1425
<212> TYPE: DNA
<213> ORGANISM: Borrelia burgdorferi

<400> SEQUENCE: 2
ctaaaatgta attttaaaag aatcgtttcc tctcaaaatt ttataagtat tttttccaac      60
ctcaagagca tcataaaatt ctcttaaatt agaaacactt tttgaattta cagaaagaat    120
tacatctcct gatttcattt taatatttga tgctaaattt ttatcaatat aatcaacaac    180 aacacccttta atccaatttc ttaaattaag ctgagcttta atatcctcaa ccaatggata    240
cacaacaaag cctggaagca tctttgaaga agaaagctct ttatccttag gtctaacagc    300
aagaacaatc tcaatatttt ttttgacatt gcctcttaag attctacat ttactttctc     360 accagcataa aaatcactaa tatatgatgt aacatcttga aaaacgctca tggaaacccc    420
attaaccttc ataataatat cccctgccct aagccctgat ttaacagcgg gtgaacccgg    480
ataaagagaa gcaataattg cagctgaaac atcattactt tcaaccccta agctttttag    540
cacctcagaa tctcttgtct ttagcggata aaaagaaatt ccaagccaag ccgattcaat    600
ttttttacct ttaaggaaaa aatctacagt gcttttaata ttgttaacag gaattgcaaa    660
acccaaccca atatttccgc cagaatttga agctatccaa gcattaattc caataaccct    720 gcccttata tttacaagag gaccacctga attaccc ctg ttgattgcag catcggtttg     780
aataaacaga ttccttgatt gcaaattagg atttgcagaa cgttgcaatc cacttacaat    840
acctgctgta actgtaaaac taaattgaaa agggctgccc actgccataa cccaatcacc    900
tatttcaagc ttatcactat ctccaagatc agctacttta atagttgcgt catcactttc    960
aaagctaata agggcaatat ccttttttc atctttgcca attaacttag ccttgtgctt   1020
ttttttatca taagatacaa cttcaagttc agttgcctta tctaccacat gactattcgt   1080
aaccacataa aataatgatt ttttttgaga atctctacca attattactc cagacccgc    1140 ccaattgctt tttctctcag aatcaaattc tggcatatca aaaagaaaa atggaatagg     1200 aaaactctgc ttgattaccc ctgttgcatg aacttccaca gatgatggta aaattttctt   1260
ggaaacctct ctaaaagaat cttgtaaggc tcgtacggta ttgtcctttt cttctgcaaa   1320
aacaatgttg cttctattag aagctaaata atgcatccca ataaaaaatc caatactcaa   1380
agccaaaaaa ctaagaagaa atccagaaaa aaactttttt tccac                   1425

<210> SEQ ID NO 3
```

```
<211> LENGTH: 474
<212> TYPE: PRT
<213> ORGANISM: Artificial Sequence
<220> FEATURE:
<223> OTHER INFORMATION: Mutant Borrelia burdorferi HtrA S226A

<400> SEQUENCE: 3
```

| | | | | | | | | | | | | | | | |
|---|---|---|---|---|---|---|---|---|---|---|---|---|---|---|---|
| Met | Glu | Lys | Lys | Phe | Phe | Ser | Gly | Phe | Leu | Leu | Ser | Phe | Leu | Ala | Leu |
| 1 | | | | 5 | | | | | 10 | | | | | 15 | |
| Ser | Ile | Gly | Phe | Phe | Ile | Gly | Met | His | Tyr | Leu | Ala | Ser | Asn | Arg | Ser |
| | | | 20 | | | | | 25 | | | | | 30 | | |
| Asn | Ile | Val | Phe | Ala | Glu | Glu | Lys | Asp | Asn | Thr | Val | Arg | Ala | Leu | Gln |
| | | 35 | | | | | 40 | | | | | 45 | | | |
| Asp | Ser | Phe | Arg | Glu | Val | Ser | Lys | Lys | Ile | Leu | Pro | Ser | Ser | Val | Glu |
| 50 | | | | | 55 | | | | | 60 | | | | | |
| Val | His | Ala | Thr | Gly | Val | Ile | Lys | Gln | Ser | Phe | Pro | Ile | Pro | Phe | Phe |
| 65 | | | | 70 | | | | | 75 | | | | | 80 | |
| Phe | Phe | Asp | Met | Pro | Glu | Phe | Asp | Ser | Glu | Arg | Lys | Ser | Asn | Trp | Ala |
| | | | | 85 | | | | | 90 | | | | | 95 | |
| Gly | Ser | Gly | Val | Ile | Ile | Gly | Arg | Asp | Ser | Gln | Lys | Lys | Ser | Leu | Phe |
| | | | 100 | | | | | 105 | | | | | 110 | | |
| Tyr | Val | Val | Thr | Asn | Ser | His | Val | Val | Asp | Lys | Ala | Thr | Glu | Leu | Glu |
| | | 115 | | | | | 120 | | | | | 125 | | | |
| Val | Val | Ser | Tyr | Asp | Lys | Lys | Lys | His | Lys | Ala | Lys | Leu | Ile | Gly | Lys |
| 130 | | | | | 135 | | | | | 140 | | | | | |
| Asp | Glu | Lys | Lys | Asp | Ile | Ala | Leu | Ile | Ser | Phe | Glu | Ser | Asp | Asp | Ala |
| 145 | | | | | 150 | | | | | 155 | | | | | 160 |
| Thr | Ile | Lys | Val | Ala | Asp | Leu | Gly | Asp | Ser | Asp | Lys | Leu | Glu | Ile | Gly |
| | | | | 165 | | | | | 170 | | | | | 175 | |
| Asp | Trp | Val | Met | Ala | Val | Gly | Ser | Pro | Phe | Gln | Phe | Ser | Phe | Thr | Val |
| | | | 180 | | | | | 185 | | | | | 190 | | |
| Thr | Ala | Gly | Ile | Val | Ser | Gly | Leu | Gln | Arg | Ser | Ala | Asn | Pro | Asn | Leu |
| | | 195 | | | | | 200 | | | | | 205 | | | |
| Gln | Ser | Arg | Asn | Leu | Phe | Ile | Gln | Thr | Asp | Ala | Ala | Ile | Asn | Arg | Gly |
| 210 | | | | | 215 | | | | | 220 | | | | | |
| Asn | Ala | Gly | Gly | Pro | Leu | Val | Asn | Ile | Lys | Gly | Glu | Val | Ile | Gly | Ile |
| 225 | | | | 230 | | | | | 235 | | | | | 240 | |
| Asn | Ala | Trp | Ile | Ala | Ser | Asn | Ser | Gly | Gly | Asn | Ile | Gly | Leu | Gly | Phe |
| | | | | 245 | | | | | 250 | | | | | 255 | |
| Ala | Ile | Pro | Val | Asn | Asn | Ile | Lys | Ser | Thr | Val | Asp | Phe | Phe | Leu | Lys |
| | | | 260 | | | | | 265 | | | | | 270 | | |
| Gly | Lys | Lys | Ile | Glu | Ser | Ala | Trp | Leu | Gly | Ile | Ser | Phe | Tyr | Pro | Leu |
| | | 275 | | | | | 280 | | | | | 285 | | | |
| Lys | Thr | Arg | Asp | Ser | Glu | Val | Leu | Lys | Ser | Leu | Gly | Val | Glu | Ser | Asn |
| 290 | | | | | 295 | | | | | 300 | | | | | |
| Asp | Val | Ser | Ala | Ala | Ile | Ile | Ala | Ser | Leu | Tyr | Pro | Gly | Ser | Pro | Ala |
| 305 | | | | 310 | | | | | 315 | | | | | 320 | |
| Val | Lys | Ser | Gly | Leu | Arg | Ala | Gly | Asp | Ile | Ile | Met | Lys | Val | Asn | Gly |
| | | | | 325 | | | | | 330 | | | | | 335 | |
| Val | Ser | Met | Ser | Val | Phe | Gln | Asp | Val | Thr | Ser | Tyr | Ile | Ser | Asp | Phe |
| | | | 340 | | | | | 345 | | | | | 350 | | |
| Tyr | Ala | Gly | Glu | Lys | Val | Asn | Val | Glu | Ile | Leu | Arg | Gly | Asn | Val | Lys |
| | | 355 | | | | | 360 | | | | | 365 | | | |
| Lys | Asn | Ile | Glu | Ile | Val | Leu | Ala | Val | Arg | Pro | Lys | Asp | Lys | Glu | Leu |
| 370 | | | | | 375 | | | | | 380 | | | | | |

```
Ser Ser Ser Lys Met Leu Pro Gly Phe Val Val Tyr Pro Leu Val Glu
385                 390                 395                 400

Asp Ile Lys Ala Gln Leu Asn Leu Arg Asn Trp Ile Lys Gly Val Val
            405                 410                 415

Val Asp Tyr Ile Asp Lys Asn Leu Ala Ser Asn Ile Lys Met Lys Ser
        420                 425                 430

Gly Asp Val Ile Leu Ser Val Asn Ser Lys Ser Val Ser Asn Leu Arg
            435                 440                 445

Glu Phe Tyr Asp Ala Leu Glu Val Gly Lys Asn Thr Tyr Lys Ile Leu
    450                 455                 460

Arg Gly Asn Asp Ser Phe Lys Ile Thr Phe
465                 470

<210> SEQ ID NO 4
<211> LENGTH: 1425
<212> TYPE: DNA
<213> ORGANISM: Artificial Sequence
<220> FEATURE:
<223> OTHER INFORMATION: nucleic acid sequence encoding mutant Borrelia
      burgdoreri HtrA S226A

<400> SEQUENCE: 4
ctaaaatgta attttaaaag aatcgtttcc tctcaaaatt ttataagtat tttttccaac      60
ctcaagagca tcataaaatt ctcttaaatt agaaacactt tttgaattta cagaaagaat    120
tacatctcct gatttcattt taatatttga tgctaaattt ttatcaatat aatcaacaac    180
aacaccttta atccaatttc ttaaattaag ctgagcttta atatcctcaa ccaatggata    240
cacaacaaag cctggaagca tctttgaaga agaaagctct ttatccttag gtctaacagc    300
aagaacaatc tcaatatttt ttttgacatt gcctcttaag atttctacat ttactttctc    360
accagcataa aaatcactaa tatatgatgt aacatcttga aaaacgctca tggaaacccc    420
attaaccttc ataataatat cccctgccct aagccctgat ttaacagcgg gtgaacccgg    480
ataaagagaa gcaataattg cagctgaaac atcattactt tcaaccccta gcttttttag    540
cacctcagaa tctcttgtct ttagcggata aaaagaaatt ccaagccaag ccgattcaat    600
ttttttacct ttaaggaaaa aatctacagt gcttttaata ttgttaacag gaattgcaaa    660
acccaaccca atatttccgc cagaatttga agctatccaa gcattaattc caataacctc    720 gcccttata tttacaagag gaccacctgc attacccctg ttgattgcag catcggtttg    780
aataaacaga ttccttgatt gcaaattagg atttgcagaa cgttgcaatc cacttacaat    840
acctgctgta actgtaaaac taaattgaaa agggctgccc actgccataa cccaatcacc    900
tatttcaagc ttatcactat ctccaagatc agctacttta atagttgcgt catcactttc    960
aaagctaata agggcaatat cctttttttc atctttgcca attaacttag ccttgtgctt   1020
ttttttatca taagatacaa cttcaagttc agttgcctta tctaccacat gactattcgt   1080
aaccacataa aataatgatt ttttttgaga atctctacca attattactc cagacccgc    1140 ccaattgctt tttctctcag aatcaaattc tggcatatca aaaagaaaa atggaatagg    1200 aaaactctgc ttgattaccc ctgttgcatg aacttccaca gatgatggta aaattttctt   1260
ggaaacctct ctaaaagaat cttgtaaggc tcgtacggta ttgtcctttt cttctgcaaa   1320
aacaatgttg cttctattag aagctaaata atgcatccca ataaaaaatc caatactcaa   1380
agccaaaaaa ctaagaagaa atccagaaaa aaacttttt tccac                    1425
```

```
<210> SEQ ID NO 5
<211> LENGTH: 474
<212> TYPE: PRT
<213> ORGANISM: Borrelia garinii

<400> SEQUENCE: 5
```

| | | | | | | | | | | | | | | |
|---|---|---|---|---|---|---|---|---|---|---|---|---|---|---|
| Met | Glu | Lys | Lys | Phe | Phe | Ser | Gly | Phe | Ile | Leu | Ser | Phe | Leu | Ala | Leu |
| 1 | | | | 5 | | | | | 10 | | | | | 15 | |
| Gly | Ile | Gly | Phe | Phe | Ile | Gly | Met | His | Tyr | Leu | Asp | Ser | Asn | Arg | Ser |
| | | | 20 | | | | | 25 | | | | | 30 | | |
| Asn | Ile | Val | Phe | Ala | Glu | Glu | Lys | Asp | Asn | Thr | Val | Gln | Ala | Leu | Gln |
| | | 35 | | | | | 40 | | | | | 45 | | | |
| Asp | Ser | Phe | Arg | Glu | Val | Ser | Lys | Lys | Ile | Leu | Ser | Ser | Val | Glu |
| | 50 | | | | | 55 | | | | | 60 | | | | |
| Val | His | Ala | Thr | Gly | Val | Ile | Lys | Gln | Ser | Phe | Pro | Ile | Pro | Phe | Phe |
| 65 | | | | | 70 | | | | | 75 | | | | | 80 |
| Phe | Phe | Asp | Met | Pro | Glu | Phe | Asp | Ser | Glu | Arg | Lys | Ser | Asn | Trp | Ala |
| | | | | 85 | | | | | 90 | | | | | 95 | |
| Gly | Ser | Gly | Val | Ile | Ile | Gly | Arg | Asp | Ser | Gln | Lys | Lys | Ser | Leu | Phe |
| | | | 100 | | | | | 105 | | | | | 110 | | |
| Tyr | Val | Val | Thr | Asn | Ser | His | Val | Val | Asp | Lys | Ala | Thr | Glu | Leu | Glu |
| | | | 115 | | | | | 120 | | | | | 125 | | |
| Val | Val | Ser | Tyr | Asp | Lys | Lys | His | Lys | Ala | Lys | Leu | Ile | Gly | Lys |
| | 130 | | | | | 135 | | | | | 140 | | | | |
| Asp | Glu | Lys | Lys | Asp | Ile | Ala | Leu | Ile | Ser | Phe | Glu | Ser | Asp | Asp | Ala |
| 145 | | | | | 150 | | | | | 155 | | | | | 160 |
| Thr | Ile | Lys | Val | Ala | Asp | Leu | Gly | Asp | Ser | Asp | Lys | Leu | Glu | Ile | Gly |
| | | | | 165 | | | | | 170 | | | | | 175 | |
| Asp | Trp | Val | Met | Ala | Val | Gly | Ser | Pro | Phe | Gln | Phe | Ser | Phe | Thr | Val |
| | | | 180 | | | | | 185 | | | | | 190 | | |
| Thr | Ala | Gly | Ile | Val | Ser | Gly | Leu | Gln | Arg | Ser | Ala | Asn | Pro | Asn | Leu |
| | | 195 | | | | | 200 | | | | | 205 | | | |
| Gln | Ser | Arg | Asn | Leu | Phe | Ile | Gln | Thr | Asp | Ala | Ala | Ile | Asn | Arg | Gly |
| | 210 | | | | | 215 | | | | | 220 | | | | |
| Asn | Ser | Gly | Gly | Pro | Leu | Val | Asn | Ile | Lys | Gly | Glu | Val | Ile | Gly | Ile |
| 225 | | | | | 230 | | | | | 235 | | | | | 240 |
| Asn | Ala | Trp | Ile | Ala | Ser | Asn | Ser | Gly | Gly | Asn | Ile | Gly | Leu | Gly | Phe |
| | | | | 245 | | | | | 250 | | | | | 255 | |
| Ala | Ile | Pro | Val | Asn | Asn | Ile | Lys | Ser | Thr | Val | Asp | Phe | Phe | Leu | Lys |
| | | | | 260 | | | | | 265 | | | | | 270 | |
| Gly | Lys | Lys | Ile | Glu | Ser | Ala | Trp | Leu | Gly | Ile | Ser | Phe | Tyr | Pro | Leu |
| | | 275 | | | | | 280 | | | | | 285 | | | |
| Lys | Thr | Arg | Asp | Ser | Glu | Val | Leu | Lys | Ser | Leu | Gly | Val | Glu | Gly | Lys |
| | 290 | | | | | 295 | | | | | 300 | | | | |
| Asp | Val | Ser | Ala | Ala | Ile | Ile | Ala | Ser | Leu | Tyr | Pro | Gly | Ser | Pro | Ala |
| 305 | | | | | 310 | | | | | 315 | | | | | 320 |
| Val | Lys | Ser | Gly | Leu | Lys | Ala | Gly | Asp | Ile | Ile | Val | Lys | Val | Asn | Gly |
| | | | | 325 | | | | | 330 | | | | | 335 | |
| Val | Ser | Met | Ser | Val | Phe | Gln | Asp | Val | Thr | Ser | Tyr | Ile | Ser | Asp | Phe |
| | | | | 340 | | | | | 345 | | | | | 350 | |
| Tyr | Ala | Gly | Glu | Lys | Val | Asn | Val | Glu | Ile | Leu | Arg | Gly | Asn | Val | Lys |
| | | 355 | | | | | 360 | | | | | 365 | | | |
| Lys | Asn | Ile | Glu | Ile | Val | Leu | Ala | Val | Arg | Pro | Lys | Asp | Lys | Glu | Leu |
| | 370 | | | | | 375 | | | | | 380 | | | | |

```
Ser Ser Ser Lys Met Leu Pro Gly Phe Ile Val Tyr Pro Leu Val Glu
385                 390                 395                 400

Asp Ile Lys Ala Gln Leu Asn Leu Arg Asn Trp Ile Lys Gly Val Val
            405                 410                 415

Val Asp Tyr Ile Asp Lys Asn Leu Ala Ser Asn Ile Lys Met Lys Ser
        420                 425                 430

Gly Asp Val Ile Leu Ser Val Asn Ser Gln Ser Val Ser Asn Leu Arg
    435                 440                 445

Glu Phe Tyr Asp Ala Leu Lys Ile Gly Lys Asn Thr Tyr Lys Ile Leu
    450                 455                 460

Arg Gly Asn Asp Ser Phe Lys Ile Ser Phe
465                 470

<210> SEQ ID NO 6
<211> LENGTH: 1425
<212> TYPE: DNA
<213> ORGANISM: Borrelia garinii

<400> SEQUENCE: 6
ctaaaacgaa attttaaaag aatcatttcc tcttaaaatt ttataagtat tttttccaat      60
cttaagagca tcataaaatt ctcttaaatt agaaacactt tgtgaattta cagaaagaat     120
cacatctcct gatttcatct taatatttga tgctaaattt ttatcaatat aatcaacaac     180
aacgccttta atccaatttc ttaaattaag ctgagcttta atatcctcaa ctaatggata     240
cacaataaaa cctggaagca ttttggaaga agaaagttct ttatccttag gtctaacagc     300
aagaacaatc tcaatatttt ttttgacatt acctcttaaa atttctacat ttactttctc     360
accagcataa aaatcgctaa tatatgatgt aacatcttga aaaacactca tagaaacccc     420
attaacctta acaataatat cgcctgcttt aagccctgac ttaacggcag gtgaacctgg     480
ataaagagag gcaataattg cagctgaaac atccttacct tcaactccta gcttttttag     540
tacttcagaa tctcttgtct ttaaaggata aaaagaaatt ccaagccatg ctgattcaat     600 tttttttacct ttaagaaaaa aatctacagt acttttaata ttattaacag gaattgcaaa     660
acctaaccca atatttcctc cagaatttga agctatccaa gcattaattc caataacttc     720
accttttata tttacaagag gaccgcctga attacctctg ttgattgcag catcagtttg     780
aataaataaa ttccttgatt gtaaattagg atttgcagag cgttgtaatc cacttacaat     840
acctgctgta actgtaaaac taaattgaaa aggactacct actgccataa cccaatcacc     900
tatttcaagc ttatcactat ctccaagatc agctacttta atagttgcat catcactttc     960
aaagctaata agagcaatat cttttttttc atctttgcca attaacttag ccttgtgctt    1020 tttttttatca taagacacaa cttcaagttc agttgcctta tctactacat gactatttgt    1080
aaccacataa aataatgatt tttttgaga tccctacca attattactc cagaccctgc     1140
ccaattgctt tttctctcag aatcaaattc tggcatatca aaaagaaaa atggaatagg     1200 aaaactctgt ttaattaccc cggttgcatg aacttctacg gacgatgata aaattttctt     1260
ggaaacttcc ctaaaagaat cttgtaaggc ttgtactgta ttgtcttttt cttctgcaaa     1320
aacaatattg cttctattag aatctaagta atgcattcca ataaaaaaac caatacctaa     1380
agccaaaaaa ctgagaataa atccagaaaa aaacttttt tccac                      1425

<210> SEQ ID NO 7
<211> LENGTH: 474
<212> TYPE: PRT
<213> ORGANISM: Borrelia afzelii
```

<400> SEQUENCE: 7

```
Met Glu Lys Lys Phe Phe Ser Gly Phe Ile Leu Ser Phe Leu Ala Leu
1               5                   10                  15

Gly Ile Gly Phe Phe Ile Gly Met His Tyr Leu Asp Ser Asn Arg Ser
            20                  25                  30

Asn Ile Val Phe Ala Glu Glu Lys Gly Asn Thr Val Gln Thr Leu Gln
        35                  40                  45

Asp Ser Phe Arg Glu Val Ser Lys Lys Ile Leu Pro Ser Ser Val Glu
    50                  55                  60

Val His Ala Thr Gly Val Ile Lys Gln Ser Phe Pro Ile Pro Phe Phe
65                  70                  75                  80

Phe Phe Asp Met Pro Glu Phe Asp Ser Glu Arg Lys Ser Asn Trp Ala
                85                  90                  95

Gly Ser Gly Val Ile Ile Gly Arg Asp Ser Lys Asn Lys Ser Leu Phe
            100                 105                 110

Tyr Val Val Thr Asn Ser His Val Val Asp Lys Ala Thr Glu Leu Glu
        115                 120                 125

Val Val Ser Tyr Asp Lys Lys His Lys Ala Lys Leu Ile Gly Lys
130                 135                 140

Asp Glu Lys Lys Asp Ile Ala Leu Ile Ser Phe Glu Ser Asp Asp Ala
145                 150                 155                 160

Thr Ile Lys Val Ala Asp Leu Gly Asp Ser Asp Lys Leu Glu Ile Gly
                165                 170                 175

Asp Trp Val Met Ala Val Gly Ser Pro Phe Gln Phe Ser Phe Thr Val
            180                 185                 190

Thr Ala Gly Ile Val Ser Gly Leu Gln Arg Ser Ala Asn Pro Asn Leu
        195                 200                 205

Gln Ser Arg Asn Leu Phe Ile Gln Thr Asp Ala Ala Ile Asn Arg Gly
    210                 215                 220

Asn Ser Gly Gly Pro Leu Val Asn Thr Lys Gly Glu Val Ile Gly Ile
225                 230                 235                 240

Asn Ala Trp Ile Ala Ser Asn Ser Gly Gly Asn Ile Gly Leu Gly Phe
                245                 250                 255

Ala Ile Pro Val Asn Asn Ile Lys Ser Thr Val Asp Phe Phe Leu Lys
            260                 265                 270

Gly Lys Lys Ile Glu Ser Ala Trp Leu Gly Ile Ser Phe Tyr Pro Leu
        275                 280                 285

Lys Thr Arg Asp Pro Glu Val Leu Lys Ser Leu Gly Val Glu Gly Asp
    290                 295                 300

Asp Val Pro Ala Ala Ile Ile Ala Ser Leu Tyr Pro Gly Ser Pro Ala
305                 310                 315                 320

Ile Lys Ser Gly Leu Arg Ala Gly Asp Ile Ile Val Lys Val Asn Gly
                325                 330                 335

Val Pro Met Ser Val Phe Gln Asp Val Thr Ser Tyr Ile Ser Asp Phe
            340                 345                 350

Tyr Ala Gly Glu Lys Ile Asn Val Glu Ile Leu Arg Gly Asn Val Lys
        355                 360                 365

Lys Asn Ile Glu Ile Ile Leu Ala Val Arg Pro Lys Asp Lys Glu Leu
    370                 375                 380

Ser Ser Ser Lys Met Phe Pro Gly Phe Val Val Tyr Pro Leu Val Glu
385                 390                 395                 400

Asp Ile Lys Ala Gln Leu Asn Leu Arg Asn Trp Thr Lys Gly Val Val
```

```
                 405                 410                 415
Val Asp Tyr Ile Asp Lys Asn Leu Ala Ser Asn Ile Lys Met Lys Ser
            420                 425                 430

Gly Asp Val Ile Leu Ser Val Asn Ser Lys Ser Val Ser Asn Leu Arg
        435                 440                 445

Glu Phe Tyr Asp Ala Leu Glu Ile Gly Lys Asn Thr Tyr Asn Ile Leu
    450                 455                 460

Arg Gly Asn Asp Ser Phe Lys Ile Ser Phe
465                 470

<210> SEQ ID NO 8
<211> LENGTH: 1425
<212> TYPE: DNA
<213> ORGANISM: Borrelia afzelii

<400> SEQUENCE: 8
ctaaaacgaa attttaaaag aatcgtttcc tcttaaaatg ttataagtat ttttttccaat      60 ctcaagagca tcataaaatt ctcttaaatt agaaacactt tttgaattta cagaaagaat     120
tacatctcct gatttcatct taatatttga tgctaaattt ttatcaatat aatcaacaac     180
aacgccttta gtccaatttc ttaaattaag ctgagcttta atatcttcaa ctaatggata     240
cacaacaaaa cctggaaaca tttttgaaga agaaagctct ttgtccttgg gtctaacagc     300
aagaataatc tcaatattct ttttaacatt acctcttaaa atttctacat tgattttctc     360
accagcataa aaatcgctaa tatatgatgt aacgtcttga aaaacactca tgggaactcc     420
attaaccttc acaataatgt ctcccgctct aagccctgac ttaatagcag gtgaacctgg     480
ataaagagaa gcaataattg cagctggaac atcatcacct tcaaccccca agcttttttag    540 cacttcagga tctcttgtct ttaatgggta aaaagaaatt ccaagccatg ctgattcaat     600
ttttttacct ttaaggaaaa aatctacggt acttttaata ttgttaacag gaattgcaaa     660
acctaaccca atatttccac cagaatttga agctatccaa gcattaatcc caataacttc     720 acctttttgta tttacaagag gtccacctga attacctcta ttgattgcag catcagtttg    780
aataaataaa tttcttgatt gtaaattagg atttgcagaa cgttgcaatc cacttacaat     840
acctgctgta actgtaaaac taaattgaaa agggctacct accgccataa cccaatcacc     900
tatttcaagc ttatcactat ccccaagatc agccacttta atagttgcat catcactttc     960
aaagctaata agcgcaatat cctttttttc atctttgcca attaacttag ccttatgctt    1020
tttcttatca taagatacaa cttcaagttc agttgcctta tctactacat gactattggt    1080
aactacataa aataatgatt tattttggga tctctacca attattactc cagaccctgc     1140
ccaattgctt tttctctcag aatcaaattc tggcatatca aaaagaaaa atggaatagg    1200 aaaactctgc ttaattaccc ctgttgcatg aacttctaca gatgatggta aaattttctt    1260
ggaaacttct ctaaaagagt cttgcaaggt ttgtactgta ttacccttttt cttctgcaaa   1320 aacaatgtta cttctattag aatctaaata atgcatccca ataaaaaacc caatacccaa    1380
agctaaaaag ctaagaataa atccagaaaa aaacttttttt tccac                   1425

<210> SEQ ID NO 9
<211> LENGTH: 437
<212> TYPE: PRT
<213> ORGANISM: Borrelia burgdorferi

<400> SEQUENCE: 9

Glu Glu Lys Asp Asn Thr Val Arg Ala Leu Gln Asp Ser Phe Arg Glu
```

-continued

```
1               5                    10                   15
Val Ser Lys Lys Ile Leu Pro Ser Ser Val Glu Val His Ala Thr Gly
            20                   25                   30
Val Ile Lys Gln Ser Phe Pro Ile Pro Phe Phe Phe Asp Met Pro
            35                   40                   45
Glu Phe Asp Ser Glu Arg Lys Ser Asn Trp Ala Gly Ser Gly Val Ile
 50                  55                   60
Ile Gly Arg Asp Ser Gln Lys Lys Ser Leu Phe Tyr Val Val Thr Asn
 65                  70                   75                   80
Ser His Val Val Asp Lys Ala Thr Glu Leu Glu Val Val Ser Tyr Asp
                 85                   90                   95
Lys Lys Lys His Lys Ala Lys Leu Ile Gly Lys Asp Glu Lys Lys Asp
                100                  105                  110
Ile Ala Leu Ile Ser Phe Glu Ser Asp Ala Thr Ile Lys Val Ala
                115                  120                  125
Asp Leu Gly Asp Ser Asp Lys Leu Glu Ile Gly Asp Trp Val Met Ala
130                  135                  140
Val Gly Ser Pro Phe Gln Phe Ser Phe Thr Val Thr Ala Gly Ile Val
145                  150                  155                  160
Ser Gly Leu Gln Arg Ser Ala Asn Pro Asn Leu Gln Ser Arg Asn Leu
                165                  170                  175
Phe Ile Gln Thr Asp Ala Ala Ile Asn Arg Gly Asn Ser Gly Pro
                180                  185                  190
Leu Val Asn Ile Lys Gly Glu Val Ile Gly Ile Asn Ala Trp Ile Ala
                195                  200                  205
Ser Asn Ser Gly Gly Asn Ile Gly Leu Gly Phe Ala Ile Pro Val Asn
210                  215                  220
Asn Ile Lys Ser Thr Val Asp Phe Phe Leu Lys Gly Lys Lys Ile Glu
225                  230                  235                  240
Ser Ala Trp Leu Gly Ile Ser Phe Tyr Pro Leu Lys Thr Arg Asp Ser
                245                  250                  255
Glu Val Leu Lys Ser Leu Gly Val Glu Ser Asn Asp Val Ser Ala Ala
                260                  265                  270
Ile Ile Ala Ser Leu Tyr Pro Gly Ser Pro Ala Val Lys Ser Gly Leu
                275                  280                  285
Arg Ala Gly Asp Ile Ile Met Lys Val Asn Gly Val Ser Met Ser Val
290                  295                  300
Phe Gln Asp Val Thr Ser Tyr Ile Ser Asp Phe Tyr Ala Gly Glu Lys
305                  310                  315                  320
Val Asn Val Glu Ile Leu Arg Gly Asn Val Lys Lys Asn Ile Glu Ile
                325                  330                  335
Val Leu Ala Val Arg Pro Lys Asp Lys Glu Leu Ser Ser Ser Lys Met
                340                  345                  350
Leu Pro Gly Phe Val Val Tyr Pro Leu Val Glu Asp Ile Lys Ala Gln
                355                  360                  365
Leu Asn Leu Arg Asn Trp Ile Lys Gly Val Val Asp Tyr Ile Asp
                370                  375                  380
Lys Asn Leu Ala Ser Asn Ile Lys Met Lys Ser Gly Asp Val Ile Leu
385                  390                  395                  400
Ser Val Asn Ser Lys Ser Val Ser Asn Leu Arg Glu Phe Tyr Asp Ala
                405                  410                  415
Leu Glu Val Gly Lys Asn Thr Tyr Lys Ile Leu Arg Gly Asn Asp Ser
                420                  425                  430
```

Phe Lys Ile Thr Phe
        435

<210> SEQ ID NO 10
<211> LENGTH: 1314
<212> TYPE: DNA
<213> ORGANISM: Borrelia burgdorferi

<400> SEQUENCE: 10

```
ctaaaatgta attttaaaag aatcgtttcc tctcaaaatt ttataagtat ttttccaac      60 ctcaagagca tcataaaatt ctcttaaatt agaaacactt tttgaattta cagaaagaat    120
tacatctcct gatttcattt taatatttga tgctaaattt ttatcaatat aatcaacaac    180
aacaccttta atccaatttc ttaaattaag ctgagcttta atatcctcaa ccaatggata    240
cacaacaaag cctggaagca tctttgaaga agaaagctct ttatccttag gtctaacagc    300
aagaacaatc tcaatatttt ttttgacatt gcctcttaag atttctacat ttactttctc    360
accagcataa aaatcactaa tatatgatgt aacatcttga aaaacgctca tggaaacccc    420
attaaccttc ataataatat cccctgccct aagccctgat ttaacagcgg gtgaacccgg    480
ataaagagaa gcaataattg cagctgaaac atcattactt tcaaccccta agcttttag     540 cacctcagaa tctcttgtct ttagcggata aaaagaaatt ccaagccaag ccgattcaat    600 tttttacct ttaaggaaaa aatctacagt gcttttaata ttgttaacag gaattgcaaa     660
acccaaccca atatttccgc cagaatttga agctatccaa gcattaattc caataacctc    720 gcccttata tttacaagag gaccacctga attaccccctg ttgattgcag catcggtttg    780
aataaacaga ttccttgatt gcaaattagg atttgcagaa cgttgcaatc cacttacaat    840
acctgctgta actgtaaaac taaattgaaa agggctgccc actgccataa cccaatcacc    900
tatttcaagc ttatcactat ctccaagatc agctacttta atagttgcgt catcactttc    960
aaagctaata agggcaatat cctttttttc atctttgcca attaacttag ccttgtgctt   1020
ttttttatca aagatacaa cttcaagttc agttgcctta tctaccacat gactattcgt    1080
aaccacataa aataatgatt ttttttgaga atctctacca attattactc cagaccccgc   1140
ccaattgctt tttctctcag aatcaaattc tggcatatca aaaagaaaa atggaatagg    1200 aaaactctgc ttgattaccc ctgttgcatg aacttccaca gatgatggta aatttctct    1260 ggaaacctct ctaaaagaat cttgtaaggc tcgtacggta ttgtcctttt cttc          1314
```

<210> SEQ ID NO 11
<211> LENGTH: 437
<212> TYPE: PRT
<213> ORGANISM: Artificial Sequence
<220> FEATURE:
<223> OTHER INFORMATION: Borrelia burgdorferi HtrA S226A mutant without
        signal sequence

<400> SEQUENCE: 11

Glu Glu Lys Asp Asn Thr Val Arg Ala Leu Gln Asp Ser Phe Arg Glu
1               5                   10                  15

Val Ser Lys Lys Ile Leu Pro Ser Val Glu Val His Ala Thr Gly
        20                  25                  30

Val Ile Lys Gln Ser Phe Pro Ile Pro Phe Phe Phe Asp Met Pro
        35                  40                  45

Glu Phe Asp Ser Glu Arg Lys Ser Asn Trp Ala Gly Ser Gly Val Ile
    50                  55                  60

```
Ile Gly Arg Asp Ser Gln Lys Lys Ser Leu Phe Tyr Val Val Thr Asn
 65                  70                  75                  80

Ser His Val Val Asp Lys Ala Thr Glu Leu Glu Val Ser Tyr Asp
                 85                  90                  95

Lys Lys Lys His Lys Ala Lys Leu Ile Gly Lys Asp Glu Lys Lys Asp
            100                 105                 110

Ile Ala Leu Ile Ser Phe Glu Ser Asp Ala Thr Ile Lys Val Ala
            115                 120                 125

Asp Leu Gly Asp Ser Asp Lys Leu Glu Ile Gly Asp Trp Val Met Ala
    130                 135                 140

Val Gly Ser Pro Phe Gln Phe Ser Phe Thr Val Thr Ala Gly Ile Val
145                 150                 155                 160

Ser Gly Leu Gln Arg Ser Ala Asn Pro Asn Leu Gln Ser Arg Asn Leu
                165                 170                 175

Phe Ile Gln Thr Asp Ala Ala Ile Asn Arg Gly Asn Ala Gly Gly Pro
                180                 185                 190

Leu Val Asn Ile Lys Gly Glu Val Ile Gly Ile Asn Ala Trp Ile Ala
                195                 200                 205

Ser Asn Ser Gly Gly Asn Ile Gly Leu Gly Phe Ala Ile Pro Val Asn
210                 215                 220

Asn Ile Lys Ser Thr Val Asp Phe Phe Leu Lys Gly Lys Lys Ile Glu
225                 230                 235                 240

Ser Ala Trp Leu Gly Ile Ser Phe Tyr Pro Leu Lys Thr Arg Asp Ser
                245                 250                 255

Glu Val Leu Lys Ser Leu Gly Val Glu Ser Asn Asp Val Ser Ala Ala
                260                 265                 270

Ile Ile Ala Ser Leu Tyr Pro Gly Ser Pro Ala Val Lys Ser Gly Leu
                275                 280                 285

Arg Ala Gly Asp Ile Ile Met Lys Val Asn Gly Val Ser Met Ser Val
                290                 295                 300

Phe Gln Asp Val Thr Ser Tyr Ile Ser Asp Phe Tyr Ala Gly Glu Lys
305                 310                 315                 320

Val Asn Val Glu Ile Leu Arg Gly Asn Val Lys Lys Asn Ile Glu Ile
                325                 330                 335

Val Leu Ala Val Arg Pro Lys Asp Lys Glu Leu Ser Ser Ser Lys Met
                340                 345                 350

Leu Pro Gly Phe Val Val Tyr Pro Leu Val Glu Asp Ile Lys Ala Gln
                355                 360                 365

Leu Asn Leu Arg Asn Trp Ile Lys Gly Val Val Asp Tyr Ile Asp
                370                 375                 380

Lys Asn Leu Ala Ser Asn Ile Lys Met Lys Ser Gly Asp Val Ile Leu
385                 390                 395                 400

Ser Val Asn Ser Lys Ser Val Ser Asn Leu Arg Glu Phe Tyr Asp Ala
                405                 410                 415

Leu Glu Val Gly Lys Asn Thr Tyr Lys Ile Leu Arg Gly Asn Asp Ser
                420                 425                 430

Phe Lys Ile Thr Phe
        435

<210> SEQ ID NO 12
<211> LENGTH: 1314
<212> TYPE: DNA
<213> ORGANISM: Artificial Sequence
<220> FEATURE:
<223> OTHER INFORMATION: Nucleic acid sequence encoding Borrelia
``` burgdorferi HtrA S226A mutant without the signal peptide

<400> SEQUENCE: 12

```
ctaaaatgta attttaaaag aatcgtttcc tctcaaaatt ttataagtat tttttccaac      60
ctcaagagca tcataaaatt ctcttaaatt agaaacactt tttgaattta cagaaagaat     120
tacatctcct gatttcattt taatatttga tgctaaattt ttatcaatat aatcaacaac     180
aacacctttta atccaatttc ttaaattaag ctgagcttta atatcctcaa ccaatggata     240
cacaacaaag cctggaagca tctttgaaga agaaagctct ttatccttag gtctaacagc     300
aagaacaatc tcaatatttt ttttgacatt gcctcttaag atttctacat ttactttctc     360
accagcataa aaatcactaa tatatgatgt aacatcttga aaaacgctca tggaaacccc     420
attaacctto ataataatat cccctgccct aagccctgat taacagcgg gtgaacccgg     480
ataaagagaa gcaataattg cagctgaaac atcattactt tcaacccta agcttttag      540
cacctcagaa tctcttgtct ttagcggata aaaagaaatt ccaagccaag ccgattcaat     600
ttttttacct ttaaggaaaa aatctacagt gcttttaata ttgttaacag gaattgcaaa     660
acccaaccca atatttccgc cagaatttga agctatccaa gcattaattc caataaccctc    720
gcccttttata tttacaagag gaccacctgc attaccctg ttgattgcag catcggtttg     780
aataaacaga ttccttgatt gcaaattagg atttgcagaa cgttgcaatc cacttacaat     840
acctgctgta actgtaaaac taaattgaaa agggctgccc actgccataa cccaatcacc     900
tatttcaagc ttatcactat ctccaagatc agctacttta atagttgcgt catcactttc     960
aaagctaata agggcaatat cctttttttc atctttgcca attaacttag ccttgtgctt    1020
tttttatca taagatacaa cttcaagttc agttgcctta tctaccacat gactattcgt    1080
aaccacataa aataatgatt tttttgaga atctctacca attattactc cagacccgc     1140
ccaattgctt tttctctcag aatcaaattc tggcatatca aaaagaaaa atggaatagg     1200
aaaactctgc ttgattaccc ctgttgcatg aacttccaca gatgatggta aattttctt     1260
ggaaacctct ctaaaagaat cttgtaaggc tcgtacggta ttgtcctttt cttc         1314
```

<210> SEQ ID NO 13
<211> LENGTH: 437
<212> TYPE: PRT
<213> ORGANISM: Borrelia garinii

<400> SEQUENCE: 13

```
Glu Glu Lys Asp Asn Thr Val Gln Ala Leu Gln Asp Ser Phe Arg Glu
1               5                  10                  15

Val Ser Lys Lys Ile Leu Ser Ser Val Glu Val His Ala Thr Gly
            20                  25                  30

Val Ile Lys Gln Ser Phe Pro Ile Pro Phe Phe Phe Asp Met Pro
        35                  40                  45

Glu Phe Asp Ser Glu Arg Lys Ser Asn Trp Ala Gly Ser Gly Val Ile
    50                  55                  60

Ile Gly Arg Asp Ser Gln Lys Lys Ser Leu Phe Tyr Val Val Thr Asn
65                  70                  75                  80

Ser His Val Val Asp Lys Ala Thr Glu Leu Glu Val Val Ser Tyr Asp
                85                  90                  95

Lys Lys Lys His Lys Ala Lys Leu Ile Gly Lys Asp Glu Lys Lys Asp
            100                 105                 110

Ile Ala Leu Ile Ser Phe Glu Ser Asp Asp Ala Thr Ile Lys Val Ala
        115                 120                 125
```

Asp Leu Gly Asp Ser Asp Lys Leu Glu Ile Gly Asp Trp Val Met Ala
            130                 135                 140

Val Gly Ser Pro Phe Gln Phe Ser Phe Thr Val Thr Ala Gly Ile Val
145                 150                 155                 160

Ser Gly Leu Gln Arg Ser Ala Asn Pro Asn Leu Gln Ser Arg Asn Leu
            165                 170                 175

Phe Ile Gln Thr Asp Ala Ala Ile Asn Arg Gly Asn Ser Gly Gly Pro
            180                 185                 190

Leu Val Asn Ile Lys Gly Glu Val Gly Ile Asn Ala Trp Ile Ala
            195                 200                 205

Ser Asn Ser Gly Gly Asn Ile Gly Leu Gly Phe Ala Ile Pro Val Asn
210                 215                 220

Asn Ile Lys Ser Thr Val Asp Phe Phe Leu Lys Gly Lys Lys Ile Glu
225                 230                 235                 240

Ser Ala Trp Leu Gly Ile Ser Phe Tyr Pro Leu Lys Thr Arg Asp Ser
            245                 250                 255

Glu Val Leu Lys Ser Leu Gly Val Glu Gly Lys Asp Val Ser Ala Ala
            260                 265                 270

Ile Ile Ala Ser Leu Tyr Pro Gly Ser Pro Ala Val Lys Ser Gly Leu
            275                 280                 285

Lys Ala Gly Asp Ile Ile Val Lys Val Asn Gly Val Ser Met Ser Val
290                 295                 300

Phe Gln Asp Val Thr Ser Tyr Ile Ser Asp Phe Tyr Ala Gly Glu Lys
305                 310                 315                 320

Val Asn Val Glu Ile Leu Arg Gly Asn Val Lys Lys Asn Ile Glu Ile
            325                 330                 335

Val Leu Ala Val Arg Pro Lys Asp Lys Glu Leu Ser Ser Ser Lys Met
            340                 345                 350

Leu Pro Gly Phe Ile Val Tyr Pro Leu Val Glu Asp Ile Lys Ala Gln
            355                 360                 365

Leu Asn Leu Arg Asn Trp Ile Lys Gly Val Val Asp Tyr Ile Asp
            370                 375                 380

Lys Asn Leu Ala Ser Asn Ile Lys Met Lys Ser Gly Asp Val Ile Leu
385                 390                 395                 400

Ser Val Asn Ser Gln Ser Val Ser Asn Leu Arg Glu Phe Tyr Asp Ala
            405                 410                 415

Leu Lys Ile Gly Lys Asn Thr Tyr Lys Ile Leu Arg Gly Asn Asp Ser
            420                 425                 430

Phe Lys Ile Ser Phe
            435

<210> SEQ ID NO 14
<211> LENGTH: 1314
<212> TYPE: DNA
<213> ORGANISM: Borrelia garinii

<400> SEQUENCE: 14
ctaaaacgaa atttaaaag aatcatttcc tcttaaaatt ttataagtat tttttccaat     60
cttaagagca tcataaaatt ctcttaaatt agaaacactt tgtgaattta cagaaagaat    120
cacatctcct gatttcatct taatatttga tgctaaattt ttatcaatat aatcaacaac    180
aacgccttta atccaatttc ttaaattaag ctgagcttta atatcctcaa ctaatggata    240
cacaataaaa cctggaagca ttttggaaga agaaagttct ttatccttag gtctaacagc    300

```
aagaacaatc tcaatatttt ttttgacatt acctcttaaa atttctacat ttactttctc    360
accagcataa aaatcgctaa tatatgatgt aacatcttga aaaacactca tagaaacccc    420 attaaccta acaataatat cgcctgcttt aagccctgac ttaacggcag gtgaacctgg     480
```

```
attaaccta acaataatat cgcctgcttt aagccctgac ttaacggcag gtgaacctgg    480
ataaagagag gcaataattg cagctgaaac atccttacct tcaactccta agcttttag    540 tacttcagaa tctcttgtct ttaaaggata aaaagaaatt ccaagccatg ctgattcaat   600
ttttttacct ttaagaaaaa aatctacagt acttttaata ttattaacag gaattgcaaa    660
acctaaccca atatttcctc cagaatttga agctatccaa gcattaattc caataacttc    720
accttttata tttacaagag gaccgcctga attacctctg ttgattgcag catcagtttg    780
aataaataaa ttccttgatt gtaaattagg atttgcagag cgttgtaatc cacttacaat    840
acctgctgta actgtaaaac taaattgaaa aggactacct actgccataa cccaatcacc    900
tatttcaagc ttatcactat ctccaagatc agctacttta atagttgcat catcactttc    960
aaagctaata agagcaatat ctttttttc atctttgcca attaacttag ccttgtgctt    1020 tttttatca taagacacaa cttcaagttc agttgcctta tctactacat gactatttgt    1080
aaccacataa aataatgatt ttttttgaga atccctacca attattactc cagaccctgc   1140
ccaattgctt tttctctcag aatcaaattc tggcatatca aaaaagaaaa atggaatagg    1200
aaaactctgt ttaattaccc cggttgcatg aacttctacg gacgatgata aaattttctt   1260
ggaaacttcc ctaaaagaat cttgtaaggc ttgtactgta ttgtcttttt cttc          1314
```

<210> SEQ ID NO 15
<211> LENGTH: 437
<212> TYPE: PRT
<213> ORGANISM: Borrelia afzelii

<400> SEQUENCE: 15

Glu Glu Lys Gly Asn Thr Val Gln Thr Leu Gln Asp Ser Phe Arg Glu
1               5                   10                  15

Val Ser Lys Lys Ile Leu Pro Ser Ser Val Glu Val His Ala Thr Gly
            20                  25                  30

Val Ile Lys Gln Ser Phe Pro Ile Pro Phe Phe Phe Asp Met Pro
        35                  40                  45

Glu Phe Asp Ser Glu Arg Lys Ser Asn Trp Ala Gly Ser Gly Val Ile
    50                  55                  60

Ile Gly Arg Asp Ser Lys Asn Lys Ser Leu Phe Tyr Val Val Thr Asn
65                  70                  75                  80

Ser His Val Val Asp Lys Ala Thr Glu Leu Glu Val Val Ser Tyr Asp
                85                  90                  95

Lys Lys Lys His Lys Ala Lys Leu Ile Gly Lys Asp Glu Lys Lys Asp
            100                 105                 110

Ile Ala Leu Ile Ser Phe Glu Ser Asp Asp Ala Thr Ile Lys Val Ala
        115                 120                 125

Asp Leu Gly Asp Ser Asp Lys Leu Glu Ile Gly Asp Trp Val Met Ala
    130                 135                 140

Val Gly Ser Pro Phe Gln Phe Ser Phe Thr Val Thr Ala Gly Ile Val
145                 150                 155                 160

Ser Gly Leu Gln Arg Ser Ala Asn Pro Asn Leu Gln Ser Arg Asn Leu
                165                 170                 175

Phe Ile Gln Thr Asp Ala Ala Ile Asn Arg Gly Asn Ser Gly Gly Pro
            180                 185                 190

Leu Val Asn Thr Lys Gly Glu Val Ile Gly Ile Asn Ala Trp Ile Ala

-continued

```
        195                 200                 205

Ser Asn Ser Gly Gly Asn Ile Gly Leu Gly Phe Ala Ile Pro Val Asn
    210                 215                 220

Asn Ile Lys Ser Thr Val Asp Phe Phe Leu Lys Gly Lys Lys Ile Glu
225                 230                 235                 240

Ser Ala Trp Leu Gly Ile Ser Phe Tyr Pro Leu Lys Thr Arg Asp Pro
                245                 250                 255

Glu Val Leu Lys Ser Leu Gly Val Glu Gly Asp Asp Val Pro Ala Ala
            260                 265                 270

Ile Ile Ala Ser Leu Tyr Pro Gly Ser Pro Ala Ile Lys Ser Gly Leu
        275                 280                 285

Arg Ala Gly Asp Ile Ile Val Lys Val Asn Gly Val Pro Met Ser Val
    290                 295                 300

Phe Gln Asp Val Thr Ser Tyr Ile Ser Asp Phe Tyr Ala Gly Glu Lys
305                 310                 315                 320

Ile Asn Val Glu Ile Leu Arg Gly Asn Val Lys Lys Asn Ile Glu Ile
                325                 330                 335

Ile Leu Ala Val Arg Pro Lys Asp Lys Glu Leu Ser Ser Ser Lys Met
            340                 345                 350

Phe Pro Gly Phe Val Val Tyr Pro Leu Val Glu Asp Ile Lys Ala Gln
        355                 360                 365

Leu Asn Leu Arg Asn Trp Thr Lys Gly Val Val Val Asp Tyr Ile Asp
    370                 375                 380

Lys Asn Leu Ala Ser Asn Ile Lys Met Lys Ser Gly Asp Val Ile Leu
385                 390                 395                 400

Ser Val Asn Ser Lys Ser Val Ser Asn Leu Arg Glu Phe Tyr Asp Ala
                405                 410                 415

Leu Glu Ile Gly Lys Asn Thr Tyr Asn Ile Leu Arg Gly Asn Asp Ser
            420                 425                 430

Phe Lys Ile Ser Phe
        435
```

<210> SEQ ID NO 16
<211> LENGTH: 1314
<212> TYPE: DNA
<213> ORGANISM: Borrelia afzelii

<400> SEQUENCE: 16

```
ctaaaacgaa attttaaaag aatcgtttcc tcttaaaatg ttataagtat tttttccaat     60
ctcaagagca tcataaaatt ctcttaaatt agaaacactt tttgaattta cagaaagaat    120
tacatctcct gatttcatct taatatttga tgctaaattt ttatcaatat aatcaacaac    180
aacgccttta gtccaatttc ttaaattaag ctgagcttta atatcttcaa ctaatggata    240
cacaacaaaa cctggaaaca tttttgaaga agaaagctct ttgtccttgg gtctaacagc    300
aagaataatc tcaatattct ttttaacatt acctcttaaa atttctacat tgattttctc    360
accagcataa aaatcgctaa tatatgatgt aacgtcttga aaaacactca tgggaactcc    420
attaaccttc acaataatgt ctcccgctct aagccctgac ttaatagcag gtgaacctgg    480
ataaagagaa gcaataattg cagctggaac atcatcacct tcaacccccca agctttttag    540 cacttcagga tctcttgtct ttaatgggta aaaagaaatt ccaagccatg ctgattcaat    600
ttttttacct ttaaggaaaa aatctacggt acttttaata ttgttaacag gaattgcaaa    660
acctaaccca atatttccac cagaatttga agctatccaa gcattaatcc caataacttc    720
```

| | |
|---|---|
| accttttgta tttacaagag gtccacctga attacctcta ttgattgcag catcagtttg | 780 |
| aataaataaa tttcttgatt gtaaattagg atttgcagaa cgttgcaatc cacttacaat | 840 |
| acctgctgta actgtaaaac taaattgaaa agggctacct accgccataa cccaatcacc | 900 |
| tatttcaagc ttatcactat ccccaagatc agccacttta atagttgcat catcactttc | 960 |
| aaagctaata agcgcaatat ccttttttc atctttgcca attaacttag ccttatgctt | 1020 |
| tttcttatca taagatacaa cttcaagttc agttgcctta tctactacat gactattggt | 1080 |
| aactacataa aataatgatt tatttttgga atctctacca attattactc cagaccctgc | 1140 |
| ccaattgctt tttctctcag aatcaaattc tggcatatca aaaagaaaa atggaatagg | 1200 |
| aaaactctgc ttaattaccc ctgttgcatg aacttctaca gatgatggta aattttctt | 1260 |
| ggaaacttct ctaaaagagt cttgcaaggt ttgtactgta ttacccttt cttc | 1314 |

<210> SEQ ID NO 17
<211> LENGTH: 336
<212> TYPE: PRT
<213> ORGANISM: Artificial Sequence
<220> FEATURE:
<223> OTHER INFORMATION: Borrelia burgdorferi HtrA amino acid sequence without signal peptide and without the PDZ2 domain

<400> SEQUENCE: 17

```
Glu Glu Lys Asp Asn Thr Val Arg Ala Leu Gln Asp Ser Phe Arg Glu
1               5                   10                  15

Val Ser Lys Lys Ile Leu Pro Ser Ser Val Glu Val His Ala Thr Gly
            20                  25                  30

Val Ile Lys Gln Ser Phe Pro Ile Pro Phe Phe Phe Asp Met Pro
        35                  40                  45

Glu Phe Asp Ser Glu Arg Lys Ser Asn Trp Ala Gly Ser Gly Val Ile
50                  55                  60

Ile Gly Arg Asp Ser Gln Lys Lys Ser Leu Phe Tyr Val Val Thr Asn
65                  70                  75                  80

Ser His Val Val Asp Lys Ala Thr Glu Leu Glu Val Val Ser Tyr Asp
                85                  90                  95

Lys Lys Lys His Lys Ala Lys Leu Ile Gly Lys Asp Glu Lys Lys Asp
            100                 105                 110

Ile Ala Leu Ile Ser Phe Glu Ser Asp Asp Ala Thr Ile Lys Val Ala
        115                 120                 125

Asp Leu Gly Asp Ser Asp Lys Leu Glu Ile Gly Asp Trp Val Met Ala
    130                 135                 140

Val Gly Ser Pro Phe Gln Phe Ser Phe Thr Val Thr Ala Gly Ile Val
145                 150                 155                 160

Ser Gly Leu Gln Arg Ser Ala Asn Pro Asn Leu Gln Ser Arg Asn Leu
                165                 170                 175

Phe Ile Gln Thr Asp Ala Ala Ile Asn Arg Gly Asn Ser Gly Gly Pro
            180                 185                 190

Leu Val Asn Ile Lys Gly Glu Val Ile Gly Ile Asn Ala Trp Ile Ala
        195                 200                 205

Ser Asn Ser Gly Gly Asn Ile Gly Leu Gly Phe Ala Ile Pro Val Asn
    210                 215                 220

Asn Ile Lys Ser Thr Val Asp Phe Phe Leu Lys Gly Lys Lys Ile Glu
225                 230                 235                 240

Ser Ala Trp Leu Gly Ile Ser Phe Tyr Pro Leu Lys Thr Arg Asp Ser
                245                 250                 255
```

```
Glu Val Leu Lys Ser Leu Gly Val Glu Ser Asn Asp Val Ser Ala Ala
            260                 265                 270

Ile Ile Ala Ser Leu Tyr Pro Gly Ser Pro Ala Val Lys Ser Gly Leu
        275                 280                 285

Arg Ala Gly Asp Ile Ile Met Lys Val Asn Gly Val Ser Met Ser Val
        290                 295                 300

Phe Gln Asp Val Thr Ser Tyr Ile Ser Asp Phe Tyr Ala Gly Glu Lys
305                 310                 315                 320

Val Asn Val Glu Ile Leu Arg Gly Asn Val Lys Lys Asn Ile Glu Ile
                325                 330                 335
```

<210> SEQ ID NO 18
<211> LENGTH: 1008
<212> TYPE: DNA
<213> ORGANISM: Artificial Sequence
<220> FEATURE:
<223> OTHER INFORMATION: Nucleic acid sequence encoding Borrelia
burgdorferi HtrA without signal peptide and without the PDZ2
domain

<400> SEQUENCE: 18

```
aatctcaata ttttttttga cattgcctct taagatttct acatttactt tctcaccagc      60
ataaaaatca ctaatatatg atgtaacatc ttgaaaaacg ctcatggaaa ccccattaac     120
cttcataata atatcccctg ccctaagccc tgatttaaca gcgggtgaac ccggataaag     180
agaagcaata attgcagctg aaacatcatt actttcaacc cctaagcttt ttagcacctc     240
agaatctctt gtctttagcg ataaaaaga aattccaagc caagccgatt caatttttt      300
acctttaagg aaaaaatcta cagtgctttt aatattgtta acaggaattg caaacccaa      360
cccaatattt ccgccagaat tgaagctat ccaagcatta attccaataa cctcgcccct     420
tatatttaca agaggaccac ctgaattacc cctgttgatt gcagcatcgg tttgaataaa     480
cagattcctt gattgcaaat taggatttgc agaacgttgc aatccactta caatacctgc     540
tgtaactgta aaactaaatt gaaaagggct gcccactgcc ataacccaat cacctatttc     600
aagcttatca ctatctccaa gatcagctac tttaatagtt gcgtcatcac tttcaaagct     660
aataagggca atatccttt tttcatcttt gccaattaac ttagccttgt gcttttttt     720
atcataagat acaacttcaa gttcagttgc cttatctacc acatgactat tcgtaaccac     780
ataaataat gattttttt gagaatctct accaattatt actccagacc ccgcccaatt     840
gctttttctc tcagaatcaa attctggcat atcaaaaaag aaaatggaa taggaaaact      900
ctgcttgatt acccctgttg catgaacttc cacagatgat ggtaaaattt tcttggaaac     960
ctctctaaaa gaatcttgta aggctcgtac ggtattgtcc ttttcttc              1008
```

<210> SEQ ID NO 19
<211> LENGTH: 336
<212> TYPE: PRT
<213> ORGANISM: Artificial Sequence
<220> FEATURE:
<223> OTHER INFORMATION: Amino acid sequence of Borrelia burgdorferi
HtrA S226A mutant without signal peptide, and without PDZ2 domain

<400> SEQUENCE: 19

```
Glu Glu Lys Asp Asn Thr Val Arg Ala Leu Gln Asp Ser Phe Arg Glu
1               5                   10                  15

Val Ser Lys Lys Ile Leu Pro Ser Ser Val Glu Val His Ala Thr Gly
            20                  25                  30

Val Ile Lys Gln Ser Phe Pro Ile Pro Phe Phe Phe Phe Asp Met Pro
```

|  |  |  |  |  | 35 |  |  |  |  | 40 |  |  |  |  | 45 |  |  |
|---|---|---|---|---|---|---|---|---|---|---|---|---|---|---|---|---|---|
| Glu | Phe | Asp | Ser | Glu | Arg | Lys | Ser | Asn | Trp | Ala | Gly | Ser | Gly | Val | Ile |  |  |
| 50 |  |  |  |  | 55 |  |  |  |  | 60 |  |  |  |  |  |  |  |

Glu Phe Asp Ser Glu Arg Lys Ser Asn Trp Ala Gly Ser Gly Val Ile
50                   55                  60

Ile Gly Arg Asp Ser Gln Lys Lys Ser Leu Phe Tyr Val Val Thr Asn
65                   70                  75                  80

Ser His Val Val Asp Lys Ala Thr Glu Leu Val Val Ser Tyr Asp
                    85                  90                  95

Lys Lys Lys His Lys Ala Lys Leu Ile Gly Lys Asp Glu Lys Lys Asp
            100                 105                 110

Ile Ala Leu Ile Ser Phe Glu Ser Asp Asp Ala Thr Ile Lys Val Ala
            115                 120                 125

Asp Leu Gly Asp Ser Asp Lys Leu Glu Ile Gly Asp Trp Val Met Ala
            130                 135                 140

Val Gly Ser Pro Phe Gln Phe Ser Phe Thr Val Thr Ala Gly Ile Val
145                 150                 155                 160

Ser Gly Leu Gln Arg Ser Ala Asn Pro Asn Leu Gln Ser Arg Asn Leu
                    165                 170                 175

Phe Ile Gln Thr Asp Ala Ala Ile Asn Arg Gly Asn Ala Gly Pro
                180                 185                 190

Leu Val Asn Ile Lys Gly Glu Val Ile Gly Ile Asn Ala Trp Ile Ala
            195                 200                 205

Ser Asn Ser Gly Gly Asn Ile Gly Leu Gly Phe Ala Ile Pro Val Asn
210                 215                 220

Asn Ile Lys Ser Thr Val Asp Phe Phe Leu Lys Gly Lys Lys Ile Glu
225                 230                 235                 240

Ser Ala Trp Leu Gly Ile Ser Phe Tyr Pro Leu Lys Thr Arg Asp Ser
                245                 250                 255

Glu Val Leu Lys Ser Leu Gly Val Glu Ser Asn Asp Val Ser Ala Ala
                260                 265                 270

Ile Ile Ala Ser Leu Tyr Pro Gly Ser Pro Ala Val Lys Ser Gly Leu
            275                 280                 285

Arg Ala Gly Asp Ile Ile Met Lys Val Asn Gly Val Ser Met Ser Val
290                 295                 300

Phe Gln Asp Val Thr Ser Tyr Ile Ser Asp Phe Tyr Ala Gly Glu Lys
305                 310                 315                 320

Val Asn Val Glu Ile Leu Arg Gly Asn Val Lys Lys Asn Ile Glu Ile
                325                 330                 335

<210> SEQ ID NO 20
<211> LENGTH: 1008
<212> TYPE: DNA
<213> ORGANISM: Artificial Sequence
<220> FEATURE:
<223> OTHER INFORMATION: Nucleic acid sequence encoding Borrelia
      burgdorferi HtrA S226A mutant without signal peptide and without
      the PDZ2 domain

<400> SEQUENCE: 20
aatctcaata ttttttttga cattgcctct taagatttct acatttactt tctcaccagc      60
ataaaaatca ctaatatatg atgtaacatc ttgaaaaacg ctcatggaaa ccccattaac     120
cttcataata atatcccctg ccctaagccc tgatttaaca gcgggtgaac ccggataaag     180
agaagcaata attgcagctg aaacatcatt actttcaacc cctaagcttt ttagcacctc     240
agaatctctt gtctttagcg gataaaagaa aattccaagc caagccgatt caattttttt     300
acctttaagg aaaaaatcta cagtgctttt aatattgtta acaggaattg caaaccccaa     360

```
cccaatattt ccgccagaat ttgaagctat ccaagcatta attccaataa cctcgccctt    420
tatatttaca agaggaccac ctgcattacc cctgttgatt gcagcatcgg tttgaataaa    480
cagattcctt gattgcaaat taggatttgc agaacgttgc aatccactta caatacctgc    540
tgtaactgta aaactaaatt gaaaagggct gcccactgcc ataacccaat cacctatttc    600
aagcttatca ctatctccaa gatcagctac tttaatagtt gcgtcatcac tttcaaagct    660
aataagggca atatccttt tttcatcttt gccaattaac ttagccttgt gcttttttt     720 atcataagat acaacttcaa gttcagttgc cttatctacc acatgactat tcgtaaccac    780
ataaaataat gattttttt gagaatctct accaattatt actccagacc ccgcccaatt    840 gcttttctc tcagaatcaa attctggcat atcaaaaag aaaaatggaa taggaaaact      900
ctgcttgatt accctgttg catgaacttc cacagatgat ggtaaattt tcttggaaac      960 ctctctaaaa gaatcttgta aggctcgtac ggtattgtcc ttttcttc                1008
```

<210> SEQ ID NO 21
<211> LENGTH: 336
<212> TYPE: PRT
<213> ORGANISM: Artificial Sequence
<220> FEATURE:
<223> OTHER INFORMATION: Borrelia garinii HtrA amino acid sequence
      without signal peptide and without the PDZ2 domain

<400> SEQUENCE: 21

```
Glu Glu Lys Asp Asn Thr Val Gln Ala Leu Gln Asp Ser Phe Arg Glu
1               5                   10                  15

Val Ser Lys Lys Ile Leu Ser Ser Val Glu Val His Ala Thr Gly
            20                  25                  30

Val Ile Lys Gln Ser Phe Pro Ile Pro Phe Phe Phe Asp Met Pro
        35                  40                  45

Glu Phe Asp Ser Glu Arg Lys Ser Asn Trp Ala Gly Ser Gly Val Ile
50                  55                  60

Ile Gly Arg Asp Ser Gln Lys Lys Ser Leu Phe Tyr Val Val Thr Asn
65                  70                  75                  80

Ser His Val Val Asp Lys Ala Thr Glu Leu Glu Val Val Ser Tyr Asp
                85                  90                  95

Lys Lys Lys His Lys Ala Lys Leu Ile Gly Lys Asp Glu Lys Lys Asp
            100                 105                 110

Ile Ala Leu Ile Ser Phe Glu Ser Asp Ala Thr Ile Lys Val Ala
        115                 120                 125

Asp Leu Gly Asp Ser Asp Lys Leu Glu Ile Gly Asp Trp Val Met Ala
    130                 135                 140

Val Gly Ser Pro Phe Gln Phe Ser Phe Thr Val Thr Ala Gly Ile Val
145                 150                 155                 160

Ser Gly Leu Gln Arg Ser Ala Asn Pro Asn Leu Gln Ser Arg Asn Leu
                165                 170                 175

Phe Ile Gln Thr Asp Ala Ala Ile Asn Arg Gly Asn Ser Gly Pro
            180                 185                 190

Leu Val Asn Ile Lys Gly Glu Val Ile Gly Ile Asn Ala Trp Ile Ala
        195                 200                 205

Ser Asn Ser Gly Gly Asn Ile Gly Leu Gly Phe Ala Ile Pro Val Asn
    210                 215                 220

Asn Ile Lys Ser Thr Val Asp Phe Phe Leu Lys Gly Lys Lys Ile Glu
225                 230                 235                 240
```

```
Ser Ala Trp Leu Gly Ile Ser Phe Tyr Pro Leu Lys Thr Arg Asp Ser
            245                 250                 255

Glu Val Leu Lys Ser Leu Gly Val Glu Gly Lys Asp Val Ser Ala Ala
        260                 265                 270

Ile Ile Ala Ser Leu Tyr Pro Gly Ser Pro Ala Val Lys Ser Gly Leu
    275                 280                 285

Lys Ala Gly Asp Ile Ile Val Lys Val Asn Gly Val Ser Met Ser Val
290                 295                 300

Phe Gln Asp Val Thr Ser Tyr Ile Ser Asp Phe Tyr Ala Gly Glu Lys
305                 310                 315                 320

Val Asn Val Glu Ile Leu Arg Gly Asn Val Lys Lys Asn Ile Glu Ile
                325                 330                 335

<210> SEQ ID NO 22
<211> LENGTH: 1008
<212> TYPE: DNA
<213> ORGANISM: Artificial Sequence
<220> FEATURE:
<223> OTHER INFORMATION: Nucleic acid sequence encoding Borrelia garinii
      HtrA without the signal peptide and without the PDZ2 domain

<400> SEQUENCE: 22
aatctcaata ttttttttga cattacctct taaaatttct acatttactt tctcaccagc      60
ataaaaatcg ctaatatatg atgtaacatc ttgaaaaaca ctcatagaaa ccccattaac     120
cttaacaata atatcgcctg ctttaagccc tgacttaacg gcaggtgaac ctggataaag     180
agaggcaata attgcagctg aaacatcctt accttcaact cctaagcttt ttagtacttc     240
agaatctctt gtctttaaag gataaaaaga aattccaagc catgctgatt caattttttt     300
acctttaaga aaaaaatcta cagtactttt aatattatta acaggaattg caaaacctaa     360
cccaatattt cctccagaat tgaagctat ccaagcatta attccaataa cttcaccttt      420
tatatttaca agaggaccgc ctgaattacc tctgttgatt gcagcatcag tttgaataaa     480
taaattcctt gattgtaaat taggatttgc agagcgttgt aatccactta caatacctgc     540
tgtaactgta aaactaaatt gaaaaggact acctactgcc ataacccaat cacctatttc     600
aagcttatca ctatctccaa gatcagctac tttaatagtt gcatcatcac tttcaaagct     660
aataagagca atatcttttt tttcatcttt gccaattaac ttagccttgt gcttttttt      720 atcataagac acaacttcaa gttcagttgc cttatctact acatgactat ttgtaaccac     780
ataaaataat gattttttt gagaatccct accaattatt actccagacc ctgcccaatt      840
gctttttctc tcagaatcaa attctggcat atcaaaaaag aaaaatggaa taggaaaact      900
ctgtttaatt accccggttg catgaacttc tacggacgat gataaaattt tcttggaaac     960
ttccctaaaa gaatcttgta aggcttgtac tgtattgtct ttttcttc                  1008

<210> SEQ ID NO 23
<211> LENGTH: 336
<212> TYPE: PRT
<213> ORGANISM: Artificial Sequence
<220> FEATURE:
<223> OTHER INFORMATION: Amino acid sequence of Borrelia afzelii HtrA
      without the signal peptide and without the PDZ2 domain

<400> SEQUENCE: 23

Glu Glu Lys Gly Asn Thr Val Gln Thr Leu Gln Asp Ser Phe Arg Glu
1               5                   10                  15

Val Ser Lys Lys Ile Leu Pro Ser Ser Val Glu Val His Ala Thr Gly
            20                  25                  30
```

```
Val Ile Lys Gln Ser Phe Pro Ile Pro Phe Phe Phe Asp Met Pro
             35                  40                  45

Glu Phe Asp Ser Glu Arg Lys Ser Asn Trp Ala Gly Ser Gly Val Ile
 50                  55                  60

Ile Gly Arg Asp Ser Lys Asn Lys Ser Leu Phe Tyr Val Val Thr Asn
 65                  70                  75                  80

Ser His Val Val Asp Lys Ala Thr Glu Leu Glu Val Val Ser Tyr Asp
             85                  90                  95

Lys Lys Lys His Lys Ala Lys Leu Ile Gly Lys Asp Glu Lys Lys Asp
                 100                 105                 110

Ile Ala Leu Ile Ser Phe Glu Ser Asp Asp Ala Thr Ile Lys Val Ala
             115                 120                 125

Asp Leu Gly Asp Ser Asp Lys Leu Glu Ile Gly Asp Trp Val Met Ala
 130                 135                 140

Val Gly Ser Pro Phe Gln Phe Ser Phe Thr Val Thr Ala Gly Ile Val
145                 150                 155                 160

Ser Gly Leu Gln Arg Ser Ala Asn Pro Asn Leu Gln Ser Arg Asn Leu
                 165                 170                 175

Phe Ile Gln Thr Asp Ala Ala Ile Asn Arg Gly Asn Ser Gly Gly Pro
             180                 185                 190

Leu Val Asn Thr Lys Gly Glu Val Ile Gly Ile Asn Ala Trp Ile Ala
             195                 200                 205

Ser Asn Ser Gly Gly Asn Ile Gly Leu Gly Phe Ala Ile Pro Val Asn
 210                 215                 220

Asn Ile Lys Ser Thr Val Asp Phe Phe Leu Lys Gly Lys Lys Ile Glu
225                 230                 235                 240

Ser Ala Trp Leu Gly Ile Ser Phe Tyr Pro Leu Lys Thr Arg Asp Pro
                 245                 250                 255

Glu Val Leu Lys Ser Leu Gly Val Glu Gly Asp Asp Val Pro Ala Ala
             260                 265                 270

Ile Ile Ala Ser Leu Tyr Pro Gly Ser Pro Ala Ile Lys Ser Gly Leu
             275                 280                 285

Arg Ala Gly Asp Ile Ile Val Lys Val Asn Gly Val Pro Met Ser Val
 290                 295                 300

Phe Gln Asp Val Thr Ser Tyr Ile Ser Asp Phe Tyr Ala Gly Glu Lys
305                 310                 315                 320

Ile Asn Val Glu Ile Leu Arg Gly Asn Val Lys Lys Asn Ile Glu Ile
                 325                 330                 335

<210> SEQ ID NO 24
<211> LENGTH: 1008
<212> TYPE: DNA
<213> ORGANISM: Artificial Sequence
<220> FEATURE:
<223> OTHER INFORMATION: Nucleic acid sequence encoding Borrelia afzelii
      HtrA without the signal peptide and without the PDZ2 domain

<400> SEQUENCE: 24
aatctcaata ttcttttta cattacctct taaaatttct acattgattt tctcaccagc      60
ataaaaatcg ctaatatatg atgtaacgtc ttgaaaaaca ctcatgggaa ctccattaac    120
cttcacaata atgtctcccg ctctaagccc tgacttaata gcaggtgaac ctggataaag    180
agaagcaata attgcagctg gaacatcatc accttcaacc cccaagcttt ttagcacttc    240
aggatctctt gtcttaatg ggtaaaaaga aattccaagc catgctgatt caattttttt     300
```

```
acctttaagg aaaaaatcta cggtactttt aatattgtta acaggaattg caaaacctaa    360
cccaatattt ccaccagaat ttgaagctat ccaagcatta atcccaataa cttcacctttt   420
tgtatttaca agaggtccac ctgaattacc tctattgatt gcagcatcag tttgaataaa    480
taaatttctt gattgtaaat taggatttgc agaacgttgc aatccactta caatacctgc    540
tgtaactgta aaactaaatt gaaaagggct acctaccgcc ataacccaat cacctatttc    600
aagcttatca ctatccccaa gatcagccac tttaatagtt gcatcatcac tttcaaagct    660
aataagcgca atatccttt tttcatcttt gccaattaac ttagccttat gcttttctt     720
atcataagat acaacttcaa gttcagttgc cttatctact acatgactat tggtaactac    780
ataaaataat gatttatttt tggaatctct accaattatt actccagacc ctgcccaatt    840
gcttttctc tcagaatcaa attctggcat atcaaaaaag aaaaatggaa taggaaaact     900
ctgcttaatt acccctgttg catgaacttc tacagatgat ggtaaaattt tcttggaaac    960
ttctctaaaa gagtcttgca aggtttgtac tgtattaccc ttttcttc                 1008
```

<210> SEQ ID NO 25
<211> LENGTH: 45
<212> TYPE: DNA
<213> ORGANISM: Artificial Sequence
<220> FEATURE:
<223> OTHER INFORMATION: Forward primer for BbHtrA

<400> SEQUENCE: 25
ctttaagaag gagatataca tatggaagaa aaagataaca ccgtg    45

<210> SEQ ID NO 26
<211> LENGTH: 50
<212> TYPE: DNA
<213> ORGANISM: Artificial Sequence
<220> FEATURE:
<223> OTHER INFORMATION: Reverse primer for BbHtrA

<400> SEQUENCE: 26
atacagctgt gcggccgcaa gctttcatta gtgatggtga tggtgatgaa    50

<210> SEQ ID NO 27
<211> LENGTH: 19
<212> TYPE: PRT
<213> ORGANISM: Artificial Sequence
<220> FEATURE:
<223> OTHER INFORMATION: BbHtrA peptide

<400> SEQUENCE: 27

Val Ser Ala Ala Ile Ile Ala Ser Leu Tyr Pro Gly Ser Pro Ala Val
1               5                   10                  15

Lys Ser Gly

<210> SEQ ID NO 28
<211> LENGTH: 5
<212> TYPE: PRT
<213> ORGANISM: Artificial Sequence
<220> FEATURE:
<223> OTHER INFORMATION: neoepitope

<400> SEQUENCE: 28

Asp Ile Pro Glu Asn
1               5

<210> SEQ ID NO 29
<211> LENGTH: 4

```
<212> TYPE: PRT
<213> ORGANISM: Artificial Sequence
<220> FEATURE:
<223> OTHER INFORMATION: neoepitope

<400> SEQUENCE: 29

Ala Arg Gly Ser
1

<210> SEQ ID NO 30
<211> LENGTH: 6
<212> TYPE: PRT
<213> ORGANISM: Artificial Sequence
<220> FEATURE:
<223> OTHER INFORMATION: neoepitope

<400> SEQUENCE: 30

Asn Ile Thr Glu Gly Glu
1               5

<210> SEQ ID NO 31
<211> LENGTH: 4
<212> TYPE: PRT
<213> ORGANISM: Artificial Sequence
<220> FEATURE:
<223> OTHER INFORMATION: cleavage site

<400> SEQUENCE: 31

Val Gln Thr Val
1

<210> SEQ ID NO 32
<211> LENGTH: 11
<212> TYPE: PRT
<213> ORGANISM: Artificial Sequence
<220> FEATURE:
<223> OTHER INFORMATION: Amino terminal peptide of recombinant aggrecan

<400> SEQUENCE: 32

Val Glu Thr Ser Asp His Asp Asn Ser Leu Ser
1               5                   10

<210> SEQ ID NO 33
<211> LENGTH: 26
<212> TYPE: PRT
<213> ORGANISM: Artificial Sequence
<220> FEATURE:
<223> OTHER INFORMATION: Bovine decorin peptide

<400> SEQUENCE: 33

Gly Leu Glu Lys Val Pro Lys Asp Leu Pro Pro Asp Thr Ala Leu Leu
1               5                   10                  15

Asp Leu Gln Asn Asn Lys Ile Thr Glu Ile
            20                  25

<210> SEQ ID NO 34
<211> LENGTH: 11
<212> TYPE: PRT
<213> ORGANISM: Artificial Sequence
<220> FEATURE:
<223> OTHER INFORMATION: Bovine decorin peptide

<400> SEQUENCE: 34

Val Val Glu Leu Gly Thr Asn Pro Leu Lys Ser
1               5                   10
```

```
<210> SEQ ID NO 35
<211> LENGTH: 26
<212> TYPE: PRT
<213> ORGANISM: Artificial Sequence
<220> FEATURE:
<223> OTHER INFORMATION: Bovine decorin peptide

<400> SEQUENCE: 35

Val Val Glu Leu Gly Thr Asn Pro Leu Lys Ser Ser Gly Ile Glu Asn
1               5                   10                  15

Gly Ala Phe Gln Gly Met Lys Lys Leu Ser
            20                  25

<210> SEQ ID NO 36
<211> LENGTH: 30
<212> TYPE: PRT
<213> ORGANISM: Artificial Sequence
<220> FEATURE:
<223> OTHER INFORMATION: Bovine decorin peptide

<400> SEQUENCE: 36

Val Val Glu Leu Gly Thr Asn Pro Leu Lys Ser Ser Gly Ile Glu Asn
1               5                   10                  15

Gly Ala Phe Gln Gly Met Lys Lys Leu Ser Tyr Ile Arg Ile
            20                  25                  30

<210> SEQ ID NO 37
<211> LENGTH: 25
<212> TYPE: PRT
<213> ORGANISM: Artificial Sequence
<220> FEATURE:
<223> OTHER INFORMATION: Bovine decorin peptide

<400> SEQUENCE: 37

Val Val Glu Leu Gly Thr Asn Pro Leu Lys Ser Ser Gly Ile Glu Asn
1               5                   10                  15

Gly Ala Phe Gln Gly Met Lys Lys Leu
            20                  25

<210> SEQ ID NO 38
<211> LENGTH: 8
<212> TYPE: PRT
<213> ORGANISM: Artificial Sequence
<220> FEATURE:
<223> OTHER INFORMATION: Bovine biglycan peptide

<400> SEQUENCE: 38

Gly Leu Pro Asp Leu Lys Leu Leu
1               5

<210> SEQ ID NO 39
<211> LENGTH: 10
<212> TYPE: PRT
<213> ORGANISM: Artificial Sequence
<220> FEATURE:
<223> OTHER INFORMATION: Bovine biglycan peptide

<400> SEQUENCE: 39

Gly Leu Pro Asp Leu Lys Leu Leu Gln Val
1               5                   10

<210> SEQ ID NO 40
<211> LENGTH: 11
<212> TYPE: PRT
<213> ORGANISM: Artificial Sequence
<220> FEATURE:
```

```
<223> OTHER INFORMATION: Bovine biglycan peptide

<400> SEQUENCE: 40

Gly Leu Pro Asp Leu Lys Leu Leu Gln Val Val
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Bovine aggrecan peptide

<400> SEQUENCE: 41

Thr Leu Pro Asn Tyr Pro Ala Ile Pro Ser Asp Ala
1               5                   10

<210> SEQ ID NO 42
<211> LENGTH: 16
<212> TYPE: PRT
<213> ORGANISM: Artificial Sequence
<220> FEATURE:
<223> OTHER INFORMATION: Bovine aggrecan peptide

<400> SEQUENCE: 42

Thr Leu Pro Asn Tyr Pro Ala Ile Pro Ser Asp Ala Thr Leu Glu Ile
1               5                   10                  15

<210> SEQ ID NO 43
<211> LENGTH: 12
<212> TYPE: PRT
<213> ORGANISM: Artificial Sequence
<220> FEATURE:
<223> OTHER INFORMATION: Bovine aggrecan peptide

<400> SEQUENCE: 43

Gly Trp Leu Ala Asp Gln Thr Val Arg Tyr Pro Ile
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Bovine fibromodulin peptide

<400> SEQUENCE: 44

Tyr Leu Gln Gly Asn Arg Ile Asn Glu Phe Ser Ile
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Bovine fibromodulin peptide

<400> SEQUENCE: 45

Val Val Asp Val Met Asn Phe Ser Lys Leu Gln Val
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Bovine fibromodulin peptide
```

```
<400> SEQUENCE: 46

Val Asp Val Met Asn Phe Ser Lys Leu Gln Val
1               5                   10

<210> SEQ ID NO 47
<211> LENGTH: 9
<212> TYPE: PRT
<213> ORGANISM: Artificial Sequence
<220> FEATURE:
<223> OTHER INFORMATION: Bovine COMP peptide

<400> SEQUENCE: 47

Val Met Trp Lys Gln Met Glu Gln Thr
1               5

<210> SEQ ID NO 48
<211> LENGTH: 12
<212> TYPE: PRT
<213> ORGANISM: Artificial Sequence
<220> FEATURE:
<223> OTHER INFORMATION: Bovine COMP peptide

<400> SEQUENCE: 48

Met Trp Lys Gln Met Glu Gln Thr Tyr Trp Gln Ala
1               5                   10

<210> SEQ ID NO 49
<211> LENGTH: 17
<212> TYPE: PRT
<213> ORGANISM: Artificial Sequence
<220> FEATURE:
<223> OTHER INFORMATION: Bovine COMP peptide

<400> SEQUENCE: 49

Met Trp Lys Gln Met Glu Gln Thr Tyr Trp Gln Ala Asn Pro Phe Arg
1               5                   10                  15

Ala

<210> SEQ ID NO 50
<211> LENGTH: 10
<212> TYPE: PRT
<213> ORGANISM: Artificial Sequence
<220> FEATURE:
<223> OTHER INFORMATION: Bovine COMP peptide

<400> SEQUENCE: 50

Trp His Thr Gly Asp Thr Ala Ser Gln Val
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Bovine COMP peptide

<400> SEQUENCE: 51

Trp His Thr Gly Asp Thr Ala Ser Gln Val Arg Leu
1               5                   10

<210> SEQ ID NO 52
<211> LENGTH: 26
<212> TYPE: PRT
<213> ORGANISM: Artificial Sequence
<220> FEATURE:
```

<223> OTHER INFORMATION: Human decorin peptide

<400> SEQUENCE: 52

Gly Leu Asp Lys Val Pro Lys Asp Leu Pro Pro Asp Thr Thr Leu Leu
1               5                   10                  15

Asp Leu Gln Asn Asn Lys Ile Thr Glu Ile
            20                  25

<210> SEQ ID NO 53
<211> LENGTH: 11
<212> TYPE: PRT
<213> ORGANISM: Artificial Sequence
<220> FEATURE:
<223> OTHER INFORMATION: Human decorin peptide

<400> SEQUENCE: 53

Val Ile Glu Leu Gly Thr Asn Pro Leu Lys Ser
1               5                   10

<210> SEQ ID NO 54
<211> LENGTH: 26
<212> TYPE: PRT
<213> ORGANISM: Artificial Sequence
<220> FEATURE:
<223> OTHER INFORMATION: Human decorin peptide

<400> SEQUENCE: 54

Val Ile Glu Leu Gly Thr Asn Pro Leu Lys Ser Ser Gly Ile Glu Asn
1               5                   10                  15

Gly Ala Phe Gln Gly Met Lys Lys Leu Ser
            20                  25

<210> SEQ ID NO 55
<211> LENGTH: 30
<212> TYPE: PRT
<213> ORGANISM: Artificial Sequence
<220> FEATURE:
<223> OTHER INFORMATION: Human decorin peptide

<400> SEQUENCE: 55

Val Ile Glu Leu Gly Thr Asn Pro Leu Lys Ser Ser Gly Ile Glu Asn
1               5                   10                  15

Gly Ala Phe Gln Gly Met Lys Lys Leu Ser Tyr Ile Arg Ile
            20                  25                  30

<210> SEQ ID NO 56
<211> LENGTH: 8
<212> TYPE: PRT
<213> ORGANISM: Artificial Sequence
<220> FEATURE:
<223> OTHER INFORMATION: Human biglycan peptide

<400> SEQUENCE: 56

Gly Leu Pro Asp Leu Lys Leu Leu
1               5

<210> SEQ ID NO 57
<211> LENGTH: 10
<212> TYPE: PRT
<213> ORGANISM: Artificial Sequence
<220> FEATURE:
<223> OTHER INFORMATION: Human biglycan peptide

<400> SEQUENCE: 57

Gly Leu Pro Asp Leu Lys Leu Leu Gln Val

```
1               5                   10
```

<210> SEQ ID NO 58
<211> LENGTH: 11
<212> TYPE: PRT
<213> ORGANISM: Artificial Sequence
<220> FEATURE:
<223> OTHER INFORMATION: Human biglycan peptide

<400> SEQUENCE: 58

```
Gly Leu Pro Asp Leu Lys Leu Leu Gln Val Val
1               5                   10
```

<210> SEQ ID NO 59
<211> LENGTH: 12
<212> TYPE: PRT
<213> ORGANISM: Artificial Sequence
<220> FEATURE:
<223> OTHER INFORMATION: Human aggrecan peptide

<400> SEQUENCE: 59

```
Ser Leu Pro Asn Tyr Pro Ala Ile Pro Ser Asp Ala
1               5                   10
```

<210> SEQ ID NO 60
<211> LENGTH: 16
<212> TYPE: PRT
<213> ORGANISM: Artificial Sequence
<220> FEATURE:
<223> OTHER INFORMATION: Human aggrecan peptide

<400> SEQUENCE: 60

```
Ser Leu Pro Asn Tyr Pro Ala Ile Pro Ser Asp Ala Thr Leu Glu Val
1               5                   10                  15
```

<210> SEQ ID NO 61
<211> LENGTH: 12
<212> TYPE: PRT
<213> ORGANISM: Artificial Sequence
<220> FEATURE:
<223> OTHER INFORMATION: Human aggrecan peptide

<400> SEQUENCE: 61

```
Gly Trp Leu Ala Asp Gln Thr Val Arg Tyr Pro Ile
1               5                   10
```

<210> SEQ ID NO 62
<211> LENGTH: 12
<212> TYPE: PRT
<213> ORGANISM: Artificial Sequence
<220> FEATURE:
<223> OTHER INFORMATION: Human fibromodulin peptide

<400> SEQUENCE: 62

```
Tyr Leu Gln Gly Asn Arg Ile Asn Glu Phe Ser Ile
1               5                   10
```

<210> SEQ ID NO 63
<211> LENGTH: 12
<212> TYPE: PRT
<213> ORGANISM: Artificial Sequence
<220> FEATURE:
<223> OTHER INFORMATION: Human fibromodulin peptide

<400> SEQUENCE: 63

```
Val Val Asp Val Val Asn Phe Ser Lys Leu Gln Val
1               5                   10
```

```
<210> SEQ ID NO 64
<211> LENGTH: 11
<212> TYPE: PRT
<213> ORGANISM: Artificial Sequence
<220> FEATURE:
<223> OTHER INFORMATION: Human fibromodulin peptide

<400> SEQUENCE: 64

Val Asp Val Val Asn Phe Ser Lys Leu Gln Val
1               5                   10

<210> SEQ ID NO 65
<211> LENGTH: 9
<212> TYPE: PRT
<213> ORGANISM: Artificial Sequence
<220> FEATURE:
<223> OTHER INFORMATION: Human COMP peptide

<400> SEQUENCE: 65

Val Met Trp Lys Gln Met Glu Gln Thr
1               5

<210> SEQ ID NO 66
<211> LENGTH: 12
<212> TYPE: PRT
<213> ORGANISM: Artificial Sequence
<220> FEATURE:
<223> OTHER INFORMATION: Human COMP peptide

<400> SEQUENCE: 66

Met Trp Lys Gln Met Glu Gln Thr Tyr Trp Gln Ala
1               5                   10

<210> SEQ ID NO 67
<211> LENGTH: 17
<212> TYPE: PRT
<213> ORGANISM: Artificial Sequence
<220> FEATURE:
<223> OTHER INFORMATION: Human COMP peptide

<400> SEQUENCE: 67

Met Trp Lys Gln Met Glu Gln Thr Tyr Trp Gln Ala Asn Pro Phe Arg
1               5                   10                  15

Ala

<210> SEQ ID NO 68
<211> LENGTH: 10
<212> TYPE: PRT
<213> ORGANISM: Artificial Sequence
<220> FEATURE:
<223> OTHER INFORMATION: Human COMP peptide

<400> SEQUENCE: 68

Trp His Thr Gly Asp Thr Glu Ser Gln Val
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Human COMP peptide

<400> SEQUENCE: 69

Trp His Thr Gly Asp Thr Glu Ser Gln Val Arg Leu
```

```
1               5                   10
```

<210> SEQ ID NO 70
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 70

```
Ala Phe Gln Thr Val Val Leu Asp
1               5
```

<210> SEQ ID NO 71
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 71

```
Ala Ile Glu Leu Glu Asp Leu Leu
1               5
```

<210> SEQ ID NO 72
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 72

```
Ala Lys Leu Thr Gly Ile Pro Lys
1               5
```

<210> SEQ ID NO 73
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 73

```
Ala Val Lys Ser Ser Thr Gly Pro
1               5
```

<210> SEQ ID NO 74
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 74

```
Cys Ile Glu Met Gly Gly Asn Pro
1               5
```

<210> SEQ ID NO 75
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 75

```
Cys Ser Asp Leu Gly Leu Glu Lys
1               5
```

```
<210> SEQ ID NO 76
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 76

Cys Val Tyr Val Arg Ala Ala Val
1               5

<210> SEQ ID NO 77
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 77

Asp Ile Lys Ala Gln Leu Asn Leu
1               5

<210> SEQ ID NO 78
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 78

Asp Thr Asn Ile Thr Thr Ile Pro
1               5

<210> SEQ ID NO 79
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 79

Phe Cys Thr Val Val Asp Val Met
1               5

<210> SEQ ID NO 80
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 80

Phe Glu Pro Gly Ala Phe Asp Gly
1               5

<210> SEQ ID NO 81
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 81

Phe Gln Thr Val Val Leu Asp Pro
1               5
```

```
<210> SEQ ID NO 82
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 82

Phe Arg Ala Val Ala Glu Pro Gly
1               5

<210> SEQ ID NO 83
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 83

Phe Arg Cys Val Thr Asp Arg Leu
1               5

<210> SEQ ID NO 84
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 84

Phe Tyr Val Val Met Trp Lys Gln
1               5

<210> SEQ ID NO 85
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 85

Gly Ile Ser Leu Phe Asn Asn Pro
1               5

<210> SEQ ID NO 86
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 86

Gly Leu Lys Leu Asn Tyr Leu Arg
1               5

<210> SEQ ID NO 87
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 87

Gly Leu Pro Ser Ala Leu Glu Gln
1               5
```

```
<210> SEQ ID NO 88
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 88

Gly Val Val Val Asp Tyr Ile Asp
1               5

<210> SEQ ID NO 89
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 89

His Glu Lys Ala Phe Ser Pro Leu
1               5

<210> SEQ ID NO 90
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 90

His Leu Tyr Ala Leu Val Leu Val
1               5

<210> SEQ ID NO 91
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 91

His Asn Asn Val Phe Ser Val Pro
1               5

<210> SEQ ID NO 92
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 92

Ile Glu Met Gly Gly Asn Pro Leu
1               5

<210> SEQ ID NO 93
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 93

Ile His Gln Leu Tyr Leu Asp Ser
1               5

<210> SEQ ID NO 94
```

```
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 94

Ile Ile Ala Ser Leu Tyr Pro Gly
1               5

<210> SEQ ID NO 95
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 95

Ile Met Lys Val Asn Gly Val Ser
1               5

<210> SEQ ID NO 96
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 96

Ile Pro Phe Phe Phe Phe Asp Met
1               5

<210> SEQ ID NO 97
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 97

Ile Gln Glu Val Gly Ser Ser Met
1               5

<210> SEQ ID NO 98
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 98

Ile Ser Glu Ala Lys Leu Thr Gly
1               5

<210> SEQ ID NO 99
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 99

Ile Ser Lys Ile Ser Pro Gly Ala
1               5

<210> SEQ ID NO 100
<211> LENGTH: 8
```

```
<212> TYPE: PRT
<213> ORGANISM: Artificial Sequence
<220> FEATURE:
<223> OTHER INFORMATION: BbHtrA protease cleavage site

<400> SEQUENCE: 100

Ile Ser Leu Phe Asn Asn Pro Val
1               5

<210> SEQ ID NO 101
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 101

Ile Ser Pro Gly Ala Phe Ala Pro
1               5

<210> SEQ ID NO 102
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 102

Ile Val Gln Thr Met Asn Ser Asp
1               5

<210> SEQ ID NO 103
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 103

Lys Asp Lys Thr Ser Tyr Arg Trp
1               5

<210> SEQ ID NO 104
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 104

Lys Glu Leu Ser Ser Ser Lys Met
1               5

<210> SEQ ID NO 105
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 105

Lys Gly Val Val Val Asp Tyr Ile
1               5

<210> SEQ ID NO 106
<211> LENGTH: 8
<212> TYPE: PRT
```

```
<213> ORGANISM: Artificial Sequence
<220> FEATURE:
<223> OTHER INFORMATION: BbHtrA protease cleavage site

<400> SEQUENCE: 106

Lys Ile Gln Ala Ile Glu Leu Glu
1               5

<210> SEQ ID NO 107
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 107

Lys Leu Gln Val Leu Arg Leu Asp
1               5

<210> SEQ ID NO 108
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 108

Lys Leu Tyr Ile Ser Lys Asn His
1               5

<210> SEQ ID NO 109
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 109

Lys Val Asp Ala Ala Ser Leu Lys
1               5

<210> SEQ ID NO 110
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 110

Leu Glu Asn Leu Tyr Leu Gln Gly
1               5

<210> SEQ ID NO 111
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 111

Leu Glu Asn Ser Gly Phe Glu Pro
1               5

<210> SEQ ID NO 112
<211> LENGTH: 8
<212> TYPE: PRT
<213> ORGANISM: Artificial Sequence
```

```
<220> FEATURE:
<223> OTHER INFORMATION: BbHtrA protease cleavage site

<400> SEQUENCE: 112

Leu Ile Leu Ile Asn Asn Lys Ile
1               5

<210> SEQ ID NO 113
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 113

Leu Lys Ala Val Lys Ser Ser Thr
1               5

<210> SEQ ID NO 114
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 114

Leu Pro Pro Ser Leu Thr Glu Leu
1               5

<210> SEQ ID NO 115
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 115

Leu Gln Asn Ser Ala Ile Ile Ala
1               5

<210> SEQ ID NO 116
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 116

Leu Arg Asn Ala Leu Trp His Thr
1               5

<210> SEQ ID NO 117
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 117

Met Cys Ser Ala Gly Trp Leu Ala
1               5

<210> SEQ ID NO 118
<211> LENGTH: 8
<212> TYPE: PRT
<213> ORGANISM: Artificial Sequence
<220> FEATURE:
```

```
<223> OTHER INFORMATION: BbHtrA protease cleavage site

<400> SEQUENCE: 118

Met Glu Gln Thr Tyr Trp Gln Ala
1               5

<210> SEQ ID NO 119
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 119

Met Lys Lys Leu Ser Tyr Ile Arg
1               5

<210> SEQ ID NO 120
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 120

Met Asn Cys Ile Glu Met Gly Gly
1               5

<210> SEQ ID NO 121
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 121

Asn Gly Ile Ser Leu Phe Asn Asn
1               5

<210> SEQ ID NO 122
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 122

Asn His Leu Val Glu Ile Pro Pro
1               5

<210> SEQ ID NO 123
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 123

Asn Lys Leu Ser Arg Val Pro Ala
1               5

<210> SEQ ID NO 124
<211> LENGTH: 8
<212> TYPE: PRT
<213> ORGANISM: Artificial Sequence
<220> FEATURE:
<223> OTHER INFORMATION: BbHtrA protease cleavage site
```

```
<400> SEQUENCE: 124

Asn Leu Pro Ser Ser Leu Val Glu
1               5

<210> SEQ ID NO 125
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 125

Asn Asn Lys Ile Ser Lys Ile Ser
1               5

<210> SEQ ID NO 126
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 126

Asn Asn Lys Leu Ser Arg Val Pro
1               5

<210> SEQ ID NO 127
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 127

Asn Gln Met Ile Val Val Glu Leu
1               5

<210> SEQ ID NO 128
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 128

Asn Gln Thr Gly Leu Leu Asp Pro
1               5

<210> SEQ ID NO 129
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 129

Asn Arg Asn Leu Lys Tyr Leu Pro
1               5

<210> SEQ ID NO 130
<211> LENGTH: 8
<212> TYPE: PRT
<213> ORGANISM: Artificial Sequence
<220> FEATURE:
<223> OTHER INFORMATION: BbHtrA protease cleavage site
```

<400> SEQUENCE: 130

Asn Trp Val Val Leu Asn Gln Gly
1               5

<210> SEQ ID NO 131
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 131

Pro Asp Thr Ala Leu Leu Asp Leu
1               5

<210> SEQ ID NO 132
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 132

Pro Asp Thr Thr Leu Leu Asp Leu
1               5

<210> SEQ ID NO 133
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 133

Pro Phe Arg Ala Val Ala Glu Pro
1               5

<210> SEQ ID NO 134
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 134

Pro Asn Trp Val Val Leu Asn Gln
1               5

<210> SEQ ID NO 135
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 135

Pro Ser Arg Met Lys Tyr Val Tyr
1               5

<210> SEQ ID NO 136
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 136

Pro Val Ser Thr Asn Leu Glu Asn
1               5

<210> SEQ ID NO 137
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 137

Gln Cys Asp Ala Gly Trp Leu Ala
1               5

<210> SEQ ID NO 138
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 138

Gln Asp Lys Val Thr Leu Pro Asn
1               5

<210> SEQ ID NO 139
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 139

Gln Leu Lys Ala Val Lys Ser Ser
1               5

<210> SEQ ID NO 140
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 140

Gln Thr Val Val Leu Asp Pro Glu
1               5

<210> SEQ ID NO 141
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 141

Arg Asn Ala Leu Trp His Thr Gly
1               5

<210> SEQ ID NO 142
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 142

```
Arg Asn Trp Ile Lys Gly Val Val
1               5

<210> SEQ ID NO 143
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 143

Arg Ser Leu Ile Leu Leu Asp Leu
1               5

<210> SEQ ID NO 144
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 144

Arg Val Pro Ala Gly Leu Pro Asp
1               5

<210> SEQ ID NO 145
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 145

Ser Phe Cys Thr Val Val Asp Val
1               5

<210> SEQ ID NO 146
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 146

Ser Phe Tyr Val Val Met Trp Lys
1               5

<210> SEQ ID NO 147
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 147

Ser Lys Asn His Leu Val Glu Ile
1               5

<210> SEQ ID NO 148
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 148

Ser Lys Ser Val Ser Asn Leu Arg
```

```
<210> SEQ ID NO 149
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 149

Ser Leu Ser Val Ser Ile Pro Glu
1               5

<210> SEQ ID NO 150
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 150

Ser Pro Gly Ala Phe Ala Pro Leu
1               5

<210> SEQ ID NO 151
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 151

Thr Lys Lys Ala Ser Tyr Ser Gly
1               5

<210> SEQ ID NO 152
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 152

Thr Ser Tyr Ile Ser Asp Phe Tyr
1               5

<210> SEQ ID NO 153
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 153

Val Phe Tyr Ala Thr Ser Pro Glu
1               5

<210> SEQ ID NO 154
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 154

Val Lys Arg Ala Tyr Tyr Asn Gly
1               5
```

```
<210> SEQ ID NO 155
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 155

Val Val Asp Val Met Asn Phe Ser
1               5

<210> SEQ ID NO 156
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 156

Val Val Glu Leu Gly Thr Asn Pro
1               5

<210> SEQ ID NO 157
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 157

Tyr Ile Arg Val Arg Phe Tyr Glu
1               5

<210> SEQ ID NO 158
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 158

Tyr Leu Arg Ile Ser Glu Ala Lys
1               5

<210> SEQ ID NO 159
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 159

Tyr Asn Gly Ile Ser Leu Phe Asn
1               5

<210> SEQ ID NO 160
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 160

Tyr Ser Gly Val Ser Leu Phe Ser
1               5
```

```
<210> SEQ ID NO 161
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 161

Tyr Val Arg Ala Ala Val Gln Leu
1               5

<210> SEQ ID NO 162
<211> LENGTH: 8
<212> TYPE: PRT
<213> ORGANISM: Artificial Sequence
<220> FEATURE:
<223> OTHER INFORMATION: BbHtrA protease cleavage site

<400> SEQUENCE: 162

Tyr Trp Gln Ala Asn Pro Phe Arg
1               5

<210> SEQ ID NO 163
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 163

Val Ser Ile Pro Gln Pro Ser Pro Leu Arg Val Leu Leu Gly Thr Ser
1               5                   10                  15

Leu Thr Ile Pro Cys Tyr Phe Ile Asp Pro Met His Pro Val Thr Thr
            20                  25                  30

Ala Pro

<210> SEQ ID NO 164
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 164

Ser Ile Pro Gln Pro Ser Pro Leu Arg Val Leu Leu Gly Thr Ser Leu
1               5                   10                  15

Thr Ile Pro Cys Tyr Phe Ile Asp Pro Met His Pro Val Thr Thr Ala
            20                  25                  30

Pro Ser

<210> SEQ ID NO 165
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 165

Leu Leu Val Ala Thr Glu Gly Arg Val Arg Val Asn Ser Ala Tyr Gln
1               5                   10                  15

Asp Lys Val Ser Leu Pro Asn Tyr Pro Ala Ile Pro Ser Asp Ala Thr
            20                  25                  30

Leu Glu
```

<210> SEQ ID NO 166
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 166

```
Ser Leu Pro Asn Tyr Pro Ala Ile Pro Ser Asp Ala Thr Leu Glu Val
1               5                   10                  15

Gln Ser Leu Arg Ser Asn Asp Ser Gly Val Tyr Arg Cys Glu Val Met
            20                  25                  30

His Gly
```

<210> SEQ ID NO 167
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 167

```
Thr Leu Glu Val Gln Ser Leu Arg Ser Asn Asp Ser Gly Val Tyr Arg
1               5                   10                  15

Cys Glu Val Met His Gly Ile Glu Asp Ser Glu Ala Thr Leu Glu Val
            20                  25                  30

Val Val
```

<210> SEQ ID NO 168
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 168

```
Ala Tyr Glu Asp Gly Phe His Gln Cys Asp Ala Gly Trp Leu Ala Asp
1               5                   10                  15

Gln Thr Val Arg Tyr Pro Ile His Thr Pro Arg Glu Gly Cys Tyr Gly
            20                  25                  30

Asp Lys
```

<210> SEQ ID NO 169
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 169

```
Gly Trp Leu Ala Asp Gln Thr Val Arg Tyr Pro Ile His Thr Pro Arg
1               5                   10                  15

Glu Gly Cys Tyr Gly Asp Lys Asp Glu Phe Pro Gly Val Arg Thr Tyr
            20                  25                  30

Gly Ile
```

<210> SEQ ID NO 170
<211> LENGTH: 34
<212> TYPE: PRT
<213> ORGANISM: Artificial Sequence
<220> FEATURE:

<223> OTHER INFORMATION: Human aggrecan peptide

<400> SEQUENCE: 170

Thr Ser Pro Glu Lys Phe Thr Phe Gln Glu Ala Ala Asn Glu Cys Arg
1               5                   10                  15
Arg Leu Gly Ala Arg Leu Ala Thr Thr Gly His Val Tyr Leu Ala Trp
            20                  25                  30
Gln Ala

<210> SEQ ID NO 171
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 171

Gly Trp Leu Ala Asp Arg Ser Val Arg Tyr Pro Ile Ser Lys Ala Arg
1               5                   10                  15
Pro Asn Cys Gly Gly Asn Leu Leu Gly Val Arg Thr Val Tyr Val His
            20                  25                  30
Ala Asn

<210> SEQ ID NO 172
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 172

Gly Tyr Pro Asp Pro Ser Ser Arg Tyr Asp Ala Ile Cys Tyr Thr Gly
1               5                   10                  15
Glu Asp Phe Val Asp Ile Pro Glu Asn Phe Phe Gly Val Gly Gly Glu
            20                  25                  30
Glu Asp

<210> SEQ ID NO 173
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 173

Ser Pro Ser Pro Leu Glu Pro Glu Glu Pro Phe Thr Phe Ala Pro Glu
1               5                   10                  15
Ile Gly Ala Thr Ala Phe Ala Glu Val Glu Asn Glu Thr Gly Glu Ala
            20                  25                  30
Thr Arg

<210> SEQ ID NO 174
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 174

Ala Tyr Glu Ala Gly Tyr Glu Gln Cys Asp Ala Gly Trp Leu Arg Asp
1               5                   10                  15

Gln Thr Val Arg Tyr Pro Ile Val Ser Pro Arg Thr Pro Cys Val Gly
            20                  25                  30

Asp Lys

<210> SEQ ID NO 175
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 175

Gly Trp Leu Ala Asp Gly Ser Leu Arg Tyr Pro Ile Val Thr Pro Arg
1               5                   10                  15

Pro Ala Cys Gly Gly Asp Lys Pro Gly Val Arg Thr Val Tyr Leu Tyr
            20                  25                  30

Pro Asn

<210> SEQ ID NO 176
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 176

Gly Leu Pro Asp Pro Leu Ser Arg His His Ala Phe Cys Phe Arg Gly
1               5                   10                  15

Ile Ser Ala Val Pro Ser Pro Gly Glu Glu Glu Gly Thr Pro Thr
            20                  25                  30

Ser Pro

<210> SEQ ID NO 177
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 177

Ser Gly Leu Pro Ser Gly Asp Leu Asp Ser Ser Gly Leu Thr Ser Thr
1               5                   10                  15

Val Gly Ser Gly Leu Thr Val Glu Ser Gly Leu Pro Ser Gly Asp Glu
            20                  25                  30

Glu Arg

<210> SEQ ID NO 178
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 178

Gly Leu Pro Ser Gly Asp Glu Glu Arg Ile Glu Trp Pro Ser Thr Pro
1               5                   10                  15

Thr Val Gly Glu Leu Pro Ser Gly Ala Glu Ile Leu Glu Gly Ser Ala
            20                  25                  30

Ser Gly

<210> SEQ ID NO 179

<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 179

Gly Asp Glu Glu Arg Ile Glu Trp Pro Ser Thr Pro Thr Val Gly Glu
1               5                   10                  15

Leu Pro Ser Gly Ala Glu Ile Leu Glu Gly Ser Ala Ser Gly Val Gly
            20                  25                  30

Asp Leu

<210> SEQ ID NO 180
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 180

Gly Leu Pro Ser Gly Glu Val Leu Glu Thr Ser Ala Ser Gly Val Gly
1               5                   10                  15

Asp Leu Ser Gly Leu Pro Ser Gly Glu Val Leu Glu Thr Thr Ala Pro
            20                  25                  30

Gly Val

<210> SEQ ID NO 181
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 181

Gly Leu Pro Ser Gly Glu Val Leu Glu Thr Ser Ala Ser Gly Val Gly
1               5                   10                  15

Asp Leu Ser Gly Leu Pro Ser Gly Glu Val Leu Glu Thr Thr Ala Pro
            20                  25                  30

Gly Val

<210> SEQ ID NO 182
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 182

Ser Gly Leu Pro Ser Gly Glu Val Leu Glu Thr Thr Ala Pro Gly Val
1               5                   10                  15

Asp Glu Ile Ser Gly Leu Pro Ser Gly Glu Val Leu Glu Thr Thr Ala
            20                  25                  30

Pro Gly

<210> SEQ ID NO 183
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 183

-continued

Ser Gly Leu Pro Ser Gly Glu Val Leu Glu Thr Thr Ala Pro Gly Val
1               5                   10                  15

Asp Glu Ile Ser Gly Leu Pro Ser Gly Glu Val Leu Glu Thr Thr Ala
            20                  25                  30

Pro Gly

<210> SEQ ID NO 184
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 184

Gly Leu Pro Ser Gly Glu Val Leu Glu Thr Ser Ala Ser Gly Val Gly
1               5                   10                  15

Asp Leu Ser Gly Leu Pro Ser Gly Glu Val Leu Glu Thr Thr Ala Pro
            20                  25                  30

Gly Val

<210> SEQ ID NO 185
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 185

Ser Val Ser Gly Val Glu Asp Ile Ser Gly Leu Pro Ser Gly Glu Val
1               5                   10                  15

Val Glu Thr Ser Ala Ser Gly Ile Glu Asp Val Ser Glu Leu Pro Ser
            20                  25                  30

Gly Glu

<210> SEQ ID NO 186
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 186

Gly Val Glu Asp Ile Ser Gly Leu Pro Ser Gly Glu Val Val Glu Thr
1               5                   10                  15

Ser Ala Ser Gly Ile Glu Asp Val Ser Glu Leu Pro Ser Gly Glu Gly
            20                  25                  30

Leu Glu

<210> SEQ ID NO 187
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 187

Ser Glu Leu Pro Ser Gly Glu Gly Leu Glu Thr Ser Ala Ser Gly Val
1               5                   10                  15

Glu Asp Leu Ser Arg Leu Pro Ser Gly Glu Glu Val Leu Glu Ile Ser
            20                  25                  30

Ala Ser

<210> SEQ ID NO 188
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 188

Gly Thr Asp Leu Ser Gly Leu Pro Ser Gly Arg Glu Gly Leu Glu Thr
1               5                   10                  15

Ser Ala Ser Gly Ala Glu Asp Leu Ser Gly Leu Pro Ser Gly Lys Glu
            20                  25                  30

Asp Leu

<210> SEQ ID NO 189
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 189

Gly Leu Pro Ser Gly Arg Glu Gly Leu Glu Thr Ser Ala Ser Gly Ala
1               5                   10                  15

Glu Asp Leu Ser Gly Leu Pro Ser Gly Lys Glu Asp Leu Val Gly Ser
            20                  25                  30

Ala Ser

<210> SEQ ID NO 190
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 190

Gly Thr Leu Gly Ser Gly Gln Ala Pro Glu Thr Ser Gly Leu Pro Ser
1               5                   10                  15

Gly Phe Ser Gly Glu Tyr Ser Gly Val Asp Leu Gly Ser Gly Pro Pro
            20                  25                  30

Ser Gly

<210> SEQ ID NO 191
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 191

Gly Leu Pro Ser Gly Phe Ser Gly Glu Tyr Ser Gly Val Asp Leu Gly
1               5                   10                  15

Ser Gly Pro Pro Ser Gly Leu Pro Asp Phe Ser Gly Leu Pro Ser Gly
            20                  25                  30

Phe Pro

<210> SEQ ID NO 192
<211> LENGTH: 34
<212> TYPE: PRT
<213> ORGANISM: Artificial Sequence

```
<220> FEATURE:
<223> OTHER INFORMATION: Human aggrecan peptide

<400> SEQUENCE: 192

Gly Leu Pro Asp Phe Ser Gly Leu Pro Ser Gly Phe Pro Thr Val Ser
1               5                   10                  15

Leu Val Asp Ser Thr Leu Val Glu Val Val Thr Ala Ser Thr Ala Ser
            20                  25                  30

Glu Leu

<210> SEQ ID NO 193
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 193

Ser Leu Val Asp Ser Thr Leu Val Glu Val Val Thr Ala Ser Thr Ala
1               5                   10                  15

Ser Glu Leu Glu Gly Arg Gly Thr Ile Gly Ile Ser Gly Ala Gly Glu
            20                  25                  30

Ile Ser

<210> SEQ ID NO 194
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 194

Thr Leu Val Glu Val Val Thr Ala Ser Thr Ala Ser Glu Leu Glu Gly
1               5                   10                  15

Arg Gly Thr Ile Gly Ile Ser Gly Ala Gly Glu Ile Ser Gly Leu Pro
            20                  25                  30

Ser Ser

<210> SEQ ID NO 195
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 195

Ser Glu Leu Glu Gly Arg Gly Thr Ile Gly Ile Ser Gly Ala Gly Glu
1               5                   10                  15

Ile Ser Gly Leu Pro Ser Ser Glu Leu Asp Ile Ser Gly Arg Ala Ser
            20                  25                  30

Gly Leu

<210> SEQ ID NO 196
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 196

Gly Leu Pro Ser Gly Thr Glu Leu Ser Gly Gln Ala Ser Gly Ser Pro
1               5                   10                  15
```

```
Asp Val Ser Gly Glu Ile Pro Gly Leu Phe Gly Val Ser Gly Gln Pro
            20                  25                  30

Ser Gly
```

<210> SEQ ID NO 197
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 197

```
Gly Thr Glu Leu Ser Gly Gln Ala Ser Gly Ser Pro Asp Val Ser Gly
1               5                   10                  15

Glu Ile Pro Gly Leu Phe Gly Val Ser Gly Gln Pro Ser Gly Phe Pro
            20                  25                  30

Asp Thr
```

<210> SEQ ID NO 198
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 198

```
Gly Leu Pro Gly Phe Ser Gly Ala Thr Ser Gly Val Pro Asp Leu Val
1               5                   10                  15

Ser Gly Thr Thr Ser Gly Ser Gly Glu Ser Ser Gly Ile Thr Phe Val
            20                  25                  30

Asp Thr
```

<210> SEQ ID NO 199
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 199

```
Ser Leu Val Glu Val Ala Pro Thr Thr Phe Lys Glu Glu Gly Leu
1               5                   10                  15

Gly Ser Val Glu Leu Ser Gly Leu Pro Ser Gly Glu Ala Asp Leu Ser
            20                  25                  30

Gly Lys
```

<210> SEQ ID NO 200
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 200

```
Ser Gly Leu Pro Ser Gly Glu Ala Asp Leu Ser Gly Lys Ser Gly Met
1               5                   10                  15

Val Asp Val Ser Gly Gln Phe Ser Gly Thr Val Asp Ser Ser Gly Phe
            20                  25                  30

Thr Ser
```

<210> SEQ ID NO 201
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 201

Gly Leu Pro Ser Gly Glu Ala Asp Leu Ser Gly Lys Ser Gly Met Val
1               5                   10                  15

Asp Val Ser Gly Gln Phe Ser Gly Thr Val Asp Ser Ser Gly Phe Thr
            20                  25                  30

Ser Gln

<210> SEQ ID NO 202
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 202

Ser Leu Val Asp Ser Thr Leu Val Glu Val Thr Ala Ser Thr Ala
1               5                   10                  15

Ser Glu Leu Glu Gly Arg Gly Thr Ile Gly Ile Ser Gly Ala Gly Glu
            20                  25                  30

Ile Ser

<210> SEQ ID NO 203
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 203

Gly Leu Ile Glu Pro Ser Gly Glu Pro Pro Gly Thr Pro Tyr Phe Ser
1               5                   10                  15

Gly Asp Phe Ala Ser Thr Thr Asn Val Ser Gly Glu Ser Ser Val Ala
            20                  25                  30

Met Gly

<210> SEQ ID NO 204
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 204

Gly Glu Pro Pro Gly Thr Pro Tyr Phe Ser Gly Asp Phe Ala Ser Thr
1               5                   10                  15

Thr Asn Val Ser Gly Glu Ser Ser Val Ala Met Gly Thr Ser Gly Glu
            20                  25                  30

Ala Ser

<210> SEQ ID NO 205
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 205

Gly Leu Pro Glu Val Thr Leu Ile Thr Ser Glu Phe Val Glu Gly Val
1               5                   10                  15

Thr Glu Pro Thr Ile Ser Gln Glu Leu Gly Gln Arg Pro Pro Val Thr
                20                  25                  30

His Thr

<210> SEQ ID NO 206
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 206

Ser Ser Val Pro Glu Ser Ser Glu Thr Ser Ala Tyr Pro Glu Ala
1               5                   10                  15

Gly Phe Gly Ala Ser Ala Ala Pro Glu Ala Ser Arg Glu Asp Ser Gly
                20                  25                  30

Ser Pro

<210> SEQ ID NO 207
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 207

Ser Val Pro Glu Ser Ser Ser Glu Thr Ser Ala Tyr Pro Glu Ala Gly
1               5                   10                  15

Phe Gly Ala Ser Ala Ala Pro Glu Ala Ser Arg Glu Asp Ser Gly Ser
                20                  25                  30

Pro Asp

<210> SEQ ID NO 208
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 208

Ala Tyr Pro Glu Ala Gly Phe Gly Ala Ser Ala Ala Pro Glu Ala Ser
1               5                   10                  15

Arg Glu Asp Ser Gly Ser Pro Asp Leu Ser Glu Thr Thr Ser Ala Phe
                20                  25                  30

His Glu

<210> SEQ ID NO 209
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 209

Ser Gly Leu Gly Val Ser Gly Ser Thr Leu Thr Phe Gln Glu Gly Glu
1               5                   10                  15

Ala Ser Ala Ala Pro Glu Val Ser Gly Glu Ser Thr Thr Thr Ser Asp
                20                  25                  30

Val Gly

<210> SEQ ID NO 210
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 210

Ser Ile Pro Glu Ser Glu Trp Thr Gln Gln Thr Gln Arg Pro Ala Glu
1               5                   10                  15

Thr His Leu Glu Ile Glu Ser Ser Leu Leu Tyr Ser Gly Glu Glu
            20                  25                  30

Thr His

<210> SEQ ID NO 211
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 211

Ser Leu Leu Tyr Ser Gly Glu Glu Thr His Thr Val Glu Thr Ala Thr
1               5                   10                  15

Ser Pro Thr Asp Ala Ser Ile Pro Ala Ser Pro Glu Trp Lys Arg Glu
            20                  25                  30

Ser Glu

<210> SEQ ID NO 212
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 212

Leu Tyr Ser Gly Glu Glu Thr His Thr Val Glu Thr Ala Thr Ser Pro
1               5                   10                  15

Thr Asp Ala Ser Ile Pro Ala Ser Pro Glu Trp Lys Arg Glu Ser Glu
            20                  25                  30

Ser Thr

<210> SEQ ID NO 213
<211> LENGTH: 34
<212> TYPE: PRT
<213> ORGANISM: Artificial Sequence
<220> FEATURE:
<223> OTHER INFORMATION: Human aggrecan peptide

<400> SEQUENCE: 213

Val Thr Pro Glu Glu Gln Glu Phe Val Asn Asn Asn Ala Gln Asp Tyr
1               5                   10                  15

Gln Trp Ile Gly Leu Asn Asp Arg Thr Ile Glu Gly Asp Phe Arg Trp
            20                  25                  30

Ser Asp

<210> SEQ ID NO 214
<211> LENGTH: 34
<212> TYPE: PRT

<213> ORGANISM: Artificial Sequence
<220> FEATURE:
<223> OTHER INFORMATION: Human biglycan peptide

<400> SEQUENCE: 214

Val Ser Leu Leu Ala Leu Ser Gln Ala Leu Pro Phe Glu Gln Arg Gly
1               5                   10                  15

Phe Trp Asp Phe Thr Leu Asp Asp Gly Pro Phe Met Met Asn Asp Glu
            20                  25                  30

Glu Ala

<210> SEQ ID NO 215
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 215

Leu Leu Ala Leu Ser Gln Ala Leu Pro Phe Glu Gln Arg Gly Phe Trp
1               5                   10                  15

Asp Phe Thr Leu Asp Asp Gly Pro Phe Met Met Asn Asp Glu Glu Ala
            20                  25                  30

Ser Gly

<210> SEQ ID NO 216
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 216

Leu Ala Leu Ser Gln Ala Leu Pro Phe Glu Gln Arg Gly Phe Trp Asp
1               5                   10                  15

Phe Thr Leu Asp Asp Gly Pro Phe Met Met Asn Asp Glu Glu Ala Ser
            20                  25                  30

Gly Ala

<210> SEQ ID NO 217
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 217

Ala Leu Ser Gln Ala Leu Pro Phe Glu Gln Arg Gly Phe Trp Asp Phe
1               5                   10                  15

Thr Leu Asp Asp Gly Pro Phe Met Met Asn Asp Glu Glu Ala Ser Gly
            20                  25                  30

Ala Asp

<210> SEQ ID NO 218
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 218

Leu Ser Gln Ala Leu Pro Phe Glu Gln Arg Gly Phe Trp Asp Phe Thr

```
                1               5                  10                  15
Leu Asp Asp Gly Pro Phe Met Met Asn Asp Glu Glu Ala Ser Gly Ala
                20                  25                  30
Asp Thr
```

<210> SEQ ID NO 219
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 219

```
Leu Pro Phe Glu Gln Arg Gly Phe Trp Asp Phe Thr Leu Asp Asp Gly
1               5                  10                  15
Pro Phe Met Met Asn Asp Glu Glu Ala Ser Gly Ala Asp Thr Ser Gly
                20                  25                  30
Val Leu
```

<210> SEQ ID NO 220
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 220

```
Gly Val Leu Asp Pro Asp Ser Val Thr Pro Thr Tyr Ser Ala Met Cys
1               5                  10                  15
Pro Phe Gly Cys His Cys His Leu Arg Val Val Gln Cys Ser Asp Leu
                20                  25                  30
Gly Leu
```

<210> SEQ ID NO 221
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 221

```
Val Leu Asp Pro Asp Ser Val Thr Pro Thr Tyr Ser Ala Met Cys Pro
1               5                  10                  15
Phe Gly Cys His Cys His Leu Arg Val Val Gln Cys Ser Asp Leu Gly
                20                  25                  30
Leu Lys
```

<210> SEQ ID NO 222
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 222

```
Leu Asp Pro Asp Ser Val Thr Pro Thr Tyr Ser Ala Met Cys Pro Phe
1               5                  10                  15
Gly Cys His Cys His Leu Arg Val Val Gln Cys Ser Asp Leu Gly Leu
                20                  25                  30
Lys Ser
```

<210> SEQ ID NO 223
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 223

Gly Leu Lys Ser Val Pro Lys Glu Ile Ser Pro Asp Thr Thr Leu Leu
1               5                   10                  15

Asp Leu Gln Asn Asn Asp Ile Ser Glu Leu Arg Lys Asp Asp Phe Lys
            20                  25                  30

Gly Leu

<210> SEQ ID NO 224
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 224

Leu Leu Asp Leu Gln Asn Asn Asp Ile Ser Glu Leu Arg Lys Asp Asp
1               5                   10                  15

Phe Lys Gly Leu Gln His Leu Tyr Ala Leu Val Leu Val Asn Asn Lys
            20                  25                  30

Ile Ser

<210> SEQ ID NO 225
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 225

Ser Glu Leu Arg Lys Asp Asp Phe Lys Gly Leu Gln His Leu Tyr Ala
1               5                   10                  15

Leu Val Leu Val Asn Asn Lys Ile Ser Lys Ile His Glu Lys Ala Phe
            20                  25                  30

Ser Pro

<210> SEQ ID NO 226
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 226

Leu Val Leu Val Asn Asn Lys Ile Ser Lys Ile His Glu Lys Ala Phe
1               5                   10                  15

Ser Pro Leu Arg Lys Leu Gln Lys Leu Tyr Ile Ser Lys Asn His Leu
            20                  25                  30

Val Glu

<210> SEQ ID NO 227
<211> LENGTH: 34
<212> TYPE: PRT
<213> ORGANISM: Artificial Sequence
<220> FEATURE:
<223> OTHER INFORMATION: Human biglycan peptide -continued

<400> SEQUENCE: 227

Val Asn Asn Lys Ile Ser Lys Ile His Glu Lys Ala Phe Ser Pro Leu
1               5                   10                  15

Arg Lys Leu Gln Lys Leu Tyr Ile Ser Lys Asn His Leu Val Glu Ile
            20                  25                  30

Pro Pro

<210> SEQ ID NO 228
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 228

Asn Asn Lys Ile Ser Lys Ile His Glu Lys Ala Phe Ser Pro Leu Arg
1               5                   10                  15

Lys Leu Gln Lys Leu Tyr Ile Ser Lys Asn His Leu Val Glu Ile Pro
            20                  25                  30

Pro Asn

<210> SEQ ID NO 229
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 229

Ser Lys Ile His Glu Lys Ala Phe Ser Pro Leu Arg Lys Leu Gln Lys
1               5                   10                  15

Leu Tyr Ile Ser Lys Asn His Leu Val Glu Ile Pro Pro Asn Leu Pro
            20                  25                  30

Ser Ser

<210> SEQ ID NO 230
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 230

Phe Ser Pro Leu Arg Lys Leu Gln Lys Leu Tyr Ile Ser Lys Asn His
1               5                   10                  15

Leu Val Glu Ile Pro Pro Asn Leu Pro Ser Ser Leu Val Glu Leu Arg
            20                  25                  30

Ile His

<210> SEQ ID NO 231
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 231

Ser Lys Asn His Leu Val Glu Ile Pro Pro Asn Leu Pro Ser Ser Leu
1               5                   10                  15

Val Glu Leu Arg Ile His Asp Asn Arg Ile Arg Lys Val Pro Lys Gly

```
                   20                  25                  30

Val Phe

<210> SEQ ID NO 232
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 232

Glu Ile Pro Pro Asn Leu Pro Ser Ser Leu Val Glu Leu Arg Ile His
1               5                   10                  15

Asp Asn Arg Ile Arg Lys Val Pro Lys Gly Val Phe Ser Gly Leu Arg
                20                  25                  30

Asn Met

<210> SEQ ID NO 233
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 233

Ser Leu Val Glu Leu Arg Ile His Asp Asn Arg Ile Arg Lys Val Pro
1               5                   10                  15

Lys Gly Val Phe Ser Gly Leu Arg Asn Met Asn Cys Ile Glu Met Gly
                20                  25                  30

Gly Asn

<210> SEQ ID NO 234
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 234

Leu Val Glu Leu Arg Ile His Asp Asn Arg Ile Arg Lys Val Pro Lys
1               5                   10                  15

Gly Val Phe Ser Gly Leu Arg Asn Met Asn Cys Ile Glu Met Gly Gly
                20                  25                  30

Asn Pro

<210> SEQ ID NO 235
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 235

Val Glu Leu Arg Ile His Asp Asn Arg Ile Arg Lys Val Pro Lys Gly
1               5                   10                  15

Val Phe Ser Gly Leu Arg Asn Met Asn Cys Ile Glu Met Gly Gly Asn
                20                  25                  30

Pro Leu

<210> SEQ ID NO 236
<211> LENGTH: 34
```

<212> TYPE: PRT
<213> ORGANISM: Artificial Sequence
<220> FEATURE:
<223> OTHER INFORMATION: Human biglycan peptide

<400> SEQUENCE: 236

Glu Leu Arg Ile His Asp Asn Arg Ile Arg Lys Val Pro Lys Gly Val
1               5                   10                  15

Phe Ser Gly Leu Arg Asn Met Asn Cys Ile Glu Met Gly Gly Asn Pro
            20                  25                  30

Leu Glu

<210> SEQ ID NO 237
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 237

Phe Ser Gly Leu Arg Asn Met Asn Cys Ile Glu Met Gly Gly Asn Pro
1               5                   10                  15

Leu Glu Asn Ser Gly Phe Glu Pro Gly Ala Phe Asp Gly Leu Lys Leu
            20                  25                  30

Asn Tyr

<210> SEQ ID NO 238
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 238

Gly Asn Pro Leu Glu Asn Ser Gly Phe Glu Pro Gly Ala Phe Asp Gly
1               5                   10                  15

Leu Lys Leu Asn Tyr Leu Arg Ile Ser Glu Ala Lys Leu Thr Gly Ile
            20                  25                  30

Pro Lys

<210> SEQ ID NO 239
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 239

Gly Phe Glu Pro Gly Ala Phe Asp Gly Leu Lys Leu Asn Tyr Leu Arg
1               5                   10                  15

Ile Ser Glu Ala Lys Leu Thr Gly Ile Pro Lys Asp Leu Pro Glu Thr
            20                  25                  30

Leu Asn

<210> SEQ ID NO 240
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 240

```
Ala Phe Asp Gly Leu Lys Leu Asn Tyr Leu Arg Ile Ser Glu Ala Lys
1               5                   10                  15

Leu Thr Gly Ile Pro Lys Asp Leu Pro Glu Thr Leu Asn Glu Leu His
            20                  25                  30

Leu Asp
```

<210> SEQ ID NO 241
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 241

```
Asn Tyr Leu Arg Ile Ser Glu Ala Lys Leu Thr Gly Ile Pro Lys Asp
1               5                   10                  15

Leu Pro Glu Thr Leu Asn Glu Leu His Leu Asp His Asn Lys Ile Gln
            20                  25                  30

Ala Ile
```

<210> SEQ ID NO 242
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 242

```
Ser Glu Ala Lys Leu Thr Gly Ile Pro Lys Asp Leu Pro Glu Thr Leu
1               5                   10                  15

Asn Glu Leu His Leu Asp His Asn Lys Ile Gln Ala Ile Glu Leu Glu
            20                  25                  30

Asp Leu
```

<210> SEQ ID NO 243
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 243

```
Lys Leu Thr Gly Ile Pro Lys Asp Leu Pro Glu Thr Leu Asn Glu Leu
1               5                   10                  15

His Leu Asp His Asn Lys Ile Gln Ala Ile Glu Leu Glu Asp Leu Leu
            20                  25                  30

Arg Tyr
```

<210> SEQ ID NO 244
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 244

```
Gly Ile Pro Lys Asp Leu Pro Glu Thr Leu Asn Glu Leu His Leu Asp
1               5                   10                  15

His Asn Lys Ile Gln Ala Ile Glu Leu Glu Asp Leu Leu Arg Tyr Ser
            20                  25                  30

Lys Leu
```

<210> SEQ ID NO 245
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 245

```
Leu Asn Glu Leu His Leu Asp His Asn Lys Ile Gln Ala Ile Glu Leu
1               5                   10                  15

Glu Asp Leu Leu Arg Tyr Ser Lys Leu Tyr Arg Leu Gly Leu Gly His
            20                  25                  30

Asn Gln
```

<210> SEQ ID NO 246
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 246

```
Ile Glu Leu Glu Asp Leu Leu Arg Tyr Ser Lys Leu Tyr Arg Leu Gly
1               5                   10                  15

Leu Gly His Asn Gln Ile Arg Met Ile Glu Asn Gly Ser Leu Ser Phe
            20                  25                  30

Leu Pro
```

<210> SEQ ID NO 247
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 247

```
Glu Leu Glu Asp Leu Leu Arg Tyr Ser Lys Leu Tyr Arg Leu Gly Leu
1               5                   10                  15

Gly His Asn Gln Ile Arg Met Ile Glu Asn Gly Ser Leu Ser Phe Leu
            20                  25                  30

Pro Thr
```

<210> SEQ ID NO 248
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 248

```
Glu Asp Leu Leu Arg Tyr Ser Lys Leu Tyr Arg Leu Gly Leu Gly His
1               5                   10                  15

Asn Gln Ile Arg Met Ile Glu Asn Gly Ser Leu Ser Phe Leu Pro Thr
            20                  25                  30

Leu Arg
```

<210> SEQ ID NO 249
<211> LENGTH: 34
<212> TYPE: PRT
<213> ORGANISM: Artificial Sequence
<220> FEATURE:

<223> OTHER INFORMATION: Human biglycan peptide

<400> SEQUENCE: 249

Tyr Arg Leu Gly Leu Gly His Asn Gln Ile Arg Met Ile Glu Asn Gly
1               5                   10                  15

Ser Leu Ser Phe Leu Pro Thr Leu Arg Glu Leu His Leu Asp Asn Asn
            20                  25                  30

Lys Leu

<210> SEQ ID NO 250
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 250

Ser Phe Leu Pro Thr Leu Arg Glu Leu His Leu Asp Asn Asn Lys Leu
1               5                   10                  15

Ala Arg Val Pro Ser Gly Leu Pro Asp Leu Lys Leu Leu Gln Val Val
            20                  25                  30

Tyr Leu

<210> SEQ ID NO 251
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 251

Phe Leu Pro Thr Leu Arg Glu Leu His Leu Asp Asn Asn Lys Leu Ala
1               5                   10                  15

Arg Val Pro Ser Gly Leu Pro Asp Leu Lys Leu Leu Gln Val Val Tyr
            20                  25                  30

Leu His

<210> SEQ ID NO 252
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 252

Leu Arg Glu Leu His Leu Asp Asn Asn Lys Leu Ala Arg Val Pro Ser
1               5                   10                  15

Gly Leu Pro Asp Leu Lys Leu Leu Gln Val Val Tyr Leu His Ser Asn
            20                  25                  30

Asn Ile

<210> SEQ ID NO 253
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 253

Ala Arg Val Pro Ser Gly Leu Pro Asp Leu Lys Leu Leu Gln Val Val
1               5                   10                  15

Tyr Leu His Ser Asn Asn Ile Thr Lys Val Gly Val Asn Asp Phe Cys
            20                  25                  30

Pro Met

<210> SEQ ID NO 254
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 254

Arg Val Pro Ser Gly Leu Pro Asp Leu Lys Leu Leu Gln Val Val Tyr
1               5                   10                  15

Leu His Ser Asn Asn Ile Thr Lys Val Gly Val Asn Asp Phe Cys Pro
            20                  25                  30

Met Gly

<210> SEQ ID NO 255
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 255

Gly Leu Pro Asp Leu Lys Leu Leu Gln Val Val Tyr Leu His Ser Asn
1               5                   10                  15

Asn Ile Thr Lys Val Gly Val Asn Asp Phe Cys Pro Met Gly Phe Gly
            20                  25                  30

Val Lys

<210> SEQ ID NO 256
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 256

Val Tyr Leu His Ser Asn Asn Ile Thr Lys Val Gly Val Asn Asp Phe
1               5                   10                  15

Cys Pro Met Gly Phe Gly Val Lys Arg Ala Tyr Tyr Asn Gly Ile Ser
            20                  25                  30

Leu Phe

<210> SEQ ID NO 257
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 257

Thr Lys Val Gly Val Asn Asp Phe Cys Pro Met Gly Phe Gly Val Lys
1               5                   10                  15

Arg Ala Tyr Tyr Asn Gly Ile Ser Leu Phe Asn Asn Pro Val Pro Tyr
            20                  25                  30

Trp Glu

<210> SEQ ID NO 258

<211> LENGTH: 34
<212> TYPE: PRT
<213> ORGANISM: Artificial Sequence
<220> FEATURE:
<223> OTHER INFORMATION: Human biglycan peptide

<400> SEQUENCE: 258

Gly Val Asn Asp Phe Cys Pro Met Gly Phe Gly Val Lys Arg Ala Tyr
1               5                   10                  15

Tyr Asn Gly Ile Ser Leu Phe Asn Asn Pro Val Pro Tyr Trp Glu Val
            20                  25                  30

Gln Pro

<210> SEQ ID NO 259
<211> LENGTH: 34
<212> TYPE: PRT
<213> ORGANISM: Artificial Sequence
<220> FEATURE:
<223> OTHER INFORMATION: Human biglycan peptide

<400> SEQUENCE: 259

Tyr Tyr Asn Gly Ile Ser Leu Phe Asn Asn Pro Val Pro Tyr Trp Glu
1               5                   10                  15

Val Gln Pro Ala Thr Phe Arg Cys Val Thr Asp Arg Leu Ala Ile Gln
            20                  25                  30

Phe Gly

<210> SEQ ID NO 260
<211> LENGTH: 33
<212> TYPE: PRT
<213> ORGANISM: Artificial Sequence
<220> FEATURE:
<223> OTHER INFORMATION: Human biglycan peptide

<400> SEQUENCE: 260

Ser Leu Phe Asn Asn Pro Val Pro Tyr Trp Glu Val Gln Pro Ala Thr
1               5                   10                  15

Phe Arg Cys Val Thr Asp Arg Leu Ala Ile Gln Phe Gly Asn Tyr Lys
            20                  25                  30

Lys

<210> SEQ ID NO 261
<211> LENGTH: 31
<212> TYPE: PRT
<213> ORGANISM: Artificial Sequence
<220> FEATURE:
<223> OTHER INFORMATION: Human biglycan peptide

<400> SEQUENCE: 261

Phe Asn Asn Pro Val Pro Tyr Trp Glu Val Gln Pro Ala Thr Phe Arg
1               5                   10                  15

Cys Val Thr Asp Arg Leu Ala Ile Gln Phe Gly Asn Tyr Lys Lys
            20                  25                  30

<210> SEQ ID NO 262
<211> LENGTH: 30
<212> TYPE: PRT
<213> ORGANISM: Artificial Sequence
<220> FEATURE:
<223> OTHER INFORMATION: Human biglycan peptide

<400> SEQUENCE: 262

Asn Asn Pro Val Pro Tyr Trp Glu Val Gln Pro Ala Thr Phe Arg Cys

```
                1               5                  10                 15
Val Thr Asp Arg Leu Ala Ile Gln Phe Gly Asn Tyr Lys Lys
            20                  25                 30
```

<210> SEQ ID NO 263
<211> LENGTH: 13
<212> TYPE: PRT
<213> ORGANISM: Artificial Sequence
<220> FEATURE:
<223> OTHER INFORMATION: Human biglycan peptide

<400> SEQUENCE: 263

```
Thr Asp Arg Leu Ala Ile Gln Phe Gly Asn Tyr Lys Lys
1               5                   10
```

<210> SEQ ID NO 264
<211> LENGTH: 34
<212> TYPE: PRT
<213> ORGANISM: Artificial Sequence
<220> FEATURE:
<223> OTHER INFORMATION: Human COMP peptide

<400> SEQUENCE: 264

```
Leu Leu Thr Leu Ala Ala Leu Gly Ala Ser Gly Gln Gly Gln Ser Pro
1               5                   10                  15
Leu Gly Ser Asp Leu Gly Pro Gln Met Leu Arg Glu Leu Gln Glu Thr
            20                  25                  30
Asn Ala
```

<210> SEQ ID NO 265
<211> LENGTH: 34
<212> TYPE: PRT
<213> ORGANISM: Artificial Sequence
<220> FEATURE:
<223> OTHER INFORMATION: Human COMP peptide

<400> SEQUENCE: 265

```
Leu Thr Leu Ala Ala Leu Gly Ala Ser Gly Gln Gly Gln Ser Pro Leu
1               5                   10                  15
Gly Ser Asp Leu Gly Pro Gln Met Leu Arg Glu Leu Gln Glu Thr Asn
            20                  25                  30
Ala Ala
```

<210> SEQ ID NO 266
<211> LENGTH: 34
<212> TYPE: PRT
<213> ORGANISM: Artificial Sequence
<220> FEATURE:
<223> OTHER INFORMATION: Human COMP peptide

<400> SEQUENCE: 266

```
Leu Ala Ala Leu Gly Ala Ser Gly Gln Gly Gln Ser Pro Leu Gly Ser
1               5                   10                  15
Asp Leu Gly Pro Gln Met Leu Arg Glu Leu Gln Glu Thr Asn Ala Ala
            20                  25                  30
Leu Gln
```

<210> SEQ ID NO 267
<211> LENGTH: 34
<212> TYPE: PRT
<213> ORGANISM: Artificial Sequence
<220> FEATURE:
<223> OTHER INFORMATION: Human COMP peptide

<400> SEQUENCE: 267

Ala Ala Leu Gly Ala Ser Gly Gln Gly Gln Ser Pro Leu Gly Ser Asp
1               5                   10                  15

Leu Gly Pro Gln Met Leu Arg Glu Leu Gln Glu Thr Asn Ala Ala Leu
            20                  25                  30

Gln Asp

<210> SEQ ID NO 268
<211> LENGTH: 34
<212> TYPE: PRT
<213> ORGANISM: Artificial Sequence
<220> FEATURE:
<223> OTHER INFORMATION: Human COMP peptide

<400> SEQUENCE: 268

Ala Leu Gly Ala Ser Gly Gln Gly Gln Ser Pro Leu Gly Ser Asp Leu
1               5                   10                  15

Gly Pro Gln Met Leu Arg Glu Leu Gln Glu Thr Asn Ala Ala Leu Gln
            20                  25                  30

Asp Val

<210> SEQ ID NO 269
<211> LENGTH: 34
<212> TYPE: PRT
<213> ORGANISM: Artificial Sequence
<220> FEATURE:
<223> OTHER INFORMATION: Human COMP peptide

<400> SEQUENCE: 269

Ser Gly Gln Gly Gln Ser Pro Leu Gly Ser Asp Leu Gly Pro Gln Met
1               5                   10                  15

Leu Arg Glu Leu Gln Glu Thr Asn Ala Ala Leu Gln Asp Val Arg Glu
            20                  25                  30

Leu Leu

<210> SEQ ID NO 270
<211> LENGTH: 34
<212> TYPE: PRT
<213> ORGANISM: Artificial Sequence
<220> FEATURE:
<223> OTHER INFORMATION: Human COMP peptide

<400> SEQUENCE: 270

Gly Ser Asp Leu Gly Pro Gln Met Leu Arg Glu Leu Gln Glu Thr Asn
1               5                   10                  15

Ala Ala Leu Gln Asp Val Arg Glu Leu Leu Arg Gln Gln Val Arg Glu
            20                  25                  30

Ile Thr

<210> SEQ ID NO 271
<211> LENGTH: 34
<212> TYPE: PRT
<213> ORGANISM: Artificial Sequence
<220> FEATURE:
<223> OTHER INFORMATION: Human COMP peptide

<400> SEQUENCE: 271

Ser Asp Leu Gly Pro Gln Met Leu Arg Glu Leu Gln Glu Thr Asn Ala
1               5                   10                  15

Ala Leu Gln Asp Val Arg Glu Leu Leu Arg Gln Gln Val Arg Glu Ile

Thr Phe

<210> SEQ ID NO 272
<211> LENGTH: 34
<212> TYPE: PRT
<213> ORGANISM: Artificial Sequence
<220> FEATURE:
<223> OTHER INFORMATION: Human COMP peptide

<400> SEQUENCE: 272

Asp Leu Gly Pro Gln Met Leu Arg Glu Leu Gln Glu Thr Asn Ala Ala
1               5                   10                  15

Leu Gln Asp Val Arg Glu Leu Leu Arg Gln Gln Val Arg Glu Ile Thr
            20                  25                  30

Phe Leu

<210> SEQ ID NO 273
<211> LENGTH: 34
<212> TYPE: PRT
<213> ORGANISM: Artificial Sequence
<220> FEATURE:
<223> OTHER INFORMATION: Human COMP peptide

<400> SEQUENCE: 273

Arg Glu Leu Leu Arg Gln Gln Val Arg Glu Ile Thr Phe Leu Lys Asn
1               5                   10                  15

Thr Val Met Glu Cys Asp Ala Cys Gly Met Gln Gln Ser Val Arg Thr
            20                  25                  30

Gly Leu

<210> SEQ ID NO 274
<211> LENGTH: 34
<212> TYPE: PRT
<213> ORGANISM: Artificial Sequence
<220> FEATURE:
<223> OTHER INFORMATION: Human COMP peptide

<400> SEQUENCE: 274

Thr Phe Leu Lys Asn Thr Val Met Glu Cys Asp Ala Cys Gly Met Gln
1               5                   10                  15

Gln Ser Val Arg Thr Gly Leu Pro Ser Val Arg Pro Leu Leu His Cys
            20                  25                  30

Ala Pro

<210> SEQ ID NO 275
<211> LENGTH: 34
<212> TYPE: PRT
<213> ORGANISM: Artificial Sequence
<220> FEATURE:
<223> OTHER INFORMATION: Human COMP peptide

<400> SEQUENCE: 275

Gly Leu Pro Ser Val Arg Pro Leu Leu His Cys Ala Pro Gly Phe Cys
1               5                   10                  15

Phe Pro Gly Val Ala Cys Ile Gln Thr Glu Ser Gly Ala Arg Cys Gly
            20                  25                  30

Pro Cys

<210> SEQ ID NO 276
<211> LENGTH: 34

<212> TYPE: PRT
<213> ORGANISM: Artificial Sequence
<220> FEATURE:
<223> OTHER INFORMATION: Human COMP peptide

<400> SEQUENCE: 276

Val Arg Pro Leu Leu His Cys Ala Pro Gly Phe Cys Phe Pro Gly Val
1               5                   10                  15

Ala Cys Ile Gln Thr Glu Ser Gly Ala Arg Cys Gly Pro Cys Pro Ala
            20                  25                  30

Gly Phe

<210> SEQ ID NO 277
<211> LENGTH: 34
<212> TYPE: PRT
<213> ORGANISM: Artificial Sequence
<220> FEATURE:
<223> OTHER INFORMATION: Human COMP peptide

<400> SEQUENCE: 277

Gly Phe Thr Gly Asn Gly Ser His Cys Thr Asp Val Asn Glu Cys Asn
1               5                   10                  15

Ala His Pro Cys Phe Pro Arg Val Arg Cys Ile Asn Thr Ser Pro Gly
            20                  25                  30

Phe Arg

<210> SEQ ID NO 278
<211> LENGTH: 34
<212> TYPE: PRT
<213> ORGANISM: Artificial Sequence
<220> FEATURE:
<223> OTHER INFORMATION: Human COMP peptide

<400> SEQUENCE: 278

Gly Trp Ala Gly Asn Gly Ile Leu Cys Gly Arg Asp Thr Asp Leu Asp
1               5                   10                  15

Gly Phe Pro Asp Glu Lys Leu Arg Cys Pro Glu Arg Gln Cys Arg Lys
            20                  25                  30

Asp Asn

<210> SEQ ID NO 279
<211> LENGTH: 34
<212> TYPE: PRT
<213> ORGANISM: Artificial Sequence
<220> FEATURE:
<223> OTHER INFORMATION: Human COMP peptide

<400> SEQUENCE: 279

Thr Val Pro Asn Ser Gly Gln Glu Asp Val Asp Arg Asp Gly Ile Gly
1               5                   10                  15

Asp Ala Cys Asp Pro Asp Ala Asp Gly Asp Gly Val Pro Asn Glu Lys
            20                  25                  30

Asp Asn

<210> SEQ ID NO 280
<211> LENGTH: 34
<212> TYPE: PRT
<213> ORGANISM: Artificial Sequence
<220> FEATURE:
<223> OTHER INFORMATION: Human COMP peptide

<400> SEQUENCE: 280

Val Arg Asn Pro Asp Gln Arg Asn Thr Asp Glu Asp Lys Trp Gly Asp
1               5                   10                  15

Ala Cys Asp Asn Cys Arg Ser Gln Lys Asn Asp Asp Gln Lys Asp Thr
            20                  25                  30

Asp Gln

<210> SEQ ID NO 281
<211> LENGTH: 34
<212> TYPE: PRT
<213> ORGANISM: Artificial Sequence
<220> FEATURE:
<223> OTHER INFORMATION: Human COMP peptide

<400> SEQUENCE: 281

Arg Asn Pro Asp Gln Arg Asn Thr Asp Glu Asp Lys Trp Gly Asp Ala
1               5                   10                  15

Cys Asp Asn Cys Arg Ser Gln Lys Asn Asp Asp Gln Lys Asp Thr Asp
            20                  25                  30

Gln Asp

<210> SEQ ID NO 282
<211> LENGTH: 34
<212> TYPE: PRT
<213> ORGANISM: Artificial Sequence
<220> FEATURE:
<223> OTHER INFORMATION: Human COMP peptide

<400> SEQUENCE: 282

Val Pro Asn Pro Gly Gln Glu Asp Ala Asp Arg Asp Gly Val Gly Asp
1               5                   10                  15

Val Cys Gln Asp Asp Phe Asp Ala Asp Lys Val Val Asp Lys Ile Asp
            20                  25                  30

Val Cys

<210> SEQ ID NO 283
<211> LENGTH: 34
<212> TYPE: PRT
<213> ORGANISM: Artificial Sequence
<220> FEATURE:
<223> OTHER INFORMATION: Human COMP peptide

<400> SEQUENCE: 283

Val Asp Lys Ile Asp Val Cys Pro Glu Asn Ala Glu Val Thr Leu Thr
1               5                   10                  15

Asp Phe Arg Ala Phe Gln Thr Val Val Leu Asp Pro Glu Gly Asp Ala
            20                  25                  30

Gln Ile

<210> SEQ ID NO 284
<211> LENGTH: 34
<212> TYPE: PRT
<213> ORGANISM: Artificial Sequence
<220> FEATURE:
<223> OTHER INFORMATION: Human COMP peptide

<400> SEQUENCE: 284

Glu Val Thr Leu Thr Asp Phe Arg Ala Phe Gln Thr Val Val Leu Asp
1               5                   10                  15

Pro Glu Gly Asp Ala Gln Ile Asp Pro Asn Trp Val Val Leu Asn Gln
            20                  25                  30

Gly Arg

<210> SEQ ID NO 285
<211> LENGTH: 34
<212> TYPE: PRT
<213> ORGANISM: Artificial Sequence
<220> FEATURE:
<223> OTHER INFORMATION: Human COMP peptide

<400> SEQUENCE: 285

Val Val Leu Asp Pro Glu Gly Asp Ala Gln Ile Asp Pro Asn Trp Val
1               5                   10                  15

Val Leu Asn Gln Gly Arg Glu Ile Val Gln Thr Met Asn Ser Asp Pro
            20                  25                  30

Gly Leu

<210> SEQ ID NO 286
<211> LENGTH: 34
<212> TYPE: PRT
<213> ORGANISM: Artificial Sequence
<220> FEATURE:
<223> OTHER INFORMATION: Human COMP peptide

<400> SEQUENCE: 286

Val Leu Asp Pro Glu Gly Asp Ala Gln Ile Asp Pro Asn Trp Val Val
1               5                   10                  15

Leu Asn Gln Gly Arg Glu Ile Val Gln Thr Met Asn Ser Asp Pro Gly
            20                  25                  30

Leu Ala

<210> SEQ ID NO 287
<211> LENGTH: 34
<212> TYPE: PRT
<213> ORGANISM: Artificial Sequence
<220> FEATURE:
<223> OTHER INFORMATION: Human COMP peptide

<400> SEQUENCE: 287

Leu Asp Pro Glu Gly Asp Ala Gln Ile Asp Pro Asn Trp Val Val Leu
1               5                   10                  15

Asn Gln Gly Arg Glu Ile Val Gln Thr Met Asn Ser Asp Pro Gly Leu
            20                  25                  30

Ala Val

<210> SEQ ID NO 288
<211> LENGTH: 34
<212> TYPE: PRT
<213> ORGANISM: Artificial Sequence
<220> FEATURE:
<223> OTHER INFORMATION: Human COMP peptide

<400> SEQUENCE: 288

Val Leu Asn Gln Gly Arg Glu Ile Val Gln Thr Met Asn Ser Asp Pro
1               5                   10                  15

Gly Leu Ala Val Gly Tyr Thr Ala Phe Asn Gly Val Asp Phe Glu Gly
            20                  25                  30

Thr Phe

<210> SEQ ID NO 289
<211> LENGTH: 34
<212> TYPE: PRT
<213> ORGANISM: Artificial Sequence
<220> FEATURE:

<223> OTHER INFORMATION: Human COMP peptide

<400> SEQUENCE: 289

Leu Asn Gln Gly Arg Glu Ile Val Gln Thr Met Asn Ser Asp Pro Gly
1               5                   10                  15
Leu Ala Val Gly Tyr Thr Ala Phe Asn Gly Val Asp Phe Glu Gly Thr
            20                  25                  30
Phe His

<210> SEQ ID NO 290
<211> LENGTH: 34
<212> TYPE: PRT
<213> ORGANISM: Artificial Sequence
<220> FEATURE:
<223> OTHER INFORMATION: Human COMP peptide

<400> SEQUENCE: 290

Met Asn Ser Asp Pro Gly Leu Ala Val Gly Tyr Thr Ala Phe Asn Gly
1               5                   10                  15
Val Asp Phe Glu Gly Thr Phe His Val Asn Thr Val Thr Asp Asp Asp
            20                  25                  30
Tyr Ala

<210> SEQ ID NO 291
<211> LENGTH: 34
<212> TYPE: PRT
<213> ORGANISM: Artificial Sequence
<220> FEATURE:
<223> OTHER INFORMATION: Human COMP peptide

<400> SEQUENCE: 291

Asn Ser Asp Pro Gly Leu Ala Val Gly Tyr Thr Ala Phe Asn Gly Val
1               5                   10                  15
Asp Phe Glu Gly Thr Phe His Val Asn Thr Val Thr Asp Asp Asp Tyr
            20                  25                  30
Ala Gly

<210> SEQ ID NO 292
<211> LENGTH: 34
<212> TYPE: PRT
<213> ORGANISM: Artificial Sequence
<220> FEATURE:
<223> OTHER INFORMATION: Human COMP peptide

<400> SEQUENCE: 292

Leu Ala Val Gly Tyr Thr Ala Phe Asn Gly Val Asp Phe Glu Gly Thr
1               5                   10                  15
Phe His Val Asn Thr Val Thr Asp Asp Asp Tyr Ala Gly Phe Ile Phe
            20                  25                  30
Gly Tyr

<210> SEQ ID NO 293
<211> LENGTH: 34
<212> TYPE: PRT
<213> ORGANISM: Artificial Sequence
<220> FEATURE:
<223> OTHER INFORMATION: Human COMP peptide

<400> SEQUENCE: 293

Gly Tyr Thr Ala Phe Asn Gly Val Asp Phe Glu Gly Thr Phe His Val
1               5                   10                  15

Asn Thr Val Thr Asp Asp Asp Tyr Ala Gly Phe Ile Phe Gly Tyr Gln
            20                  25                  30

Asp Ser

<210> SEQ ID NO 294
<211> LENGTH: 34
<212> TYPE: PRT
<213> ORGANISM: Artificial Sequence
<220> FEATURE:
<223> OTHER INFORMATION: Human COMP peptide

<400> SEQUENCE: 294

Asp Phe Glu Gly Thr Phe His Val Asn Thr Val Thr Asp Asp Tyr
1               5                   10                  15

Ala Gly Phe Ile Phe Gly Tyr Gln Asp Ser Ser Ser Phe Tyr Val Val
            20                  25                  30

Met Trp

<210> SEQ ID NO 295
<211> LENGTH: 34
<212> TYPE: PRT
<213> ORGANISM: Artificial Sequence
<220> FEATURE:
<223> OTHER INFORMATION: Human COMP peptide

<400> SEQUENCE: 295

Val Thr Asp Asp Asp Tyr Ala Gly Phe Ile Phe Gly Tyr Gln Asp Ser
1               5                   10                  15

Ser Ser Phe Tyr Val Val Met Trp Lys Gln Met Glu Thr Tyr Trp
            20                  25                  30

Gln Ala

<210> SEQ ID NO 296
<211> LENGTH: 34
<212> TYPE: PRT
<213> ORGANISM: Artificial Sequence
<220> FEATURE:
<223> OTHER INFORMATION: Human COMP peptide

<400> SEQUENCE: 296

Thr Asp Asp Asp Tyr Ala Gly Phe Ile Phe Gly Tyr Gln Asp Ser Ser
1               5                   10                  15

Ser Phe Tyr Val Val Met Trp Lys Gln Met Glu Gln Thr Tyr Trp Gln
            20                  25                  30

Ala Asn

<210> SEQ ID NO 297
<211> LENGTH: 34
<212> TYPE: PRT
<213> ORGANISM: Artificial Sequence
<220> FEATURE:
<223> OTHER INFORMATION: Human COMP peptide

<400> SEQUENCE: 297

Val Val Met Trp Lys Gln Met Glu Gln Thr Tyr Trp Gln Ala Asn Pro
1               5                   10                  15

Phe Arg Ala Val Ala Glu Pro Gly Ile Gln Leu Lys Ala Val Lys Ser
            20                  25                  30

Ser Thr

<210> SEQ ID NO 298

```
<211> LENGTH: 34
<212> TYPE: PRT
<213> ORGANISM: Artificial Sequence
<220> FEATURE:
<223> OTHER INFORMATION: Human COMP peptide

<400> SEQUENCE: 298

Val Met Trp Lys Gln Met Glu Gln Thr Tyr Trp Gln Ala Asn Pro Phe
1               5                   10                  15
Arg Ala Val Ala Glu Pro Gly Ile Gln Leu Lys Ala Val Lys Ser Ser
            20                  25                  30
Thr Gly

<210> SEQ ID NO 299
<211> LENGTH: 34
<212> TYPE: PRT
<213> ORGANISM: Artificial Sequence
<220> FEATURE:
<223> OTHER INFORMATION: Human COMP peptide

<400> SEQUENCE: 299

Tyr Trp Gln Ala Asn Pro Phe Arg Ala Val Ala Glu Pro Gly Ile Gln
1               5                   10                  15
Leu Lys Ala Val Lys Ser Ser Thr Gly Pro Gly Glu Gln Leu Arg Asn
            20                  25                  30
Ala Leu

<210> SEQ ID NO 300
<211> LENGTH: 34
<212> TYPE: PRT
<213> ORGANISM: Artificial Sequence
<220> FEATURE:
<223> OTHER INFORMATION: Human COMP peptide

<400> SEQUENCE: 300

Val Ala Glu Pro Gly Ile Gln Leu Lys Ala Val Lys Ser Ser Thr Gly
1               5                   10                  15
Pro Gly Glu Gln Leu Arg Asn Ala Leu Trp His Thr Gly Asp Thr Glu
            20                  25                  30
Ser Gln

<210> SEQ ID NO 301
<211> LENGTH: 34
<212> TYPE: PRT
<213> ORGANISM: Artificial Sequence
<220> FEATURE:
<223> OTHER INFORMATION: Human COMP peptide

<400> SEQUENCE: 301

Ala Glu Pro Gly Ile Gln Leu Lys Ala Val Lys Ser Ser Thr Gly Pro
1               5                   10                  15
Gly Glu Gln Leu Arg Asn Ala Leu Trp His Thr Gly Asp Thr Glu Ser
            20                  25                  30
Gln Val

<210> SEQ ID NO 302
<211> LENGTH: 34
<212> TYPE: PRT
<213> ORGANISM: Artificial Sequence
<220> FEATURE:
<223> OTHER INFORMATION: Human COMP peptide

<400> SEQUENCE: 302
```

Lys Ala Val Lys Ser Ser Thr Gly Pro Gly Glu Gln Leu Arg Asn Ala
1               5                   10                  15

Leu Trp His Thr Gly Asp Thr Glu Ser Gln Val Arg Leu Leu Trp Lys
            20                  25                  30

Asp Pro

<210> SEQ ID NO 303
<211> LENGTH: 34
<212> TYPE: PRT
<213> ORGANISM: Artificial Sequence
<220> FEATURE:
<223> OTHER INFORMATION: Human COMP peptide

<400> SEQUENCE: 303

Val Lys Ser Ser Thr Gly Pro Gly Glu Gln Leu Arg Asn Ala Leu Trp
1               5                   10                  15

His Thr Gly Asp Thr Glu Ser Gln Val Arg Leu Leu Trp Lys Asp Pro
            20                  25                  30

Arg Asn

<210> SEQ ID NO 304
<211> LENGTH: 34
<212> TYPE: PRT
<213> ORGANISM: Artificial Sequence
<220> FEATURE:
<223> OTHER INFORMATION: Human COMP peptide

<400> SEQUENCE: 304

Lys Ser Ser Thr Gly Pro Gly Glu Gln Leu Arg Asn Ala Leu Trp His
1               5                   10                  15

Thr Gly Asp Thr Glu Ser Gln Val Arg Leu Leu Trp Lys Asp Pro Arg
            20                  25                  30

Asn Val

<210> SEQ ID NO 305
<211> LENGTH: 34
<212> TYPE: PRT
<213> ORGANISM: Artificial Sequence
<220> FEATURE:
<223> OTHER INFORMATION: Human COMP peptide

<400> SEQUENCE: 305

Ser Thr Gly Pro Gly Glu Gln Leu Arg Asn Ala Leu Trp His Thr Gly
1               5                   10                  15

Asp Thr Glu Ser Gln Val Arg Leu Leu Trp Lys Asp Pro Arg Asn Val
            20                  25                  30

Gly Trp

<210> SEQ ID NO 306
<211> LENGTH: 34
<212> TYPE: PRT
<213> ORGANISM: Artificial Sequence
<220> FEATURE:
<223> OTHER INFORMATION: Human COMP peptide

<400> SEQUENCE: 306

Thr Gly Pro Gly Glu Gln Leu Arg Asn Ala Leu Trp His Thr Gly Asp
1               5                   10                  15

Thr Glu Ser Gln Val Arg Leu Leu Trp Lys Asp Pro Arg Asn Val Gly
            20                  25                  30

Trp Lys

<210> SEQ ID NO 307
<211> LENGTH: 34
<212> TYPE: PRT
<213> ORGANISM: Artificial Sequence
<220> FEATURE:
<223> OTHER INFORMATION: Human COMP peptide

<400> SEQUENCE: 307

Leu Trp His Thr Gly Asp Thr Glu Ser Gln Val Arg Leu Leu Trp Lys
1               5                   10                  15

Asp Pro Arg Asn Val Gly Trp Lys Asp Lys Lys Ser Tyr Arg Trp Phe
            20                  25                  30

Leu Gln

<210> SEQ ID NO 308
<211> LENGTH: 34
<212> TYPE: PRT
<213> ORGANISM: Artificial Sequence
<220> FEATURE:
<223> OTHER INFORMATION: Human COMP peptide

<400> SEQUENCE: 308

Leu Trp Lys Asp Pro Arg Asn Val Gly Trp Lys Asp Lys Lys Ser Tyr
1               5                   10                  15

Arg Trp Phe Leu Gln His Arg Pro Gln Val Gly Tyr Ile Arg Val Arg
            20                  25                  30

Phe Tyr

<210> SEQ ID NO 309
<211> LENGTH: 34
<212> TYPE: PRT
<213> ORGANISM: Artificial Sequence
<220> FEATURE:
<223> OTHER INFORMATION: Human COMP peptide

<400> SEQUENCE: 309

Gly Trp Lys Asp Lys Lys Ser Tyr Arg Trp Phe Leu Gln His Arg Pro
1               5                   10                  15

Gln Val Gly Tyr Ile Arg Val Arg Phe Tyr Glu Gly Pro Glu Leu Val
            20                  25                  30

Ala Asp

<210> SEQ ID NO 310
<211> LENGTH: 34
<212> TYPE: PRT
<213> ORGANISM: Artificial Sequence
<220> FEATURE:
<223> OTHER INFORMATION: Human COMP peptide

<400> SEQUENCE: 310

Gly Tyr Ile Arg Val Arg Phe Tyr Glu Gly Pro Glu Leu Val Ala Asp
1               5                   10                  15

Ser Asn Val Val Leu Asp Thr Thr Met Arg Gly Gly Arg Leu Gly Val
            20                  25                  30

Phe Cys

<210> SEQ ID NO 311
<211> LENGTH: 34
<212> TYPE: PRT
<213> ORGANISM: Artificial Sequence
<220> FEATURE:
<223> OTHER INFORMATION: Human COMP peptide

<400> SEQUENCE: 311

Arg Phe Tyr Glu Gly Pro Glu Leu Val Ala Asp Ser Asn Val Val Leu
1               5                   10                  15

Asp Thr Thr Met Arg Gly Gly Arg Leu Gly Val Phe Cys Phe Ser Gln
            20                  25                  30

Glu Asn

<210> SEQ ID NO 312
<211> LENGTH: 34
<212> TYPE: PRT
<213> ORGANISM: Artificial Sequence
<220> FEATURE:
<223> OTHER INFORMATION: Human COMP peptide

<400> SEQUENCE: 312

Ala Asp Ser Asn Val Val Leu Asp Thr Thr Met Arg Gly Gly Arg Leu
1               5                   10                  15

Gly Val Phe Cys Phe Ser Gln Glu Asn Ile Ile Trp Ala Asn Leu Arg
            20                  25                  30

Tyr Arg

<210> SEQ ID NO 313
<211> LENGTH: 34
<212> TYPE: PRT
<213> ORGANISM: Artificial Sequence
<220> FEATURE:
<223> OTHER INFORMATION: Human COMP peptide

<400> SEQUENCE: 313

Val Leu Asp Thr Thr Met Arg Gly Gly Arg Leu Gly Val Phe Cys Phe
1               5                   10                  15

Ser Gln Glu Asn Ile Ile Trp Ala Asn Leu Arg Tyr Arg Cys Asn Asp
            20                  25                  30

Thr Ile

<210> SEQ ID NO 314
<211> LENGTH: 34
<212> TYPE: PRT
<213> ORGANISM: Artificial Sequence
<220> FEATURE:
<223> OTHER INFORMATION: Human COMP peptide

<400> SEQUENCE: 314

Leu Asp Thr Thr Met Arg Gly Gly Arg Leu Gly Val Phe Cys Phe Ser
1               5                   10                  15

Gln Glu Asn Ile Ile Trp Ala Asn Leu Arg Tyr Arg Cys Asn Asp Thr
            20                  25                  30

Ile Pro

<210> SEQ ID NO 315
<211> LENGTH: 34
<212> TYPE: PRT
<213> ORGANISM: Artificial Sequence
<220> FEATURE:
<223> OTHER INFORMATION: Human decorin peptide

<400> SEQUENCE: 315

Leu Leu Leu Leu Ala Gln Val Ser Trp Ala Gly Pro Phe Gln Gln Arg
1               5                   10                  15

```
Gly Leu Phe Asp Phe Met Leu Glu Asp Glu Ala Ser Gly Ile Gly Pro
            20                  25                  30
Glu Val

<210> SEQ ID NO 316
<211> LENGTH: 34
<212> TYPE: PRT
<213> ORGANISM: Artificial Sequence
<220> FEATURE:
<223> OTHER INFORMATION: Human decorin peptide

<400> SEQUENCE: 316

Leu Leu Ala Gln Val Ser Trp Ala Gly Pro Phe Gln Gln Arg Gly Leu
1               5                   10                  15

Phe Asp Phe Met Leu Glu Asp Glu Ala Ser Gly Ile Gly Pro Glu Val
            20                  25                  30

Pro Asp

<210> SEQ ID NO 317
<211> LENGTH: 34
<212> TYPE: PRT
<213> ORGANISM: Artificial Sequence
<220> FEATURE:
<223> OTHER INFORMATION: Human decorin peptide

<400> SEQUENCE: 317

Leu Ala Gln Val Ser Trp Ala Gly Pro Phe Gln Gln Arg Gly Leu Phe
1               5                   10                  15

Asp Phe Met Leu Glu Asp Glu Ala Ser Gly Ile Gly Pro Glu Val Pro
            20                  25                  30

Asp Asp

<210> SEQ ID NO 318
<211> LENGTH: 34
<212> TYPE: PRT
<213> ORGANISM: Artificial Sequence
<220> FEATURE:
<223> OTHER INFORMATION: Human decorin peptide

<400> SEQUENCE: 318

Leu Gly Pro Val Cys Pro Phe Arg Cys Gln Cys His Leu Arg Val Val
1               5                   10                  15

Gln Cys Ser Asp Leu Gly Leu Asp Lys Val Pro Lys Asp Leu Pro Pro
            20                  25                  30

Asp Thr

<210> SEQ ID NO 319
<211> LENGTH: 34
<212> TYPE: PRT
<213> ORGANISM: Artificial Sequence
<220> FEATURE:
<223> OTHER INFORMATION: Human decorin peptide

<400> SEQUENCE: 319

Gly Leu Asp Lys Val Pro Lys Asp Leu Pro Pro Asp Thr Thr Leu Leu
1               5                   10                  15

Asp Leu Gln Asn Asn Lys Ile Thr Glu Ile Lys Asp Gly Asp Phe Lys
            20                  25                  30

Asn Leu
```

```
<210> SEQ ID NO 320
<211> LENGTH: 34
<212> TYPE: PRT
<213> ORGANISM: Artificial Sequence
<220> FEATURE:
<223> OTHER INFORMATION: Human decorin peptide

<400> SEQUENCE: 320

Leu Leu Asp Leu Gln Asn Asn Lys Ile Thr Glu Ile Lys Asp Gly Asp
1               5                   10                  15

Phe Lys Asn Leu Lys Asn Leu His Ala Leu Ile Leu Val Asn Asn Lys
            20                  25                  30

Ile Ser

<210> SEQ ID NO 321
<211> LENGTH: 34
<212> TYPE: PRT
<213> ORGANISM: Artificial Sequence
<220> FEATURE:
<223> OTHER INFORMATION: Human decorin peptide

<400> SEQUENCE: 321

Thr Glu Ile Lys Asp Gly Asp Phe Lys Asn Leu Lys Asn Leu His Ala
1               5                   10                  15

Leu Ile Leu Val Asn Asn Lys Ile Ser Lys Val Ser Pro Gly Ala Phe
            20                  25                  30

Thr Pro

<210> SEQ ID NO 322
<211> LENGTH: 34
<212> TYPE: PRT
<213> ORGANISM: Artificial Sequence
<220> FEATURE:
<223> OTHER INFORMATION: Human decorin peptide

<400> SEQUENCE: 322

Lys Asn Leu His Ala Leu Ile Leu Val Asn Asn Lys Ile Ser Lys Val
1               5                   10                  15

Ser Pro Gly Ala Phe Thr Pro Leu Val Lys Leu Glu Arg Leu Tyr Leu
            20                  25                  30

Ser Lys

<210> SEQ ID NO 323
<211> LENGTH: 34
<212> TYPE: PRT
<213> ORGANISM: Artificial Sequence
<220> FEATURE:
<223> OTHER INFORMATION: Human decorin peptide

<400> SEQUENCE: 323

Asn Asn Lys Ile Ser Lys Val Ser Pro Gly Ala Phe Thr Pro Leu Val
1               5                   10                  15

Lys Leu Glu Arg Leu Tyr Leu Ser Lys Asn Gln Leu Lys Glu Leu Pro
            20                  25                  30

Glu Lys

<210> SEQ ID NO 324
<211> LENGTH: 34
<212> TYPE: PRT
<213> ORGANISM: Artificial Sequence
<220> FEATURE:
<223> OTHER INFORMATION: Human decorin peptide
```

-continued

<400> SEQUENCE: 324

Ser Lys Val Ser Pro Gly Ala Phe Thr Pro Leu Val Lys Leu Glu Arg
1               5                   10                  15

Leu Tyr Leu Ser Lys Asn Gln Leu Lys Glu Leu Pro Glu Lys Met Pro
            20                  25                  30

Lys Thr

<210> SEQ ID NO 325
<211> LENGTH: 34
<212> TYPE: PRT
<213> ORGANISM: Artificial Sequence
<220> FEATURE:
<223> OTHER INFORMATION: Human decorin peptide

<400> SEQUENCE: 325

Lys Val Ser Pro Gly Ala Phe Thr Pro Leu Val Lys Leu Glu Arg Leu
1               5                   10                  15

Tyr Leu Ser Lys Asn Gln Leu Lys Glu Leu Pro Glu Lys Met Pro Lys
            20                  25                  30

Thr Leu

<210> SEQ ID NO 326
<211> LENGTH: 34
<212> TYPE: PRT
<213> ORGANISM: Artificial Sequence
<220> FEATURE:
<223> OTHER INFORMATION: Human decorin peptide

<400> SEQUENCE: 326

Ser Pro Gly Ala Phe Thr Pro Leu Val Lys Leu Glu Arg Leu Tyr Leu
1               5                   10                  15

Ser Lys Asn Gln Leu Lys Glu Leu Pro Glu Lys Met Pro Lys Thr Leu
            20                  25                  30

Gln Glu

<210> SEQ ID NO 327
<211> LENGTH: 34
<212> TYPE: PRT
<213> ORGANISM: Artificial Sequence
<220> FEATURE:
<223> OTHER INFORMATION: Human decorin peptide

<400> SEQUENCE: 327

Ala Phe Thr Pro Leu Val Lys Leu Glu Arg Leu Tyr Leu Ser Lys Asn
1               5                   10                  15

Gln Leu Lys Glu Leu Pro Glu Lys Met Pro Lys Thr Leu Gln Glu Leu
            20                  25                  30

Arg Ala

<210> SEQ ID NO 328
<211> LENGTH: 34
<212> TYPE: PRT
<213> ORGANISM: Artificial Sequence
<220> FEATURE:
<223> OTHER INFORMATION: Human decorin peptide

<400> SEQUENCE: 328

Phe Thr Pro Leu Val Lys Leu Glu Arg Leu Tyr Leu Ser Lys Asn Gln
1               5                   10                  15

Leu Lys Glu Leu Pro Glu Lys Met Pro Lys Thr Leu Gln Glu Leu Arg
            20                  25                  30

Ala His

<210> SEQ ID NO 329
<211> LENGTH: 34
<212> TYPE: PRT
<213> ORGANISM: Artificial Sequence
<220> FEATURE:
<223> OTHER INFORMATION: Human decorin peptide

<400> SEQUENCE: 329

Tyr Leu Ser Lys Asn Gln Leu Lys Glu Leu Pro Glu Lys Met Pro Lys
1               5                   10                  15

Thr Leu Gln Glu Leu Arg Ala His Glu Asn Glu Ile Thr Lys Val Arg
            20                  25                  30

Lys Val

<210> SEQ ID NO 330
<211> LENGTH: 34
<212> TYPE: PRT
<213> ORGANISM: Artificial Sequence
<220> FEATURE:
<223> OTHER INFORMATION: Human decorin peptide

<400> SEQUENCE: 330

Ser Lys Asn Gln Leu Lys Glu Leu Pro Glu Lys Met Pro Lys Thr Leu
1               5                   10                  15

Gln Glu Leu Arg Ala His Glu Asn Glu Ile Thr Lys Val Arg Lys Val
            20                  25                  30

Thr Phe

<210> SEQ ID NO 331
<211> LENGTH: 34
<212> TYPE: PRT
<213> ORGANISM: Artificial Sequence
<220> FEATURE:
<223> OTHER INFORMATION: Human decorin peptide

<400> SEQUENCE: 331

Lys Glu Leu Pro Glu Lys Met Pro Lys Thr Leu Gln Glu Leu Arg Ala
1               5                   10                  15

His Glu Asn Glu Ile Thr Lys Val Arg Lys Val Thr Phe Asn Gly Leu
            20                  25                  30

Asn Gln

<210> SEQ ID NO 332
<211> LENGTH: 34
<212> TYPE: PRT
<213> ORGANISM: Artificial Sequence
<220> FEATURE:
<223> OTHER INFORMATION: Human decorin peptide

<400> SEQUENCE: 332

Thr Phe Asn Gly Leu Asn Gln Met Ile Val Ile Glu Leu Gly Thr Asn
1               5                   10                  15

Pro Leu Lys Ser Ser Gly Ile Glu Asn Gly Ala Phe Gln Gly Met Lys
            20                  25                  30

Lys Leu

<210> SEQ ID NO 333
<211> LENGTH: 34
<212> TYPE: PRT

<213> ORGANISM: Artificial Sequence
<220> FEATURE:
<223> OTHER INFORMATION: Human decorin peptide

<400> SEQUENCE: 333

Val Ile Glu Leu Gly Thr Asn Pro Leu Lys Ser Ser Gly Ile Glu Asn
1               5                   10                  15

Gly Ala Phe Gln Gly Met Lys Lys Leu Ser Tyr Ile Arg Ile Ala Asp
            20                  25                  30

Thr Asn

<210> SEQ ID NO 334
<211> LENGTH: 34
<212> TYPE: PRT
<213> ORGANISM: Artificial Sequence
<220> FEATURE:
<223> OTHER INFORMATION: Human decorin peptide

<400> SEQUENCE: 334

Gly Thr Asn Pro Leu Lys Ser Ser Gly Ile Glu Asn Gly Ala Phe Gln
1               5                   10                  15

Gly Met Lys Lys Leu Ser Tyr Ile Arg Ile Ala Asp Thr Asn Ile Thr
            20                  25                  30

Ser Ile

<210> SEQ ID NO 335
<211> LENGTH: 34
<212> TYPE: PRT
<213> ORGANISM: Artificial Sequence
<220> FEATURE:
<223> OTHER INFORMATION: Human decorin peptide

<400> SEQUENCE: 335

Thr Asn Pro Leu Lys Ser Ser Gly Ile Glu Asn Gly Ala Phe Gln Gly
1               5                   10                  15

Met Lys Lys Leu Ser Tyr Ile Arg Ile Ala Asp Thr Asn Ile Thr Ser
            20                  25                  30

Ile Pro

<210> SEQ ID NO 336
<211> LENGTH: 34
<212> TYPE: PRT
<213> ORGANISM: Artificial Sequence
<220> FEATURE:
<223> OTHER INFORMATION: Human decorin peptide

<400> SEQUENCE: 336

Ser Gly Ile Glu Asn Gly Ala Phe Gln Gly Met Lys Lys Leu Ser Tyr
1               5                   10                  15

Ile Arg Ile Ala Asp Thr Asn Ile Thr Ser Ile Pro Gln Gly Leu Pro
            20                  25                  30

Pro Ser

<210> SEQ ID NO 337
<211> LENGTH: 34
<212> TYPE: PRT
<213> ORGANISM: Artificial Sequence
<220> FEATURE:
<223> OTHER INFORMATION: Human decorin peptide

<400> SEQUENCE: 337

Gly Ile Glu Asn Gly Ala Phe Gln Gly Met Lys Lys Leu Ser Tyr Ile

```
                1               5                  10                  15
Arg Ile Ala Asp Thr Asn Ile Thr Ser Ile Pro Gln Gly Leu Pro Pro
                20                  25                  30
Ser Leu
```

<210> SEQ ID NO 338
<211> LENGTH: 34
<212> TYPE: PRT
<213> ORGANISM: Artificial Sequence
<220> FEATURE:
<223> OTHER INFORMATION: Human decorin peptide

<400> SEQUENCE: 338

```
Ala Phe Gln Gly Met Lys Lys Leu Ser Tyr Ile Arg Ile Ala Asp Thr
1               5                   10                  15
Asn Ile Thr Ser Ile Pro Gln Gly Leu Pro Pro Ser Leu Thr Glu Leu
                20                  25                  30
His Leu
```

<210> SEQ ID NO 339
<211> LENGTH: 34
<212> TYPE: PRT
<213> ORGANISM: Artificial Sequence
<220> FEATURE:
<223> OTHER INFORMATION: Human decorin peptide

<400> SEQUENCE: 339

```
Ser Tyr Ile Arg Ile Ala Asp Thr Asn Ile Thr Ser Ile Pro Gln Gly
1               5                   10                  15
Leu Pro Pro Ser Leu Thr Glu Leu His Leu Asp Gly Asn Lys Ile Ser
                20                  25                  30
Arg Val
```

<210> SEQ ID NO 340
<211> LENGTH: 34
<212> TYPE: PRT
<213> ORGANISM: Artificial Sequence
<220> FEATURE:
<223> OTHER INFORMATION: Human decorin peptide

<400> SEQUENCE: 340

```
Leu Thr Glu Leu His Leu Asp Gly Asn Lys Ile Ser Arg Val Asp Ala
1               5                   10                  15
Ala Ser Leu Lys Gly Leu Asn Asn Leu Ala Lys Leu Gly Leu Ser Phe
                20                  25                  30
Asn Ser
```

<210> SEQ ID NO 341
<211> LENGTH: 34
<212> TYPE: PRT
<213> ORGANISM: Artificial Sequence
<220> FEATURE:
<223> OTHER INFORMATION: Human decorin peptide

<400> SEQUENCE: 341

```
Ser Arg Val Asp Ala Ala Ser Leu Lys Gly Leu Asn Asn Leu Ala Lys
1               5                   10                  15
Leu Gly Leu Ser Phe Asn Ser Ile Ser Ala Val Asp Asn Gly Ser Leu
                20                  25                  30
Ala Asn
```

<210> SEQ ID NO 342
<211> LENGTH: 34
<212> TYPE: PRT
<213> ORGANISM: Artificial Sequence
<220> FEATURE:
<223> OTHER INFORMATION: Human decorin peptide

<400> SEQUENCE: 342

```
Ala Ser Leu Lys Gly Leu Asn Asn Leu Ala Lys Leu Gly Leu Ser Phe
1               5                   10                  15

Asn Ser Ile Ser Ala Val Asp Asn Gly Ser Leu Ala Asn Thr Pro His
            20                  25                  30

Leu Arg
```

<210> SEQ ID NO 343
<211> LENGTH: 34
<212> TYPE: PRT
<213> ORGANISM: Artificial Sequence
<220> FEATURE:
<223> OTHER INFORMATION: Human decorin peptide

<400> SEQUENCE: 343

```
Ser Leu Lys Gly Leu Asn Asn Leu Ala Lys Leu Gly Leu Ser Phe Asn
1               5                   10                  15

Ser Ile Ser Ala Val Asp Asn Gly Ser Leu Ala Asn Thr Pro His Leu
            20                  25                  30

Arg Glu
```

<210> SEQ ID NO 344
<211> LENGTH: 34
<212> TYPE: PRT
<213> ORGANISM: Artificial Sequence
<220> FEATURE:
<223> OTHER INFORMATION: Human decorin peptide

<400> SEQUENCE: 344

```
Leu Asn Asn Leu Ala Lys Leu Gly Leu Ser Phe Asn Ser Ile Ser Ala
1               5                   10                  15

Val Asp Asn Gly Ser Leu Ala Asn Thr Pro His Leu Arg Glu Leu His
            20                  25                  30

Leu Asp
```

<210> SEQ ID NO 345
<211> LENGTH: 34
<212> TYPE: PRT
<213> ORGANISM: Artificial Sequence
<220> FEATURE:
<223> OTHER INFORMATION: Human decorin peptide

<400> SEQUENCE: 345

```
Asn Asn Leu Ala Lys Leu Gly Leu Ser Phe Asn Ser Ile Ser Ala Val
1               5                   10                  15

Asp Asn Gly Ser Leu Ala Asn Thr Pro His Leu Arg Glu Leu His Leu
            20                  25                  30

Asp Asn
```

<210> SEQ ID NO 346
<211> LENGTH: 34
<212> TYPE: PRT
<213> ORGANISM: Artificial Sequence
<220> FEATURE:
<223> OTHER INFORMATION: Human decorin peptide

<400> SEQUENCE: 346

Ala Lys Leu Gly Leu Ser Phe Asn Ser Ile Ser Ala Val Asp Asn Gly
1               5                   10                  15
Ser Leu Ala Asn Thr Pro His Leu Arg Glu Leu His Leu Asp Asn Asn
            20                  25                  30
Lys Leu

<210> SEQ ID NO 347
<211> LENGTH: 34
<212> TYPE: PRT
<213> ORGANISM: Artificial Sequence
<220> FEATURE:
<223> OTHER INFORMATION: Human decorin peptide

<400> SEQUENCE: 347

Lys Leu Gly Leu Ser Phe Asn Ser Ile Ser Ala Val Asp Asn Gly Ser
1               5                   10                  15
Leu Ala Asn Thr Pro His Leu Arg Glu Leu His Leu Asp Asn Asn Lys
            20                  25                  30
Leu Thr

<210> SEQ ID NO 348
<211> LENGTH: 34
<212> TYPE: PRT
<213> ORGANISM: Artificial Sequence
<220> FEATURE:
<223> OTHER INFORMATION: Human decorin peptide

<400> SEQUENCE: 348

Ser Phe Asn Ser Ile Ser Ala Val Asp Asn Gly Ser Leu Ala Asn Thr
1               5                   10                  15
Pro His Leu Arg Glu Leu His Leu Asp Asn Asn Lys Leu Thr Arg Val
            20                  25                  30
Pro Gly

<210> SEQ ID NO 349
<211> LENGTH: 34
<212> TYPE: PRT
<213> ORGANISM: Artificial Sequence
<220> FEATURE:
<223> OTHER INFORMATION: Human decorin peptide

<400> SEQUENCE: 349

Ser Ala Val Asp Asn Gly Ser Leu Ala Asn Thr Pro His Leu Arg Glu
1               5                   10                  15
Leu His Leu Asp Asn Asn Lys Leu Thr Arg Val Pro Gly Gly Leu Ala
            20                  25                  30
Glu His

<210> SEQ ID NO 350
<211> LENGTH: 34
<212> TYPE: PRT
<213> ORGANISM: Artificial Sequence
<220> FEATURE:
<223> OTHER INFORMATION: Human decorin peptide

<400> SEQUENCE: 350

Val Asp Asn Gly Ser Leu Ala Asn Thr Pro His Leu Arg Glu Leu His
1               5                   10                  15
Leu Asp Asn Asn Lys Leu Thr Arg Val Pro Gly Gly Leu Ala Glu His

```
                    20                  25                  30

Lys Tyr

<210> SEQ ID NO 351
<211> LENGTH: 34
<212> TYPE: PRT
<213> ORGANISM: Artificial Sequence
<220> FEATURE:
<223> OTHER INFORMATION: Human decorin peptide

<400> SEQUENCE: 351

Ala Asn Thr Pro His Leu Arg Glu Leu His Leu Asp Asn Asn Lys Leu
1               5                   10                  15

Thr Arg Val Pro Gly Gly Leu Ala Glu His Lys Tyr Ile Gln Val Val
                20                  25                  30

Tyr Leu

<210> SEQ ID NO 352
<211> LENGTH: 34
<212> TYPE: PRT
<213> ORGANISM: Artificial Sequence
<220> FEATURE:
<223> OTHER INFORMATION: Human decorin peptide

<400> SEQUENCE: 352

Thr Arg Val Pro Gly Gly Leu Ala Glu His Lys Tyr Ile Gln Val Val
1               5                   10                  15

Tyr Leu His Asn Asn Asn Ile Ser Val Val Gly Ser Ser Asp Phe Cys
                20                  25                  30

Pro Pro

<210> SEQ ID NO 353
<211> LENGTH: 34
<212> TYPE: PRT
<213> ORGANISM: Artificial Sequence
<220> FEATURE:
<223> OTHER INFORMATION: Human decorin peptide

<400> SEQUENCE: 353

Arg Val Pro Gly Gly Leu Ala Glu His Lys Tyr Ile Gln Val Val Tyr
1               5                   10                  15

Leu His Asn Asn Asn Ile Ser Val Val Gly Ser Ser Asp Phe Cys Pro
                20                  25                  30

Pro Gly

<210> SEQ ID NO 354
<211> LENGTH: 34
<212> TYPE: PRT
<213> ORGANISM: Artificial Sequence
<220> FEATURE:
<223> OTHER INFORMATION: Human decorin peptide

<400> SEQUENCE: 354

Gly Leu Ala Glu His Lys Tyr Ile Gln Val Val Tyr Leu His Asn Asn
1               5                   10                  15

Asn Ile Ser Val Val Gly Ser Ser Asp Phe Cys Pro Pro Gly His Asn
                20                  25                  30

Thr Lys

<210> SEQ ID NO 355
<211> LENGTH: 34
```

```
<212> TYPE: PRT
<213> ORGANISM: Artificial Sequence
<220> FEATURE:
<223> OTHER INFORMATION: Human decorin peptide

<400> SEQUENCE: 355

Val Tyr Leu His Asn Asn Asn Ile Ser Val Val Gly Ser Ser Asp Phe
1               5                   10                  15

Cys Pro Pro Gly His Asn Thr Lys Lys Ala Ser Tyr Ser Gly Val Ser
            20                  25                  30

Leu Phe

<210> SEQ ID NO 356
<211> LENGTH: 34
<212> TYPE: PRT
<213> ORGANISM: Artificial Sequence
<220> FEATURE:
<223> OTHER INFORMATION: Human decorin peptide

<400> SEQUENCE: 356

Ser Val Val Gly Ser Ser Asp Phe Cys Pro Pro Gly His Asn Thr Lys
1               5                   10                  15

Lys Ala Ser Tyr Ser Gly Val Ser Leu Phe Ser Asn Pro Val Gln Tyr
            20                  25                  30

Trp Glu

<210> SEQ ID NO 357
<211> LENGTH: 34
<212> TYPE: PRT
<213> ORGANISM: Artificial Sequence
<220> FEATURE:
<223> OTHER INFORMATION: Human decorin peptide

<400> SEQUENCE: 357

Val Gly Ser Ser Asp Phe Cys Pro Pro Gly His Asn Thr Lys Lys Ala
1               5                   10                  15

Ser Tyr Ser Gly Val Ser Leu Phe Ser Asn Pro Val Gln Tyr Trp Glu
            20                  25                  30

Ile Gln

<210> SEQ ID NO 358
<211> LENGTH: 34
<212> TYPE: PRT
<213> ORGANISM: Artificial Sequence
<220> FEATURE:
<223> OTHER INFORMATION: Human decorin peptide

<400> SEQUENCE: 358

Gly Ser Ser Asp Phe Cys Pro Pro Gly His Asn Thr Lys Lys Ala Ser
1               5                   10                  15

Tyr Ser Gly Val Ser Leu Phe Ser Asn Pro Val Gln Tyr Trp Glu Ile
            20                  25                  30

Gln Pro

<210> SEQ ID NO 359
<211> LENGTH: 34
<212> TYPE: PRT
<213> ORGANISM: Artificial Sequence
<220> FEATURE:
<223> OTHER INFORMATION: Human decorin peptide

<400> SEQUENCE: 359
```

-continued

Ser Tyr Ser Gly Val Ser Leu Phe Ser Asn Pro Val Gln Tyr Trp Glu
1               5                   10                  15

Ile Gln Pro Ser Thr Phe Arg Cys Val Tyr Val Arg Ser Ala Ile Gln
            20                  25                  30

Leu Gly

<210> SEQ ID NO 360
<211> LENGTH: 34
<212> TYPE: PRT
<213> ORGANISM: Artificial Sequence
<220> FEATURE:
<223> OTHER INFORMATION: Human decorin peptide

<400> SEQUENCE: 360

Gly Val Ser Leu Phe Ser Asn Pro Val Gln Tyr Trp Glu Ile Gln Pro
1               5                   10                  15

Ser Thr Phe Arg Cys Val Tyr Val Arg Ser Ala Ile Gln Leu Gly Asn
            20                  25                  30

Tyr Lys

<210> SEQ ID NO 361
<211> LENGTH: 32
<212> TYPE: PRT
<213> ORGANISM: Artificial Sequence
<220> FEATURE:
<223> OTHER INFORMATION: Human decorin peptide

<400> SEQUENCE: 361

Ser Leu Phe Ser Asn Pro Val Gln Tyr Trp Glu Ile Gln Pro Ser Thr
1               5                   10                  15

Phe Arg Cys Val Tyr Val Arg Ser Ala Ile Gln Leu Gly Asn Tyr Lys
            20                  25                  30

<210> SEQ ID NO 362
<211> LENGTH: 30
<212> TYPE: PRT
<213> ORGANISM: Artificial Sequence
<220> FEATURE:
<223> OTHER INFORMATION: Human decorin peptide

<400> SEQUENCE: 362

Phe Ser Asn Pro Val Gln Tyr Trp Glu Ile Gln Pro Ser Thr Phe Arg
1               5                   10                  15

Cys Val Tyr Val Arg Ser Ala Ile Gln Leu Gly Asn Tyr Lys
            20                  25                  30

<210> SEQ ID NO 363
<211> LENGTH: 29
<212> TYPE: PRT
<213> ORGANISM: Artificial Sequence
<220> FEATURE:
<223> OTHER INFORMATION: Human decorin peptide

<400> SEQUENCE: 363

Ser Asn Pro Val Gln Tyr Trp Glu Ile Gln Pro Ser Thr Phe Arg Cys
1               5                   10                  15

Val Tyr Val Arg Ser Ala Ile Gln Leu Gly Asn Tyr Lys
            20                  25

<210> SEQ ID NO 364
<211> LENGTH: 8
<212> TYPE: PRT
<213> ORGANISM: Artificial Sequence

```
<220> FEATURE:
<223> OTHER INFORMATION: Human decorin peptide

<400> SEQUENCE: 364

Ala Ile Gln Leu Gly Asn Tyr Lys
1               5

<210> SEQ ID NO 365
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 365

Ser Leu Leu Leu Leu Ala Gly Leu Phe Ser Leu Ser Gln Ala Gln Tyr
1               5                   10                  15

Glu Asp Asp Pro His Trp Trp Phe His Tyr Leu Arg Ser Gln Gln Ser
            20                  25                  30

Thr Tyr

<210> SEQ ID NO 366
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 366

Leu Leu Leu Leu Ala Gly Leu Phe Ser Leu Ser Gln Ala Gln Tyr Glu
1               5                   10                  15

Asp Asp Pro His Trp Trp Phe His Tyr Leu Arg Ser Gln Gln Ser Thr
            20                  25                  30

Tyr Tyr

<210> SEQ ID NO 367
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 367

Leu Leu Ala Gly Leu Phe Ser Leu Ser Gln Ala Gln Tyr Glu Asp Asp
1               5                   10                  15

Pro His Trp Trp Phe His Tyr Leu Arg Ser Gln Gln Ser Thr Tyr Tyr
            20                  25                  30

Asp Pro

<210> SEQ ID NO 368
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 368

Leu Ala Gly Leu Phe Ser Leu Ser Gln Ala Gln Tyr Glu Asp Asp Pro
1               5                   10                  15

His Trp Trp Phe His Tyr Leu Arg Ser Gln Gln Ser Thr Tyr Tyr Asp
            20                  25                  30

Pro Tyr
```

-continued

```
<210> SEQ ID NO 369
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 369

Gly Leu Phe Ser Leu Ser Gln Ala Gln Tyr Glu Asp Asp Pro His Trp
1               5                   10                  15

Trp Phe His Tyr Leu Arg Ser Gln Gln Ser Thr Tyr Tyr Asp Pro Tyr
            20                  25                  30

Asp Pro

<210> SEQ ID NO 370
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 370

Leu Phe Ser Leu Ser Gln Ala Gln Tyr Glu Asp Asp Pro His Trp Trp
1               5                   10                  15

Phe His Tyr Leu Arg Ser Gln Gln Ser Thr Tyr Tyr Asp Pro Tyr Asp
            20                  25                  30

Pro Tyr

<210> SEQ ID NO 371
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 371

Tyr Tyr Asp Pro Tyr Asp Pro Tyr Glu Thr Tyr Glu Pro Tyr
1               5                   10                  15

Pro Tyr Gly Val Asp Glu Gly Pro Ala Tyr Thr Tyr Gly Ser Pro Ser
            20                  25                  30

Pro Pro

<210> SEQ ID NO 372
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 372

Lys Tyr Leu Pro Phe Val Pro Ser Arg Met Lys Tyr Val Tyr Phe Gln
1               5                   10                  15

Asn Asn Gln Ile Thr Ser Ile Gln Glu Gly Val Phe Asp Asn Ala Thr
            20                  25                  30

Gly Leu

<210> SEQ ID NO 373
<211> LENGTH: 34
<212> TYPE: PRT
<213> ORGANISM: Artificial Sequence
<220> FEATURE:
```

<223> OTHER INFORMATION: Human fibromodulin peptide

<400> SEQUENCE: 373

Thr Ser Ile Gln Glu Gly Val Phe Asp Asn Ala Thr Gly Leu Leu Trp
1               5                   10                  15
Ile Ala Leu His Gly Asn Gln Ile Thr Ser Asp Lys Val Gly Arg Lys
            20                  25                  30
Val Phe

<210> SEQ ID NO 374
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 374

Val Phe Asp Asn Ala Thr Gly Leu Leu Trp Ile Ala Leu His Gly Asn
1               5                   10                  15
Gln Ile Thr Ser Asp Lys Val Gly Arg Lys Val Phe Ser Lys Leu Arg
            20                  25                  30
His Leu

<210> SEQ ID NO 375
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 375

Thr Gly Leu Leu Trp Ile Ala Leu His Gly Asn Gln Ile Thr Ser Asp
1               5                   10                  15
Lys Val Gly Arg Lys Val Phe Ser Lys Leu Arg His Leu Glu Arg Leu
            20                  25                  30
Tyr Leu

<210> SEQ ID NO 376
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 376

Phe Ser Lys Leu Arg His Leu Glu Arg Leu Tyr Leu Asp His Asn Asn
1               5                   10                  15
Leu Thr Arg Met Pro Gly Pro Leu Pro Arg Ser Leu Arg Glu Leu His
            20                  25                  30
Leu Asp

<210> SEQ ID NO 377
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 377

Tyr Leu Asp His Asn Asn Leu Thr Arg Met Pro Gly Pro Leu Pro Arg
1               5                   10                  15

-continued

Ser Leu Arg Glu Leu His Leu Asp His Asn Gln Ile Ser Arg Val Pro
            20                  25                  30

Asn Asn

<210> SEQ ID NO 378
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 378

Arg Met Pro Gly Pro Leu Pro Arg Ser Leu Arg Glu Leu His Leu Asp
1               5                   10                  15

His Asn Gln Ile Ser Arg Val Pro Asn Asn Ala Leu Glu Gly Leu Glu
            20                  25                  30

Asn Leu

<210> SEQ ID NO 379
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 379

Leu Arg Glu Leu His Leu Asp His Asn Gln Ile Ser Arg Val Pro Asn
1               5                   10                  15

Asn Ala Leu Glu Gly Leu Glu Asn Leu Thr Ala Leu Tyr Leu Gln His
            20                  25                  30

Asn Glu

<210> SEQ ID NO 380
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 380

Ser Arg Val Pro Asn Asn Ala Leu Glu Gly Leu Glu Asn Leu Thr Ala
1               5                   10                  15

Leu Tyr Leu Gln His Asn Glu Ile Gln Glu Val Gly Ser Ser Met Arg
            20                  25                  30

Gly Leu

<210> SEQ ID NO 381
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 381

Leu Glu Gly Leu Glu Asn Leu Thr Ala Leu Tyr Leu Gln His Asn Glu
1               5                   10                  15

Ile Gln Glu Val Gly Ser Ser Met Arg Gly Leu Arg Ser Leu Ile Leu
            20                  25                  30

Leu Asp

<210> SEQ ID NO 382

```
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 382

Leu Tyr Leu Gln His Asn Glu Ile Gln Glu Val Gly Ser Ser Met Arg
1               5                   10                  15

Gly Leu Arg Ser Leu Ile Leu Leu Asp Leu Ser Tyr Asn His Leu Arg
            20                  25                  30

Lys Val

<210> SEQ ID NO 383
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 383

Gly Ser Ser Met Arg Gly Leu Arg Ser Leu Ile Leu Leu Asp Leu Ser
1               5                   10                  15

Tyr Asn His Leu Arg Lys Val Pro Asp Gly Leu Pro Ser Ala Leu Glu
            20                  25                  30

Gln Leu

<210> SEQ ID NO 384
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 384

Leu Ile Leu Leu Asp Leu Ser Tyr Asn His Leu Arg Lys Val Pro Asp
1               5                   10                  15

Gly Leu Pro Ser Ala Leu Glu Gln Leu Tyr Met Glu His Asn Asn Val
            20                  25                  30

Tyr Thr

<210> SEQ ID NO 385
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 385

Leu Leu Asp Leu Ser Tyr Asn His Leu Arg Lys Val Pro Asp Gly Leu
1               5                   10                  15

Pro Ser Ala Leu Glu Gln Leu Tyr Met Glu His Asn Asn Val Tyr Thr
            20                  25                  30

Val Pro

<210> SEQ ID NO 386
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 386
```

```
Ser Tyr Asn His Leu Arg Lys Val Pro Asp Gly Leu Pro Ser Ala Leu
1               5                   10                  15

Glu Gln Leu Tyr Met Glu His Asn Asn Val Tyr Thr Val Pro Asp Ser
            20                  25                  30

Tyr Phe

<210> SEQ ID NO 387
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 387

Ala Leu Glu Gln Leu Tyr Met Glu His Asn Asn Val Tyr Thr Val Pro
1               5                   10                  15

Asp Ser Tyr Phe Arg Gly Ala Pro Lys Leu Leu Tyr Val Arg Leu Ser
            20                  25                  30

His Asn

<210> SEQ ID NO 388
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 388

Leu Glu Gln Leu Tyr Met Glu His Asn Asn Val Tyr Thr Val Pro Asp
1               5                   10                  15

Ser Tyr Phe Arg Gly Ala Pro Lys Leu Leu Tyr Val Arg Leu Ser His
            20                  25                  30

Asn Ser

<210> SEQ ID NO 389
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 389

Tyr Thr Val Pro Asp Ser Tyr Phe Arg Gly Ala Pro Lys Leu Leu Tyr
1               5                   10                  15

Val Arg Leu Ser His Asn Ser Leu Thr Asn Asn Gly Leu Ala Ser Asn
            20                  25                  30

Thr Phe

<210> SEQ ID NO 390
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 390

Val Pro Asp Ser Tyr Phe Arg Gly Ala Pro Lys Leu Leu Tyr Val Arg
1               5                   10                  15

Leu Ser His Asn Ser Leu Thr Asn Asn Gly Leu Ala Ser Asn Thr Phe
            20                  25                  30
```

Asn Ser

<210> SEQ ID NO 391
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 391

```
Leu Tyr Val Arg Leu Ser His Asn Ser Leu Thr Asn Asn Gly Leu Ala
1               5                   10                  15

Ser Asn Thr Phe Asn Ser Ser Ser Leu Leu Glu Leu Asp Leu Ser Tyr
            20                  25                  30

Asn Gln
```

<210> SEQ ID NO 392
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 392

```
Arg Leu Ser His Asn Ser Leu Thr Asn Asn Gly Leu Ala Ser Asn Thr
1               5                   10                  15

Phe Asn Ser Ser Ser Leu Leu Glu Leu Asp Leu Ser Tyr Asn Gln Leu
            20                  25                  30

Gln Lys
```

<210> SEQ ID NO 393
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 393

```
Ser His Asn Ser Leu Thr Asn Asn Gly Leu Ala Ser Asn Thr Phe Asn
1               5                   10                  15

Ser Ser Ser Leu Leu Glu Leu Asp Leu Ser Tyr Asn Gln Leu Gln Lys
            20                  25                  30

Ile Pro
```

<210> SEQ ID NO 394
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 394

```
Thr Asn Asn Gly Leu Ala Ser Asn Thr Phe Asn Ser Ser Ser Leu Leu
1               5                   10                  15

Glu Leu Asp Leu Ser Tyr Asn Gln Leu Gln Lys Ile Pro Pro Val Asn
            20                  25                  30

Thr Asn
```

<210> SEQ ID NO 395
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 395

Asn Asn Gly Leu Ala Ser Asn Thr Phe Asn Ser Ser Leu Leu Glu
1               5                   10                  15

Leu Asp Leu Ser Tyr Asn Gln Leu Gln Lys Ile Pro Pro Val Asn Thr
            20                  25                  30

Asn Leu

<210> SEQ ID NO 396
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 396

Phe Asn Ser Ser Leu Leu Glu Leu Asp Leu Ser Tyr Asn Gln Leu
1               5                   10                  15

Gln Lys Ile Pro Pro Val Asn Thr Asn Leu Glu Asn Leu Tyr Leu Gln
            20                  25                  30

Gly Asn

<210> SEQ ID NO 397
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 397

Ser Ser Leu Leu Glu Leu Asp Leu Ser Tyr Asn Gln Leu Gln Lys Ile
1               5                   10                  15

Pro Pro Val Asn Thr Asn Leu Glu Asn Leu Tyr Leu Gln Gly Asn Arg
            20                  25                  30

Ile Asn

<210> SEQ ID NO 398
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 398

Ser Leu Leu Glu Leu Asp Leu Ser Tyr Asn Gln Leu Gln Lys Ile Pro
1               5                   10                  15

Pro Val Asn Thr Asn Leu Glu Asn Leu Tyr Leu Gln Gly Asn Arg Ile
            20                  25                  30

Asn Glu

<210> SEQ ID NO 399
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 399

Leu Leu Glu Leu Asp Leu Ser Tyr Asn Gln Leu Gln Lys Ile Pro Pro
1               5                   10                  15

```
Val Asn Thr Asn Leu Glu Asn Leu Tyr Leu Gln Gly Asn Arg Ile Asn
            20                  25                  30

Glu Phe

<210> SEQ ID NO 400
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 400

Leu Glu Leu Asp Leu Ser Tyr Asn Gln Leu Gln Lys Ile Pro Pro Val
1               5                   10                  15

Asn Thr Asn Leu Glu Asn Leu Tyr Leu Gln Gly Asn Arg Ile Asn Glu
            20                  25                  30

Phe Ser

<210> SEQ ID NO 401
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 401

Glu Leu Asp Leu Ser Tyr Asn Gln Leu Gln Lys Ile Pro Pro Val Asn
1               5                   10                  15

Thr Asn Leu Glu Asn Leu Tyr Leu Gln Gly Asn Arg Ile Asn Glu Phe
            20                  25                  30

Ser Ile

<210> SEQ ID NO 402
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 402

Tyr Asn Gln Leu Gln Lys Ile Pro Pro Val Asn Thr Asn Leu Glu Asn
1               5                   10                  15

Leu Tyr Leu Gln Gly Asn Arg Ile Asn Glu Phe Ser Ile Ser Ser Phe
            20                  25                  30

Cys Thr

<210> SEQ ID NO 403
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 403

Asn Thr Asn Leu Glu Asn Leu Tyr Leu Gln Gly Asn Arg Ile Asn Glu
1               5                   10                  15

Phe Ser Ile Ser Ser Phe Cys Thr Val Val Asp Val Val Asn Phe Ser
            20                  25                  30

Lys Leu
```

```
<210> SEQ ID NO 404
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 404

Asn Leu Glu Asn Leu Tyr Leu Gln Gly Asn Arg Ile Asn Glu Phe Ser
1               5                   10                  15

Ile Ser Ser Phe Cys Thr Val Val Asp Val Val Asn Phe Ser Lys Leu
            20                  25                  30

Gln Val

<210> SEQ ID NO 405
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 405

Tyr Leu Gln Gly Asn Arg Ile Asn Glu Phe Ser Ile Ser Ser Phe Cys
1               5                   10                  15

Thr Val Val Asp Val Val Asn Phe Ser Lys Leu Gln Val Leu Arg Leu
            20                  25                  30

Asp Gly

<210> SEQ ID NO 406
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 406

Val Val Asp Val Val Asn Phe Ser Lys Leu Gln Val Leu Arg Leu Asp
1               5                   10                  15

Gly Asn Glu Ile Lys Arg Ser Ala Met Pro Ala Asp Ala Pro Leu Cys
            20                  25                  30

Leu Arg

<210> SEQ ID NO 407
<211> LENGTH: 34
<212> TYPE: PRT
<213> ORGANISM: Artificial Sequence
<220> FEATURE:
<223> OTHER INFORMATION: Human fibromodulin peptide

<400> SEQUENCE: 407

Val Asp Val Val Asn Phe Ser Lys Leu Gln Val Leu Arg Leu Asp Gly
1               5                   10                  15

Asn Glu Ile Lys Arg Ser Ala Met Pro Ala Asp Ala Pro Leu Cys Leu
            20                  25                  30

Arg Leu

<210> SEQ ID NO 408
<211> LENGTH: 34
<212> TYPE: PRT
<213> ORGANISM: Artificial Sequence
<220> FEATURE:
<223> OTHER INFORMATION: Human fibromodulin peptide
```

```
<400> SEQUENCE: 408

Val Asn Phe Ser Lys Leu Gln Val Leu Arg Leu Asp Gly Asn Glu Ile
1               5                   10                  15

Lys Arg Ser Ala Met Pro Ala Asp Ala Pro Leu Cys Leu Arg Leu Ala
            20                  25                  30

Ser Leu

<210> SEQ ID NO 409
<211> LENGTH: 31
<212> TYPE: PRT
<213> ORGANISM: Artificial Sequence
<220> FEATURE:
<223> OTHER INFORMATION: Human fibromodulin peptide

<400> SEQUENCE: 409

Gln Val Leu Arg Leu Asp Gly Asn Glu Ile Lys Arg Ser Ala Met Pro
1               5                   10                  15

Ala Asp Ala Pro Leu Cys Leu Arg Leu Ala Ser Leu Ile Glu Ile
            20                  25                  30

<210> SEQ ID NO 410
<211> LENGTH: 29
<212> TYPE: PRT
<213> ORGANISM: Artificial Sequence
<220> FEATURE:
<223> OTHER INFORMATION: Human fibromodulin peptide

<400> SEQUENCE: 410

Leu Arg Leu Asp Gly Asn Glu Ile Lys Arg Ser Ala Met Pro Ala Asp
1               5                   10                  15

Ala Pro Leu Cys Leu Arg Leu Ala Ser Leu Ile Glu Ile
            20                  25

<210> SEQ ID NO 411
<211> LENGTH: 28
<212> TYPE: PRT
<213> ORGANISM: Artificial Sequence
<220> FEATURE:
<223> OTHER INFORMATION: Human fibromodulin peptide

<400> SEQUENCE: 411

Arg Leu Asp Gly Asn Glu Ile Lys Arg Ser Ala Met Pro Ala Asp Ala
1               5                   10                  15

Pro Leu Cys Leu Arg Leu Ala Ser Leu Ile Glu Ile
            20                  25

<210> SEQ ID NO 412
<211> LENGTH: 18
<212> TYPE: PRT
<213> ORGANISM: Artificial Sequence
<220> FEATURE:
<223> OTHER INFORMATION: Human fibromodulin peptide

<400> SEQUENCE: 412

Ala Met Pro Ala Asp Ala Pro Leu Cys Leu Arg Leu Ala Ser Leu Ile
1               5                   10                  15

Glu Ile

<210> SEQ ID NO 413
<211> LENGTH: 6
<212> TYPE: PRT
<213> ORGANISM: Artificial Sequence
<220> FEATURE:
```

<223> OTHER INFORMATION: Human fibromodulin peptide

<400> SEQUENCE: 413

Ala Ser Leu Ile Glu Ile
1               5

<210> SEQ ID NO 414
<211> LENGTH: 5
<212> TYPE: PRT
<213> ORGANISM: Artificial Sequence
<220> FEATURE:
<223> OTHER INFORMATION: Human fibromodulin peptide

<400> SEQUENCE: 414

Ser Leu Ile Glu Ile
1               5

<210> SEQ ID NO 415
<211> LENGTH: 360
<212> TYPE: PRT
<213> ORGANISM: Bos taurus

<400> SEQUENCE: 415

Met Lys Ala Thr Ile Ile Phe Leu Leu Val Ala Gln Val Ser Trp Ala
1               5                   10                  15

Gly Pro Phe Gln Gln Lys Gly Leu Phe Asp Phe Met Leu Glu Asp Glu
                20                  25                  30

Ala Ser Gly Ile Gly Pro Glu Glu His Phe Pro Glu Val Pro Glu Ile
            35                  40                  45

Glu Pro Met Gly Pro Val Cys Pro Phe Arg Cys Gln Cys His Leu Arg
    50                  55                  60

Val Val Gln Cys Ser Asp Leu Gly Leu Glu Lys Val Pro Lys Asp Leu
65                  70                  75                  80

Pro Pro Asp Thr Ala Leu Leu Asp Leu Gln Asn Asn Lys Ile Thr Glu
                85                  90                  95

Ile Lys Asp Gly Asp Phe Lys Asn Leu Lys Asn Leu His Thr Leu Ile
                100                 105                 110

Leu Ile Asn Asn Lys Ile Ser Lys Ile Ser Pro Gly Ala Phe Ala Pro
            115                 120                 125

Leu Val Lys Leu Glu Arg Leu Tyr Leu Ser Lys Asn Gln Leu Lys Glu
        130                 135                 140

Leu Pro Glu Lys Met Pro Lys Thr Leu Gln Glu Leu Arg Val His Glu
145                 150                 155                 160

Asn Glu Ile Thr Lys Val Arg Lys Ser Val Phe Asn Gly Leu Asn Gln
                165                 170                 175

Met Ile Val Val Glu Leu Gly Thr Asn Pro Leu Lys Ser Ser Gly Ile
            180                 185                 190

Glu Asn Gly Ala Phe Gln Gly Met Lys Lys Leu Ser Tyr Ile Arg Ile
        195                 200                 205

Ala Asp Thr Asn Ile Thr Thr Ile Pro Gln Gly Leu Pro Pro Ser Leu
    210                 215                 220

Thr Glu Leu His Leu Asp Gly Asn Lys Ile Thr Lys Val Asp Ala Ala
225                 230                 235                 240

Ser Leu Lys Gly Leu Asn Asn Leu Ala Lys Leu Gly Leu Ser Phe Asn
                245                 250                 255

Ser Ile Ser Ala Val Asp Asn Gly Ser Leu Ala Asn Thr Pro His Leu
            260                 265                 270

```
Arg Glu Leu His Leu Asn Asn Asn Lys Leu Val Lys Val Pro Gly Gly
            275                 280                 285

Leu Ala Asp His Lys Tyr Ile Gln Val Val Tyr Leu His Asn Asn Asn
        290                 295                 300

Ile Ser Ala Ile Gly Ser Asn Asp Phe Cys Pro Pro Gly Tyr Asn Thr
305                 310                 315                 320

Lys Lys Ala Ser Tyr Ser Gly Val Ser Leu Phe Ser Asn Pro Val Gln
                325                 330                 335

Tyr Trp Glu Ile Gln Pro Ser Thr Phe Arg Cys Val Tyr Val Arg Ala
            340                 345                 350

Ala Val Gln Leu Gly Asn Tyr Lys
        355                 360

<210> SEQ ID NO 416
<211> LENGTH: 369
<212> TYPE: PRT
<213> ORGANISM: Bos taurus

<400> SEQUENCE: 416

Met Trp Pro Leu Trp Pro Leu Ala Ala Leu Leu Ala Leu Ser Gln Ala
1               5                   10                  15

Leu Pro Phe Glu Gln Lys Ala Phe Trp Asp Phe Thr Leu Asp Asp Gly
            20                  25                  30

Leu Pro Met Leu Asn Asp Glu Glu Ala Ser Gly Ala Glu Thr Thr Ser
        35                  40                  45

Gly Ile Pro Asp Leu Asp Ser Leu Pro Pro Thr Tyr Ser Ala Met Cys
50                  55                  60

Pro Phe Gly Cys His Cys His Leu Arg Val Val Gln Cys Ser Asp Leu
65                  70                  75                  80

Gly Leu Lys Ala Val Pro Lys Glu Ile Ser Pro Asp Thr Thr Leu Leu
                85                  90                  95

Asp Leu Gln Asn Asn Asp Ile Ser Glu Leu Arg Lys Asp Asp Phe Lys
            100                 105                 110

Gly Leu Gln His Leu Tyr Ala Leu Val Leu Val Asn Asn Lys Ile Ser
        115                 120                 125

Lys Ile His Glu Lys Ala Phe Ser Pro Leu Arg Lys Leu Gln Lys Leu
130                 135                 140

Tyr Ile Ser Lys Asn His Leu Val Glu Ile Pro Pro Asn Leu Pro Ser
145                 150                 155                 160

Ser Leu Val Glu Leu Arg Ile His Asp Asn Arg Ile Arg Lys Val Pro
                165                 170                 175

Lys Gly Val Phe Ser Gly Leu Arg Asn Met Asn Cys Ile Glu Met Gly
            180                 185                 190

Gly Asn Pro Leu Glu Asn Ser Gly Phe Glu Pro Gly Ala Phe Asp Gly
        195                 200                 205

Leu Lys Leu Asn Tyr Leu Arg Ile Ser Glu Ala Lys Leu Thr Gly Ile
210                 215                 220

Pro Lys Asp Leu Pro Glu Thr Leu Asn Glu Leu His Leu Asp His Asn
225                 230                 235                 240

Lys Ile Gln Ala Ile Glu Leu Glu Asp Leu Leu Arg Tyr Ser Lys Leu
                245                 250                 255

Tyr Arg Leu Gly Leu Gly His Asn Gln Ile Arg Met Ile Glu Asn Gly
            260                 265                 270

Ser Leu Ser Phe Leu Pro Thr Leu Arg Glu Leu His Leu Asp Asn Asn
        275                 280                 285
```

-continued

```
Lys Leu Ser Arg Val Pro Ala Gly Leu Pro Asp Leu Lys Leu Gln
    290                 295                 300

Val Val Tyr Leu His Thr Asn Asn Ile Thr Lys Val Gly Val Asn Asp
305                 310                 315                 320

Phe Cys Pro Val Gly Phe Gly Val Lys Arg Ala Tyr Tyr Asn Gly Ile
                325                 330                 335

Ser Leu Phe Asn Asn Pro Val Pro Tyr Trp Glu Val Gln Pro Ala Thr
            340                 345                 350

Phe Arg Cys Val Thr Asp Arg Leu Ala Ile Gln Phe Gly Asn Tyr Lys
        355                 360                 365

Lys

<210> SEQ ID NO 417
<211> LENGTH: 376
<212> TYPE: PRT
<213> ORGANISM: Bos taurus

<400> SEQUENCE: 417

Met Gln Trp Ala Ser Ile Leu Leu Ala Gly Leu Cys Ser Leu Ser
1               5                   10                  15

Trp Ala Gln Tyr Glu Glu Asp Ser His Trp Trp Phe Gln Phe Leu Arg
                20                  25                  30

Asn Gln Gln Ser Thr Tyr Asp Asp Pro Tyr Asp Pro Tyr Pro Tyr Glu
            35                  40                  45

Pro Tyr Glu Pro Tyr Pro Tyr Gly Gly Glu Glu Gly Pro Ala Tyr Ala
        50                  55                  60

Tyr Gly Ser Pro Pro Gln Pro Glu Pro Arg Asp Cys Pro Gln Glu Cys
65                  70                  75                  80

Asp Cys Pro Pro Asn Phe Pro Thr Ala Met Tyr Cys Asn Arg Asn
                85                  90                  95

Leu Lys Tyr Leu Pro Phe Val Pro Ser Arg Met Lys Tyr Val Tyr Phe
            100                 105                 110

Gln Asn Asn Gln Ile Ser Ser Ile Gln Glu Gly Val Phe Asp Asn Ala
        115                 120                 125

Thr Gly Leu Leu Trp Ile Ala Leu His Gly Asn Gln Ile Thr Ser Asp
    130                 135                 140

Lys Val Gly Lys Val Phe Ser Lys Leu Arg His Leu Glu Arg Leu
145                 150                 155                 160

Tyr Leu Asp His Asn Asn Leu Thr Arg Ile Pro Ser Pro Leu Pro Arg
                165                 170                 175

Ser Leu Arg Glu Leu His Leu Asp His Asn Gln Ile Ser Arg Val Pro
            180                 185                 190

Asn Asn Ala Leu Glu Gly Leu Glu Asn Leu Thr Ala Leu Tyr Leu His
        195                 200                 205

His Asn Glu Ile Gln Glu Val Gly Ser Ser Met Lys Gly Leu Arg Ser
    210                 215                 220

Leu Ile Leu Leu Asp Leu Ser Tyr Asn His Leu Arg Lys Val Pro Asp
225                 230                 235                 240

Gly Leu Pro Ser Ala Leu Glu Gln Leu Tyr Leu Glu His Asn Asn Val
                245                 250                 255

Phe Ser Val Pro Asp Ser Tyr Phe Arg Gly Ser Pro Lys Leu Leu Tyr
            260                 265                 270

Val Arg Leu Ser His Asn Ser Leu Thr Asn Asn Gly Leu Ala Ser Asn
        275                 280                 285
```

```
Thr Phe Asn Ser Ser Leu Leu Glu Leu Asp Leu Ser Tyr Asn Gln
    290                 295                 300

Leu Gln Lys Ile Pro Pro Val Ser Thr Asn Leu Glu Asn Leu Tyr Leu
305                 310                 315                 320

Gln Gly Asn Arg Ile Asn Glu Phe Ser Ile Ser Ser Phe Cys Thr Val
                325                 330                 335

Val Asp Val Met Asn Phe Ser Lys Leu Gln Val Leu Arg Leu Asp Gly
            340                 345                 350

Asn Glu Ile Lys Arg Ser Ala Met Pro Ala Asp Ala Pro Leu Cys Leu
                355                 360                 365

Arg Leu Ala Ser Leu Ile Glu Ile
370                 375

<210> SEQ ID NO 418
<211> LENGTH: 756
<212> TYPE: PRT
<213> ORGANISM: Bos taurus

<400> SEQUENCE: 418

Met Val Leu Ala Ala Arg Val Leu Leu Leu Thr Leu Ala Ala Leu
1               5                   10                  15

Gly Ala Ser Gly Gln Gly Gln Met Pro Leu Gly Gly Asp Leu Gly Pro
                20                  25                  30

Gln Met Leu Arg Glu Leu Gln Thr Asn Ala Ala Leu Gln Asp Val
                35                  40                  45

Arg Asp Leu Leu Arg Gln Gln Val Lys Glu Ile Thr Phe Leu Lys Asn
50                  55                  60

Thr Val Met Glu Cys Asp Ala Cys Gly Met Gln Pro Ala Arg Thr Pro
65                  70                  75                  80

Lys Leu Thr Val Arg Pro Leu Ser Gln Cys Ser Pro Gly Phe Cys Phe
                85                  90                  95

Pro Gly Val Ala Cys Thr Glu Thr Ala Asn Gly Ala Arg Cys Gly Pro
                100                 105                 110

Cys Pro Glu Gly Phe Thr Gly Asn Gly Ser His Cys Ala Asp Val Asn
                115                 120                 125

Glu Cys Thr Ala His Pro Cys Phe Pro Arg Val Arg Cys Ile Asn Thr
                130                 135                 140

Ser Pro Gly Phe Arg Cys Glu Ala Cys Pro Pro Gly Phe Ser Gly Pro
145                 150                 155                 160

Thr His Glu Gly Val Gly Leu Ala Phe Ala Lys Ala Asn Lys Gln Val
                165                 170                 175

Cys Thr Asp Ile Asn Glu Cys Glu Thr Gly Gln His Asn Cys Val Pro
                180                 185                 190

Asn Ser Val Cys Val Asn Thr Val Gly Ser Phe Gln Cys Gly Pro Cys
                195                 200                 205

Gln Pro Gly Phe Val Gly Asp Gln Ala Ser Gly Cys Arg Arg Pro
                210                 215                 220

Gln Arg Phe Cys Pro Asp Gly Thr Pro Ser Pro Cys His Glu Lys Ala
225                 230                 235                 240

Asp Cys Val Leu Glu Arg Asp Gly Ser Arg Ser Cys Val Cys Ala Val
                245                 250                 255

Gly Trp Ala Gly Asn Gly Leu Ile Cys Gly Arg Asp Thr Asp Leu Asp
                260                 265                 270

Gly Phe Pro Asp Glu Lys Leu Arg Cys Ser Glu Arg Gln Cys Arg Lys
```

```
                275                 280                 285
Asp Asn Cys Val Thr Val Pro Asn Ser Gly Gln Glu Asp Val Asp Gln
290                 295                 300
Asp Gly Ile Gly Asp Ala Cys Asp Pro Asp Ala Asp Gly Asp Gly Val
305                 310                 315                 320
Leu Asn Glu Lys Asp Asn Cys Pro Leu Val Arg Asn Pro Asp Gln Arg
                325                 330                 335
Asn Thr Asp Gly Asp Lys Trp Gly Asp Ala Cys Asp Asn Cys Arg Ser
                340                 345                 350
Gln Lys Asn Asp Asp Gln Lys Asp Thr Asp Lys Asp Gly Arg Gly Asp
                355                 360                 365
Ala Cys Asp Asp Asp Ile Asp Gly Asp Arg Ile Arg Asn Pro Val Asp
                370                 375                 380
Asn Cys Pro Lys Val Pro Asn Ser Asp Gln Lys Asp Thr Asp Gly Asp
385                 390                 395                 400
Gly Val Gly Asp Ala Cys Asp Asn Cys Pro Gln Lys Ser Asn Ala Asp
                405                 410                 415
Gln Arg Asp Val Asp His Asp Phe Val Gly Asp Ala Cys Asp Ser Asp
                420                 425                 430
Gln Asp Gln Asp Gly Asp Gly His Gln Asp Ser Lys Asp Asn Cys Pro
                435                 440                 445
Thr Val Pro Asn Ser Ala Gln Gln Asp Ser Asp His Asp Gly Gln Gly
                450                 455                 460
Asp Ala Cys Asp Asp Asp Asp Asn Asp Gly Val Pro Asp Ser Arg
465                 470                 475                 480
Asp Asn Cys Arg Leu Val Pro Asn Pro Gly Gln Glu Asp Met Asp Arg
                485                 490                 495
Asp Gly Val Gly Asp Ala Cys Gln Gly Asp Phe Asp Ala Asp Lys Val
                500                 505                 510
Val Asp Lys Ile Asp Val Cys Pro Glu Asn Ala Glu Val Thr Leu Thr
                515                 520                 525
Asp Phe Arg Ala Phe Gln Thr Val Leu Asp Pro Glu Gly Asp Ala
                530                 535                 540
Gln Ile Asp Pro Asn Trp Val Val Leu Asn Gln Gly Met Glu Ile Val
545                 550                 555                 560
Gln Thr Met Asn Ser Asp Pro Gly Leu Ala Val Gly Tyr Thr Ala Phe
                565                 570                 575
Asn Gly Val Asp Phe Glu Gly Thr Phe His Val Asn Thr Ala Thr Asp
                580                 585                 590
Asp Asp Tyr Ala Gly Phe Ile Phe Gly Tyr Gln Asp Ser Ser Ser Phe
                595                 600                 605
Tyr Val Val Met Trp Lys Gln Met Glu Gln Thr Tyr Trp Gln Ala Asn
                610                 615                 620
Pro Phe Arg Ala Val Ala Glu Pro Gly Ile Gln Leu Lys Ala Val Lys
625                 630                 635                 640
Ser Ser Thr Gly Pro Gly Glu Gln Leu Arg Asn Ala Leu Trp His Thr
                645                 650                 655
Gly Asp Thr Ala Ser Gln Val Arg Leu Leu Trp Lys Asp Pro Arg Asn
                660                 665                 670
Val Gly Trp Lys Asp Lys Thr Ser Tyr Arg Trp Phe Leu Gln His Arg
                675                 680                 685
Pro Gln Val Gly Tyr Ile Arg Val Arg Phe Tyr Glu Gly Pro Glu Leu
                690                 695                 700
```

Val Ala Asp Ser Asn Val Ile Leu Asp Thr Thr Met Arg Gly Gly Arg
705                 710                 715                 720

Leu Gly Val Phe Cys Phe Ser Gln Glu Asn Ile Ile Trp Ala Asn Leu
            725                 730                 735

Arg Tyr Arg Cys Asn Asp Thr Ile Pro Glu Asp Tyr Glu Ala Gln Arg
            740                 745                 750

Leu Leu Gln Ala
        755

<210> SEQ ID NO 419
<211> LENGTH: 2364
<212> TYPE: PRT
<213> ORGANISM: Bos taurus

<400> SEQUENCE: 419

Met Thr Thr Leu Leu Leu Val Phe Val Thr Leu Arg Val Ile Thr Ala
1               5                   10                  15

Ala Ile Ser Val Glu Val Ser Glu Pro Asp Asn Ser Leu Ser Val Ser
                20                  25                  30

Ile Pro Glu Pro Ser Pro Leu Arg Val Leu Gly Ser Ser Leu Thr
            35                  40                  45

Ile Pro Cys Tyr Phe Ile Asp Pro Met His Pro Val Thr Thr Ala Pro
50                  55                  60

Ser Thr Ala Pro Leu Ala Pro Arg Ile Lys Trp Ser Arg Ile Ser Lys
65                  70                  75                  80

Glu Lys Glu Val Val Leu Leu Val Ala Thr Glu Gly Arg Val Arg Val
                85                  90                  95

Asn Ser Ala Tyr Gln Asp Lys Val Thr Leu Pro Asn Tyr Pro Ala Ile
                100                 105                 110

Pro Ser Asp Ala Thr Leu Glu Ile Gln Asn Met Arg Ser Asn Asp Ser
            115                 120                 125

Gly Ile Leu Arg Cys Glu Val Met His Gly Ile Glu Asp Ser Gln Ala
            130                 135                 140

Thr Leu Glu Val Val Val Lys Gly Ile Val Phe His Tyr Arg Ala Ile
145                 150                 155                 160

Ser Thr Arg Tyr Thr Leu Asp Phe Asp Arg Ala Gln Arg Ala Cys Leu
                165                 170                 175

Gln Asn Ser Ala Ile Ile Ala Thr Pro Glu Gln Leu Gln Ala Ala Tyr
            180                 185                 190

Glu Asp Gly Phe His Gln Cys Asp Ala Gly Trp Leu Ala Asp Gln Thr
            195                 200                 205

Val Arg Tyr Pro Ile His Thr Pro Arg Glu Gly Cys Tyr Gly Asp Lys
210                 215                 220

Asp Glu Phe Pro Gly Val Arg Thr Tyr Gly Ile Arg Asp Thr Asn Glu
225                 230                 235                 240

Thr Tyr Asp Val Tyr Cys Phe Ala Glu Glu Met Glu Gly Glu Val Phe
                245                 250                 255

Tyr Ala Thr Ser Pro Glu Lys Phe Thr Phe Gln Glu Ala Ala Asn Glu
            260                 265                 270

Cys Arg Arg Leu Gly Ala Arg Leu Ala Thr Thr Gly Gln Leu Tyr Leu
            275                 280                 285

Ala Trp Gln Gly Gly Met Asp Met Cys Ser Ala Gly Trp Leu Ala Asp
        290                 295                 300

Arg Ser Val Arg Tyr Pro Ile Ser Lys Ala Arg Pro Asn Cys Gly Gly

```
              305                 310                 315                 320
Asn Leu Leu Gly Val Arg Thr Val Tyr Leu His Ala Asn Gln Thr Gly
                    325                 330                 335

Tyr Pro Asp Pro Ser Arg Tyr Asp Ala Ile Cys Tyr Thr Gly Glu
                340                 345                 350

Asp Phe Val Asp Ile Pro Glu Ser Phe Phe Gly Val Gly Gly Glu
            355                 360                 365

Asp Ile Thr Ile Gln Thr Val Thr Trp Pro Asp Val Glu Leu Pro Leu
370                 375                 380

Pro Arg Asn Ile Thr Glu Gly Glu Ala Arg Gly Ser Val Ile Leu Thr
385                 390                 395                 400

Ala Lys Pro Asp Phe Glu Val Ser Pro Thr Ala Pro Glu Pro Glu Glu
                405                 410                 415

Pro Phe Thr Phe Val Pro Glu Val Arg Ala Thr Ala Phe Pro Glu Val
                420                 425                 430

Glu Asn Arg Thr Glu Glu Ala Thr Arg Pro Trp Ala Phe Pro Arg Glu
            435                 440                 445

Ser Thr Pro Gly Leu Gly Ala Pro Thr Ala Phe Thr Ser Glu Asp Leu
    450                 455                 460

Val Val Gln Val Thr Leu Ala Pro Gly Ala Ala Glu Val Pro Gly Gln
465                 470                 475                 480

Pro Arg Leu Pro Gly Gly Val Val Phe His Tyr Arg Pro Gly Ser Ser
                485                 490                 495

Arg Tyr Ser Leu Thr Phe Glu Glu Ala Lys Gln Ala Cys Leu Arg Thr
            500                 505                 510

Gly Ala Ile Ile Ala Ser Pro Glu Gln Leu Gln Ala Ala Tyr Glu Ala
            515                 520                 525

Gly Tyr Glu Gln Cys Asp Ala Gly Trp Leu Gln Asp Gln Thr Val Arg
            530                 535                 540

Tyr Pro Ile Val Ser Pro Arg Thr Pro Cys Val Gly Asp Lys Asp Ser
545                 550                 555                 560

Ser Pro Gly Val Arg Thr Tyr Gly Val Arg Pro Pro Ser Glu Thr Tyr
                565                 570                 575

Asp Val Tyr Cys Tyr Val Asp Arg Leu Glu Gly Glu Val Phe Phe Ala
            580                 585                 590

Thr Arg Leu Glu Gln Phe Thr Phe Trp Glu Ala Gln Glu Phe Cys Glu
            595                 600                 605

Ser Gln Asn Ala Thr Leu Ala Thr Thr Gly Gln Leu Tyr Ala Ala Trp
    610                 615                 620

Ser Arg Gly Leu Asp Lys Cys Tyr Ala Gly Trp Leu Ala Asp Gly Ser
625                 630                 635                 640

Leu Arg Tyr Pro Ile Val Thr Pro Arg Pro Ala Cys Gly Gly Asp Lys
                645                 650                 655

Pro Gly Val Arg Thr Val Tyr Leu Tyr Pro Asn Gln Thr Gly Leu Leu
                660                 665                 670

Asp Pro Leu Ser Arg His His Ala Phe Cys Phe Arg Gly Val Ser Ala
            675                 680                 685

Ala Pro Ser Pro Glu Glu Glu Gly Ser Ala Pro Thr Ala Gly Pro
            690                 695                 700

Asp Val Glu Glu Trp Met Val Thr Gln Val Gly Pro Gly Val Ala Ala
705                 710                 715                 720

Val Pro Ile Gly Glu Glu Thr Thr Ala Ile Pro Gly Phe Thr Val Glu
                725                 730                 735
```

-continued

Pro Glu Asn Lys Thr Glu Trp Glu Leu Ala Tyr Thr Pro Ala Gly Thr
            740                 745                 750

Leu Pro Leu Pro Gly Ile Pro Pro Thr Trp Pro Thr Gly Glu Ala
        755                 760                 765

Thr Glu Glu His Thr Gly Pro Ser Ala Thr Glu Val Pro Ser Ala
    770                 775                 780

Ser Glu Lys Pro Phe Pro Ser Glu Pro Phe Pro Glu Pro
785                 790                 795                 800

Phe Pro Ser Glu Lys Pro Phe Pro Glu Glu Leu Phe Pro Ser Glu
                805                 810                 815

Lys Pro Phe Ser Glu Lys Pro Phe Pro Ser Glu Glu Pro Phe Pro
            820                 825                 830

Ser Glu Lys Pro Phe Pro Glu Glu Leu Phe Pro Ser Glu Lys Pro
        835                 840                 845

Ile Pro Ser Glu Glu Pro Phe Pro Ser Glu Glu Pro Phe Pro Ser Glu
    850                 855                 860

Lys Pro Phe Pro Pro Glu Glu Pro Phe Pro Ser Glu Lys Pro Ile Pro
865                 870                 875                 880

Ser Glu Glu Pro Phe Pro Ser Lys Pro Phe Pro Ser Glu Glu Pro
                885                 890                 895

Phe Pro Ser Glu Glu Pro Ser Thr Leu Ser Ala Pro Val Pro Ser Arg
            900                 905                 910

Thr Glu Leu Pro Ser Ser Gly Glu Val Ser Gly Val Pro Glu Ile Ser
        915                 920                 925

Gly Asp Phe Thr Gly Ser Gly Glu Ile Ser Gly His Leu Asp Phe Ser
    930                 935                 940

Gly Gln Pro Ser Gly Glu Ser Ala Ser Gly Leu Pro Ser Glu Asp Leu
945                 950                 955                 960

Asp Ser Ser Gly Leu Thr Ser Thr Val Gly Ser Gly Leu Pro Val Glu
                965                 970                 975

Ser Gly Leu Pro Ser Gly Glu Glu Arg Ile Thr Trp Thr Ser Ala
            980                 985                 990

Pro Lys Val Asp Arg Leu Pro Ser Gly Gly Glu Gly Pro Glu Val Ser
        995                 1000                1005

Gly Val Glu Asp Ile Ser Gly Leu Pro Ser Gly Gly Glu Val His
    1010                1015                1020

Leu Glu Ile Ser Ala Ser Gly Val Glu Asp Ile Ser Gly Leu Pro
    1025                1030                1035

Ser Gly Gly Glu Val His Leu Glu Ile Ser Ala Ser Gly Val Glu
    1040                1045                1050

Asp Leu Ser Arg Ile Pro Ser Gly Glu Gly Pro Glu Ile Ser Ala
    1055                1060                1065

Ser Gly Val Glu Asp Ile Ser Gly Leu Pro Ser Gly Glu Glu Gly
    1070                1075                1080

His Leu Glu Ile Ser Ala Ser Gly Val Glu Asp Leu Ser Gly Ile
    1085                1090                1095

Pro Ser Gly Glu Gly Pro Val Ser Ala Ser Gly Val Glu Asp
    1100                1105                1110

Leu Ile Gly Leu Pro Ser Gly Glu Gly Pro Glu Val Ser Ala Ser
    1115                1120                1125

Gly Val Glu Asp Leu Ser Arg Leu Pro Ser Gly Glu Gly Pro Glu
    1130                1135                1140

| | | | | | | | | | | |
|---|---|---|---|---|---|---|---|---|---|---|
| Val | Ser | Ala | Ser | Gly | Val | Glu | Asp | Leu | Ser | Gly | Leu | Pro | Ser | Gly |
| | | 1145 | | | | 1150 | | | | 1155 | | | | |
| Glu | Gly | Pro | Glu | Val | Ser | Val | Ser | Gly | Val | Glu | Asp | Leu | Ser | Arg |
| 1160 | | | | | 1165 | | | | | 1170 | | | | |
| Leu | Pro | Ser | Gly | Gly | Pro | Glu | Val | Ser | Ala | Ser | Gly | Val | Glu |
| 1175 | | | | | 1180 | | | | | 1185 | | | | |
| Asp | Leu | Ser | Arg | Leu | Pro | Ser | Gly | Gly | Pro | Glu | Ile | Ser | Val |
| 1190 | | | | | 1195 | | | | | 1200 | | | | |
| Ser | Gly | Val | Glu | Asp | Ile | Ser | Ile | Leu | Pro | Ser | Gly | Glu | Gly | Pro |
| 1205 | | | | | 1210 | | | | | 1215 | | | | |
| Glu | Val | Ser | Ala | Ser | Gly | Val | Glu | Asp | Leu | Ser | Val | Leu | Pro | Ser |
| 1220 | | | | | 1225 | | | | | 1230 | | | | |
| Gly | Glu | Gly | His | Leu | Glu | Ile | Ser | Thr | Ser | Gly | Val | Glu | Asp | Leu |
| 1235 | | | | | 1240 | | | | | 1245 | | | | |
| Ser | Val | Leu | Pro | Ser | Gly | Glu | Gly | His | Leu | Glu | Thr | Ser | Ser | Gly |
| 1250 | | | | | 1255 | | | | | 1260 | | | | |
| Val | Glu | Asp | Ile | Ser | Arg | Leu | Pro | Ser | Gly | Glu | Gly | Pro | Glu | Val |
| 1265 | | | | | 1270 | | | | | 1275 | | | | |
| Ser | Ala | Ser | Gly | Val | Glu | Asp | Leu | Ser | Val | Leu | Pro | Ser | Gly | Glu |
| 1280 | | | | | 1285 | | | | | 1290 | | | | |
| Asp | His | Leu | Glu | Ile | Ser | Ala | Ser | Gly | Val | Glu | Asp | Leu | Gly | Val |
| 1295 | | | | | 1300 | | | | | 1305 | | | | |
| Leu | Pro | Ser | Gly | Glu | Asp | His | Leu | Glu | Ile | Ser | Ala | Ser | Gly | Val |
| 1310 | | | | | 1315 | | | | | 1320 | | | | |
| Glu | Asp | Ile | Ser | Arg | Leu | Pro | Ser | Gly | Glu | Gly | Pro | Glu | Val | Ser |
| 1325 | | | | | 1330 | | | | | 1335 | | | | |
| Ala | Ser | Gly | Val | Glu | Asp | Leu | Ser | Val | Leu | Pro | Ser | Gly | Glu | Gly |
| 1340 | | | | | 1345 | | | | | 1350 | | | | |
| His | Leu | Glu | Ile | Ser | Ala | Ser | Gly | Val | Glu | Asp | Leu | Ser | Arg | Leu |
| 1355 | | | | | 1360 | | | | | 1365 | | | | |
| Pro | Ser | Gly | Gly | Glu | Asp | His | Leu | Glu | Thr | Ser | Ala | Ser | Gly | Val |
| 1370 | | | | | 1375 | | | | | 1380 | | | | |
| Gly | Asp | Leu | Ser | Gly | Leu | Pro | Ser | Gly | Arg | Glu | Gly | Leu | Glu | Ile |
| 1385 | | | | | 1390 | | | | | 1395 | | | | |
| Ser | Ala | Ser | Gly | Ala | Gly | Asp | Leu | Ser | Gly | Leu | Thr | Ser | Gly | Lys |
| 1400 | | | | | 1405 | | | | | 1410 | | | | |
| Glu | Asp | Leu | Thr | Gly | Ser | Ala | Ser | Gly | Ala | Leu | Asp | Leu | Gly | Arg |
| 1415 | | | | | 1420 | | | | | 1425 | | | | |
| Ile | Pro | Ser | Val | Thr | Leu | Gly | Ser | Gly | Gln | Ala | Pro | Glu | Ala | Ser |
| 1430 | | | | | 1435 | | | | | 1440 | | | | |
| Gly | Leu | Pro | Ser | Gly | Phe | Ser | Gly | Glu | Tyr | Ser | Gly | Val | Asp | Leu |
| 1445 | | | | | 1450 | | | | | 1455 | | | | |
| Glu | Ser | Gly | Pro | Ser | Ser | Gly | Leu | Pro | Asp | Phe | Ser | Gly | Leu | Pro |
| 1460 | | | | | 1465 | | | | | 1470 | | | | |
| Ser | Gly | Phe | Pro | Thr | Val | Ser | Leu | Val | Asp | Thr | Thr | Leu | Val | Glu |
| 1475 | | | | | 1480 | | | | | 1485 | | | | |
| Val | Val | Thr | Ala | Thr | Thr | Ala | Gly | Glu | Leu | Glu | Gly | Arg | Gly | Thr |
| 1490 | | | | | 1495 | | | | | 1500 | | | | |
| Ile | Asp | Ile | Ser | Gly | Ala | Gly | Glu | Thr | Ser | Gly | Leu | Pro | Phe | Ser |
| 1505 | | | | | 1510 | | | | | 1515 | | | | |
| Glu | Leu | Asp | Ile | Ser | Gly | Gly | Ala | Ser | Gly | Leu | Ser | Ser | Gly | Ala |
| 1520 | | | | | 1525 | | | | | 1530 | | | | |
| Glu | Leu | Ser | Gly | Gln | Ala | Ser | Gly | Ser | Pro | Asp | Ile | Ser | Gly | Glu |

-continued

```
            1535                1540                1545

Thr Ser Gly Leu Phe Gly Val Ser Gly Gln Pro Ser Gly Phe Pro
        1550                1555                1560

Asp Ile Ser Gly Glu Thr Ser Gly Leu Leu Glu Val Ser Gly Gln
        1565                1570                1575

Pro Ser Gly Phe Tyr Gly Glu Ile Ser Gly Val Thr Glu Leu Ser
        1580                1585                1590

Gly Leu Ala Ser Gly Gln Pro Glu Ile Ser Gly Glu Ala Ser Gly
        1595                1600                1605

Ile Leu Ser Gly Leu Gly Pro Pro Phe Gly Ile Thr Asp Leu Ser
        1610                1615                1620

Gly Glu Ala Pro Gly Ile Pro Asp Leu Ser Gly Gln Pro Ser Gly
        1625                1630                1635

Leu Pro Glu Phe Ser Gly Thr Ala Ser Gly Ile Pro Asp Leu Val
        1640                1645                1650

Ser Ser Ala Val Ser Gly Ser Gly Glu Ser Ser Gly Ile Thr Phe
        1655                1660                1665

Val Asp Thr Ser Leu Val Glu Val Thr Pro Thr Thr Phe Lys Glu
        1670                1675                1680

Glu Glu Gly Leu Gly Ser Val Glu Leu Ser Gly Leu Pro Ser Gly
        1685                1690                1695

Glu Leu Gly Val Ser Gly Thr Ser Gly Leu Ala Asp Val Ser Gly
        1700                1705                1710

Leu Ser Ser Gly Ala Ile Asp Ser Ser Gly Phe Thr Ser Gln Pro
        1715                1720                1725

Pro Glu Phe Ser Gly Leu Pro Ser Gly Val Thr Glu Val Ser Gly
        1730                1735                1740

Glu Ala Ser Gly Ala Glu Ser Gly Ser Ser Leu Pro Ser Gly Ala
        1745                1750                1755

Tyr Asp Ser Ser Gly Leu Pro Ser Gly Phe Pro Thr Val Ser Phe
        1760                1765                1770

Val Asp Arg Thr Leu Val Glu Ser Val Thr Gln Ala Pro Thr Ala
        1775                1780                1785

Gln Glu Ala Gly Glu Gly Pro Ser Gly Ile Leu Glu Leu Ser Gly
        1790                1795                1800

Ala Pro Ser Gly Ala Pro Asp Met Ser Gly Asp His Leu Gly Ser
        1805                1810                1815

Leu Asp Gln Ser Gly Leu Gln Ser Gly Leu Val Glu Pro Ser Gly
        1820                1825                1830

Glu Pro Ala Ser Thr Pro Tyr Phe Ser Gly Asp Phe Ser Gly Thr
        1835                1840                1845

Thr Asp Val Ser Gly Glu Ser Ser Ala Ala Thr Ser Thr Ser Gly
        1850                1855                1860

Glu Ala Ser Gly Leu Pro Glu Val Thr Leu Ile Thr Ser Glu Leu
        1865                1870                1875

Val Glu Gly Val Thr Glu Pro Thr Val Ser Gln Glu Leu Gly Gln
        1880                1885                1890

Arg Pro Pro Val Thr Tyr Thr Pro Gln Leu Phe Glu Ser Ser Gly
        1895                1900                1905

Glu Ala Ser Ala Ser Gly Asp Val Pro Arg Phe Pro Gly Ser Gly
        1910                1915                1920

Val Glu Val Ser Ser Val Pro Glu Ser Ser Gly Glu Thr Ser Ala
        1925                1930                1935
```

-continued

```
Tyr Pro Glu Ala Glu Val Gly Ala Ser Ala Pro Glu Ala Ser
    1940            1945            1950

Gly Gly Ala Ser Gly Ser Pro Asn Leu Ser Glu Thr Thr Ser Thr
    1955            1960            1965

Phe His Glu Ala Asp Leu Glu Gly Thr Ser Gly Leu Gly Val Ser
    1970            1975            1980

Gly Ser Pro Ser Ala Phe Pro Glu Gly Pro Thr Glu Gly Leu Ala
    1985            1990            1995

Thr Pro Glu Val Ser Gly Glu Ser Thr Thr Ala Phe Asp Val Ser
    2000            2005            2010

Val Glu Ala Ser Gly Ser Pro Ser Ala Thr Pro Leu Ala Ser Gly
    2015            2020            2025

Asp Arg Thr Asp Thr Ser Gly Asp Leu Ser Gly His Thr Ser Gly
    2030            2035            2040

Leu Asp Ile Val Ile Ser Thr Thr Ile Pro Glu Ser Glu Trp Thr
    2045            2050            2055

Gln Gln Thr Gln Arg Pro Ala Glu Ala Arg Leu Glu Ile Glu Ser
    2060            2065            2070

Ser Ser Pro Val His Ser Gly Glu Glu Ser Gln Thr Ala Asp Thr
    2075            2080            2085

Ala Thr Ser Pro Thr Asp Ala Ser Ile Pro Ala Ser Ala Gly Gly
    2090            2095            2100

Thr Asp Asp Ser Glu Ala Thr Thr Thr Asp Ile Asp Glu Cys Leu
    2105            2110            2115

Ser Ser Pro Cys Leu Asn Gly Ala Thr Cys Val Asp Ala Ile Asp
    2120            2125            2130

Ser Phe Thr Cys Leu Cys Leu Pro Ser Tyr Gln Gly Asp Val Cys
    2135            2140            2145

Glu Ile Gln Lys Leu Cys Glu Gly Trp Thr Lys Phe Gln Gly
    2150            2155            2160

His Cys Tyr Arg His Phe Pro Asp Arg Ala Thr Trp Val Asp Ala
    2165            2170            2175

Glu Ser Gln Cys Arg Lys Gln Ser His Leu Ser Ser Ile Val
    2180            2185            2190

Thr Pro Glu Glu Gln Glu Phe Val Asn Asn Asn Ala Gln Asp Tyr
    2195            2200            2205

Gln Trp Ile Gly Leu Asn Asp Lys Thr Ile Glu Gly Asp Phe Arg
    2210            2215            2220

Trp Ser Asp Gly His Ser Leu Gln Phe Glu Asn Trp Arg Pro Asn
    2225            2230            2235

Gln Pro Asp Asn Phe Phe Ala Thr Gly Glu Asp Cys Val Val Met
    2240            2245            2250

Ile Trp His Glu Lys Gly Glu Trp Asn Asp Val Pro Cys Asn Tyr
    2255            2260            2265

Gln Leu Pro Phe Thr Cys Lys Lys Gly Thr Val Ala Cys Gly Glu
    2270            2275            2280

Pro Pro Val Val Glu His Ala Arg Ile Phe Gly Gln Lys Lys Asp
    2285            2290            2295

Arg Tyr Glu Ile Asn Ala Leu Val Arg Tyr Gln Cys Thr Glu Gly
    2300            2305            2310

Phe Ile Gln Gly His Val Pro Thr Ile Arg Cys Gln Pro Ser Gly
    2315            2320            2325
```

His Trp Glu Glu Pro Arg Ile Thr Cys Thr Asp Pro Ala Thr Tyr
    2330                2335                2340

Lys Arg Arg Leu Gln Lys Arg Ser Ser Arg Pro Leu Arg Arg Ser
2345                2350                2355

His Pro Ser Thr Ala His
    2360

<210> SEQ ID NO 420
<211> LENGTH: 359
<212> TYPE: PRT
<213> ORGANISM: Homo sapiens

<400> SEQUENCE: 420

Met Lys Ala Thr Ile Ile Leu Leu Leu Ala Gln Val Ser Trp Ala
1               5                   10                  15

Gly Pro Phe Gln Gln Arg Gly Leu Phe Asp Phe Met Leu Glu Asp
                20                  25                  30

Ala Ser Gly Ile Gly Pro Glu Val Pro Asp Asp Arg Asp Phe Glu Pro
                35                  40                  45

Ser Leu Gly Pro Val Cys Pro Phe Arg Cys Gln Cys His Leu Arg Val
50                  55                  60

Val Gln Cys Ser Asp Leu Gly Leu Asp Lys Val Pro Lys Asp Leu Pro
65                  70                  75                  80

Pro Asp Thr Thr Leu Leu Asp Leu Gln Asn Asn Lys Ile Thr Glu Ile
                85                  90                  95

Lys Asp Gly Asp Phe Lys Asn Leu Lys Asn Leu His Ala Leu Ile Leu
                100                 105                 110

Val Asn Asn Lys Ile Ser Lys Val Ser Pro Gly Ala Phe Thr Pro Leu
                115                 120                 125

Val Lys Leu Glu Arg Leu Tyr Leu Ser Lys Asn Gln Leu Lys Glu Leu
130                 135                 140

Pro Glu Lys Met Pro Lys Thr Leu Gln Glu Leu Arg Ala His Glu Asn
145                 150                 155                 160

Glu Ile Thr Lys Val Arg Lys Val Thr Phe Asn Gly Leu Asn Gln Met
                165                 170                 175

Ile Val Ile Glu Leu Gly Thr Asn Pro Leu Lys Ser Ser Gly Ile Glu
                180                 185                 190

Asn Gly Ala Phe Gln Gly Met Lys Lys Leu Ser Tyr Ile Arg Ile Ala
                195                 200                 205

Asp Thr Asn Ile Thr Ser Ile Pro Gln Gly Leu Pro Pro Ser Leu Thr
210                 215                 220

Glu Leu His Leu Asp Gly Asn Lys Ile Ser Arg Val Asp Ala Ala Ser
225                 230                 235                 240

Leu Lys Gly Leu Asn Asn Leu Ala Lys Leu Gly Leu Ser Phe Asn Ser
                245                 250                 255

Ile Ser Ala Val Asp Asn Gly Ser Leu Ala Asn Thr Pro His Leu Arg
                260                 265                 270

Glu Leu His Leu Asp Asn Asn Lys Leu Thr Arg Val Pro Gly Gly Leu
                275                 280                 285

Ala Glu His Lys Tyr Ile Gln Val Val Tyr Leu His Asn Asn Asn Ile
                290                 295                 300

Ser Val Val Gly Ser Ser Asp Phe Cys Pro Pro Gly His Asn Thr Lys
305                 310                 315                 320

Lys Ala Ser Tyr Ser Gly Val Ser Leu Phe Ser Asn Pro Val Gln Tyr
                325                 330                 335

```
Trp Glu Ile Gln Pro Ser Thr Phe Arg Cys Val Tyr Val Arg Ser Ala
            340                 345                 350

Ile Gln Leu Gly Asn Tyr Lys
        355

<210> SEQ ID NO 421
<211> LENGTH: 368
<212> TYPE: PRT
<213> ORGANISM: Homo sapiens

<400> SEQUENCE: 421

Met Trp Pro Leu Trp Arg Leu Val Ser Leu Leu Ala Leu Ser Gln Ala
1               5                   10                  15

Leu Pro Phe Glu Gln Arg Gly Phe Trp Asp Phe Thr Leu Asp Asp Gly
            20                  25                  30

Pro Phe Met Met Asn Asp Glu Glu Ala Ser Gly Ala Asp Thr Ser Gly
        35                  40                  45

Val Leu Asp Pro Asp Ser Val Thr Pro Thr Tyr Ser Ala Met Cys Pro
50                  55                  60

Phe Gly Cys His Cys His Leu Arg Val Val Gln Cys Ser Asp Leu Gly
65                  70                  75                  80

Leu Lys Ser Val Pro Lys Glu Ile Ser Pro Asp Thr Thr Leu Leu Asp
                85                  90                  95

Leu Gln Asn Asn Asp Ile Ser Glu Leu Arg Lys Asp Asp Phe Lys Gly
            100                 105                 110

Leu Gln His Leu Tyr Ala Leu Val Leu Val Asn Asn Lys Ile Ser Lys
        115                 120                 125

Ile His Glu Lys Ala Phe Ser Pro Leu Arg Lys Leu Gln Lys Leu Tyr
130                 135                 140

Ile Ser Lys Asn His Leu Val Glu Ile Pro Pro Asn Leu Pro Ser Ser
145                 150                 155                 160

Leu Val Glu Leu Arg Ile His Asp Asn Arg Ile Arg Lys Val Pro Lys
                165                 170                 175

Gly Val Phe Ser Gly Leu Arg Asn Met Asn Cys Ile Glu Met Gly Gly
            180                 185                 190

Asn Pro Leu Glu Asn Ser Gly Phe Glu Pro Gly Ala Phe Asp Gly Leu
        195                 200                 205

Lys Leu Asn Tyr Leu Arg Ile Ser Glu Ala Lys Leu Thr Gly Ile Pro
210                 215                 220

Lys Asp Leu Pro Glu Thr Leu Asn Glu Leu His Leu Asp His Asn Lys
225                 230                 235                 240

Ile Gln Ala Ile Glu Leu Glu Asp Leu Leu Arg Tyr Ser Lys Leu Tyr
                245                 250                 255

Arg Leu Gly Leu Gly His Asn Gln Ile Arg Met Ile Glu Asn Gly Ser
            260                 265                 270

Leu Ser Phe Leu Pro Thr Leu Arg Glu Leu His Leu Asp Asn Asn Lys
        275                 280                 285

Leu Ala Arg Val Pro Ser Gly Leu Pro Asp Leu Lys Leu Leu Gln Val
        290                 295                 300

Val Tyr Leu His Ser Asn Asn Ile Thr Lys Val Gly Val Asn Asp Phe
305                 310                 315                 320

Cys Pro Met Gly Phe Gly Val Lys Arg Ala Tyr Tyr Asn Gly Ile Ser
                325                 330                 335

Leu Phe Asn Asn Pro Val Pro Tyr Trp Glu Val Gln Pro Ala Thr Phe
```

```
            340                 345                 350
Arg Cys Val Thr Asp Arg Leu Ala Ile Gln Phe Gly Asn Tyr Lys Lys
            355                 360             365
```

<210> SEQ ID NO 422
<211> LENGTH: 376
<212> TYPE: PRT
<213> ORGANISM: Homo sapiens

<400> SEQUENCE: 422

```
Met Gln Trp Thr Ser Leu Leu Leu Ala Gly Leu Phe Ser Leu Ser
1               5                   10                  15

Gln Ala Gln Tyr Glu Asp Pro His Trp Trp Phe His Tyr Leu Arg
            20                  25                  30

Ser Gln Gln Ser Thr Tyr Tyr Asp Pro Tyr Asp Pro Tyr Pro Tyr Glu
            35                  40                  45

Thr Tyr Glu Pro Tyr Pro Tyr Gly Val Asp Glu Gly Pro Ala Tyr Thr
        50                  55                  60

Tyr Gly Ser Pro Ser Pro Asp Pro Arg Asp Cys Pro Gln Glu Cys
65                  70                  75                  80

Asp Cys Pro Pro Asn Phe Pro Thr Ala Met Tyr Cys Asp Asn Arg Asn
                85                  90                  95

Leu Lys Tyr Leu Pro Phe Val Pro Ser Arg Met Lys Tyr Val Tyr Phe
            100                 105                 110

Gln Asn Asn Gln Ile Thr Ser Ile Gln Glu Gly Val Phe Asp Asn Ala
            115                 120                 125

Thr Gly Leu Leu Trp Ile Ala Leu His Gly Asn Gln Ile Thr Ser Asp
130                 135                 140

Lys Val Gly Arg Lys Val Phe Ser Lys Leu Arg His Leu Glu Arg Leu
145                 150                 155                 160

Tyr Leu Asp His Asn Asn Leu Thr Arg Met Pro Gly Pro Leu Pro Arg
                165                 170                 175

Ser Leu Arg Glu Leu His Leu Asp His Asn Gln Ile Ser Arg Val Pro
            180                 185                 190

Asn Asn Ala Leu Glu Gly Leu Glu Asn Leu Thr Ala Leu Tyr Leu Gln
            195                 200                 205

His Asn Glu Ile Gln Glu Val Gly Ser Ser Met Arg Gly Leu Arg Ser
        210                 215                 220

Leu Ile Leu Leu Asp Leu Ser Tyr Asn His Leu Arg Lys Val Pro Asp
225                 230                 235                 240

Gly Leu Pro Ser Ala Leu Glu Gln Leu Tyr Met Glu His Asn Asn Val
                245                 250                 255

Tyr Thr Val Pro Asp Ser Tyr Phe Arg Gly Ala Pro Lys Leu Leu Tyr
            260                 265                 270

Val Arg Leu Ser His Asn Ser Leu Thr Asn Asn Gly Leu Ala Ser Asn
            275                 280                 285

Thr Phe Asn Ser Ser Ser Leu Leu Glu Leu Asp Leu Ser Tyr Asn Gln
        290                 295                 300

Leu Gln Lys Ile Pro Pro Val Asn Thr Asn Leu Glu Asn Leu Tyr Leu
305                 310                 315                 320

Gln Gly Asn Arg Ile Asn Glu Phe Ser Ile Ser Ser Phe Cys Thr Val
                325                 330                 335

Val Asp Val Val Asn Phe Ser Lys Leu Gln Val Leu Arg Leu Asp Gly
            340                 345                 350
```

-continued

```
Asn Glu Ile Lys Arg Ser Ala Met Pro Ala Asp Ala Pro Leu Cys Leu
            355                 360                 365

Arg Leu Ala Ser Leu Ile Glu Ile
    370                 375

<210> SEQ ID NO 423
<211> LENGTH: 757
<212> TYPE: PRT
<213> ORGANISM: Homo sapiens

<400> SEQUENCE: 423

Met Val Pro Asp Thr Ala Cys Val Leu Leu Thr Leu Ala Ala Leu
1               5                   10                  15

Gly Ala Ser Gly Gln Gly Gln Ser Pro Leu Gly Ser Asp Leu Gly Pro
                20                  25                  30

Gln Met Leu Arg Glu Leu Gln Glu Thr Asn Ala Ala Leu Gln Asp Val
            35                  40                  45

Arg Glu Leu Leu Arg Gln Gln Val Arg Glu Ile Thr Phe Leu Lys Asn
    50                  55                  60

Thr Val Met Glu Cys Asp Ala Cys Gly Met Gln Gln Ser Val Arg Thr
65                  70                  75                  80

Gly Leu Pro Ser Val Arg Pro Leu Leu His Cys Ala Pro Gly Phe Cys
                85                  90                  95

Phe Pro Gly Val Ala Cys Ile Thr Glu Ser Gly Ala Arg Cys Gly
                100                 105                 110

Pro Cys Pro Ala Gly Phe Thr Gly Asn Gly Ser His Cys Thr Asp Val
            115                 120                 125

Asn Glu Cys Asn Ala His Pro Cys Phe Pro Arg Val Arg Cys Ile Asn
    130                 135                 140

Thr Ser Pro Gly Phe Arg Cys Glu Ala Cys Pro Pro Gly Tyr Ser Gly
145                 150                 155                 160

Pro Thr His Gln Gly Val Gly Leu Ala Phe Ala Lys Ala Asn Lys Gln
                165                 170                 175

Val Cys Thr Asp Ile Asn Glu Cys Glu Thr Gly Gln His Asn Cys Val
            180                 185                 190

Pro Asn Ser Val Cys Ile Asn Thr Arg Gly Ser Phe Gln Cys Gly Pro
    195                 200                 205

Cys Gln Pro Gly Phe Val Gly Asp Gln Ala Ser Gly Cys Gln Arg Arg
210                 215                 220

Ala Gln Arg Phe Cys Pro Asp Gly Ser Pro Ser Glu Cys His Glu His
225                 230                 235                 240

Ala Asp Cys Val Leu Glu Arg Asp Gly Ser Arg Ser Cys Val Cys Ala
                245                 250                 255

Val Gly Trp Ala Gly Asn Gly Ile Leu Cys Gly Arg Asp Thr Asp Leu
            260                 265                 270

Asp Gly Phe Pro Asp Glu Lys Leu Arg Cys Pro Glu Arg Gln Cys Arg
    275                 280                 285

Lys Asp Asn Cys Val Thr Val Pro Asn Ser Gly Gln Glu Asp Val Asp
290                 295                 300

Arg Asp Gly Ile Gly Asp Ala Cys Asp Pro Asp Ala Asp Gly Asp Gly
305                 310                 315                 320

Val Pro Asn Glu Lys Asp Asn Cys Pro Leu Val Arg Asn Pro Asp Gln
                325                 330                 335

Arg Asn Thr Asp Glu Asp Lys Trp Gly Asp Ala Cys Asp Asn Cys Arg
            340                 345                 350
```

```
Ser Gln Lys Asn Asp Asp Gln Lys Asp Thr Asp Gln Asp Gly Arg Gly
        355                 360                 365
Asp Ala Cys Asp Asp Ile Asp Gly Asp Arg Ile Arg Asn Gln Ala
    370                 375                 380
Asp Asn Cys Pro Arg Val Pro Asn Ser Asp Gln Lys Asp Ser Asp Gly
385                 390                 395                 400
Asp Gly Ile Gly Asp Ala Cys Asp Asn Cys Pro Gln Lys Ser Asn Pro
                405                 410                 415
Asp Gln Ala Asp Val Asp His Asp Phe Val Gly Asp Ala Cys Asp Ser
            420                 425                 430
Asp Gln Asp Gln Asp Gly Asp Gly His Gln Asp Ser Arg Asp Asn Cys
        435                 440                 445
Pro Thr Val Pro Asn Ser Ala Gln Glu Asp Ser Asp His Asp Gly Gln
    450                 455                 460
Gly Asp Ala Cys Asp Asp Asp Asp Asn Asp Gly Val Pro Asp Ser
465                 470                 475                 480
Arg Asp Asn Cys Arg Leu Val Pro Asn Pro Gly Gln Glu Asp Ala Asp
                485                 490                 495
Arg Asp Gly Val Gly Asp Val Cys Gln Asp Phe Asp Ala Asp Lys
            500                 505                 510
Val Val Asp Lys Ile Asp Val Cys Pro Glu Asn Ala Glu Val Thr Leu
        515                 520                 525
Thr Asp Phe Arg Ala Phe Gln Thr Val Val Leu Asp Pro Glu Gly Asp
    530                 535                 540
Ala Gln Ile Asp Pro Asn Trp Val Val Leu Asn Gln Gly Arg Glu Ile
545                 550                 555                 560
Val Gln Thr Met Asn Ser Asp Pro Gly Leu Ala Val Gly Tyr Thr Ala
                565                 570                 575
Phe Asn Gly Val Asp Phe Glu Gly Thr Phe His Val Asn Thr Val Thr
            580                 585                 590
Asp Asp Asp Tyr Ala Gly Phe Ile Phe Gly Tyr Gln Asp Ser Ser Ser
        595                 600                 605
Phe Tyr Val Val Met Trp Lys Gln Met Glu Gln Thr Tyr Trp Gln Ala
    610                 615                 620
Asn Pro Phe Arg Ala Val Ala Glu Pro Gly Ile Gln Leu Lys Ala Val
625                 630                 635                 640
Lys Ser Ser Thr Gly Pro Gly Glu Gln Leu Arg Asn Ala Leu Trp His
                645                 650                 655
Thr Gly Asp Thr Glu Ser Gln Val Arg Leu Leu Trp Lys Asp Pro Arg
            660                 665                 670
Asn Val Gly Trp Lys Asp Lys Lys Ser Tyr Arg Trp Phe Leu Gln His
        675                 680                 685
Arg Pro Gln Val Gly Tyr Ile Arg Val Arg Phe Tyr Glu Gly Pro Glu
    690                 695                 700
Leu Val Ala Asp Ser Asn Val Val Leu Asp Thr Thr Met Arg Gly Gly
705                 710                 715                 720
Arg Leu Gly Val Phe Cys Phe Ser Gln Glu Asn Ile Ile Trp Ala Asn
                725                 730                 735
Leu Arg Tyr Arg Cys Asn Asp Thr Ile Pro Glu Asp Tyr Glu Thr His
            740                 745                 750
Gln Leu Arg Gln Ala
        755
```

<210> SEQ ID NO 424
<211> LENGTH: 2415
<212> TYPE: PRT
<213> ORGANISM: Homo sapiens

<400> SEQUENCE: 424

```
Met Thr Thr Leu Leu Trp Val Phe Val Thr Leu Arg Val Ile Thr Ala
1               5                   10                  15

Ala Val Thr Val Glu Thr Ser Asp His Asp Asn Ser Leu Ser Val Ser
            20                  25                  30

Ile Pro Gln Pro Ser Pro Leu Arg Val Leu Leu Gly Thr Ser Leu Thr
        35                  40                  45

Ile Pro Cys Tyr Phe Ile Asp Pro Met His Pro Val Thr Thr Ala Pro
    50                  55                  60

Ser Thr Ala Pro Leu Ala Pro Arg Ile Lys Trp Ser Arg Val Ser Lys
65                  70                  75                  80

Glu Lys Glu Val Val Leu Leu Val Ala Thr Glu Gly Arg Val Arg Val
                85                  90                  95

Asn Ser Ala Tyr Gln Asp Lys Val Ser Leu Pro Asn Tyr Pro Ala Ile
            100                 105                 110

Pro Ser Asp Ala Thr Leu Glu Val Gln Ser Leu Arg Ser Asn Asp Ser
        115                 120                 125

Gly Val Tyr Arg Cys Glu Val Met His Gly Ile Glu Asp Ser Glu Ala
    130                 135                 140

Thr Leu Glu Val Val Lys Gly Ile Val Phe His Tyr Arg Ala Ile
145                 150                 155                 160

Ser Thr Arg Tyr Thr Leu Asp Phe Asp Arg Ala Gln Arg Ala Cys Leu
                165                 170                 175

Gln Asn Ser Ala Ile Ile Ala Thr Pro Glu Gln Leu Gln Ala Ala Tyr
            180                 185                 190

Glu Asp Gly Phe His Gln Cys Asp Ala Gly Trp Leu Ala Asp Gln Thr
        195                 200                 205

Val Arg Tyr Pro Ile His Thr Pro Arg Glu Gly Cys Tyr Gly Asp Lys
    210                 215                 220

Asp Glu Phe Pro Gly Val Arg Thr Tyr Gly Ile Arg Asp Thr Asn Glu
225                 230                 235                 240

Thr Tyr Asp Val Tyr Cys Phe Ala Glu Glu Met Glu Gly Glu Val Phe
                245                 250                 255

Tyr Ala Thr Ser Pro Glu Lys Phe Thr Phe Gln Glu Ala Ala Asn Glu
            260                 265                 270

Cys Arg Arg Leu Gly Ala Arg Leu Ala Thr Thr Gly His Val Tyr Leu
        275                 280                 285

Ala Trp Gln Ala Gly Met Asp Met Cys Ser Ala Gly Trp Leu Ala Asp
    290                 295                 300

Arg Ser Val Arg Tyr Pro Ile Ser Lys Ala Arg Pro Asn Cys Gly Gly
305                 310                 315                 320

Asn Leu Leu Gly Val Arg Thr Val Tyr Val His Ala Asn Gln Thr Gly
                325                 330                 335

Tyr Pro Asp Pro Ser Ser Arg Tyr Asp Ala Ile Cys Tyr Thr Gly Glu
            340                 345                 350

Asp Phe Val Asp Ile Pro Glu Asn Phe Phe Gly Val Gly Gly Glu Glu
        355                 360                 365

Asp Ile Thr Val Gln Thr Val Thr Trp Pro Asp Met Glu Leu Pro Leu
    370                 375                 380
```

```
Pro Arg Asn Ile Thr Glu Gly Glu Ala Arg Gly Ser Val Ile Leu Thr
385                 390                 395                 400

Val Lys Pro Ile Phe Glu Val Ser Pro Ser Pro Leu Glu Pro Glu Glu
            405                 410                 415

Pro Phe Thr Phe Ala Pro Glu Ile Gly Ala Thr Ala Phe Ala Glu Val
        420                 425                 430

Glu Asn Glu Thr Gly Glu Ala Thr Arg Pro Trp Gly Phe Pro Thr Pro
            435                 440                 445

Gly Leu Gly Pro Ala Thr Ala Phe Thr Ser Glu Asp Leu Val Val Gln
        450                 455                 460

Val Thr Ala Val Pro Gly Gln Pro His Leu Pro Gly Val Val Phe
465                 470                 475                 480

His Tyr Arg Pro Gly Pro Thr Arg Tyr Ser Leu Thr Phe Glu Glu Ala
            485                 490                 495

Gln Gln Ala Cys Pro Gly Thr Gly Ala Val Ile Ala Ser Pro Glu Gln
                500                 505                 510

Leu Gln Ala Ala Tyr Glu Ala Gly Tyr Glu Gln Cys Asp Ala Gly Trp
            515                 520                 525

Leu Arg Asp Gln Thr Val Arg Tyr Pro Ile Val Ser Pro Arg Thr Pro
530                 535                 540

Cys Val Gly Asp Lys Asp Ser Ser Pro Gly Val Arg Thr Tyr Gly Val
545                 550                 555                 560

Arg Pro Ser Thr Glu Thr Tyr Asp Val Tyr Cys Phe Val Asp Arg Leu
                565                 570                 575

Glu Gly Glu Val Phe Phe Ala Thr Arg Leu Glu Gln Phe Thr Phe Gln
                580                 585                 590

Glu Ala Leu Glu Phe Cys Glu Ser His Asn Ala Thr Ala Thr Thr Gly
            595                 600                 605

Gln Leu Tyr Ala Ala Trp Ser Arg Gly Leu Asp Lys Cys Tyr Ala Gly
        610                 615                 620

Trp Leu Ala Asp Gly Ser Leu Arg Tyr Pro Ile Val Thr Pro Arg Pro
625                 630                 635                 640

Ala Cys Gly Gly Asp Lys Pro Gly Val Arg Thr Val Tyr Leu Tyr Pro
                645                 650                 655

Asn Gln Thr Gly Leu Pro Asp Pro Leu Ser Arg His His Ala Phe Cys
            660                 665                 670

Phe Arg Gly Ile Ser Ala Val Pro Ser Pro Gly Glu Glu Glu Gly Gly
        675                 680                 685

Thr Pro Thr Ser Pro Ser Gly Val Glu Glu Trp Ile Val Thr Gln Val
        690                 695                 700

Val Pro Gly Val Ala Ala Val Pro Val Glu Glu Thr Thr Ala Val
705                 710                 715                 720

Pro Ser Gly Glu Thr Thr Ala Ile Leu Glu Phe Thr Thr Glu Pro Glu
            725                 730                 735

Asn Gln Thr Glu Trp Glu Pro Ala Tyr Thr Pro Val Gly Thr Ser Pro
            740                 745                 750

Leu Pro Gly Ile Leu Pro Thr Trp Pro Pro Thr Gly Ala Glu Thr Glu
            755                 760                 765

Glu Ser Thr Glu Gly Pro Ser Ala Thr Glu Val Pro Ser Ala Ser Glu
            770                 775                 780

Glu Pro Ser Pro Ser Glu Val Pro Phe Pro Ser Glu Glu Pro Ser Pro
785                 790                 795                 800
```

-continued

```
Ser Glu Glu Pro Phe Pro Ser Val Arg Pro Phe Pro Ser Val Glu Leu
            805                 810                 815

Phe Pro Ser Glu Glu Pro Phe Pro Ser Lys Glu Pro Ser Pro Ser Glu
        820                 825                 830

Glu Pro Ser Ala Ser Glu Glu Pro Tyr Thr Pro Ser Pro Pro Glu Pro
        835                 840                 845

Ser Trp Thr Glu Leu Pro Ser Ser Gly Glu Glu Ser Gly Ala Pro Asp
    850                 855                 860

Val Ser Gly Asp Phe Thr Gly Ser Gly Asp Val Ser Gly His Leu Asp
865                 870                 875                 880

Phe Ser Gly Gln Leu Ser Gly Asp Arg Ala Ser Gly Leu Pro Ser Gly
        885                 890                 895

Asp Leu Asp Ser Ser Gly Leu Thr Ser Thr Val Gly Ser Gly Leu Thr
        900                 905                 910

Val Glu Ser Gly Leu Pro Ser Gly Asp Glu Glu Arg Ile Glu Trp Pro
        915                 920                 925

Ser Thr Pro Thr Val Gly Glu Leu Pro Ser Gly Ala Glu Ile Leu Glu
    930                 935                 940

Gly Ser Ala Ser Gly Val Gly Asp Leu Ser Gly Leu Pro Ser Gly Glu
945                 950                 955                 960

Val Leu Glu Thr Ser Ala Ser Gly Val Gly Asp Leu Ser Gly Leu Pro
            965                 970                 975

Ser Gly Glu Val Leu Glu Thr Ala Pro Gly Val Glu Asp Ile Ser
            980                 985                 990

Gly Leu Pro Ser Gly Glu Val Leu Glu Thr Thr Ala Pro Gly Val Glu
        995                 1000                1005

Asp Ile Ser Gly Leu Pro Ser Gly Glu Val Leu Glu Thr Thr Ala
    1010                1015                1020

Pro Gly Val Glu Asp Ile Ser Gly Leu Pro Ser Gly Glu Val Leu
    1025                1030                1035

Glu Thr Thr Ala Pro Gly Val Glu Asp Ile Ser Gly Leu Pro Ser
    1040                1045                1050

Gly Glu Val Leu Glu Thr Thr Ala Pro Gly Val Glu Asp Ile Ser
    1055                1060                1065

Gly Leu Pro Ser Gly Glu Val Leu Glu Thr Ala Ala Pro Gly Val
    1070                1075                1080

Glu Asp Ile Ser Gly Leu Pro Ser Gly Glu Val Leu Glu Thr Ala
    1085                1090                1095

Ala Pro Gly Val Glu Asp Ile Ser Gly Leu Pro Ser Gly Glu Val
    1100                1105                1110

Leu Glu Thr Ala Ala Pro Gly Val Glu Asp Ile Ser Gly Leu Pro
    1115                1120                1125

Ser Gly Glu Val Leu Glu Thr Ala Ala Pro Gly Val Glu Asp Ile
    1130                1135                1140

Ser Gly Leu Pro Ser Gly Glu Val Leu Glu Thr Ala Ala Pro Gly
    1145                1150                1155

Val Glu Asp Ile Ser Gly Leu Pro Ser Gly Glu Val Leu Glu Thr
    1160                1165                1170

Ala Ala Pro Gly Val Glu Asp Ile Ser Gly Leu Pro Ser Gly Glu
    1175                1180                1185

Val Leu Glu Thr Ala Ala Pro Gly Val Glu Asp Ile Ser Gly Leu
    1190                1195                1200

Pro Ser Gly Glu Val Leu Glu Thr Ala Ala Pro Gly Val Glu Asp
```

```
                1205                1210                1215

Ile Ser Gly Leu Pro Ser Gly Glu Val Leu Glu Thr Ala Ala Pro
        1220                1225                1230

Gly Val Glu Asp Ile Ser Gly Leu Pro Ser Gly Glu Val Leu Glu
    1235                1240                1245

Thr Ala Ala Pro Gly Val Glu Asp Ile Ser Gly Leu Pro Ser Gly
        1250                1255                1260

Glu Val Leu Glu Thr Ala Ala Pro Gly Val Glu Asp Ile Ser Gly
    1265                1270                1275

Leu Pro Ser Gly Glu Val Leu Glu Thr Thr Ala Pro Gly Val Glu
        1280                1285                1290

Glu Ile Ser Gly Leu Pro Ser Gly Val Leu Glu Thr Thr Ala
        1295                1300                1305

Pro Gly Val Asp Glu Ile Ser Gly Leu Pro Ser Gly Glu Val Leu
    1310                1315                1320

Glu Thr Thr Ala Pro Gly Val Glu Glu Ile Ser Gly Leu Pro Ser
    1325                1330                1335

Gly Glu Val Leu Glu Thr Ser Thr Ser Ala Val Gly Asp Leu Ser
    1340                1345                1350

Gly Leu Pro Ser Gly Gly Glu Val Leu Glu Ile Ser Val Ser Gly
    1355                1360                1365

Val Glu Asp Ile Ser Gly Leu Pro Ser Gly Glu Val Val Glu Thr
    1370                1375                1380

Ser Ala Ser Gly Ile Glu Asp Val Ser Glu Leu Pro Ser Gly Glu
    1385                1390                1395

Gly Leu Glu Thr Ser Ala Ser Gly Val Glu Asp Leu Ser Arg Leu
    1400                1405                1410

Pro Ser Gly Glu Glu Val Leu Glu Ile Ser Ala Ser Gly Phe Gly
    1415                1420                1425

Asp Leu Ser Gly Val Pro Ser Gly Gly Glu Gly Leu Glu Thr Ser
    1430                1435                1440

Ala Ser Glu Val Gly Thr Asp Leu Ser Gly Leu Pro Ser Gly Arg
    1445                1450                1455

Glu Gly Leu Glu Thr Ser Ala Ser Gly Ala Glu Asp Leu Ser Gly
    1460                1465                1470

Leu Pro Ser Gly Lys Glu Asp Leu Val Gly Ser Ala Ser Gly Asp
    1475                1480                1485

Leu Asp Leu Gly Lys Leu Pro Ser Gly Thr Leu Gly Ser Gly Gln
    1490                1495                1500

Ala Pro Glu Thr Ser Gly Leu Pro Ser Gly Phe Ser Gly Glu Tyr
    1505                1510                1515

Ser Gly Val Asp Leu Gly Ser Gly Pro Pro Ser Gly Leu Pro Asp
    1520                1525                1530

Phe Ser Gly Leu Pro Ser Gly Phe Pro Thr Val Ser Leu Val Asp
    1535                1540                1545

Ser Thr Leu Val Glu Val Val Thr Ala Ser Thr Ala Ser Glu Leu
    1550                1555                1560

Glu Gly Arg Gly Thr Ile Gly Ile Ser Gly Ala Gly Glu Ile Ser
    1565                1570                1575

Gly Leu Pro Ser Ser Glu Leu Asp Ile Ser Gly Arg Ala Ser Gly
    1580                1585                1590

Leu Pro Ser Gly Thr Glu Leu Ser Gly Gln Ala Ser Gly Ser Pro
    1595                1600                1605
```

```
Asp Val Ser Gly Glu Ile Pro Gly Leu Phe Gly Val Ser Gly Gln
    1610              1615                1620

Pro Ser Gly Phe Pro Asp Thr Ser Gly Glu Thr Ser Gly Val Thr
    1625              1630                1635

Glu Leu Ser Gly Leu Ser Ser Gly Gln Pro Gly Val Ser Gly Glu
    1640              1645                1650

Ala Ser Gly Val Leu Tyr Gly Thr Ser Gln Pro Phe Gly Ile Thr
    1655              1660                1665

Asp Leu Ser Gly Glu Thr Ser Gly Val Pro Asp Leu Ser Gly Gln
    1670              1675                1680

Pro Ser Gly Leu Pro Gly Phe Ser Gly Ala Thr Ser Gly Val Pro
    1685              1690                1695

Asp Leu Val Ser Gly Thr Thr Ser Gly Ser Gly Glu Ser Ser Gly
    1700              1705                1710

Ile Thr Phe Val Asp Thr Ser Leu Val Glu Val Ala Pro Thr Thr
    1715              1720                1725

Phe Lys Glu Glu Glu Gly Leu Gly Ser Val Glu Leu Ser Gly Leu
    1730              1735                1740

Pro Ser Gly Glu Ala Asp Leu Ser Gly Lys Ser Gly Met Val Asp
    1745              1750                1755

Val Ser Gly Gln Phe Ser Gly Thr Val Asp Ser Ser Gly Phe Thr
    1760              1765                1770

Ser Gln Thr Pro Glu Phe Ser Gly Leu Pro Ser Gly Ile Ala Glu
    1775              1780                1785

Val Ser Gly Glu Ser Ser Arg Ala Glu Ile Gly Ser Ser Leu Pro
    1790              1795                1800

Ser Gly Ala Tyr Tyr Gly Ser Gly Thr Pro Ser Ser Phe Pro Thr
    1805              1810                1815

Val Ser Leu Val Asp Arg Thr Leu Val Glu Ser Val Thr Gln Ala
    1820              1825                1830

Pro Thr Ala Gln Glu Ala Gly Glu Gly Pro Ser Gly Ile Leu Glu
    1835              1840                1845

Leu Ser Gly Ala His Ser Gly Ala Pro Asp Met Ser Gly Glu His
    1850              1855                1860

Ser Gly Phe Leu Asp Leu Ser Gly Leu Gln Ser Gly Leu Ile Glu
    1865              1870                1875

Pro Ser Gly Glu Pro Pro Gly Thr Pro Tyr Phe Ser Gly Asp Phe
    1880              1885                1890

Ala Ser Thr Thr Asn Val Ser Gly Glu Ser Ser Val Ala Met Gly
    1895              1900                1905

Thr Ser Gly Glu Ala Ser Gly Leu Pro Glu Val Thr Leu Ile Thr
    1910              1915                1920

Ser Glu Phe Val Glu Gly Val Thr Glu Pro Thr Ile Ser Gln Glu
    1925              1930                1935

Leu Gly Gln Arg Pro Pro Val Thr His Thr Pro Gln Leu Phe Glu
    1940              1945                1950

Ser Ser Gly Lys Val Ser Thr Ala Gly Asp Ile Ser Gly Ala Thr
    1955              1960                1965

Pro Val Leu Pro Gly Ser Gly Val Glu Val Ser Ser Val Pro Glu
    1970              1975                1980

Ser Ser Ser Glu Thr Ser Ala Tyr Pro Glu Ala Gly Phe Gly Ala
    1985              1990                1995
```

```
Ser Ala Ala Pro Glu Ala Ser Arg Glu Asp Ser Gly Ser Pro Asp
    2000                2005                2010

Leu Ser Glu Thr Thr Ser Ala Phe His Glu Ala Asn Leu Glu Arg
    2015                2020                2025

Ser Ser Gly Leu Gly Val Ser Gly Ser Thr Leu Thr Phe Gln Glu
    2030                2035                2040

Gly Glu Ala Ser Ala Ala Pro Glu Val Ser Gly Glu Ser Thr Thr
    2045                2050                2055

Thr Ser Asp Val Gly Thr Glu Ala Pro Gly Leu Pro Ser Ala Thr
    2060                2065                2070

Pro Thr Ala Ser Gly Asp Arg Thr Glu Ile Ser Gly Asp Leu Ser
    2075                2080                2085

Gly His Thr Ser Gln Leu Gly Val Val Ile Ser Thr Ser Ile Pro
    2090                2095                2100

Glu Ser Glu Trp Thr Gln Gln Thr Gln Arg Pro Ala Glu Thr His
    2105                2110                2115

Leu Glu Ile Glu Ser Ser Ser Leu Leu Tyr Ser Gly Glu Glu Thr
    2120                2125                2130

His Thr Val Glu Thr Ala Thr Ser Pro Thr Asp Ala Ser Ile Pro
    2135                2140                2145

Ala Ser Pro Glu Trp Lys Arg Glu Ser Glu Ser Thr Ala Ala Ala
    2150                2155                2160

Pro Ala Arg Ser Cys Ala Glu Glu Pro Cys Gly Ala Gly Thr Cys
    2165                2170                2175

Lys Glu Thr Glu Gly His Val Ile Cys Leu Cys Pro Pro Gly Tyr
    2180                2185                2190

Thr Gly Glu His Cys Asn Ile Asp Gln Glu Val Cys Glu Glu Gly
    2195                2200                2205

Trp Asn Lys Tyr Gln Gly His Cys Tyr Arg His Phe Pro Asp Arg
    2210                2215                2220

Glu Thr Trp Val Asp Ala Glu Arg Arg Cys Arg Glu Gln Gln Ser
    2225                2230                2235

His Leu Ser Ser Ile Val Thr Pro Glu Glu Gln Glu Phe Val Asn
    2240                2245                2250

Asn Asn Ala Gln Asp Tyr Gln Trp Ile Gly Leu Asn Asp Arg Thr
    2255                2260                2265

Ile Glu Gly Asp Phe Arg Trp Ser Asp Gly His Pro Met Gln Phe
    2270                2275                2280

Glu Asn Trp Arg Pro Asn Gln Pro Asp Asn Phe Phe Ala Ala Gly
    2285                2290                2295

Glu Asp Cys Val Val Met Ile Trp His Glu Lys Gly Glu Trp Asn
    2300                2305                2310

Asp Val Pro Cys Asn Tyr His Leu Pro Phe Thr Cys Lys Lys Gly
    2315                2320                2325

Thr Val Ala Cys Gly Glu Pro Pro Val Val Glu His Ala Arg Thr
    2330                2335                2340

Phe Gly Gln Lys Lys Asp Arg Tyr Glu Ile Asn Ser Leu Val Arg
    2345                2350                2355

Tyr Gln Cys Thr Glu Gly Phe Val Gln Arg His Met Pro Thr Ile
    2360                2365                2370

Arg Cys Gln Pro Ser Gly His Trp Glu Glu Pro Arg Ile Thr Cys
    2375                2380                2385

Thr Asp Ala Thr Thr Tyr Lys Arg Arg Leu Gln Lys Arg Ser Ser
```

```
                2390              2395               2400
Arg His  Pro Arg Arg Ser Arg  Pro Ser Thr Ala His
    2405              2410               2415
```

<210> SEQ ID NO 425
<211> LENGTH: 143
<212> TYPE: PRT
<213> ORGANISM: Homo sapiens

<400> SEQUENCE: 425

```
Ala Val Leu Pro Gln Glu Glu Gly Ser Gly Gly Gly Gln Leu Val
1               5                   10                  15

Thr Glu Val Thr Lys Lys Glu Asp Ser Cys Gln Leu Gly Tyr Ser Ala
                20                  25                  30

Gly Pro Cys Met Gly Met Thr Ser Arg Tyr Phe Tyr Asn Gly Thr Ser
            35                  40                  45

Met Ala Cys Glu Thr Phe Gln Tyr Gly Gly Cys Met Gly Asn Gly Asn
    50                  55                  60

Asn Phe Val Thr Glu Lys Glu Cys Leu Gln Thr Cys Arg Thr Val Ala
65                  70                  75                  80

Ala Cys Asn Leu Pro Ile Val Arg Gly Pro Cys Arg Ala Phe Ile Gln
                85                  90                  95

Leu Trp Ala Phe Asp Ala Val Lys Gly Lys Cys Val Leu Phe Pro Tyr
            100                 105                 110

Gly Gly Cys Gln Gly Asn Gly Asn Lys Phe Tyr Ser Glu Lys Glu Cys
        115                 120                 125

Arg Glu Tyr Cys Gly Val Pro Gly Asp Gly Asp Glu Glu Leu Leu
    130                 135                 140
```

<210> SEQ ID NO 426
<211> LENGTH: 168
<212> TYPE: PRT
<213> ORGANISM: Glycine max

<400> SEQUENCE: 426

```
Met Pro Ser Thr Trp Gly Ala Ala Gly Gly Gly Leu Lys Leu Gly Arg
1               5                   10                  15

Thr Gly Asn Ser Asn Cys Pro Val Thr Val Leu Gln Asp Tyr Ser Glu
                20                  25                  30

Ile Phe Arg Gly Thr Pro Val Lys Phe Ser Ile Pro Gly Ile Ser Pro
            35                  40                  45

Gly Ile Ile Phe Thr Gly Thr Pro Leu Glu Ile Glu Phe Ala Glu Lys
    50                  55                  60

Pro Tyr Cys Ala Glu Ser Ser Lys Trp Val Ala Phe Val Asp Asn Glu
65                  70                  75                  80

Ile Gln Lys Ala Cys Val Gly Ile Gly Gly Pro Glu Gly His Pro Gly
                85                  90                  95

Gln Gln Thr Phe Ser Gly Thr Phe Ser Ile Gln Lys Tyr Lys Phe Gly
            100                 105                 110

Tyr Lys Leu Val Phe Cys Ile Thr Gly Ser Gly Thr Cys Leu Asp Ile
        115                 120                 125

Gly Arg Phe Asp Ala Lys Asn Gly Glu Gly Gly Arg Arg Leu Asn Leu
    130                 135                 140

Thr Glu His Glu Ala Phe Asp Ile Val Phe Ile Glu Ala Ser Lys Val
145                 150                 155                 160

Asp Gly Ile Ile Lys Ser Val Val
                165
```